(12) United States Patent
Hua et al.

(10) Patent No.: US 12,383,581 B2
(45) Date of Patent: Aug. 12, 2025

(54) COMPOSITIONS AND METHODS FOR TARGETING CD13 AND TIM-3 WITH CAR T CELLS TO TREAT ACUTE MYELOID LEUKEMIA

(71) Applicant: THE TRUSTEES OF THE UNIVERSITY OF PENNSYLVANIA, Philadelphia, PA (US)

(72) Inventors: Xianxin Hua, Wynnewood, PA (US); Xin He, Philadelphia, PA (US); Xuyao Zhang, Shanghai (CN)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 54 days.

(21) Appl. No.: 17/767,831

(22) PCT Filed: Oct. 9, 2020

(86) PCT No.: PCT/US2020/055138
§ 371 (c)(1),
(2) Date: Apr. 8, 2022

(87) PCT Pub. No.: WO2021/072312
PCT Pub. Date: Apr. 15, 2021

(65) Prior Publication Data
US 2024/0082302 A1 Mar. 14, 2024

Related U.S. Application Data

(60) Provisional application No. 62/913,915, filed on Oct. 11, 2019.

(51) Int. Cl.
*A61K 35/17* (2025.01)
*A61K 40/11* (2025.01)
(Continued)

(52) U.S. Cl.
CPC ............. *A61K 35/17* (2013.01); *A61K 40/11* (2025.01); *A61K 40/31* (2025.01); *A61K 40/421* (2025.01);
(Continued)

(58) Field of Classification Search
CPC ................ A61K 35/17; A61K 39/4611; A61K 39/4631; A61K 39/464411;
(Continued)

(56) References Cited

U.S. PATENT DOCUMENTS 9,605,070 B2    3/2017   Sabatos-Peyton et al.
2014/0050708 A1 2/2014   Powell et al.
(Continued)

FOREIGN PATENT DOCUMENTS

WO   2011/155607 A1   12/2011
WO   2016/014576 A1    1/2016
(Continued)

OTHER PUBLICATIONS

Williams, B.A., et al.(2019) Antibody therapies for Acute Myeloid Leukeima: unconjugated, toxin-conjugated, radio-conjugated and multivalent formats Journal of clinical medicine 8(1261); 1-31 (Year: 2019).*

(Continued)

*Primary Examiner* — Scarlett Y Goon
*Assistant Examiner* — Audrey L Buttice
(74) *Attorney, Agent, or Firm* — Saul Ewing LLP; Kathryn Doyle; Alireza Behrooz

(57) ABSTRACT

The present invention includes compositions and methods for treating AML utilizing bispecific CARs. In certain aspects, the invention includes a bispecific split CAR which binds CD13 and TIM-3 on AML cells.

15 Claims, 21 Drawing Sheets

Specification includes a Sequence Listing.

(51) Int. Cl.
  *A61K 40/31* (2025.01)
  *A61K 40/42* (2025.01)
  *A61P 35/02* (2006.01)
  *C07K 16/28* (2006.01)
  *C07K 16/40* (2006.01)

(52) U.S. Cl.
  CPC ...... *A61K 40/4224* (2025.01); *A61K 40/4244* (2025.01); *A61P 35/02* (2018.01); *C07K 16/2803* (2013.01); *C07K 16/40* (2013.01); *A61K 2239/13* (2023.05); *A61K 2239/17* (2023.05); *A61K 2239/21* (2023.05); *A61K 2239/22* (2023.05); *A61K 2239/29* (2023.05); *A61K 2239/48* (2023.05)

(58) Field of Classification Search
  CPC ........ A61K 39/464454; A61K 2239/13; A61K 2239/17; A61K 2239/21; A61K 2239/22; A61K 2239/29; A61K 2239/48; A61K 39/464429; A61K 2039/505; A61K 2039/507; A61K 2039/804; A61P 35/02; C07K 16/2803; C07K 16/40; C07K 16/2896; C07K 2317/22; C07K 2317/31; C07K 2317/569; C07K 2317/622; C07K 2319/03; C07K 14/70521; C07K 14/7051; C07K 14/705
  See application file for complete search history.

(56) References Cited

U.S. PATENT DOCUMENTS

| | | | |
|---|---|---|---|
| 2015/0218274 A1 | 8/2015 | Sabatos-Peyton et al. |
| 2016/0075769 A1 | 3/2016 | Agrosavfe |
| 2016/0362472 A1 | 12/2016 | Bitter et al. |
| 2017/0296623 A1 | 10/2017 | Cellectis |
| 2018/0280551 A1 | 4/2018 | Rashidian et al. |

FOREIGN PATENT DOCUMENTS

| | | | | |
|---|---|---|---|---|
| WO | 2017/079400 A1 | 5/2017 | | |
| WO | 2017/222593 A1 | 12/2017 | | |
| WO | 2018/068053 A2 | 4/2018 | | |
| WO | 2018/120842 A1 | 7/2018 | | |
| WO | 2018/156434 A1 | 8/2018 | | |
| WO | WO-2018161017 A1 * | 9/2018 | ........... | A61K 31/505 |
| WO | 2019/032661 A1 | 2/2019 | | |
| WO | 2019/074542 A1 | 4/2019 | | |
| WO | 2019/118518 A2 | 6/2019 | | |
| WO | 2019/210155 A1 | 10/2019 | | |

OTHER PUBLICATIONS

Gould, N., et al (2014) Computational tools and algorithms for designing and customized synthetic genes Frontiers in Bioengineering and Biotechnology 2(41); 1-14 (Year: 2014).*
Lee, H.K et al., "CD13 and CD33 CAR-T cells for the treatment of myeloid malignancies", Annals of Oncology, vol. 29, Oct. 1, 2018, pp. viii360-viii361.
He, X et al., "Bispecific and split CAR T cells targeting CD13 and TIM3 eradicate acute myeloid leukemia", Blood, Mar. 5, 2020, 135(10):713-723.
Kaneko, T. et al.,"A Bispecific Antibody Enhances Cytokine-Induced Killer-Mediated Cytolysis Of Autologous Acute Myeloid Leukemia Cells", Blood, American Society of Hematology, US, vol. 81, No. 5, Mar. 1, 1993, pp. 1333-1341.
Kikushige Y., et al., "TIM-3 is a promising target to selectively kill acute myeloid leukemia stem cells", Cell Stem Cell Dec. 3, 2010;7(6):708-717.
Rodgers, D.T. et al., "Switch-mediated activation and retargeting of CAR-T cells for B-cell malignancies", Proceedings of the National Academy of Sciences of the United States of America, Jan. 12, 2016, 113(4):E459-468.
Taussig D.C., et al. "Hematopoietic stem cells express multiple myeloid markers: implications for the origin and targeted therapy of acute myeloid leukemia" Blood, Dec. 15, 2005, 106(13):4086-4092.
Zahnd C., et al., "Directed in vitro evolution and crystallographic analysis of a peptide-binding single chain antibody fragment (scFv) with low picomolar affinity", Jan. 30, 2004 J Biol Chem. Apr. 30, 2004; 279(18):18870-18877.
Hoseini, S.S. et al., "Acute myeloid leukemia targets for bispecific antibodies", Blood Cancer Journal, Feb. 3, 2017, 7(2):e522.
International Search Report and Written Opinion dated Feb. 9, 2021 of corresponding International Patent Application No. PCT/US2020/055138.
Partial Supplementary European Search Report dated Oct. 30, 2023, of corresponding European Patent Application No. 20874662.8.
Extended European Search Report issued Jan. 30, 2024 in European Patent Application No. EP20874662.8.

* cited by examiner

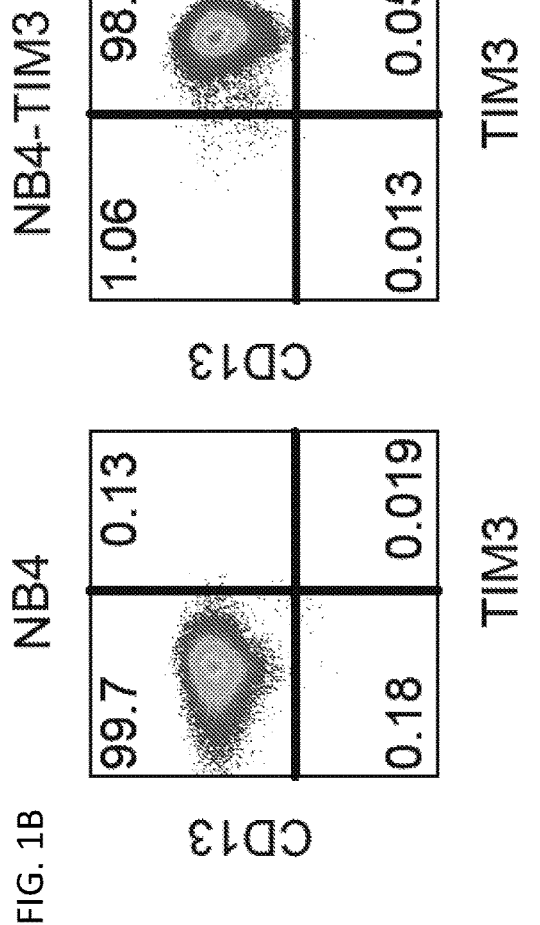
FIG. 1A
FIG. 1B
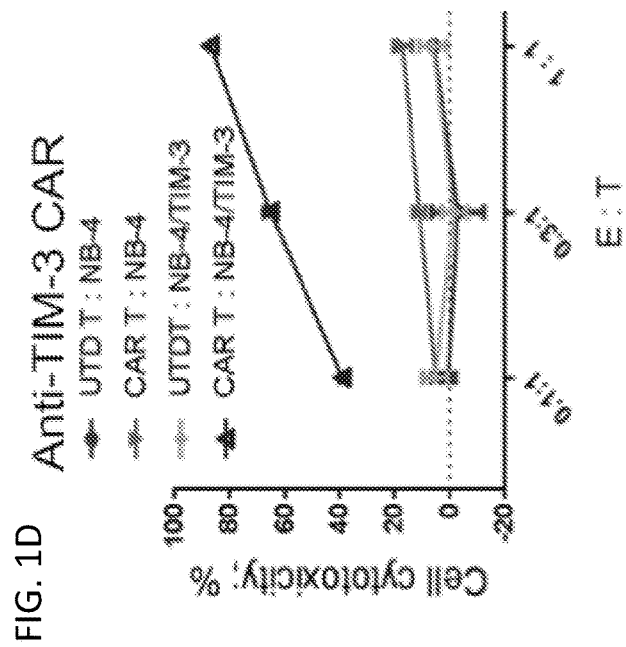
FIG. 1C
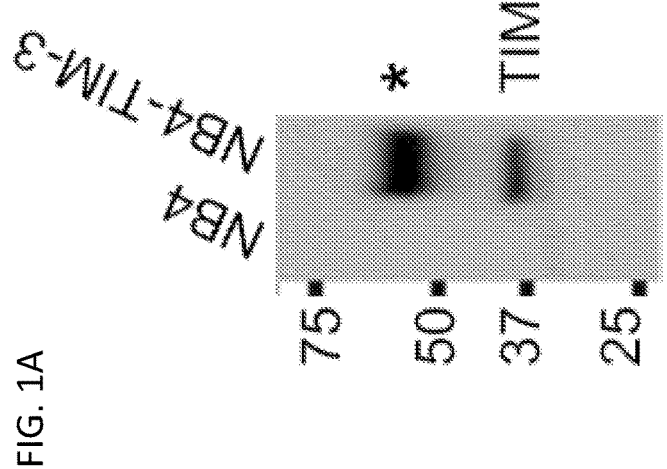
FIG. 1D

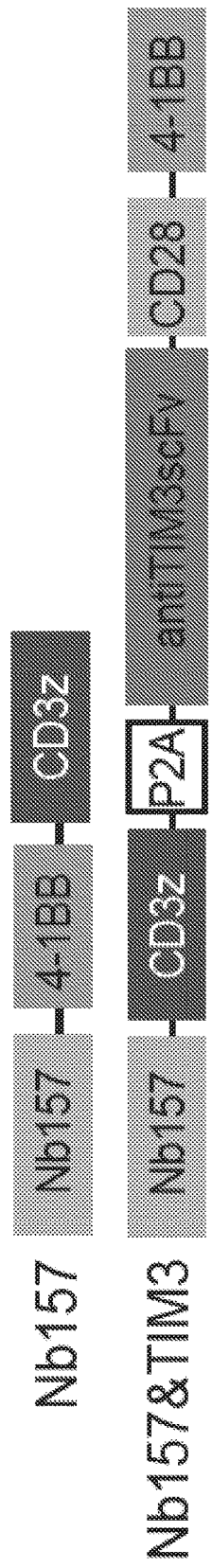
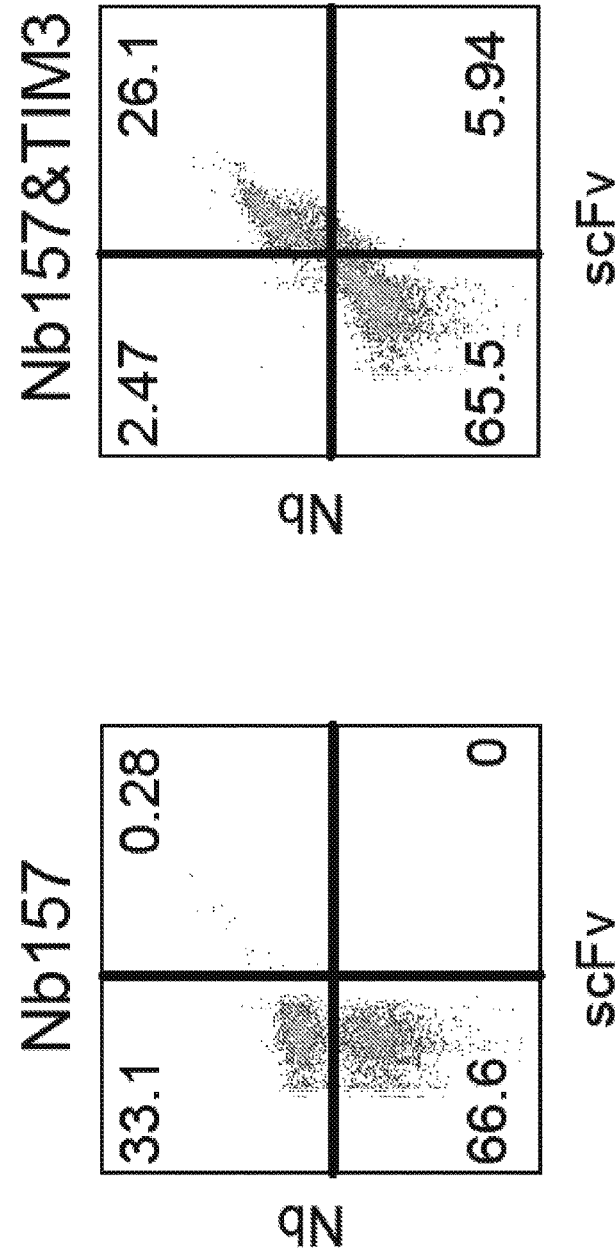
FIG. 3A
FIG. 3B

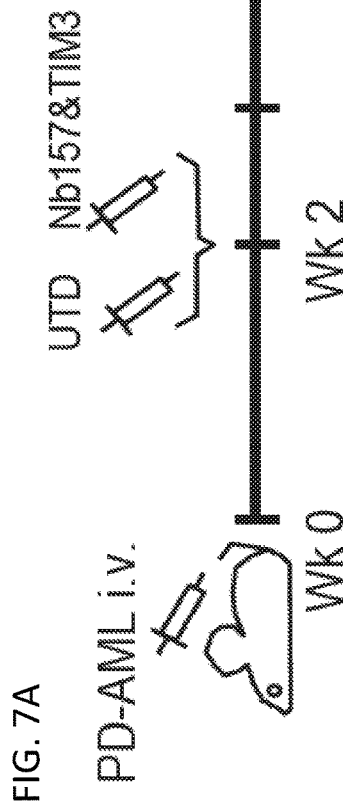
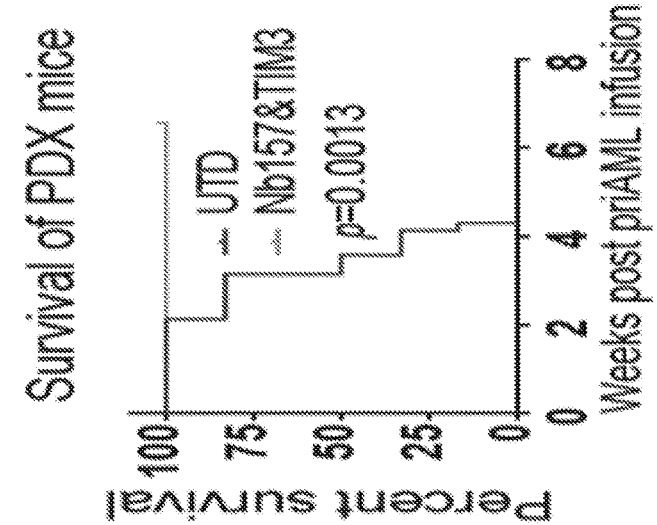
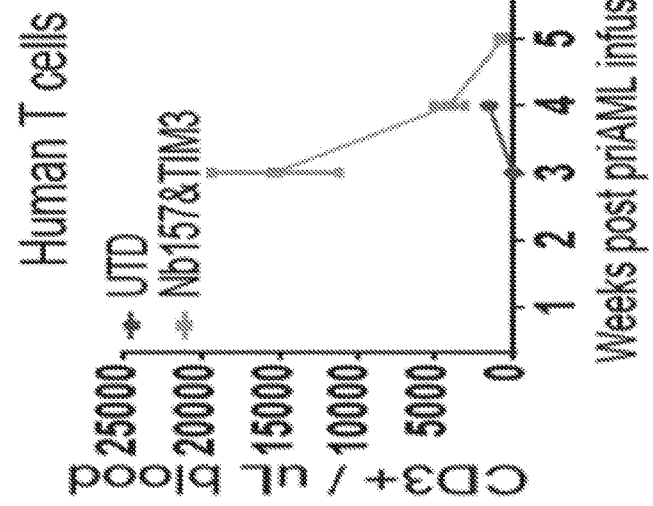
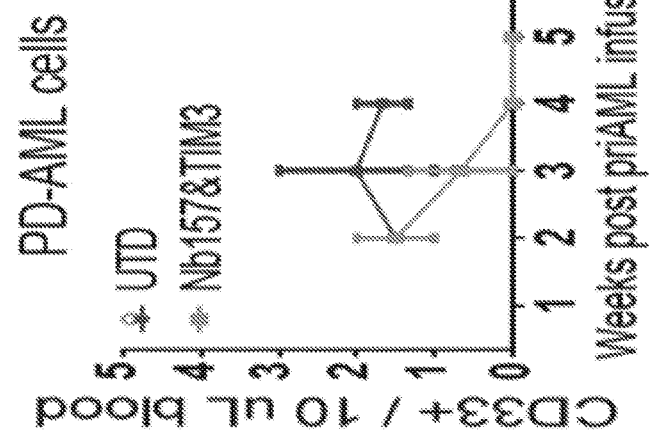
FIG. 7A
FIG. 7B
FIG. 7C
FIG. 7D

COMPOSITIONS AND METHODS FOR TARGETING CD13 AND TIM-3 WITH CAR T CELLS TO TREAT ACUTE MYELOID LEUKEMIA

CROSS-REFERENCE TO RELATED APPLICATION

The present application is a 35 U.S.C. § 371 national phase application from, and claims priority to, International Application No. PCT/US2020/055138, filed Oct. 9, 2020, and is entitled to priority under 35 U.S.C. § 119 (e) to U.S. Provisional Patent Application No. 62/913,915, filed Oct. 11, 2019, all of which are incorporated herein by reference in their entireties.

REFERENCE TO AN ELECTRONIC SEQUENCE LISTING

The instant application contains a Sequence Listing which has been submitted in ASCII format via EFS-Web and is hereby incorporated by reference in its entirety. Said ASCII copy, created on Sep. 25, 2024 is named "046483-7259US1 (02850).txt and is 136,499 bytes in size.

BACKGROUND OF THE INVENTION

Acute myeloid leukemia (AML) is a major form of acute leukemia in elder adults. The treatment of AML has changed little in the past decades and the overall 5-year survival rate remains very poor in AML patients. AML relapse from chemotherapy is highly aggressive with poor prognosis. While adaptive cell therapy via chimeric antigen receptor (CAR)-expressing T cells is quite successful for treating acute and chronic lymphoblastic leukemia by targeting CD19, this approach has not yet been extensively explored for AML. There is an urgent need to develop potent antibodies against AML-specific surface targets to improve the therapy.

The CAR structure generally comprises an extracellular antigen recognition region and intracellular activation region. The recognition region typically comprises a single-chain variable fragment (scFv), composed of an antibody's heavy and light variable regions. The activation signal is transduced by the intracellular domains of the CD3 zeta, co-stimulatory 4-1BB and/or CD28. The co-stimulatory signals prolong survival and enhance cytotoxicity of CAR T cells to eliminate the cancer cells. CAR T cells targeting CD33, a cell surface lectin, and CD123, a subunit of IL-3 receptor, were tested for suppressing AML, but the approach was hindered by side effects.

A need exists for novel approaches for improving CAR T cell-mediated AML therapy. The present invention addresses this need.

SUMMARY OF THE INVENTION

As described herein, the present invention relates to compositions and methods for treating AML utilizing bispecific CARs (e.g. bispecific split CARs which bind CD13 and TIM-3 on AML cells.)

In one aspect, the invention provides a bispecific chimeric antigen receptor (CAR) comprising a first antigen binding domain capable of binding CD13, a first intracellular domain, a second antigen binding domain capable of binding TIM-3, a transmembrane domain, and a second intracellular domain.

In certain embodiments, the first and/or second antigen binding domain is selected from the group consisting of an antibody, a nanobody, a Fab, or an scFv.

In certain embodiments, the second antigen binding domain comprises a nanobody, wherein the nanobody is Nb157.

In certain embodiments, the first antigen binding domain comprises the amino acid sequence set forth in SEQ ID NO: 1.

In certain embodiments, the second antigen binding domain comprises the amino acid sequence set forth in SEQ ID NO: 6.

In certain embodiments, the second antigen binding domain comprises an amino acid sequence selected from the group consisting of SEQ ID NO: 20, 22, 24, 26, 28, 30, and 32. In certain embodiments, the second antigen binding domain is encoded by a nucleotide sequence selected from the group consisting of SEQ ID NO: 19, 21, 23, 25, 27, 29, and 31.

In certain embodiments, the transmembrane domain comprises CD28.

In certain embodiments, the first intracellular domain is selected from the group consisting of 4-1BB, CD28, and CD3 zeta. In certain embodiments, the second intracellular domain is selected from the group consisting of 4-1BB, CD28, and CD3 zeta.

In certain embodiments, the bispecific CAR further comprises a hinge domain selected from the group consisting of a CD8 hinge, an IgG3s hinge, and an IgG4m hinge.

In certain embodiments, the bispecific CAR is encoded by a nucleotide sequence selected from the group consisting of SEQ ID NOs: 33-39.

In another aspect, the invention provides an inducible bispecific CAR comprising a first antigen binding domain capable of binding Peptide-Neo-Epitope (PNE), a first transmembrane domain, a first intracellular domain, a second antigen binding domain capable of binding TIM-3, a transmembrane domain, and a second intracellular domain.

In certain embodiments, the first and/or second antigen binding domain is selected from the group consisting of an antibody, a Fab, or an scFv.

In certain embodiments, the second antigen binding domain comprises the amino acid sequence set forth in any one of SEQ ID NOs: 6, 20, 22, 24, 26, 28, 30, and 32.

In certain embodiments, the first and/or second transmembrane domain comprises CD28.

In certain embodiments, the first intracellular domain comprises CD3 zeta. In certain embodiments, the second intracellular domain comprises 4-1BB.

In certain embodiments, the CAR further comprises a hinge domain selected from the group consisting of a CD8 hinge, an IgG3s hinge, and an IgG4m hinge.

In another aspect, the invention provides a chimeric antigen receptor (CAR) comprising an antigen binding domain specific for TIM-3, a transmembrane domain, and an intracellular signaling domain.

In certain embodiments, the antigen binding domain is selected from the group consisting of an antibody, a nanobody, a Fab, or an scFv.

In certain embodiments, the antigen binding domain comprises the amino acid sequence set forth in any one of SEQ ID NOs: 6, 20, 22, 24, 26, 28, 30, and 32.

In certain embodiments, the CAR further comprises a hinge domain selected from the group consisting of a CD8 hinge, an IgG3s hinge, and an IgG4m hinge.

In certain embodiments, the transmembrane domain is selected from the group consisting of CD8, CD28, and ICOS.

In certain embodiments, the intracellular domain comprises 4-1BB and CD3 zeta.

In certain embodiments, the CAR comprises the amino acid sequence of SEQ ID NO: 13. In certain embodiments, the CAR is encoded by the nucleotide sequence of SEQ ID NO: 14.

In another aspect, the invention provides a modified T cell or precursor thereof, comprising any of the CARs or bispecific CARs contemplated herein.

In certain embodiments, the T cell is autologous.

In another aspect, the invention provides a nucleic acid encoding any of the CARs or bispecific CARs contemplated herein.

In another aspect, the invention provides a method for treating cancer in a subject in need thereof. The method comprises administering to the subject a modified T cell or precursor thereof comprising the any of the CARs or bispecific CARs contemplated herein. In certain embodiments, the cancer is acute myeloid leukemia (AML).

BRIEF DESCRIPTION OF THE DRAWINGS

The following detailed description of specific embodiments of the invention will be better understood when read in conjunction with the appended drawings. For the purpose of illustrating the invention, there are shown in the drawings exemplary embodiments. It should be understood, however, that the invention is not limited to the precise arrangements and instrumentalities of the embodiments shown in the drawings.

FIGS. 1A-1D are series of images and graphs depicting an anti-TIM3 CAR that empowers T cells to specifically kill TIM-3 expressing AML cells. FIG. 1A illustrates confirmation of TIM-3 expression in NB4-TIM-3 cell lines by Western Blot. The star indicates the glycosylated TIM-3 protein. FIG. 1B shows flow cytometry analysis of NB4 and NB4-TIM3 cells by staining them with the antibodies targeting either CD13 and TIM3, indicating that NB4 cells only expressed CD13 and NB4-TIM3 cells expressed both CD13 and TIM3. FIG. 1C is a schematic diagram of an anti-TIM3 CAR. FIG. 1D illustrates cytotoxity of the anti-TIM-3 CAR T against NB4-TIM-3 cells. NB4 or NB4-TIM-3 cells were incubated with anti-TIM-3-scFv-CAR T cells overnight. Untransduced (UTD) T cells were used as a negative control. Cytotoxicity was detected by flow cytometry analysis of the survial THP-1 cells. The data demonstrate that anti-TIM3 CAR T cells specifically kill TIM-3-expressing myeloid leukemia cells.

FIGS. 3A-3C illustrate and compare a $2^{nd}$ generation CAR targeting CD13 and a bispecific split CAR targeting both CD13 and TIM3. FIG. 3A is a schematic showing a 2nd generation CAR targeting CD13 (Nb157) and a bispecific split CAR (BissCAR) targeting both CD13 and TIM3 (Nb157 & TIM3). FIG. 3B illustrates cell surface expression of the respective CARs on the transduced CAR T cells. FIG. 3C illustrates each CARs ability to kill NB4 or NB4-TIM3 cells in vitro (FIG. 3C).

FIG. 4A is a schematic diagram of combinatorial bispecific and split CARs of the Nb157 (anti-CD13) and anti-TIM3 system. Nb157 linked with CD3z recognized CD13 on normal HSCs or LSCs. Anti-TIM3 linked with CD28 and 4-1BB recognized TIM3 only on LSCs. Such Biss CAR T cells can be fully activated only by LSCs but not by HSCs. FIG. 4B shows flow cytometry data showing the expression of TIM3, CD90, and CD13 on normal donor bone marrow cells (ND-BM) and patient-derived AML (PD-AML) cells, which were gated on $CD45^+Lin^-CD34^+CD38^-$ subsets. Flow cytometry analysis showed that normal donor (ND) bone marrow $CD34^+/CD38^-/CD90$ cells, an HSC-enriched population, identifiable in the ND sample, but very low in AML patient derived leukemia sample (PD-AML) (FIG. 4B, top panels). In contrast, the TIM3/CD13 double positive cells from the $CD34^+/CD38^-$ cell population were significantly increased in the PD-AML sample.

FIGS. 7A-7H illustrate BissCAR T cells targeting CD13 and TIM3 erradicate AML PDXs, but with reduced toxicity to human HSCs in vivo. FIG. 7A is a schematic diagram of an AML PDX mice treated with control or BissCAR T cells. Twenty million patient derived AML cells were injected into each NSG mouse, followed by injection of 5 million BissCAR T cells or UTD T cells, 2 weeks later. Human peripheral blood CD3+ cells were analyzed by serial bleeding weekly. FIGS. 7B-7C depict patient-derived AML cells or T cells in mouse peripheral blood were monitored weekly by staining with anti-human CD33 or anti-human CD3 antibodies. FIG. 7D shows mice survival was monitored and recorded (n=6 per group). FIG. 7E is a schematic diagram of HIS mice for evaluation of human HSC toxicity. A total of 1.5 million normal donor bone marrow (BM) CD34+ cells were injected into each NSG mouse. Four weeks later, 3 million Nb157 anti-TIM3 BissCAR T cells, or conventional Nb157 CARs, or UTD T cells were injected intravenously, followed by flow cytometry analysis of peripheral blood and bone marrow (n=5 per group for Biss CAR and UTD cells; n=3 per group of Nb157 cells). FIG. 7F shows bone marrow of HIS mice, which were treated with T cells for 3 weeks, was analyzed by flow cytometry after staining with CD45/Lin/CD34/CD38/7-AAD. Representative fluorescence-activate cell sorting plots were used to identify HSC ($CD34^+CD38^+$) and myeloid progenitors ($CD34^+CD38^+$). FIG. 7G shows HSCs ($CD45^+Lin^-CD34^+CD38^+$) in the bone marrow of HIS mice were analyzed by flow cytometry 3 weeks after the initial treatment. FIG. 7H shows myeloid progenitors ($CD45^+Lin\ CD34^+CD38^-$) in the bone marrow of HIS mice were analyzed by flow cytometry 3 weeks after the initial treatment. In FIG. 7G-7I, n=5 per group for BissCAR T cells and UTD T cells, n=3 per group for Nb157 T cells. *P<. 05, P<01, *P<. 001, Student t test.

FIG. 10A is a schematic illustrating construction of bispecific CARs using newly generated anti-TIM3 VHHs. FIGS. 10B-10C illustrate expression of the bispecific CARs on primary human T cells.

FIGS. 12A-12E illustrate the specificity of the various bispecific CARTs in suppressing tumors in vivo. The antitumor effects of bispecific CAR T cells against NB4-CD13KO (FIG. 12A), NB4 (FIG. 12B) and NB4-TIM3 (FIG. 12C) tumors were evaluated. Various NB4 cells were injected subcutaneously into each flank of a NSG mice (n=3), and the indicated CARTs (5*10$^6$) were injected into each mouse via tail vein at 7 days after tumor cell injection. The number of human T cells in peripheral blood of mice bearing NB4-CD13KO, NB4 and NB4-TIM3 tumors was measured by flow cytometry 7 days (FIG. 12D) and 14 days (FIG. 12E) after T cell infusion.

FIG. 13A shows the number of colonies from control (UTD) or the bispecific CART treated plates. FIG. 13B is a linear graph comparing the dose-dependent effect of the CARTs based on colony number.

DETAILED DESCRIPTION

Definitions

Figure 2:
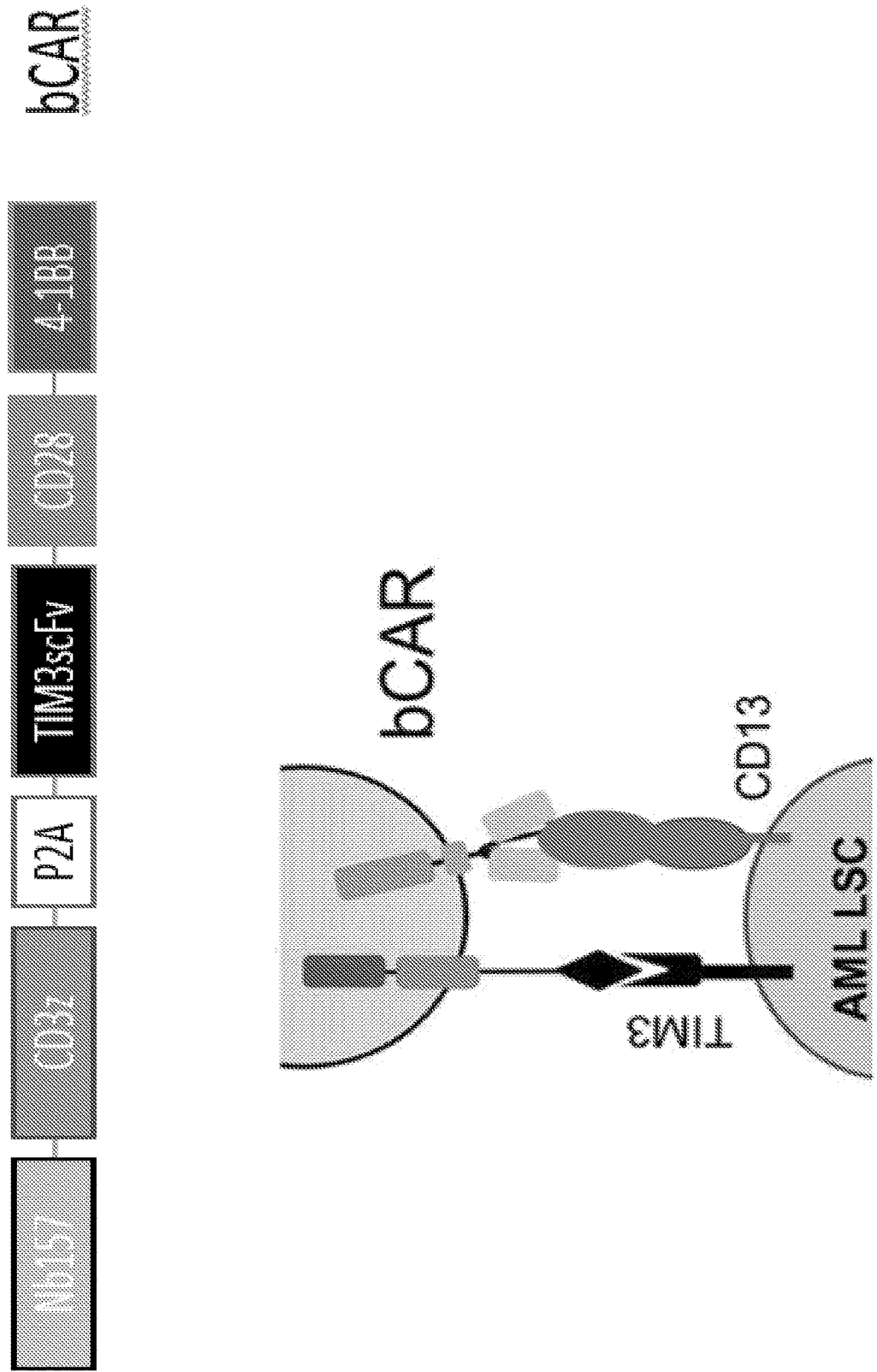
FIG. 2 illustrates a bispecific split CAR (BissCAR) that can specifically kill tumor cells expressing both TIM-3 and CD13.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

"Allogeneic" refers to a graft derived from a different animal of the same species.

"Alloantigen" refers to an antigen present only in some individuals of a species and capable of inducing the production of an alloantibody by individuals which lack it.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F (ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. α and β light chains refer to the two major antibody light chain isotypes.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene"

at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

"Allogeneic" refers to any material derived from a different animal of the same species. The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CAR has specificity to a selected target, for example a tumor antigen. CARs may also comprise an intracellular activation domain, a transmembrane domain and an extracellular domain comprising an antigen binding region.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. Preferably, the epitope is about 4-18 amino acids, more preferably about 5-16 amino acids, and even more most preferably 6-14 amino acids, more preferably about 7-12, and most preferably about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide of the present invention can be an epitope.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

The term "immunostimulatory" is used herein to refer to increasing overall immune response.

The term "immunosuppressive" is used herein to refer to reducing overall immune response.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Octretotide" is an octapeptide that mimics natural somatostatin. It is a long-acting analog of somatostatin. It is sold under the brand name Sandostatin (Novartis Pharmaceuticals). d-Phe-Cys-Phe-d-Trp-Lys-Thr-Cys-Thr-ol (SEQ ID NO: 40)

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "self-antigen" as used herein is defined as an antigen that is expressed by a host cell or tissue. Self-antigens may be tumor antigens, but in certain embodiments, are expressed in both normal and tumor cells. A skilled artisan would readily understand that a self-antigen may be overexpressed in a cell.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

As used herein, a switchable CAR (sCAR) refers to a CAR comprising a Peptide-Neo-Epitope (PNE) binding domain, a transmembrane domain, and an intracellular domain.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha ($\alpha$) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

"Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver. A transplant can also refer to any material that is to be administered to a host. For example, a transplant can refer to a nucleic acid or a protein.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

"Xenogeneic" refers to any material derived from an animal of a different species.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

Acute myeloid leukemia (AML) patients relapsing after chemotherapy have a poor overall 5-year survival prognosis. The present invention provides CAR T cells possessing the necessary specificity towards AML cancer cells while avoiding on-target, off-tumor effects. CD13 is upregulated in AML cells in over 80% of AML patients, but is also moderately expressed in a few types of normal tissues including HSCs. TIM-3 is expressed on the surface of LSCs in many types of human acute myeloid leukemia (AML), but not on hematopoietic stem cells (HSCs). Targeting both TIM3 and CD13, as disclosed herein, provides the specificity needed to target the AML tumor while sparing HSCs and the healthy myeloid compartment of the hemopoietic system.

The present invention includes compositions and methods for bispecific and inducible CAR T cells that specifically kill cancer cells (e.g. AML leukemia stem cells (LSCs)) that commonly express both TIM-3 and CD13.

Chimeric Antigen Receptor

Certain embodiments of the invention include chimeric antigen receptors (CARs), including bispecific CARs comprising the following components: At least one antigen binding domain, at least one transmembrane domain, and at least one intracellular domain. The CARs may optionally comprise a hinge domain.

a) Antigen Binding Domain

In one embodiment, the CAR (or bispecific CAR) of the invention comprises an antigen binding domain that is a variable domain heavy-chain camelid antibody (VHH), also referred to as a nanobody (Nb). In another embodiment, the CAR comprises an antigen binding domain that binds to TIM-3. In another embodiment, the CAR comprises an antigen binding domain that binds to CD13. In another embodiment, the CAR comprises an antigen binding domain that binds to Peptide-Neo-Epitope (PNE).

The choice of antigen binding domain(s) depends upon the type of CAR (TIM-3 specific, bispecific, or switchable) being generated. The antigen binding domain(s) may also be chosen depending on the type and number of antigens that are present on the surface of a target cell. For example, the antigen binding domain may be chosen to recognize an antigen that acts as a cell surface marker on a target cell associated with a particular disease state.

The antigen binding domain can include any domain that binds to the antigen and may include, but is not limited to, a nanobody, a monoclonal antibody, a polyclonal antibody, a synthetic antibody, a human antibody, a humanized antibody, a non-human antibody, and any fragment thereof. Thus, in one embodiment, the antigen binding domain portion comprises a mammalian antibody or a fragment thereof.

In some instances, the antigen binding domain may be derived from the same species in which the CAR will ultimately be used. For example, for use in humans, the antigen binding domain of the CAR may comprise a human antibody as described elsewhere herein, or a fragment thereof.

The antigen binding domain may be operably linked to another domain of the CAR, such as the transmembrane domain or the intracellular domain, both described elsewhere herein, for expression in the cell. In one embodiment, a nucleic acid encoding the antigen binding domain is operably linked to a nucleic acid encoding a transmembrane domain and a nucleic acid encoding an intracellular domain.

The antigen binding domains described herein can be combined with any of the transmembrane domains described herein, any of the intracellular domains or cytoplasmic domains described herein, or any of the other domains described herein that may be included in the CAR.

In certain embodiments, the antigen binding domain is nanobody Nb157 (VHH157). In certain embodiments, the antigen binding domain comprises the amino acid sequence of SEQ ID NO: 1. In certain embodiments, the antigen binding domain is encoded by the nucleotide sequence of SEQ ID NO: 2. In certain embodiments, the antigen binding domain comprises a CDR1 sequence comprising the amino acid sequence SYSMA (SEQ ID NO: 3). In certain embodiments, the antigen binding domain comprises a CDR2 sequence comprising the amino acid sequence GIYPSDGKTRYADFVKGR (SEQ ID NO: 4). In certain embodiments, the antigen binding domain comprises a CDR3 sequence comprising the amino acid sequence ARGITGLGP (SEQ ID NO: 5).

In certain embodiments, the antigen binding domain comprises a TIM-3 binding domain. In certain embodiments, the antigen binding domain comprises an anti-TIM-3 antibody. Antibody molecules to TIM-3 include, but are not limited to, those disclosed in U.S. Pat. No. 9,605,070B2, contents of which are incorporated in their entirety herein. In certain embodiments, the antigen binding domain comprises the amino acid sequence of SEQ ID NO: 6. In certain embodiments, the antigen binding domain is encoded by the nucleotide sequence of SEQ ID NO: 7. In certain embodiments, the antigen binding domain comprises a CDR1 sequence comprising the amino acid sequence of SEQ ID NO: 8. In certain embodiments, the antigen binding domain comprises a CDR2 sequence comprising the amino acid sequence of SEQ ID NO: 9. In certain embodiments, the antigen binding domain comprises a CDR3 sequence comprising the amino acid sequence of SEQ ID NO: 10.

In certain embodiments, the antigen binding domain comprises an anti-TIM-3 nanobody or VHH. In certain embodiments, the nanobody comprises an amino acid sequence selected from the group consisting of SEQ ID NO:

20, 22, 24, 26, 28, 30, and 32. In certain embodiments, the nanobody is encoded by a nucleotide sequence selected from the group consisting of SEQ ID NO: 19, 21, 23, 25, 27, 29, and 31.

In certain embodiments, the antigen binding domain comprises a PNE-binding domain.

In certain embodiments, the antigen binding domain comprises the amino acid sequence of SEQ ID NO: 11. In certain embodiments, the antigen binding domain is encoded by the nucleotide sequence of SEQ ID NO: 12.

Tolerable variations of the antigen binding domain will be known to those of skill in the art, while maintaining specific binding to the antigen. For example, in some embodiments the antigen binding domain comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the amino acid sequences set forth in SEQ ID NOs: 1, 3-6, 8-11, 20, 22, 24, 26, 28, 30, and 32. In some embodiments the antigen binding domain is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 2, 7, 12, 19, 21, 23, 25, 27, 29, and 31.

Amino acid sequence of Nb 157
(SEQ ID NO: 1)
AAQAAQVQLQESGGGLVQPGGSLSLSCTASGFTFSSYSMAWVRQAPGKG

PEWVSGIYPSDGKTRYADFVKGRFSISRDNAKNMLYLQMNNLEPEDTAL

YYCARGITGLGPRGQGTQVTVSSAA

Nucleotide sequence of Nb 157
(SEQ ID NO: 2)
gcggcccaggtgcagctgcaggagtctggggggaggcttggtgcagcctg gggggtctctgagcctctcctgtacagcctctggattcacgttcagtag ttactccatggcctgggtccgccaggctccagggaagggacccgaatgg gtctcagggatttaccttctgatggtaagacaaggtatgcagacttcg tgaagggccgattcagcatctccagagacaacgccaagaatatgttgta tctgcaaatgaacaacctggaacctgaggacacggccctatattactgt gcgagaggtatcaccggattgggaccccggggccaggggacccaggtca ccgtctcctcagcggccgcc Amino acid sequence of TIM-3 scFv
(SEQ ID NO: 6)
QVQLQQPGAELVKPGASVKMSCKASGYTFTSYNMHWIKQTPGQGLEWIG

DIYPGNGDTSYNQKFKGKATLTADKSSSTVYMQLSSLTSEDSAVYYCAR

VGGAFPMDYWGQGTSVTVSSGGGGSGGGGSGGGGSGGGGSDIVLTQSPA

SLAVSLGQRATISCRASESVEYYGTSLMQWYQQKPGQPPKLLIYAASNV

ESGVPARFSGSGSGTDFSLNIHPVEEDDIAIYFCQQSRKDPSTFGGGTK

LEIK

Nucleotide sequence of TIM-3 scFv
(SEQ ID NO: 7)
CAGGTGCAACTGCAGCAGCCTGGGGCTGAGCTGGTGAAGCCTGGGGCCT

CAGTGAAGATGTCCTGCAAGGCTTCTGGCTACACATTTACCAGTTACAA

TATGCACTGGATAAAGCAGACACCTGGACAGGGCCTGGAATGGATTGGA

GATATTTATCCAGGAAATGGTGATACTTCCTACAATCAGAAATTCAAAG

GCAAGGCCACATTGACTGCAGACAAATCCTCCAGCACAGTCTACATGCA

GCTCAGCAGCCTGACATCTGAGGACTCTGCGGTCTATTACTGTGCAAGA

GTGGGGGGTGCCTTTCCTATGGACTACTGGGGTCAAGGAACCTCAGTCA

CCGTCTCCTCAGGAGGCGGAGGATCTGGCGGCGGAGGAAGTGGCGGAGG

GGGATCAGGGGGAGGCGGATCTGACATTGTGCTCACCCAATCTCCAGCT

TCTTTGGCTGTGTCTCTAGGGCAGAGAGCCACCATCTCCTGCAGAGCCA

GTGAAAGTGTTGAATATTATGGCACAAGTTTAATGCAGTGGTACCAACA

GAAACCAGGACAGCCACCCAAACTCCTCATCTATGCTGCATCCAACGTA

GAATCTGGGGTCCCTGCCAGGTTTAGTGGCAGTGGGTCTGGGACAGACT

TCAGCCTCAACATCCATCCTGTGGAGGAGGATGATATTGCAATATATTT

CTGTCAGCAAAGTAGGAAGGATCCTTCGACGTTCGGTGGAGGCACCAAG

CTGGAGATCAAA

TIM-3 CDR1 AA sequence
(SEQ ID NO: 8)
GYTFTSYNMH

TIM-3 CDR2 AA sequence
(SEQ ID NO: 9)
DIYPGNGDTSYNQKFKG

TIM-3 CDR3 AA sequence
(SEQ ID NO: 10)
VGGAFPMDY

PNE scFv AA sequence
(SEQ ID NO: 11)
HAARPDAVVTQESALTSSPGETVTLTCRSSTGAVTTSNYASWVQEKPDH

LFTGLIGGTNNRAPGVPARFSGSLIGDKAALTITGAQTEDEAIYFCVLW

YSDHWVFGGGTKLTVLGGGGSGGGGSGGGGSGGGGSDVQLQESGPGLV

APSQSLSITCTVSGFLLTDYGVNWVRQSPGKGLEWLGVIWGDGITDYNS

ALKSRLSVTKDNSKSQVFLKMNSLQSGDSARYYCVTGLFDYWGQGTTLT

VSS

PNE scFv nucleotide sequence
(SEQ ID NO: 12)
CATGCCGCTAGACCTGATGCCGTCGTGACCCAGGAAAGCGCCCTGACAA

GCAGCCCTGGCGAGACAGTGACCCTGACCTGCAGATCTAGCACAGGCGC

CGTGACCACCAGCAACTACGCCAGCTGGGTGCAGGAAAAGCCCGACCAC

CTGTTCACCGGCCTGATCGGCGGCACCAACAATAGAGCACCTGGCGTGC

CCGCCAGATTCAGCGGCTCTCTGATCGGAGATAAGGCCGCCCTGACCAT

CACTGGCGCCCAGACAGAGGACGAGGCCATCTACTTTTGCGTGCTGTGG

TACAGCGACCACTGGGTGTTCGGCGGAGGCACCAAGCTGACAGTGCTGG

GCGGAGGCGGAGGATCTGGCGGCGGAGGAAGTGGCGGAGGGGGATCAGG

GGGAGGCGGATCTGATGTGCAGCTGCAGGAATCTGGCCCAGGACTGGTG

```
-continued
GCCCCTAGCCAGAGCCTGAGCATCACCTGTACCGTGTCCGGCTTCCTGC

TGACCGACTACGGCGTGAACTGGGTGCGCCAGTCTCCTGGCAAGGGCCT

GGAATGGCTGGGAGTGATCTGGGGCGACGGAATCACCGACTACAACTCC

GCCCTGAAGTCCCGGCTGAGCGTGACCAAGGACAACAGCAAGAGCCAGG

TGTTCCTGAAGATGAACAGCCTGCAGAGCGGCGACAGCGCCCGGTACTA

TTGTGTGACCGGCCTGTTCGACTACTGGGGCCAGGGCACAACCCTGACC

GTGTCTAGC
``` b) Transmembrane Domain

With respect to the transmembrane domain, the CAR (or bispecific CAR) is designed to comprise a transmembrane domain that connects the antigen binding domain of the CAR to the intracellular domain. In one embodiment, the transmembrane domain is naturally associated with one or more of the domains in the CAR. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, ICOS, CD3 epsilon, CD45, CD4, CD5, CD8, CD9, CD16, CD22, CD33, CD37, CD64, CD80, CD86, CD134, CD137, CD154, Toll-like receptor 1 (TLR1), TLR2, TLR3, TLR4, TLR5, TLR6, TLR7, TLR8, and TLR9.

The transmembrane domains described herein be combined with any of the antigen binding domains described herein, any of the intracellular domains or cytoplasmic domains described herein, or any of the other domains described herein that may be included in the CAR.

In some instances, a variety of hinges can be employed as well including but not limited to the Ig (immunoglobulin) hinge, and the CD8 hinge. The transmembrane domain may be combined with any hinge domain and/or may comprise one or more transmembrane domains described herein. In one embodiment, the transmembrane domain comprises a CD28 transmembrane domain. In another embodiment, the transmembrane domain comprises a CD8 transmembrane domain. In another embodiment, the transmembrane domain comprises a CD8 hinge domain and a CD8 transmembrane domain. In certain embodiments, the hinge domain is selected from the group consisting of a CD8 hinge, an IgG3s hinge, and an IgG4m hinge.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

Between the extracellular domain and the transmembrane domain of the CAR, or between the intracellular domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

c) Intracellular Domain

The intracellular domain or otherwise the cytoplasmic domain of the CAR (or bispecific CAR) is responsible for activation of the cell in which the CAR is expressed. Examples of an intracellular domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

The intracellular domain of the chimeric membrane protein is responsible for activation of at least one of effector functions of the T cell. While usually the entire intracellular domain can be employed, in many cases it is not necessary to use the entire chain. To the extent that a truncated portion of the intracellular signaling domain is used, such truncated portion may be used in place of the intact chain as long as it transduces the effector function signal. The intracellular domain includes any truncated portion of the intracellular domain sufficient to transduce the effector function signal.

In one embodiment, the intracellular domain of the CAR includes any portion of one or more co-stimulatory molecules, such as at least one signaling domain from CD3, CD8, CD27, CD28, ICOS, 4-IBB, PD-1, any derivative or variant thereof, any synthetic sequence thereof that has the same functional capability, and any combination thereof.

Examples of the intracellular domain include a fragment or domain from one or more molecules or receptors including, but are not limited to, TCR, CD3 zeta, CD3 gamma, CD3 delta, CD3 epsilon, CD86, common FcR gamma, FcR beta (Fc Epsilon Rib), CD79a, CD79b, Fcgamma Rlla, DAP10, DAP 12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD 160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1 Id, ITGAE, CD 103, ITGAL, CD 11 a, LFA-1, ITGAM, CD lib, ITGAX, CD 11c, ITGB1, CD29, ITGB2, CD 18, LFA-1, ITGB7, TNFR2, TRANCE/RANKL, DNAM1 (CD226), SLAMF4 (CD244, 2B4), CD84, CD 96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD 162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

The intracellular domains described herein can be combined with any of the antigen binding domains described herein, any of the transmembrane domains described herein, or any of the other domains described herein that may be included in the CAR.

In certain embodiments, the CAR comprises a TIM-3 scFv, an IgG4 hinge region, a CD8 transmembrane domain, a 4-1BB intracellular domain and CD3zeta intracellular domain. In certain embodiments, the CAR comprises the amino acid set forth in SEQ ID NO: 13. In certain embodiments, the CAR is encoded by the nucleotide sequence set forth in SEQ ID NO: 14.

Tolerable variations of the CAR sequences will be known to those of skill in the art. For example, in some embodiments the CAR comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequence set forth in SEQ ID NOs: 13. In some embodiments the CAR is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO: 33 or 35.

```
TIM-3 CAR amino acid sequence
                                          (SEQ ID NO: 13)
MALPVTALLLPLALLLHAARPGSAAQAAQVQLQQPGAELVKPGASVKMS

CKASGYTFTSYNMHWIKQTPGQGLEWIGDIYPGNGDTSYNQKFKGKATL

TADKSSSTVYMQLSSLTSEDSAVYYCARVGGAFPMDYWGQGTSVTVSSG

GGGSGGGGSGGGGSGGGGSDIVLTQSPASLAVSLGQRATISCRASESVE

YYGTSLMQWYQQKPGQPPKLLIYAASNVESGVPARFSGSGSGTDFSLNI

HPVEEDDIAIYFCQQSRKDPSTFGGGTKLEIKHMGQAGQSGESKYGPPC

PPCPASYIWAPLAGTCGVLLLSLVITLYCKRGRKKLLYIFKQPFMRPVQ

TTQEEDGCSCRFPEEEEGGCELRVKFSRSADAPAYKQGQNQLYNELNLG

RREEYDVLDKRRGRDPEMGGKPRRKNPQEGLYNELQKDKMAEAYSEIGM

KGERRRGKGHDGLYQGLSTATKDTYDALHMQALPPR

TIM-3 CAR nucleotide sequence
                                          (SEQ ID NO: 14)
ATGGCCTTACCAGTGACCGCCTTGCTCCTGCCGCTGGCCTTGCTGCTCC

ACGCCGCCAGGCCGGGATCCGCGGCCCAGGCGGCCCAGGTGCAACTGCA

GCAGCCTGGGGCTGAGCTGGTGAAGCCTGGGGCCTCAGTGAAGATGTCC

TGCAAGGCTTCTGGCTACACATTTACCAGTTACAATATGCACTGGATAA

AGCAGACACCTGGACAGGGCCTGGAATGGATTGGAGATATTTATCCAGG

AAATGGTGATACTTCCTACAATCAGAAATTCAAAGGCAAGGCCACATTG

ACTGCAGACAAATCCTCCAGCACAGTCTACATGCAGCTCAGCAGCCTGA

CATCTGAGGACTCTGCGGTCTATTACTGTGCAAGAGTGGGGGGTGCCTT

TCCTATGGACTACTGGGGTCAAGGAACCTCAGTCACCGTCTCCTCAGGA

GGCGGAGGATCTGGCGGCGGAGGAAGTGGCGGAGGGGGATCAGGGGGAG

GCGGATCTGACATTGTGCTCACCCAATCTCCAGCTTCTTTGGCTGTGTC

TCTAGGGCAGAGAGCCACCATCTCCTGCAGAGCCAGTGAAAGTGTTGAA

TATTATGGCACAAGTTTAATGCAGTGGTACCAACAGAAACCAGGACAGC

CACCCAAACTCCTCATCTATGCTGCATCCAACGTAGAATCTGGGGTCCC

TGCCAGGTTTAGTGGCAGTGGGTCTGGGACAGACTTCAGCCTCAACATC
```

```
-continued
CATCCTGTGGAGGAGGATGATATTGCAATATATTTCTGTCAGCAAAGTA

GGAAGGATCCTTCGACGTTCGGTGGAGGCACCAAGCTGGAGATCAAACA

TATGGGCCAGGCCGGCCAGTCCGGAGAGAGCAAGTACGGCCCTCCCTGC

CCCCCTTGCCCTGCTAGCTACATCTGGGCGCCCTTGGCCGGGACTTGTG

GGGTCCTTCTCCTGTCACTGGTTATCACCCTTTACTGCAAACGGGGCAG

AAAGAAACTCCTGTATATATTCAAACAACCATTTATGAGACCAGTACAA

ACTACTCAAGAGGAAGATGGCTGTAGCTGCCGATTTCCAGAAGAAGAAG

AAGGAGGATGTGAACTGAGAGTGAAGTTCAGCAGGAGCGCAGACGCCCC

CGCGTACAAGCAGGGCCAGAACCAGCTCTATAACGAGCTCAATCTAGGA

CGAAGAGAGGAGTACGATGTTTTGGACAAGAGACGTGGCCGGGACCCTG

AGATGGGGGGAAAGCCGAGAAGGAAGAACCCTCAGGAAGGCCTGTACAA

TGAACTGCAGAAAGATAAGATGGCGGAGGCCTACAGTGAGATTGGGATG

AAAGGCGAGCGCCGGAGGGGCAAGGGGCACGATGGCCTTTACCAGGGTC

TCAGTACAGCCACCAAGGACACCTACGACGCCCTTCACATGCAGGCCCT

GCCCCCTCGCTAA
```

Included in the invention are isolated polypeptides comprising CARs, isolated nucleic acids comprising CARs, vectors comprising nucleic acids comprising CARs, and modified cells (e.g. T cells) comprising CARs, nucleic acids encoding CARs, or vectors comprising CARs.

Bispecific CARs

Certain aspects of the invention provide bispecific CARs. A bispecific CAR comprises two different binding specificities and thus binds to two different antigens. In certain embodiments, the bispecific CAR comprises a first antigen binding domain that binds to a first antigen and a second antigen binding domain that binds to a second antigen.

In one aspect, the invention provides a bispecific CAR comprising a first antigen binding domain capable of binding CD13, and a second antigen binding domain capable of binding TIM-3. In certain embodiments, the bispecific CAR comprises a first antigen binding domain capable of binding CD13, a first intracellular domain, a second antigen binding domain capable of binding TIM-3, a transmembrane domain, and a second intracellular domain.

In certain embodiments, the first and/or second antigen binding domain of the bispecific CAR is selected from the group consisting of an antibody, a nanobody, a Fab, an scFv, or any fragment thereof. The antigen binding domains of the bispecific CAR can be combined with any of the transmembrane domains described herein, any of the intracellular domains described herein, any of the hinge domains described herein, or any of the other domains described herein that may be included in the bi-specific CAR.

In certain embodiments, the bispecific CAR comprises a first antigen binding domain comprising a nanobody and a second antigen binding domain comprising an scFv. In certain embodiments, the first antigen binding domain comprising a nanobody is capable of specifically binding CD13 and/or the second antigen binding domain comprising an scFv is capable of specifically binding TIM-3. In certain embodiments, the bi-specific CAR comprises a first antigen binding domain comprising a nanobody capable of binding CD13, a CD3 zeta intracellular domain, a linker, a second antigen binding domain capable of binding TIM-3, a CD28 transmembrane domain, and a 4-1BB intracellular domain.

In certain embodiments, the nanobody capable of binding CD13 is Nb157 and may comprise SEQ ID NO: 1. In certain embodiments, the bi-specific CAR comprises the amino acid sequence set forth in SEQ ID NO: 15, and may be encoded by the nucleotide sequence set forth in SEQ ID NO: 16.

In certain embodiments, the bispecific CAR comprises a first antigen binding domain capbable of binding CD13 and a second antigen binding domain capable of binding TIM-3. In certain embodiments, the first antigen binding domain comprises a first nanobody and the second antigen binding comprises a second nanobody. In certain embodiments, the second antigen binding domain comprises an anti-TIM-3 nanobody (VHH). In certain embodiments, the CAR comprises an anti-TIM-3 nanobody comprising an amino acid sequence selected from the group consisting of SEQ ID NO: 20, 22, 24, 26, 28, 30, and 32. In certain embodiments, the CAR comprises an anti-TIM-3 nanobody encoded by a nucleotide sequence selected from the group consisting of SEQ ID NO: 19, 21, 23, 25, 27, 29, and 31. In certain embodiments, the bispecific CAR is encoded by a nucleotide sequence selected from the group consisting of SEQ ID NOs: 33-39.

In certain embodiments, the bispecific CAR may comprise a first nucleic acid sequence encoding a first CAR and a second nucleic acid sequence encoding a second CAR, wherein the first nucleic acid sequence and the second nucleic acid sequence are separated by a linker. Any linker known to one of ordinary skill in the art may be used. In certain embodiments, the linker comprises a cleavage site and/or a self-cleaving peptide. In certain embodiments, the linker is a 2A peptide. In certain embodiments, the 2A peptide is selected from the group consisting of porcine teschovirus-1 2A (P2A), Thoseaasigna virus 2A (T2A), equine rhinitis A virus 2A (E2A), and foot-and-mouth disease virus 2A (F2A).

The bispecific CAR, while exhibiting a dual-specificity, may also exhibit split-signaling properties. For example, the a CAR-T cell comprising a TIM-3-specific CAR operably linked to 4-1BBz and a CD13-specific CAR operably linked to CD3z will signal through both 4-1BB and CD3z and synergize to kill target cells when the bispecific CARs bind to the two respective antigens on the cancer cells. In addition, whem TIM-3-specific CAR linked to CD3z and a CD13-specific CAR linked to 41BB or CD23/4-1BB domain, they can also synergize to kill the target cells when the target cells express both of the respective cell surface antigens.

In certain embodiments, the bispecific CAR comprises a bispecific antibody. In such embodiments, the bispecific antibody comprises an antigen binding domain comprising a first and a second single chain variable fragment (scFv) molecules. The first and a second scFv are capable of binding two different antigens.

Also provided in the invention is a bispecific CAR comprising an inducible (switchable) element. For example, the bispecific CAR may comprise a switchable CAR (sCAR). In certain embodiments, the sCAR refers to a CAR comprising a Peptide-Neo-Epitope (PNE) binding domain, and optionally a transmembrane domain, and/or an intracellular domain. The switchable CAR can be used in conjunction with a molecule comprising a nanobody fused to a PNE molecule (e.g. a switchable CAR system). When the nanobody-PNE molecule comes into contact with the sCAR, the "switch" is turned on and the CAR T cell is activated.

The nanoboby can be fused to the C-terminal region of the PNE or the N-terminal region of the PNE. In certain embodiments, nanobody comprises Nb157 (VHH157) and is fused to the C-terminal region of PNE. In certain embodiments, nanobody is Nb157 and is fused to the N-terminal region of PNE.

In certain embodiments, the inducible bispecific CAR comprises a first antigen binding domain capable of binding Peptide-Neo-Epitope (PNE), a first transmembrane domain, a first intracellular domain, a second antigen binding domain capable of binding TIM-3, a transmembrane domain, and a second intracellular domain. In certain embodiments, the first and/or second transmembrane domain comprises CD28. In certain embodiments, the first intracellular domain comprises CD3 zeta. In certain embodiments, the second intracellular domain comprises 4-1BB. In certain embodiments, the inducible bispecific CAR comprises the amino acid sequence set forth in SEQ ID NO: 17, which may be encoded by the nucleotide sequence set forth in SEQ ID NO: 18.

Included in the invention are isolated polypeptides comprising CARs, isolated nucleic acids comprising CARs, vectors comprising nucleic acids comprising CARs, and modified cells (e.g. T cells) comprising CARs, nucleic acids encoding CARs, or vectors comprising CARs.

Tolerable variations of the CAR sequences will be known to those of skill in the art. For example, in some embodiments the CAR comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to any of the amino acid sequences set forth in SEQ ID NOs: 15 or 17. In some embodiments the CAR is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the nucleic acid sequence set forth in SEQ ID NO: 16 or 18.

```
TIM-3&CD13 bispecific CAR amino acid sequence
                                          (SEQ ID NO: 15)
MALPVTALLLPLALLLHAARPGSAAQAAQVQLQESGGGLVQPGGSLSLSCTASG
FTFSSYSMAWVRQAPGKGPEWVSGIYPSDGKTRYADFVKGRFSISRDNAKNMLY
LQMNNLEPEDTALYYCARGITGLGPRGQGTQVTVSSAAATSGQTVSSESKYGPP
CPPCPYIWAPLAGTCGVLLLSLVITLYCRVKFSRSADAPAYKQGQNQLYNELNLG
RREEYDVLDKRRGRDPEMGGKPRRKNPQEGLYNELQKDKMAEAYSEIGMKGER
RRGKGHDGLYQGLSTATKDTYDALHMQALPPRLEGSGATNFSLLKQAGDVEEN
PGPPRMALPVTALLLPLALLLHAARPGSAAQAAQVQLQQPGAELVKPGASVKMS
CKASGYTFTSYNMHWIKQTPGQGLEWIGDIYPGNGDTSYNQKFKGKATLTADKS
SSTVYMQLSSLTSEDSAVYYCARVGGAFPMDYWGQGTSVTVSSGGGGSGGGGS
GGGGSGGGGSDIVLTQSPASLAVSLGQRATISCRASESVEYYGTSLMQWYQQKP
GQPPKLLIYAASNVESGVPARFSGSGSGTDFSLNIHPVEEDDIAIYFCQQSRKDPST
```

-continued

FGGGTKLEIKHMGKHLCPSPLFPGPSKPFWVLVVVGGVLACYSLLVTVAFIIFWV
RSKRSRLLHSDYMNMTPRRPGPTRKHYQPYAPPRDFAAYRSKRGRKKLLYIFKQ
PFMRPVQTTQEEDGCSCRFPEEEEGGCEL

TIM-3&CD13 bispecific CAR nucleotide sequence
(SEQ ID NO: 16)

```
ATGGCCTTACCAGTGACCGCCTTGCTCCTGCCGCTGGCCTTGCTGCTCCACGC
CGCCAGGCCGGGATCCGCGGCCCAGGCGGCCCAGGTGCAGCTGCAGGAGTCT
GGGGGAGGCTTGGTGCAGCCTGGGGGGTCTCTGAGCCTCTCCTGTACAGCCTC
TGGATTCACGTTCAGTAGTTACTCCATGGCCTGGGTCCGCCAGGCTCCAGGGA
AGGGACCCGAATGGGTCTCAGGGATTTACCCTTCTGATGGTAAGACAAGGTA
TGCAGACTTCGTGAAGGGCCGATTCAGCATCTCCAGAGACAACGCCAAGAAT
ATGTTGTATCTGCAAATGAACAACCTGGAACCTGAGGACACGGCCCTATATT
ACTGTGCGAGAGGTATCACCGGATTGGGACCCCGGGGCCAGGGGACCCAGGT
CACCGTCTCCTCAGCGGCCGCCACTAGTGGCCAGACCGTGTCTAGCGAGTCTA
AGTACGCCCTCCCTGCCCTCCTTGCCCATACATCTGGGCGCCCTTGGCCGGG
ACTTGTGGGGTCCTTCTCCTGTCACTGGTTATCACCCTTTACTGCAGAGTGAA
GTTCAGCAGGAGCGCAGACGCCCCCGCGTACAAGCAGGGCCAGAACCAGCTC
TATAACGAGCTCAATCTAGGACGAAGAGAGGAGTACGATGTTTTGGACAAGA
GACGTGGCCGGGACCCTGAGATGGGGGGAAAGCCGAGAAGGAAGAACCCTC
AGGAAGGCCTGTACAATGAACTGCAGAAAGATAAGATGGCGGAGGCCTACA
GTGAGATTGGGATGAAAGGCGAGCGCCGGAGGGGCAAGGGGCACGATGGCC
TTTACCAGGGTCTCAGTACAGCCACCAAGGACACCTACGACGCCCTTCACAT
GCAGGCCCTGCCCCCTCGCCTCGAGGGAAGCGGAGCTACTAACTTCAGCCTG
CTGAAGCAGGCTGGAGACGTGGAGGAGAACCCTGGACCTCCTAGGATGGCCT
TACCAGTGACCGCCTTGCTCCTGCCGCTGGCCTTGCTGCTCCACGCCGCCAGG
CCGGGATCCGCGGCCCAGGCGGCCCAGGTGCAACTGCAGCAGCCTGGGGCTG
AGCTGGTGAAGCCTGGGGCCTCAGTGAAGATGTCCTGCAAGGCTTCTGGCTA
CACATTTACCAGTTACAATATGCACTGGATAAAGCAGACACCTGGACAGGGC
CTGGAATGGATTGGAGATATTTATCCAGGAAATGGTGATACTTCCTACAATCA
GAAATTCAAAGGCAAGGCCACATTGACTGCAGACAAATCCTCCAGCACAGTC
TACATGCAGCTCAGCAGCCTGACATCTGAGGACTCTGCGGTCTATTACTGTGC
AAGAGTGGGGGGTGCCTTTCCTATGGACTACTGGGGTCAAGGAACCTCAGTC
ACCGTCTCCTCAGGAGGCGGAGGATCTGGCGGCGGAGGAAGTGGCGGAGGG
GGATCAGGGGGAGGCGGATCTGACATTGTGCTCACCCAATCTCCAGCTTCTTT
GGCTGTGTCTCTAGGGCAGAGAGCCACCATCTCCTGCAGAGCCAGTGAAAGT
GTTGAATATTATGGCACAAGTTTAATGCAGTGGTACCAACAGAAACCAGGAC
AGCCACCCAAACTCCTCATCTATGCTGCATCCAACGTAGAATCTGGGGTCCCT
GCCAGGTTTAGTGGCAGTGGGTCTGGGACAGACTTCAGCCTCAACATCCATCC
TGTGGAGGAGGATGATATTGCAATATATTTCTGTCAGCAAAGTAGGAAGGAT
CCTTCGACGTTCGGTGGAGGCACCAAGCTGGAGATCAAACATATGGGGAAAC
ACCTTTGTCCAAGTCCCCTATTTCCCGGACCTTCTAAGCCCTTTTGGGTGCTGG
TGGTGGTTGGTGGAGTCCTGGCTTGCTATAGCTTGCTAGTAACAGTGGCCTTT
ATTATTTTCTGGGTGAGGAGTAAGAGGAGCAGGCTCCTGCACAGTGACTACA
TGAACATGACTCCCCGCCGCCCGGGCCCACCCGCAAGCATTACCAGCCCTA
TGCCCCACCACGCGACTTCGCAGCCTATCGCTCCAAACGGGGCAGAAAGAA
CTCCTGTATATATTCAAACAACCATTTATGAGACCAGTACAAACTACTCAAGA
GGAAGATGGCTGTAGCTGCCGATTTCCAGAAGAAGAAGAAGGAGGATGTGA
ACTGTAA
```

Figure 8A:
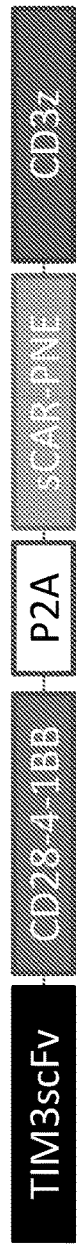
FIGS. 8A-8B illustrate a TIM-3& PNE inducible bispecific CAR.
Figure 8B:
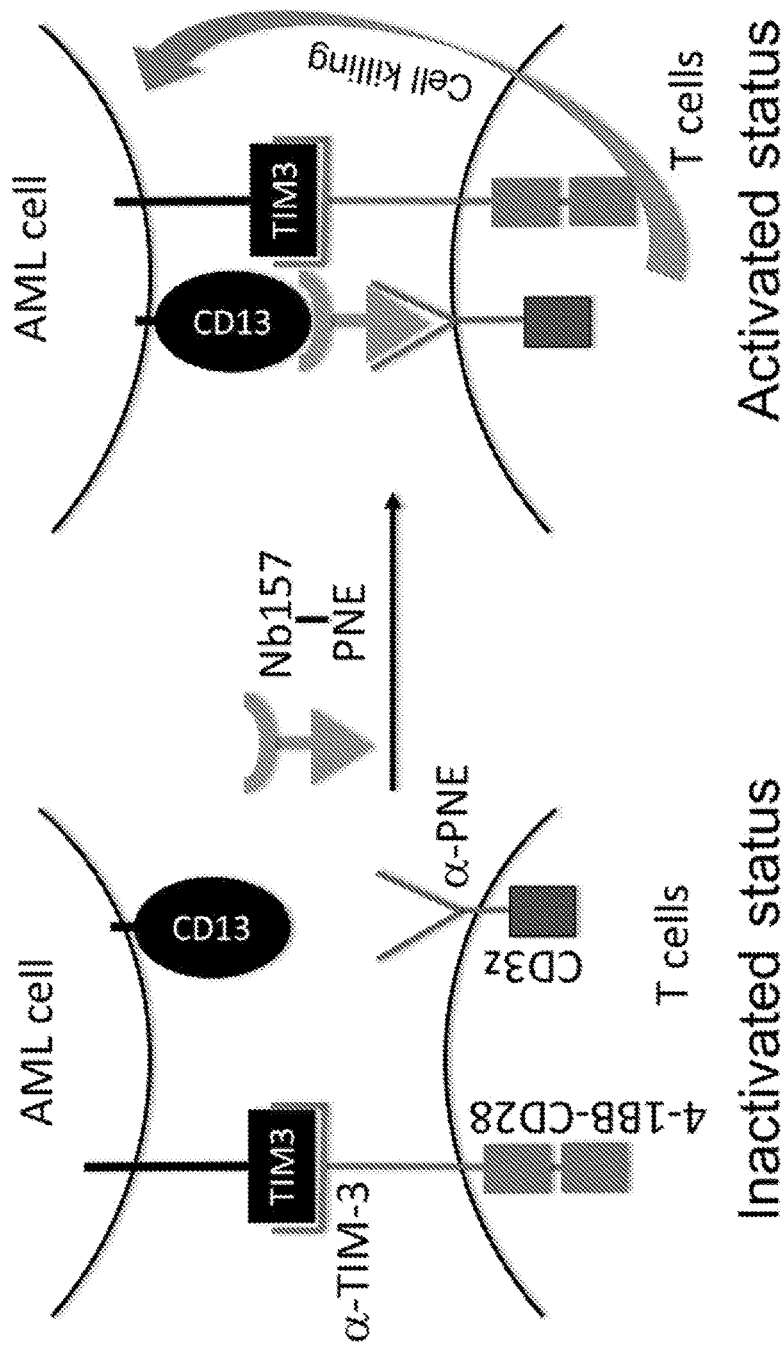

TIM-3&PNE inducible bispecific CAR amino acid sequence (FIGs. 8A-8B)
(SEQ ID NO: 17)

MALPVTALLLPLALLLHAARPGSAAQAAQVQLQQPGAELVKPGASVKMSCKAS
GYTFTSYNMHWIKQTPGQGLEWIGDIYPGNGDTSYNQKFKGKATLTADKSSSTV
YMQLSSLTSEDSAVYYCARVGGAFPMDYWGQGTSVTVSSGGGGSGGGGSGGG
GSGGGGGSDIVLTQSPASLAVSLGQRATISCRASESVEYYGTSLMQWYQQKPGQPP
KLLIYAASNVESGVPARFSGSGSGTDFSLNIHPVEEDDIAIYFCQQSRKDPSTFGGG
TKLEIKHMGKHLCPSPLFPGPSKPFWVLVVVGGVLACYSLLVTVAFIIFWVRSKR
SRLLHSDYMNMTPRRPGPTRKHYQPYAPPRDFAAYRSKRGRKKLLYIFKQPFMR
PVQTTQEEDGCCRFPEEEEGGCELLEGSGATNFSLLKQAGDVEENPGPPRMALP
VTALLLPLALLLHAARPDAVVTQESALTSSPGETVTLTCRSSTGAVTTSNYASWV
QEKPDHLFTGLIGGTNNRAPGVPARFSGSLIGDKAALTITGAQTEDEAIYFCVLW
YSDHWVFGGGTKLTVLGGGGSGGGGSGGGGSGGGGSDVQLQESGPGLVAPSQ
SLSITCTVSGFLLTDYGVNWVRQSPGKGLEWLGVIWGDGITDYNSALKSRLSVTK
DNSKSQVFLKMNSLQSGDSARYYCVTGLFDYWGQGTTLTVSSESKYGPPCPPCP
YIWAPLAGTCGVLLLSLVITLYCRVKFSRSADAPAYKQGQNQLYNELNLGRREE
YDVLDKRRGRDPEMGGKPRRKNPQEGLYNELQKDKMAEAYSEIGMKGERRRG
KGHDGLYQGLSTATKDTYDALHMQALPPR

TIM-3&PNE inducible bispecific CAR nucleotide sequence (FIGs. 8A-8B)
(SEQ ID NO: 18)

```
ATGGCCTTACCAGTGACCGCCTTGCTCCTGCCGCTGGCCTTGCTGCTCCACGC
CGCCAGGCCGGGATCCGCGGCCCAGGCGGCCCAGGTGCAACTGCAGCAGCCT
GGGGCTGAGCTGGTGAAGCCTGGGGCCTCAGTGAAGATGTCCTGCAAGGCTT
CTGGCTACACATTTACCAGTTACAATATGCACTGGATAAAGCAGACACCTGG
ACAGGGCCTGGAATGGATTGGAGATATTTATCCAGGAAATGGTGATACTTCC
TACAATCAGAAATTCAAAGGCAAGGCCACATTGACTGCAGACAAATCCTCCA
GCACAGTCTACATGCAGCTCAGCAGCCTGACATCTGAGGACTCTGCGGTCTAT
TACTGTGCAAGAGTGGGGGGTGCCTTTCCTATGGACTACTGGGGTCAAGGAA
CCTCAGTCACCGTCTCCTCAGGAGGCGGAGGATCTGGCGGCGGAGGAAGTGG
CGGAGGGGGATCAGGGGGAGGCGGATCTGACATTGTGCTCACCCAATCTCCA
```

-continued

```
GCTTCTTTGGCTGTGTCTCTAGGGCAGAGAGCCACCATCTCCTGCAGAGCCAG
TGAAAGTGTTGAATATTATGGCACAAGTTTAATGCAGTGGTACCAACAGAAA
CCAGGACAGCCACCCAAACTCCTCATCTATGCTGCATCCAACGTAGAATCTG
GGGTCCCTGCCAGGTTTAGTGGCAGTGGGTCTGGGACAGACTTCAGCCTCAA
CATCCATCCTGTGGAGGAGGATGATATTGCAATATATTTCTGTCAGCAAAGTA
GGAAGGATCCTTCGACGTTCGGTGGAGGCACCAAGCTGGAGATCAAACATAT
GGGGAAACACCTTTGTCCAAGTCCCCTATTTCCCGGACCTTCTAAGCCCTTTT
GGGTGCTGGTGGTGGTTGGTGGAGTCCTGGCTTGCTATAGCTTGCTAGTAACA
GTGGCCTTTATTATTTTCTGGGTGAGGAGTAAGAGGAGCAGGCTCCTGCACAG
TGACTACATGAACATGACTCCCCGCCGCCCCGGGCCCACCCGCAAGCATTAC
CAGCCCTATGCCCCACCACGCGACTTCGCAGCCTATCGCTCCAAACGGGGCA
GAAAGAAACTCCTGTATATATTCAAACAACCATTTATGAGACCAGTACAAAC
TACTCAAGAGGAAGATGGCTGTAGCTGCCGATTTCCAGAAGAAGAAGAAGGA
GGATGTGAACTGCTCGAGGGAAGCGGAGCTACTAACTTCAGCCTGCTGAAGC
AGGCTGGAGACGTGGAGGAGAACCCTGGACCTCCTAGGATGGCTCTGCCTGT
GACAGCTCTGCTGCTGCCTCTGGCCCTGCTGCTGCATGCCGCTAGACCTGATG
CCGTCGTGACCCAGGAAAGCGCCCTGACAAGCAGCCCTGGCGAGACAGTGAC
CCTGACCTGCAGATCTAGCACAGGCGCCGTGACCACCAGCAACTACGCCAGC
TGGGTGCAGGAAAAGCCCGACCACCTGTTCACCGGCCTGATCGGCGGCACCA
ACAATAGAGCACCTGGCGTGCCCGCCAGATTCAGCGGCTCTCTGATCGGAGA
TAAGGCCGCCCTGACCATCACTGGCGCCCAGACAGAGGACGAGGCCATCTAC
TTTTGCGTGCTGTGGTACAGCGACCACTGGGTGTTCGGCGGAGGCACCAAGCT
GACAGTGCTGGGCGGAGGCGGAGGATCTGGCGGCGGAGGAAGTGGCGGAGG
GGGATCAGGGGGAGGCGGATCTGATGTGCAGCTGCAGGAATCTGGCCCAGGA
CTGGTGGCCCCTAGCCAGAGCCTGAGCATCACCTGTACCGTGTCCGGCTTCCT
GCTGACCGACTACGGCGTGAACTGGGTGCGCCAGTCTCCTGGCAAGGGCCTG
GAATGGCTGGGAGTGATCTGGGGCGACGGAATCACCGACTACAACTCCGCCC
TGAAGTCCCGGCTGAGCGTGACCAAGGACAACAGCAAGAGCCAGGTGTTCCT
GAAGATGAACAGCCTGCAGAGCGGCGACAGCGCCCGGTACTATTGTGTGACC
GGCCTGTTCGACTACTGGGGCCAGGGCACAACCCTGACCGTGTCTAGCGAGT
CTAAGTACGGCCCTCCCTGCCCTCCTTGCCCATACATCTGGGCGCCCTTGGCC
GGGACTTGTGGGGTCCTTCTCCTGTCACTGGTTATCACCCTTTACTGCAGAGT
GAAGTTCAGCAGGAGCGCAGACGCCCCGCGTACAAGCAGGGCCAGAACCA
GCTCTATAACGAGCTCAATCTAGGACGAAGAGAGGAGTACGATGTTTTGGAC
AAGAGACGTGGCCGGGACCCTGAGATGGGGGGAAAGCCGAGAAGGAAGAAC
CCTCAGGAAGGCCTGTACAATGAACTGCAGAAAGATAAGATGGCGGAGGCCT
ACAGTGAGATTGGGATGAAAGGCGAGCGCCGGAGGGGCAAGGGGCACGATG
GCCTTTACCAGGGTCTCAGTACAGCCACCAAGGACACCTACGACGCCCTTCA
CATGCAGGCCCTGCCCCCTCGCTAA

BiCAR2 VHH12                                                    (SEQ ID NO: 33)

GTGCACGAGTGGGTTACATCGAACTGGATCTCAACAGCGGTAAGATCCTTGA
GAGTTTTCGCCCCGAAGAACGTTTTCCAATGATGAGCACTTTTAAAGTTCTGC
TATGTGGCGCGGTATTATCCCGTATTGACGCCGGGCAAGAGCAACTCGGTCG
CCGCATACACTATTCTCAGAATGACTTGGTTGAGTACTCACCAGTCACAGAAA
AGCATCTTACGGATGGCATGACAGTCATAAGAGAATTATGCAGTGCTGCCATAAC
CATGAGTGATAACACTGCGGCCAACTTACTTCTGACAACGATCGGAGGACCG
AAGGAGCTAACCGCTTTTTTGCACAACATGGGGGATCATGTAACTCGCCTTGA
TCGTTGGGAACCGGAGCTGAATGAAGCCATACCAAACGACGAGCGTGACACC
ACGATGCCTGTAGCAATGGCAACAACGTTGCGCAAACTATTAACTGGCGAAC
TACTTACTCTAGCTTCCCGGCAACAATTAATAGACTGGATGGAGGCGGATAA
AGTTGCAGGACCACTTCTGCGCTCGGCCCTTCCGGCTGGCTGGTTTATTGCTG
ATAAATCTGGAGCCGGTGAGCGTGGGTCTCGCGGTATCATTGCAGCACTGGG
GCCAGATGGTAAGCCCTCCCGTATCGTAGTTATCTACACGACGGGGAGTCAG
GCAACTATGGATGAACGAAATAGACAGATCGCTGAGATAGGTGCCTCACTGA
TTAAGCATTGGTAACTGTCAGACCAAGTTTACTCATATATACTTTAGATTGAT
TTAAAACTTCATTTTTAATTTAAAAGGATCTAGGTGAAGATCCTTTTTGATAA
TCTCATGACCAAAATCCCTTAACGTGAGTTTTCGTTCCACTGAGCGTCAGACC
CCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGG
ATCAAGAGCTACCAACTCTTTTTCCGAAGGTAACTGGCTTCAGCAGAGCGCA
GATACCAAATACTGTTCTTCTAGTGTAGCCGTAGTTAGGCCACCACTTCAAGA
ACTCTGTAGCACCGCCTACATACCTCGCTCTGCTAATCGTTACCAGTGGCT
GCTGCCAGTGGCGATAAGTCGTGTCTTACCGGGTTGGACTCAAGACGATAGTT
ACCGGATAAGGCGCAGCGGTCGGGCTGAACGGGGGGTTCGTGCACACAGCCC
AGCTTGGAGCGAACGACCTACACCGAACTGAGATACCTACAGCGTGAGCTAT
GAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACG
CCTGGTATCTTTATAGTCCTGTCGGGTTTCGCCACCTCTGACTTGAGCGTCGAT
TTTTGTGATGCTCGTCAGGGGGCGGAGCCTATGGAAAAACGCCAGCAACGC
GGCCTTTTTACGGTTCCTGGCCTTTTGCTGGCCTTTTGCTCACATGTTCTTTCCT
GCGTTATCCCCTGATTCTGTGGATAACCGTATTACCGCCTTTGAGTGAGCTGA
TACCGCTCGCCGCAGCCGAACGACCGAGCGCAGCGAGTCAGTGAGCGAGGA
AGCGGAAGAGCGCCCAATACGCAAACCGCCTCTCCCCGCGCGTTGGCCGATT
CATTAATGCAGCTGGCACGACAGGTTTCCCGACTGGAAAGCGGGCAGTGAGC
GCAACGCAATTAATGTGAGTTAGCTCACTCATTAGGCACCCCAGGCTTTACAC
TTTATGCTTCCGGCTCGTATGTTGTGTGGAATTGTGAGCGGATAACAATTTCA
CACAGGAAACAGCTATGACCATGATTACGCCAAGCGCGCAATTAACCCTCAC
TAAAGGGAACAAAAGCTGGAGCTGCAAGCTTAATGTAGTCTTATGCAATACT
CTTGTAGTCTTGCAACATGGTAACGATGAGTTAGCAACATGCCTTACAAGGA
```

```
GAGAAAAAGCACCGTGCATGCCGATTGGTGGAAGTAAGGTGGTACGATCGTG
CCTTATTAGGAAGGCAACAGACGGGTCTGACATGGATTGGACGAACCACTGA
ATTGCCGCATTGCAGAGATATTGTATTTAAGTGCCTAGCTCGATACATAAACG
GGTCTCTCTGGTTAGACCAGATCTGAGCCTGGGAGCTCTCTGGCTAACTAGGG
AACCCACTGCTTAAGCCTCAATAAAGCTTGCCTTGAGTGCTTCAAGTAGTGTG
TGCCCGTCTGTTGTGTGACTCTGGTAACTAGAGATCCCTCAGACCCTTTTAGT
CAGTGTGGAAAATCTCTAGCAGTGGCGCCCGAACAGGGACTTGAAAGCGAAA
GGGAAACCAGAGGAGCTCTCTCGACGCAGGACTCGGCTTGCTGAAGCGCGCA
CGGCAAGAGGCGAGGGGCGGCGACTGGTGAGTACGCCAAAAATTTTGACTAG
CGGAGGCTAGAAGGAGAGAGATGGGTGCGAGAGCGTCAGTATTAAGCGGGG
GAGAATTAGATCGCGATGGGAAAAAATTCGGTTAAGGCCAGGGGGAAAGAA
AAAATATAAATTAAAACATATAGTATGGGCAAGCAGGGAGCTAGAACGATTC
GCAGTTAATCCTGGCCTGTTAGAAACATCAGAAGGCTGTAGACAAATACTGG
GACAGCTACAACCATCCCTTCAGACAGGATCAGAAGAACTTAGATCATTATA
TAATACAGTAGCAACCCTCTATTGTGTGCATCAAAGGATAGAGATAAAAGAC
ACCAAGGAAGCTTTAGACAAGATAGAGGAAGAGCAAACAAAAGTAAGACC
ACCGCACAGCAAGCGGCCGCTGATCTTCAGACCTGGAGGAGGAGATATGAGG
GACAATTGGAGAAGTGAATTATATAAATATAAAGTAGTAAAAATTGAACCAT
TAGGAGTAGCACCCACCAAGGCAAAGAGAAGAGTGGTGCAGAGAGAAAAAA
GAGCAGTGGGAATAGGAGCTTTGTTCCTTGGGTTCTTGGGAGCAGCAGGAAG
CACTATGGGCGCAGCGTCAATGACGCTGACGGTACAGGCCAGACAATTATTG
TCTGGTATAGTGCAGCAGCAGAACAATTTGCTGAGGGCTATTGAGGCGCAAC
AGCATCTGTTGCAACTCACAGTCTGGGGCATCAAGCAGCTCCAGGCAAGAAT
CCTGGCTGTGGAAAGATACCTAAAGGATCAACAGCTCCTGGGGATTTGGGGT
TGCTCTGGAAAACTCATTTGCACCACTGCTGTGCCTTGGAATGCTAGTTGGAG
TAATAAATCTCTGGAACAGATTTGGAATCACACGACCTGGATGGAGTGGGAC
AGAGAAATTAACAATTACACAAGCTTAATACACTCCTTAATTGAAGAATCGC
AAAACCAGCAAGAAAAGAATGAACAAGAATTATTGGAATTAGATAAATGGG
CAAGTTTGTGGAATTGGTTTAACATAACAAATTGGCTGTGGTATATAAAATTA
TTCATAATGATAGTAGGAGGCTTGGTAGGTTTAAGAATAGTTTTTGCTGTACT
TTCTATAGTGAATAGAGTTAGGCAGGGATATTCACCATTATCGTTTCAGACCC
ACCTCCCAACCCCGAGGGGACCCGACAGGCCCGAAGGAATAGAAGAAGAAG
GTGGAGAGAGAGACAGAGACAGATCCATTCGATTAGTGAACGGATCTCGACG
GTATCGATTAGACTGTAGCCCAGGAATATGGCAGCTAGATTGTACACATTTAG
AAGGAAAAGTTATCTTGGTAGCAGTTCATGTAGCCAGTGGATATATAGAAGC
AGAAGTAATTCCAGCAGAGACAGGGCAAGAAACAGCATACTTCCTCTTAAAA
TTAGCAGGAAGATGGCCAGTAAAAACAGTACATACAGACAATGGCAGCAATT
TCACCAGTACTACAGTTAAGGCCGCCTGTTGGTGGGCGGGGATCAAGCAGGA
ATTTGGCATTCCCTACAATCCCCAAAGTCAAGGAGTAATAGAATCTATGAATA
AAGAATTAAAGAAAATTATAGGACAGGTAAGAGATCAGGCTGAACATCTTAA
GACAGCAGTACAAATGGCAGTATTCATCCACAATTTTAAAAGAAAAGGGGGG
ATTGGGGGGTACAGTGCAGGGGAAAGAATAGTAGACATAATAGCAACAGAC
ATACAAACTAAAGAATTACAAAAACAAATTACAAAAATTCAAAATTTTCGGG
TTTATTACAGGGACAGCAGAGATCCAGTTTGGCTGCATACGCGTCGTGAGGCT
CCGGTGCCCGTCAGTGGGCAGAGCGCACATCGCCCACAGTCCCCGAGAAGTT
GGGGGGAGGGGTCGGCAATTGAACCGGTGCCTAGAGAAGGTGGCGCGGGGT
AAACTGGGAAAGTGATGTCGTGTACTGGCTCCGCCTTTTTCCCGAGGGTGGGG
GAGAACCGTATATAAGTGCAGTAGTCGCCGTGAACGTTCTTTTTCGCAACGGG
TTTGCCGCCAGAACACAGGTAAGTGCCGTGTGTGGTTCCCGCGGGCCTGGCCT
CTTTTACGGGTTATGGCCCTTGCGTGCCTTGAATTACTTCCACCTGGCTGCAGT
ACGTGATTCTTGATCCCGAGCTTCGGGTTGGAAGTGGGTGGGAGAGTTCGAG
GCCTTGCGCTTAAGGAGCCCCTTCGCCTCGTGCTTGAGTTGAGGCCTGGCCTG
GGCGCTGGGGCCGCCGCGTGCGAATCTGGTGGCACCTTCGCGCCTGTCTCGCT
GCTTTCGATAAGTCTCTAGCCATTTAAAATTTTTGATGACCTGCTGCGACGCTT
TTTTTCTGGCAAGATAGTCTTGTAAATGCGGGCCAAGATCTGCACACTGGTAT
TTCGGTTTTTGGGGCCGCGGGCGGCGACGGGGCCCGTGCGTCCCAGCGCACA
TGTTCGGCGAGGCGGGGCCTGCGAGCGCGGCCACCGAGAATCGGACGGGGGT
AGTCTCAAGCTGGCCGGCCTGCTCGGTGCCTGGCCTCGCGCCGCCGTGTATC
GCCCCGCCCTGGGCGGCAAGGCTGGCCCGGTCGGCACCAGTTGCGTGAGCGG
AAAGATGGCCGCTTCCCGGCCCTGCTGCAGGGAGCTCAAAATGGAGGACGCG
GCGCTCGGGAGAGCGGGCGGGTGAGTCACCCACACAAAGGAAAAGGGCCTT
TCCGTCCTCAGCCGTCGCTTCATGTGACTCCACTGAGTACCGGGCGCCGTCCA
GGCACCTCGATTAGTTCTCGTGCTTTTGGAGTACGTCGTCTTTAGGTTGGGGG
GAGGGGTTTTATGCGATGGAGTTTCCCCACACTGAGTGGGTGGAGACTGAAG
TTAGGCCAGCTTGGCACTTGATGTAATTCTCCTTGGAATTTGCCCTTTTTGAGT
TTGGATCTTGGTTCATTCTCAAGCCTCAGACAGTGGTTCAAAGTTTTTTTCTTC
CATTTCAGGTGTCGTGAGCTAGCTCTAGAATGGCCTTACCAGTGACCGCCTTG
CTCCTGCCGCTGGCCTTGCTGCTCCACGCCGCCAGGCCGcaggtgcagctgcaggagtctg
ggggaggcttggtgcagcctgggggggtctctgagcctctcctgtacagcctctggattcacgttc
agtagttactccatggcctgggtccgccaggctccagggaagggaccccgaatgggtctcaggga
tttaccttctgatggtaagacaaggtatgcagacttcgtgaagggccgattcagcatctccagagac
aacgccaagaatatgttgtatctgcaaatgaacaacctgaaacctgaggacacggccctatattactgtg
cgagaggtatcaccggattgggaccccggggccaggggacccaggtcaccgtctcctcagcggccgccac
tagtGAGTCTAAGTACGGCCCTCCCTGCCCTCCTTGCCCATACATCTGGGCGCCC
TTGGCCGGGACTTGTGGGGTCCTTCTCCTGTCACTGGTTATCACCCTTTACTGC
AAACGGGGCAGAAAGAAACTCCTGTATATATTCAAACAACCATTTATGAGAC
CAGTACAAACTACTCAAGAGGAAGATGGCTGTAGCTGCCGATTTCCAGAAGA
AGAAGAGGAGGATGTGAACTGCTCGAGGGAAGCGGAGCTACTAACTTCAG
CCTGCTGAAGCAGGCTGGAGACGTGGAGGAGAACCCTGGACCTCCTAGGATG
GCCTTACCAGTGACCGCCTTGCTCCTGCCGCTGGCCTTGCTGCTCCACGCCGC
CAGGCCGGGATCCCAGGTGCAGCTGCAGGAGTCTGGAGGAGGATTGGTGCAG
```

```
-continued
ACTGGGGACTCTCTGAGACTCTCCTGTGTAGTCTCTGGAGGCACCTTCAGAAA
CTATGTTATGGGCTGGTTCCGCCAGGCTCCAGGGAAGGAGCGTGAGTTTGTGT
CTGCTATGAACTGGAGTGGCGGCATCACAGTCTATGCAGACTCCGTGAAGGG
CCGATTCACCATCTCCAGAGACAACGCCAAGAACGCGGTGTATCTGCAAATG
GGCAGCCTGAAACCTGGCGACACGGCCGTTTATTACTGTGCAGCTGCTGCAAT
CGATGGTGGAACCGTCAGAAGCATTAACAGTTATGCCTACTGGGGCCAGGGG
ACCCAGGTCACCGTCTCCTCAGCGGCCGCCACTAGTTCCGGAACCACTACACC
AGCGCCCAGACCACCTACCCCGGCTCCTACCATCGCATCTCAGCCCTTGAGTC
TTAGACCCGAGGCATGTCGGCCAGCGGCGGGGGGCGCAGTGCACACGAGGG
GGCTGGACTTCGCCTGTGATTACATCTGGGCGCCCTTGGCCGGGACTTGTGGG
GTCCTTCTCCTGTCACTGGTTATCACCCTTTACTGCAGAGTGAAGTTCAGCAG
GAGCGCAGACGCCCCCGCGTACAAGCAGGGCCAGAACCAGCTCTATAACGA
GCTCAATCTAGGACGAAGAGAGGAGTACGATGTTTTGGACAAGAGACGTGGC
CGGGACCCTGAGATGGGGGGAAAGCCGAGAAGGAAGAACCCTCAGGAAGGC
CTGTACAATGAACTGCAGAAAGATAAGATGGCGGAGGCCTACAGTGAGATTG
GGATGAAAGCGAGCGCCGGAGGGGCAAGGGGCACGATGGCCTTTACCAGG
GTCTCAGTACAGCCACCAAGGACACCTACGACGCCCTTCACATGCAGGCCCT
GCCCCCTCGCTAAGTCGACAATCAACCTCTGGATTACAAAATTTGTGAAAGAT
TGACTGGTATTCTTAACTATGTTGCTCCTTTTACGCTATGTGGATACGCTGCTT
TAATGCCTTTGTATCATGCTATTGCTTCCCGTATGGCTTTCATTTTCTCCTCCTT
GTATAAATCCTGGTTGCTGTCTCTTTATGAGGAGTTGTGGCCCGTTGTCAGGC
AACGTGGCGTGGTGTGCACTGTGTTTGCTGACGCAACCCCCACTGGTTGGGGC
ATTGCCACCACCTGTCAGCTCCTTTCCGGGACTTTCGCTTTCCCCCTCCCTATT
GCCACGGCGGAACTCATCGCCGCCTGCCTTGCCCGCTGCTGGACAGGGGCTC
GGCTGTTGGGCACTGACAATTCCGTGGTGTTGTCGGGGAAGCTGACGTCCTTT
CCTTGGCTGCTCGCCTGTGTTGCCACCTGGATTCTGCGCGGGACGTCCTTCTG
CTACGTCCCTTCGGCCCTCAATCCAGCGGACCTTCCTTCCCGCGGCCTGCTGC
CGGCTCTGCGGCCTCTTCCGCGTCTTCGCCTTCGCCCTCAGACGAGTCGGATC
TCCCTTTGGGCCGCCTCCCCGCCTGGAATTCGAGCTCGGTACCTTTAAGACCA
ATGACTTACAAGGCAGCTGTAGATCTTAGCCACTTTTTAAAAGAAAAGGGGG
GACTGGAAGGGCTAATTCACTCCCAACGAAGACAAGATCTGCTTTTTGCTTGT
ACTGGGTCTCTCTGGTTAGACCAGATCTGAGCCTGGGAGCTCTCTGGCTAACT
AGGGAACCCACTGCTTAAGCCTCAATAAAGCTTGCCTTGAGTGCTTCAAGTAG
TGTGTGCCCGTCTGTTGTGTGACTCTGGTAACTAGAGATCCCTCAGACCCTTTT
AGTCAGTGTGGAAAATCTCTAGCAGTAGTAGTTCATGTCATCTTATTATTCAG
TATTTATAACTTGCAAAGAAATGAATATCAGAGAGTGAGAGGAACTTGTTTA
TTGCAGCTTATAATGGTTACAAATAAAGCAATAGCATCACAAATTTCACAAAT
AAAGCATTTTTTTCACTGCATTCTAGTTGTGGTTTGTCCAAACTCATCAATGTA
TCTTATCATGTCTGGCTCTAGCTATCCCGCCCCTAACTCCGCCCCAGTTCCGCCC
ATTCTCCGCCCCATGGCTGACTAATTTTTTTTATTTATGCAGAGGCCGAGGCC
GCCTCGGCCTCTGAGCTATTCCAGAAGTAGTGAGGAGGCTTTTTTGGAGGCCT
AGCTAGGGACGTACCCAATTCGCCCTATAGTGAGTCGTATTACGCGCGCTCAC
TGGCCGTCGTTTTACAACGTCGTGACTGGGAAAACCCTGGCGTTACCCAACTT
AATCGCCTTGCAGCACATCCCCCTTTCGCCAGCTGGCGTAATAGCGAAGAGG
CCCGCACCGATCGCCCTTCCCAACAGTTGCGCAGCCTGAATGGCGAATGGGA
CGCGCCCTGTAGCGGCGCATTAAGCGCGGCGGGTGTGGTGGTTACGCGCAGC
GTGACCGCTACACTTGCCAGCGCCCTAGCGCCCGCTCCTTTCGCTTTCTTCCCT
TCCTTTCTCGCCACGTTCGCCGGCTTTCCCCGTCAAGCTCTAAATCGGGGGCT
CCCTTTAGGGTTCCGATTTAGTGCTTTACGGCACCTCGACCCCAAAAAACTTG
ATTAGGGTGATGGTTCACGTAGTGGGCCATCGCCCTGATAGACGGTTTTTCGC
CCTTTGACGTTGGAGTCCACGTTCTTTAATAGTGGACTCTTGTTCCAAACTGG
AACAACACTCAACCCTATCTCGGTCTATTCTTTTGATTTATAAGGGATTTTGCC
GATTTCGGCCTATTGGTTAAAAAATGAGCTGATTTAACAAAAATTTAACGCGA
ATTTTAACAAAATATTAACGCTTACAATTTAGGTGGCACTTTTCGGGGAAATG
TGCGCGGAACCCCTATTTGTTTATTTTTCTAAATACATTCAAATATGTATCCGC
TCATGAGACAATAACCCTGATAAATGCTTCAATAATATTGAAAAAGGAAGAG
TATGAGTATTCAACATTTCCGTGTCGCCCTTATTCCCTTTTTTGCGGCATTTTG
CCTTCCTGTTTTTGCTCACCCAGAAACGCTGGTGAAAGTAAAAGATGCTGAAG
ATCAGTTGG BiCAR2 VHH13                                                              (SEQ ID NO: 34)

GTGCACGAGTGGGTTACATCGAACTGGATCTCAACAGCGGTAAGATCCTTGA
GAGTTTTCGCCCCGAAGAACGTTTTCCAATGATGAGCACTTTTAAAGTTCTGC
TATGTGGCGCGGTATTATCCCGTATTGACGCCGGGCAAGAGCAACTCGGTCG
CCGCATACACTATTCTCAGAATGACTTGGTTGAGTACTCACCAGTCACAGAAA
AGCATCTTACGGATGGCATGACAGTAAGAGAATTATGCAGTGCTGCCATAAC
CATGAGTGATAACACTGCGGCCAACTTACTTCTGACAACGATCGGAGGACCG
AAGGAGCTAACCGCTTTTTTGCACAACATGGGGGATCATGTAACTCGCCTTGA
TCGTTGGGAACCGGAGCTGAATGAAGCCATACCAAACGACGAGCGTGACACC
ACGATGCCTGTAGCAATGGCAACAACGTTGCGCAAACTATTAACTGGCGAAC
TACTTACTCTAGCTTCCCGGCAACAATTAATAGACTGGATGGAGGCGGATAA
AGTTGCAGGACCACTTCTGCGCTCGGCCCTTCCGGCTGGCTGGTTTATTGCTG
ATAAATCTGGAGCCGGTGAGCGTGGGTCTCGCGGTATCATTGCAGCACTGGG
GCCAGATGGTAAGCCCTCCCGTATCGTAGTTATCTACACGACGGGGAGTCAG
GCAACTATGGATGAACGAAATAGACAGATCGCTGAGATAGGTGCCTCACTGA
TTAAGCATTGGTAACTGTCAGACCAAGTTTACTCATATATACTTTAGATTGAT
TTAAAACTTCATTTTTAATTTAAAAGGATCTAGGTGAAGATCCTTTTTGATAA
TCTCATGACCAAAATCCCTTAACGTGAGTTTTCGTTCCACTGAGCGTCAGACC
CCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGG
```

-continued

```
ATCAAGAGCTACCAACTCTTTTTCCGAAGGTAACTGGCTTCAGCAGAGCGCA
GATACCAAATACTGTTCTTCTAGTGTAGCCGTAGTTAGGCCACCACTTCAAGA
ACTCTGTAGCACCGCCTACATACCTCGCTCTGCTAATCCTGTTACCAGTGGCT
GCTGCCAGTGGCGATAAGTCGTGTCTTACCGGGTTGGACTCAAGACGATAGTT
ACCGGATAAGGCGCAGCGGTCGGGCTGAACGGGGGGTTCGTGCACACAGCCC
AGCTTGGAGCGAACGACCTACACCGAACTGAGATACCTACAGCGTGAGCTAT
GAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACG
CCTGGTATCTTTATAGTCCTGTCGGGTTTCGCCACCTCTGACTTGAGCGTCGAT
TTTTGTGATGCTCGTCAGGGGGCGGAGCCTATGGAAAAACGCCAGCAACGC
GGCCTTTTTACGGTTCCTGGCCTTTTGCTGGCCTTTTGCTCACATGTTCTTTCCT
GCGTTATCCCCTGATTCTGTGGATAACCGTATTACCGCCTTTGAGTGAGCTGA
TACCGCTCGCCGCAGCCGAACGACCGAGCGCAGCGAGTCAGTGAGCGAGGA
AGCGGAAGAGCGCCCAATACGCAAACCGCCTCTCCCCGCGCGTTGGCCGATT
CATTAATGCAGCTGGCACGACAGGTTTCCCGACTGGAAAGCGGGCAGTGAGC
GCAACGCAATTAATGTGAGTTAGCTCACTCATTAGGCACCCCAGGCTTTACAC
TTTATGCTTCCGGCTCGTATGTTGTGTGGAATTGTGAGCGGATAACAATTTCA
CACAGGAAACAGCTATGACCATGATTACGCCAAGCGCGCAATTAACCCTCAC
TAAAGGGAACAAAAGCTGGAGCTGCAAGCTTAATGTAGTCTTATGCAATACT
CTTGTAGTCTTGCAACATGGTAACGATGAGTTAGCAACATGCCTTACAAGGA
GAGAAAAAGCACCGTGCATGCCGATTGGTGGAAGTAAGGTGGTACGATCGTG
CCTTATTAGGAAGGCAACAGACGGGTCTGACATGGATTGGACGAACCACTGA
ATTGCCGCATTGCAGAGATATTGTATTTAAGTGCCTAGCTCGATACATAAACG
GGTCTCTCTGGTTAGACCAGATCTGAGCCTGGGAGCTCTCTGGCTAACTAGGG
AACCCACTGCTTAAGCCTCAATAAAGCTTGCCTTGAGTGCTTCAAGTAGTGTG
TGCCCGTCTGTTGTGTGACTCTGGTAACTAGAGATCCCTCAGACCCTTTTAGT
CAGTGTGGAAAATCTCTAGCAGTGGCGCCCGAACAGGGACTTGAAAGCGAAA
GGGAAACCAGAGGAGCTCTCTCGACGCAGGACTCGGCTTGCTGAAGCGCGCA
CGGCAAGAGGCGAGGGGCGGCGACTGGTGAGTACGCCAAAAATTTTGACTAG
CGGAGGCTAGAAGGAGAGAGATGGGTGCGAGAGCGTCAGTATTAAGCGGGG
GAGAATTAGATCGCGATGGGAAAAAATTCGGTTAAGGCCAGGGGGAAAGAA
AAAATATAAATTAAAACATATAGTATGGGCAAGCAGGGAGCTAGAACGATTC
GCAGTTAATCCTGGCCTGTTAGAAACATCAGAAGGCTGTAGACAAATACTGG
GACAGCTACAACCATCCCTTCAGACAGGATCAGAAGAACTTAGATCATTATA
TAATACAGTAGCAACCCTCTATTGTGTGCATCAAAGGATAGAGATAAAAGAC
ACCAAGGAAGCTTTAGACAAGATAGAGGAAGAGCAAACAAAAGTAAGACC
ACCGCACAGCAAGCGGCCGCTGATCTTCAGACCTGGAGGAGGAGATATGAGG
GACAATTGGAGAAGTGAATTATATAAATATAAAGTAGTAAAAATTGAACCAT
TAGGAGTAGCACCCACCAAGGCAAAGAGAAGAGTGGTGCAGAGAGAAAAA
GAGCAGTGGGAATAGGAGCTTTGTTCCTTGGGTTCTTGGGAGCAGCAGGAAG
CACTATGGGCGCAGCGTCAATGACGCTGACGGTACAGGCCAGACAATTATTG
TCTGGTATAGTGCAGCAGCAGAACAATTTGCTGAGGGCTATTGAGGCGCAAC
AGCATCTGTTGCAACTCACAGTCTGGGGCATCAAGCAGCTCCAGGCAAGAAT
CCTGGCTGTGGAAAGATACCTAAAGGATCAACAGCTCCTGGGGATTTGGGGT
TGCTCTGGAAAACTCATTTGCACCACTGCTGTGCCTTGGAATGCTAGTTGGAG
TAATAAATCTCTGGAACAGATTTGGAATCACACGACCTGGATGGAGTGGGAC
AGAGAAATTAACAATTACACAAGCTTAATACACTCCTTAATTGAAGAATCGC
AAAACCAGCAAGAAAAGAATGAACAAGAATTATTGGAATTAGATAAATGGG
CAAGTTTGTGGAATTGGTTTAACATAACAAATTGGCTGTGGTATATAAAATTA
TTCATAATGATAGTAGGAGGCTTGGTAGGTTTAAGAATAGTTTTTGCTGTACT
TTCTATAGTGAATAGAGTTAGGCAGGGATATTCACCATTATCGTTTCAGACCC
ACCTCCCAACCCCGAGGGGACCCGACAGGCCCGAAGGAATAGAAGAAGAAG
GTGGAGAGAGAGACAGAGACAGATCCATTCGATTAGTGAACGGATCTCGACG
GTATCGATTAGACTGTAGCCCAGGAATATGGCAGCTAGATTGTACACATTTAG
AAGGAAAAGTTATCTTGGTAGCAGTTCATGTAGCCAGTGGATATATAGAAGC
AGAAGTAATTCCAGCAGAGACAGGGCAAGAAACAGCATACTTCCTCTTAAAA
TTAGCAGGAAGATGGCCAGTAAAAACAGTACATACAGACAATGGCAGCAATT
TCACCAGTACTACAGTTAAGGCCGCCTGTTGGTGGGCGGGATCAAGCAGGA
ATTTGGCATTCCCTACAATCCCCAAAGTCAAGGAGTAATAGAATCTATGAATA
AAGAATTAAAGAAAATTATAGGACAGGTAAGAGATCAGGCTGAACATCTTAA
GACAGCAGTACAAATGGCAGTATTCATCCACAATTTTAAAAGAAAAGGGGGG
ATTGGGGGGTACAGTGCAGGGGAAAGAATAGTAGACATAATAGCAACAGAC
ATACAAACTAAAGAATTACAAAAACAAATTACAAAAATTCAAAATTTTCGGG
TTTATTACAGGGACAGCAGAGATCCAGTTTGGCTGCATACGCGTCGTGAGGCT
CCGGTGCCCGTCAGTGGGCAGAGCGCACATCGCCCACAGTCCCCGAGAAGTT
GGGGGGAGGGGTCGGCAATTGAACCGGTGCCTAGAGAAGGTGGCGCGGGGT
AAACTGGGAAAGTGATGTCGTGTACTGGCTCCGCCTTTTTCCCGAGGGTGGGG
GAGAACCGTATATAAGTGCAGTAGTCGCCGTGAACGTTCTTTTTCGCAACGGG
TTTGCCGCCAGAACACAGGTAAGTGCCGTGTGTGGTTCCCGCGGGCCTGGCCT
CTTTACGGGTTATGGCCCTTGCGTGCCTTGAATTACTTCCACCTGGCTGCAGT
ACGTGATTCTTGATCCCGAGCTTCGGGTTGGAAGTGGGTGGGAGAGTTCGAG
GCCTTGCGCTTAAGGAGCCCCTTCGCCTCGTGCTTGAGTTGAGGCCTGGCCTG
GGCGCTGGGGCCGCCGCGTGCGAATCTGGTGGCACCTTCGCGCCTGTCTCGCT
GCTTTCGATAAGTCTCTAGCCATTTAAAATTTTTGATGACCTGCTGCGACGCTT
TTTTTCTGGCAAGATAGTCTTGTAAATGCGGGCCAAGATCTGCACACTGGTAT
TTCGGTTTTTGGGGCCGCGGGCGGCGACGGGGCCCGTGCGTCCCAGCGCACA
TGTTCGGCGAGGCGGGCCTGCGAGCGCGGCCACCGAGAATCGGACGGGGGT
AGTCTCAAGCTGGCCGGCCTGCTCTGGTGCCTGGCCTCGCGCCGCCGTGTATC
GCCCCGCCCTGGGCGGCAAGGCTGGCCCGGTCGGCACCAGTTGCGTGAGCGG
AAAGATGGCCGCTTCCCGGCCCTGCTGCAGGGAGCTCAAAATGGAGGACGCG
GCGCTCGGGAGAGCGGGCGGGTGAGTCACCCACACAAAGGAAAAGGGCCTT
```

```
-continued
TCCGTCCTCAGCCGTCGCTTCATGTGACTCCACTGAGTACCGGGCGCCGTCCA
GGCACCTCGATTAGTTCTCGTGCTTTTGGAGTACGTCGTCTTTAGGTTGGGGG
GAGGGGTTTTATGCGATGGAGTTTCCCCACACTGAGTGGGTGGAGACTGAAG
TTAGGCCAGCTTGGCACTTGATGTAATTCTCCTTGGAATTTGCCCTTTTTGAGT
TTGGATCTTGGTTCATTCTCAAGCCTCAGACAGTGGTTCAAAGTTTTTTTCTTC
CATTTCAGGTGTCGTGAGCTAGCTCTAGAGCCAGCATGGCCTTACCAGTGACC
GCCTTGCTCCTGCCGCTGGCCTTGCTGCTCCACGCCGCCAGGCCGcaggtgcagctgc
aggagtctgggggaggcttggtgcagcctggggggtctctgagcctctcctgtacagcctctgg
attcacgttcagtagttactccatggcctgggtccgccaggctccagggaagggacccgaatgggtct
cagggatttacccttctgatggtaagacaaggtatgcagacttcgtgaagggccgattcagcatctcca
gagacaacgccaagaatatgttgtatctgcaaatgaacaacctggaacctgaggacacggccctatatt
actgtgcgagaggtatcaccggattgggaccccggggccaggggacccaggtcaccgtctcctcagcg
gccgccactagtGAGTCTAAGTACGGCCCTCCCTGCCCTCCTTGCCCATACATCTGG
GCGCCCTTGGCCGGGACTTGTGGGGTCCTTCTCCTGTCACTGGTTATCACCCTT
TACTGCAAACGGGGCAGAAAGAAACTCCTGTATATATTCAAACAACCATTTA
TGAGACCAGTACAAACTACTCAAGAGGAAGATGGCTGTAGCTGCCGATTTCC
AGAAGAAGAAGAAGGAGGATGTGAACTGCTCGAGGGAAGCGGAGCTACTAA
CTTCAGCCTGCTGAAGCAGGCTGGAGACGTGGAGGAGAACCCTGGACCTCCT
AGGATGGCCTTACCAGTGACCGCCTTGCTCCTGCCGCTGGCCTTGCTGCTCCA
CGCCGCCAGGCCGGGATCCCAGGTGCAGCTGCAGGAGTCTGGAGGAGGATTG
GTGCAGGCTGGGGGCTCTCTGAGCCTCTCCTGTGCAGCCTCTGGACGCACCTT
CAAGAACTATCTCATGGCCTGGTTCCGCCAGACTCCAGGGAAGGAGCGTGAG
TTTGTGGCAGCTATTACTCAGCTTGGTACTAGATCATTAAATGAAGACTTCGT
GAAGGGCCGATTCACCATCTCCAGGGACAACGCCAAGAACACGGTGTATCTG
CAAATGAACGACCTGAAAACTGACGACACGGGCGTTTATTCTTGTGCAGCAA
GCCTACAGAGTGGGGGGTCACTACGGTACGCGAAGTATGACTATTGGGGCCA
GGGGACCCAGGTCACCGTCTCCTCAGCGGCCGCCACTAGTTCCGGAACCACT
ACACCAGCGCCCAGACCACCTACCCCGGCTCCTACCATCGCATCTCAGCCCTT
GAGTCTTAGACCCGAGGCATGTCGGCCAGCGGCGGGGGGCGCAGTGCACACG
AGGGGGCTGGACTTCGCCTGTGATTACATCTGGGCGCCCTTGGCCGGGACTTG
TGGGGTCCTTCTCCTGTCACTGGTTATCACCCTTTACTGCAGAGTGAAGTTCA
GCAGGAGCGCAGACGCCCCCGCGTACAAGCAGGGCCAGAACCAGCTCTATA
ACGAGCTCAATCTAGGACGAAGAGAGGAGTACGATGTTTTGGACAAGAGACG
TGGCCGGGACCCTGAGATGGGGGGAAAGCCGAGAAGGAAGAACCCTCAGGA
AGGCCTGTACAATGAACTGCAGAAAGATAAGATGGCGGAGGCCTACAGTGA
GATTGGGATGAAAGGCGAGCGCCGGAGGGGCAAGGGGCACGATGGCCTTTA
CCAGGGTCTCAGTACAGCCACCAAGGACACCTACGACGCCCTTCACATGCAG
GCCCTGCCCCCTCGCTAAGTCGACAATCAACCTCTGGATTACAAAATTTGTGA
AAGATTGACTGGTATTCTTAACTATGTTGCTCCTTTTACGCTATGTGGATACGC
TGCTTTAATGCCTTTGTATCATGCTATTGCTTCCCGTATGGCTTTCATTTTCTCC
TCCTTGTATAAATCCTGGTTGCTGTCTCTTTATGAGGAGTTGTGGCCCGTTGTC
AGGCAACGTGGCGTGGTGTGCACTGTGTTTGCTGACGCAACCCCCACTGGTTG
GGGCATTGCCACCACCTGTCAGCTCCTTTCCGGGACTTTCGCTTTCCCCCTCCC
TATTGCCACGGCGGAACTCATCGCCGCCTGCCTTGCCCGCTGCTGGACAGGG
GCTCGGCTGTTGGGCACTGACAATTCCGTGGTGTTGTCGGGGAAGCTGACGTC
CTTTCCTTGGCTGCTCGCCTGTGTTGCCACCTGGATTCTGCGCGGGACGTCCTT
CTGCTACGTCCCTTCGGCCCTCAATCCAGCGGACCTTCCTTCCCGCGGCCTGC
TGCCGGCTCTGCGGCCTCTTCCGCGTCTTCGCCTTCGCCCTCAGACGAGTCGG
ATCTCCCTTTGGGCCGCCTCCCCGCCTGGAATTCGAGCTCGGTACCTTTAAGA
CCAATGACTTACAAGGCAGCTGTAGATCTTAGCCACTTTTTAAAAGAAAGG
GGGGACTGGAAGGGCTAATTCACTCCCAACGAAGACAAGATCTGCTTTTTGC
TTGTACTGGGTCTCTCTGGTTAGACCAGATCTGAGCCTGGGAGCTCTCTGGCT
AACTAGGGAACCCACTGCTTAAGCCTCAATAAAGCTTGCCTTGAGTGCTTCAA
GTAGTGTGTGCCCGTCTGTTGTGTGACTCTGGTAACTAGAGATCCCTCAGACC
CTTTTAGTCAGTGTGGAAAATCTCTAGCAGTAGTAGTTCATGTCATCTTATTAT
TCAGTATTTATAACTTGCAAAGAAATGAATATCAGAGAGTGAGAGGAACTTG
TTTATTGCAGCTTATAATGGTTACAAATAAAGCAATAGCATCACAAATTTCAC
AAATAAAGCATTTTTTTCACTGCATTCTAGTTGTGGTTTGTCCAAACTCATCAA
TGTATCTTATCATGTCTGGCTCTAGCTATCCCGCCCCTAACTCCGCCCAGTTCC
GCCCATTCTCCGCCCCATGGCTGACTAATTTTTTTATTTATGCAGAGGCCGA
GGCCGCCTCGGCCTCTGAGCTATTCCAGAAGTAGTGAGGAGGCTTTTTTGGAG
GCCTAGCTAGGGACGTACCCAATTCGCCCTATAGTGAGTCGTATTACGCGCGC
TCACTGGCCGTCGTTTTACAACGTCGTGACTGGGAAAACCCTGGCGTTACCCA
ACTTAATCGCCTTGCAGCACATCCCCCTTTCGCCAGCTGGCGTAATAGCGAAG
AGGCCCGCACCGATCGCCCTTCCCAACAGTTGCGCAGCCTGAATGGCGAATG
GGACGCGCCCTGTAGCGGCGCATTAAGCGCGGCGGGTGTGGTGGTTACGCGC
AGCGTGACCGCTACACTTGCCAGCGCCCTAGCGCCCGCTCCTTTCGCTTTCTT
CCCTTCCTTTCTCGCCACGTTCGCCGGCTTTCCCCGTCAAGCTCTAAATCGGG
GGCTCCCTTTAGGGTTCCGATTTAGTGCTTTACGGCACCTCGACCCCAAAAAA
CTTGATTAGGGTGATGGTTCACGTAGTGGGCCATCGCCCTGATAGACGGTTTT
TCGCCCTTTGACGTTGGAGTCCACGTTCTTTAATAGTGGACTCTTGTTCCAAAC
TGGAACAACACTCAACCCTATCTCGGTCTATTCTTTTGATTTATAAGGGATTTT
GCCGATTTCGGCCTATTGGTTAAAAAATGAGCTGATTTAACAAAAATTTAACG
CGAATTTTAACAAAATATTAACGCTTACAATTTAGGTGGCACTTTTCGGGGAA
ATGTGCGCGGAACCCCTATTTGTTTATTTTTCTAAATACATTCAAATATGTATC
CGCTCATGAGACAATAACCCTGATAAATGCTTCAATAATATTGAAAAGGAA
GAGTATGAGTATTCAACATTTCCGTGTCGCCCTTATTCCCTTTTTTGCGGCATT
TTGCCTTCCTGTTTTTGCTCACCCAGAAACGCTGGTGAAAGTAAAAGATGCTG
AAGATCAGTTGG
```

BiCAR2 VHH28

(SEQ ID NO: 35)

GTGCACGAGTGGGTTACATCGAACTGGATCTCAACAGCGGTAAGATCCTTGA
GAGTTTTCGCCCCGAAGAACGTTTTCCAATGATGAGCACTTTTAAAGTTCTGC
TATGTGGCGCGGTATTATCCCGTATTGACGCCGGGCAAGAGCAACTCGGTCG
CCGCATACACTATTCTCAGAATGACTTGGTTGAGTACTCACCAGTCACAGAAA
AGCATCTTACGGATGGCATGACAGTAAGAGAATTATGCAGTGCTGCCATAAC
CATGAGTGATAACACTGCGGCCAACTTACTTCTGACAACGATCGGAGGACCG
AAGGAGCTAACCGCTTTTTTGCACAACATGGGGGATCATGTAACTCGCCTTGA
TCGTTGGGAACCGGAGCTGAATGAAGCCATACCAAACGACGAGCGTGACACC
ACGATGCCTGTAGCAATGGCAACAACGTTGCGCAAACTATTAACTGGCGAAC
TACTTACTCTAGCTTCCCGGCAACAATTAATAGACTGGATGGAGGCGGATAA
AGTTGCAGGACCACTTCTGCGCTCGGCCCTTCCGGCTGGCTGGTTTATTGCTG
ATAAATCTGGACCGGTGAGCGTGGGTCTCGCGGTATCATTGCAGCACTGGG
GCCAGATGGTAAGCCCTCCCGTATCGTAGTTATCTACACGACGGGGAGTCAG
GCAACTATGGATGAACGAAATAGACAGATCGCTGAGATAGGTGCCTCACTGA
TTAAGCATTGGTAACTGTCAGACCAAGTTTACTCATATATACTTTAGATTGAT
TTAAAACTTCATTTTTAATTTAAAAGGATCTAGGTGAAGATCCTTTTTGATAA
TCTCATGACCAAAATCCCTTAACGTGAGTTTTCGTTCCACTGAGCGTCAGACC
CCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGG
ATCAAGAGCTACCAACTCTTTTTCCGAAGGTAACTGGCTTCAGCAGAGCGCA
GATACCAAATACTGTTCTTCTAGTGTAGCCGTAGTTAGGCCACCACTTCAAGA
ACTCTGTAGCACCGCCTACATACCTCGCTCTGCTAATCCTGTTACCAGTGGCT
GCTGCCAGTGGCGATAAGTCGTGTCTTACCGGGTTGGACTCAAGACGATAGTT
ACCGGATAAGGCGCAGCGGTCGGGCTGAACGGGGGGTTCGTGCACACAGCCC
AGCTTGGAGCGAACGACCTACACCGAACTGAGATACCTACAGCGTGAGCTAT
GAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACG
CCTGGTATCTTTATAGTCCTGTCGGGTTTCGCCACCTCTGACTTGAGCGTCGAT
TTTTGTGATGCTCGTCAGGGGGCGGAGCCTATGGAAAAACGCCAGCAACGC
GGCCTTTTTACGGTTCCTGGCCTTTTGCTGGCCTTTTGCTCACATGTTCTTTCCT
GCGTTATCCCCTGATTCTGTGGATAACCGTATTACCGCCTTTGAGTGAGCTGA
TACCGCTCGCCGCAGCCGAACGACCGAGCGCAGCGAGTCAGTGAGCGAGGA
AGCGGAAGAGCGCCCAATACGCAAACCGCCTCTCCCCGCGCGTTGGCCGATT
CATTAATGCAGCTGGCACGACAGGTTTCCCGACTGGAAAGCGGGCAGTGAGC
GCAACGCAATTAATGTGAGTTAGCTCACTCATTAGGCACCCCAGGCTTTACAC
TTTATGCTTCCGGCTCGTATGTTGTGTGGAATTGTGAGCGGATAACAATTTCA
CACAGGAAACAGCTATGACCATGATTACGCCAAGCGCGCAATTAACCCTCAC
TAAAGGGAACAAAAGCTGGAGCTGCAAGCTTAATGTAGTCTTATGCAATACT
CTTGTAGTCTTGCAACATGGTAACGATGAGTTAGCAACATGCCTTACAAGGA
GAGAAAAAGCACCGTGCATGCCGATTGGTGGAAGTAAGGTGGTACGATCGTG
CCTTATTAGGAAGGCAACAGACGGGTCTGACATGGATTGGACGAACCACTGA
ATTGCCGCATTGCAGAGATATTGTATTTAAGTGCCTAGCTCGATACATAAACG
GGTCTCTCTGGTTAGACCAGATCTGAGCCTGGGAGCTCTCTGGCTAACTAGGG
AACCCACTGCTTAAGCCTCAATAAAGCTTGCCTTGAGTGCTTCAAGTAGTGTG
TGCCCGTCTGTTGTGTGACTCTGGTAACTAGAGATCCCTCAGACCCTTTTAGT
CAGTGTGGAAAATCTCTAGCAGTGGCGCCCGAACAGGGACTTGAAAGCGAAA
GGGAAACCAGAGGAGCTCTCTCGACGCAGGACTCGGCTTGCTGAAGCGCGCA
CGGCAAGAGGCGAGGGGCGGCGACTGGTGAGTACGCCAAAAATTTTGACTAG
CGGAGGCTAGAAGGAGAGAGATGGGTGCGAGAGCGTCAGTATTAAGCGGGG
GAGAATTAGATCGCGATGGGAAAAAATTCGGTTAAGGCCAGGGGGAAAGAA
AAAATATAAATTAAAACATATAGTATGGGCAAGCAGGGAGCTAGAACGATTC
GCAGTTAATCCTGGCCTGTTAGAAACATCAGAAGGCTGTAGACAAATACTGG
GACAGCTACAACCATCCCTTCAGACAGGATCAGAAGAACTTAGATCATTATA
TAATACAGTAGCAACCCTCTATTGTGTGCATCAAAGGATAGAGATAAAAGAC
ACCAAGGAAGCTTTAGACAAGATAGAGGAAGAGCAAAACAAAAGTAAGACC
ACCGCACAGCAAGCGGCCGCTGATCTTCAGACCTGGAGGAGGAGATATGAGG
GACAATTGGAGAAGTGAATTATATAAATATAAAGTAGTAAAAATTGAACCAT
TAGGAGTAGCACCCACCAAGGCAAAGAGAAGAGTGGTGCAGAGAGAAAAA
GAGCAGTGGGAATAGGAGCTTTGTTCCTTGGGTTCTTGGGAGCAGCAGGAAG
CACTATGGGCGCAGCGTCAATGACGCTGACGGTACAGGCCAGACAATTATTG
TCTGGTATAGTGCAGCAGCAGAACAATTTGCTGAGGGCTATTGAGGCGCAAC
AGCATCTGTTGCAACTCACAGTCTGGGGCATCAAGCAGCTCCAGGCAAGAAT
CCTGGCTGTGGAAAGATACCTAAAGGATCAACAGCTCCTGGGGATTTGGGGT
TGCTCTGGAAAACTCATTTGCACCACTGCTGTGCCTTGGAATGCTAGTTGGAG
TAATAAATCTCTGGAACAGATTTGGAATCACACGACCTGATGGAGTGGCAAC
AGAGAAATTAACAATTACACAAGCTTAATACACTCCTTAATTGAAGAATCGC
AAAACCAGCAAGAAAAGAATGAACAAGAATTATTGGAATTAGATAAATGGG
CAAGTTTGTGGAATTGGTTTAACATAACAAATTGGCTGTGGTATATAAAATTA
TTCATAATGATAGTAGGAGGCTTGGTAGGTTTAAGAATAGTTTTTGCTGTACT
TTCTATAGTGAATAGAGTTAGGCAGGGATATTCACCATTATCGTTTCAGACCC
ACCTCCCAACCCCGAGGGGACCCGACAGGCCCGAAGGAATAGAAGAAGAAG
GTGGAGAGAGAGACAGAGACAGATCCATTCGATTAGTGAACGGATCTCGACG
GTATCGATTAGACTGTAGCCCAGGAATATGGCAGCTAGATTGTACACATTTAG
AAGGAAAAGTTATCTTGGTAGCAGTTCATGTAGCCAGTGGATATATAGAAGC
AGAAGTAATTCCAGCAGAGACAGGGCAAGAAACAGCATACTTCCTCTTAAAA
TTAGCAGGAAGATGGCCAGTAAAAACAGTACATAGACAATGGCAGCAATT
TCACCAGTACTACAGTTAAGGCCGCCTGTTGGTGGGCGGGATCAAGCAGGA
ATTTGGCATTCCCTACAATCCCCAAAGTCAAGGAGTAATAGAATCTATGAATA

-continued

```
AAGAATTAAAGAAAATTATAGGACAGGTAAGAGATCAGGCTGAACATCTTAA
GACAGCAGTACAAATGGCAGTATTCATCCACAATTTTAAAAGAAAAGGGGGG
ATTGGGGGGTACAGTGCAGGGGAAAGAATAGTAGACATAATAGCAACAGAC
ATACAAACTAAAGAATTACAAAAACAAATTACAAAAATTCAAATTTTCGGG
TTTATTACAGGGACAGCAGAGATCCAGTTTGGCTGCATACGCGTCGTGAGGCT
CCGGTGCCCGTCAGTGGGCAGAGCGCACATCGCCCACAGTCCCCGAGAAGTT
GGGGGGAGGGGTCGGCAATTGAACCGGTGCCTAGAGAAGGTGGCGCGGGGT
AAACTGGGAAAGTGATGTCGTGTACTGGCTCCGCCTTTTTCCCGAGGGTGGGG
GAGAACCGTATATAAGTGCAGTAGTCGCCGTGAACGTTCTTTTTCGCAACGGG
TTTGCCGCCAGAACACAGGTAAGTGCCGTGTGTGGTTCCCGCGGGCCTGGCCT
CTTTACGGGTTATGGCCCTTGCGTGCCTTGAATTACTTCCACCTGGCTGCAGT
ACGTGATTCTTGATCCCGAGCTTCGGGTTGGAAGTGGGTGGGAGAGTTCGAG
GCCTTGCGCTTAAGGAGCCCCTTCGCCTCGTGCTTGAGTTGAGGCCTGGCCTG
GGCGCTGGGGCCGCCGCGTGCGAATCTGGTGGCACCTTCGCGCCTGTCTCGCT
GCTTTCGATAAGTCTCTAGCCATTTAAAATTTTTGATGACCTGCTGCGACGCTT
TTTTTCTGGCAAGATAGTCTTGTAAATGCGGGCCAAGATCTGCACACTGGTAT
TTCGGTTTTTGGGGCCGCGGGCGGCGACGGGGCCCGTGCGTCCCAGCGCACA
TGTTCGGCGAGGCGGGGCCTGCGAGCGCGGCCACCGAGAATCGGACGGGGGT
AGTCTCAAGCTGGCCGGCCTGCTCTGGTGCCTGGCCTCGCGCCGCCGTGTATC
GCCCCGCCCTGGGCGGCAAGGCTGGCCCGGTCGGCACCAGTTGCGTGAGCGG
AAAGATGGCCGCTTCCCGGCCCTGCTGCAGGGAGCTCAAAATGGAGGACGCG
GCGCTCGGGAGAGCGGGCGGGTGAGTCACCCACACAAAGGAAAAGGGCCTT
TCCGTCCTCAGCCGTCGCTTCATGTGACTCCACTGAGTACCGGGCGCCGTCCA
GGCACCTCGATTAGTTCTCGTGCTTTTGGAGTACGTCGTCTTTAGGTTGGGGG
GAGGGGTTTTATGCGATGGAGTTTCCCCACACTGAGTGGGTGGAGACTGAAG
TTAGGCCAGCTTGGCACTTGATGTAATTCTCCTTGGAATTTGCCCTTTTTGAGT
TTGGATCTTGGTTCATTCTCAAGCCTCAGACAGTGGTTCAAAGTTTTTTTCTTC
CATTTCAGGTGTCGTGAGCTAGCTCTAGAGCCAGCATGGCCTTACCAGTGACC
GCCTTGCTCCTGCCGCTGGCCTTGCTGCTCCACGCCGCCAGGCCGcaggtgcagctgc
aggagtctgggggaggcttggtgcagcctggggggtctctgagcctctcctgtacag
cctctggattcacgttcagtagttactccatggcctgggtccgccaggctccaggga
agggacccgaatggggtctcagggatttacccttctgatggtaagacaaggtatgcag
acttcgtgaagggccgattcagcatctccagagacaacgccaagaatatgttgtatct
gcaaatgaacaacctggaacctgaggacacggccctatattactgtgcgagaggtatca
ccggattgggaccccggggccaggggaccaggtcaccgtctcctcagcg
gccgccactagtGAGTCTAAGTACGGCCCTCCCTGCCCTCCTTGCCCATACATCTGG
GCGCCCTTGGCCGGGACTTGTGGGGTCCTTCTCCTGTCACTGGTTATCACCCTT
TACTGCAAACGGGGCAGAAAGAAACTCCTGTATATATTCAAACAACCATTTA
TGAGACCAGTACAAACTACTCAAGAGGAAGATGGCTGTAGCTGCCGATTTCC
AGAAGAAGAAGAAGGAGGATGTGAACTGCTCGAGGGAAGCGGAGCTACTAA
CTTCAGCCTGCTGAAGCAGGCTGGAGACGTGGAGGAGAACCCTGGACCTCCT
AGGATGGCCTTACCAGTGACCGCCTTGCTCCTGCCGCTGGCCTTGCTGCTCCA
CGCCGCCAGGCCGGGATCCCAGGTGCAGCTGCAGGAGTCTGGGGGAGGATTG
GTGCAGGCTGGGGGCTCTCTGAGACTCTCCTGTGCAGCCTCTGAAGGCACCGT
CAGCACCTACACCATGGCCTGGTTCCGCCAGGCTCCAGGGAAGGAGCGTGAG
TTTGTAGCCAGGATTACTGGTGTTAGTACGGCTGTGAAGGGCCGGTTCACCTT
CTCCAGAGACGAGCCCAAAAACACAGTGTATCTGCAAATGAACAGCCTGAAA
CCTGAGGACACGGCCGTCTATTACTGCGCGGCACACTATTTGGGTGGTCGTCC
AGATATGCCGACTCAGTATCAATACTTGGGCCAGGGGACCCAGGTCACCGTC
TCCTCAGCGGCCGCCACTAGTTCCGGAACCACTACACCAGCGCCCAGACCAC
CTACCCCGGCTCCTACCATCGCATCTCAGCCCTTGAGTCTTAGACCCGAGGCA
TGTCGGCCAGCGGCGGGGGCGCAGTGCACACGAGGGGGCTGGACTTCGCCT
GTGATTACATCTGGGCGCCCTTGGCCGGGACTTGTGGGGTCCTTCTCCTGTCA
CTGGTTATCACCCTTTACTGCAGAGTGAAGTTCAGCAGGAGCGCAGACGCCC
CCGCGTACAAGCAGGGCCAGAACCAGCTCTATAACGAGCTCAATCTAGGACG
AAGAGAGGAGTACGATGTTTTGGACAAGAGACGTGGCCGGGACCCTGAGATG
GGGGGAAAGCCGAGAAGGAAGAACCCTCAGGAAGGCCTGTACAATGAACTG
CAGAAAGATAAGATGGCGGAGGCCTACAGTGAGATTGGGATGAAAGGCGAG
CGCCGGAGGGGCAAGGGGCACGATGGCCTTTACCAGGGTCTCAGTACAGCCA
CCAAGGACACCTACGACGCCCTTCACATGCAGGCCCTGCCCCCTCGCTAAGTC
GACAATCAACCTCTGGATTACAAAATTTGTGAAAGATTGACTGGTATTCTTAA
CTATGTTGCTCCTTTTACGCTATGTGGATACGCTGCTTTAATGCCTTTGTATCA
TGCTATTGCTTCCCGTATGGCTTTCATTTTCTCCTCCTTGTATAAATCCTGGTT
GCTGTCTCTTTATGAGGAGTTGTGGCCCGTTGTCAGGCAACGTGGCGTGGTGT
GCACTGTGTTTGCTGACGCAACCCCCACTGGTTGGGGCATTGCCACCACCTGT
CAGCTCCTTTCCGGGACTTTCGCTTTCCCCCTCCCTATTGCCACGGCGGAACTC
ATCGCCGCCTGCCTTGCCCGCTGCTGGACAGGGGCTCGGCTGTTGGGCACTGA
CAATTCCGTGGTGTTGTCGGGGAAGCTGACGTCCTTTCCTTGGCTGCTCGCCT
GTGTTGCCACCTGGATTCTGCGCGGGACGTCCTTCTGCTACGTCCCTTCGGCC
CTCAATCCAGCGGACCTTCCTTCCCGCGGCCTGCTGCCGGCTCTGCGGCCTCT
TCCGCGTCTTCGCCTTCGCCCTCAGACGAGTCGGATCTCCCTTTGGGCCGCCT
CCCCGCCTGGAATTCGAGCTCGGTACCTTTAAGACCAATGACTTACAAGGCA
GCTGTAGATCTTAGCCACTTTTTAAAAGAAAAGGGGGGACTGGAAGGGCTAA
TTCACTCCCAACGAAGACAAGATCTGCTTTTTGCTTGTACTGGGTCTCTCTGGT
TAGACCAGATCTGAGCCTGGGAGCTCTCTGGCTAACTAGGGAACCCACTGCTT
AAGCCTCAATAAAGCTTGCCTTGAGTGCTTCAAGTAGTGTGTGCCCGTCTGTT
GTGTGACTCTGGTAACTAGAGATCCCTCAGACCCTTTTAGTCAGTGTGGAAAA
TCTCTAGCAGTAGTAGTTCATGTCATCTTATTATTCAGTATTTATAACTTGCAA
AGAAATGAATATCAGAGAGTGAGAGGAACTTGTTTATTGCAGCTTATAATGG
TTACAAATAAAGCAATAGCATCACAAATTTCACAAATAAAGCATTTTTTTCAC
TGCATTCTAGTTGTGGTTTGTCCAAACTCATCAATGTATCTTATCATGTCTGGC
```

-continued

TCTAGCTATCCCGCCCCTAACTCCGCCCAGTTCCGCCCATTCTCCGCCCCATG
GCTGACTAATTTTTTTATTTATGCAGAGGCCGAGGCCGCCTCGGCCTCTGAG
CTATTCCAGAAGTAGTGAGGAGGCTTTTTGGAGGCCTAGCTAGGGACGTAC
CCAATTCGCCCTATAGTGAGTCGTATTACGCGCGCTCACTGGCCGTCGTTTTA
CAACGTCGTGACTGGGAAAACCCTGGCGTTACCCAACTTAATCGCCTTGCAGC
ACATCCCCCTTTCGCCAGCTGGCGTAATAGCGAAGAGGCCCGCACCGATCGC
CCTTCCCAACAGTTGCGCAGCCTGAATGGCGAATGGGACGCGCCCTGTAGCG
GCGCATTAAGCGCGGCGGGTGTGGTGGTTACGCGCAGCGTGACCGCTACACT
TGCCAGCGCCCTAGCGCCCGCTCCTTTCGCTTTCTTCCCTTCCTTTCTCGCCAC
GTTCGCCGGCTTTCCCCGTCAAGCTCTAAATCGGGGGCTCCCTTTAGGGTTCC
GATTTAGTGCTTTACGGCACCTCGACCCCAAAAAACTTGATTAGGGTGATGGT
TCACGTAGTGGGCCATCGCCCTGATAGACGGTTTTTCGCCCTTTGACGTTGGA
GTCCACGTTCTTTAATAGTGGACTCTTGTTCCAAACTGGAACAACACTCAACC
CTATCTCGGTCTATTCTTTTGATTTATAAGGGATTTTGCCGATTTCGGCCTATT
GGTTAAAAAATGAGCTGATTTAACAAAAATTTAACGCGAATTTTAACAAAAT
ATTAACGCTTACAATTTAGGTGGCACTTTTCGGGGAAATGTGCGCGGAACCCC
TATTTGTTTATTTTTCTAAATACATTCAAATATGTATCCGCTCATGAGACAATA
ACCCTGATAAATGCTTCAATAATATTGAAAAAGGAAGAGTATGAGTATTCAA
CATTTCCGTGTCGCCCTTATTCCCTTTTTTGCGGCATTTTGCCTTCCTGTTTTTG
CTCACCCAGAAACGCTGGTGAAAGTAAAAGATGCTGAAGATCAGTTGG

BiCAR2 VHH30

(SEQ ID NO: 36)

GTGCACGAGTGGGTTACATCGAACTGGATCTCAACAGCGGTAAGATCCTTGA
GAGTTTTCGCCCCGAAGAACGTTTTCCAATGATGAGCACTTTTAAAGTTCTGC
TATGTGGCGCGGTATTATCCCGTATTGACGCCGGGCAAGAGCAACTCGGTCG
CCGCATACACTATTCTCAGAATGACTTGGTTGAGTACTCACCAGTCACAGAAA
AGCATCTTACGGATGGCATGACAGTAAGAGAATTATGCAGTGCTGCCATAAC
CATGAGTGATAACACTGCGGCCAACTTACTTCTGACAACGATCGGAGGACCG
AAGGAGCTAACCGCTTTTTTGCACAACATGGGGGATCATGTAACTCGCCTTGA
TCGTTGGGAACCGGAGCTGAATGAAGCCATACCAAACGACGAGCGTGACACC
ACGATGCCTGTAGCAATGGCAACAACGTTGCGCAAACTATTAACTGGCGAAC
TACTTACTCTAGCTTCCCGGCAACAATTAATAGACTGGATGGAGGCGGATAA
AGTTGCAGGACCACTTCTGCGCTCGGCCCTTCCGGCTGGCTGGTTTATTGCTG
ATAAATCTGGAGCCGGTGAGCGTGGGTCTCGCGGTATCATTGCAGCACTGGG
GCCAGATGGTAAGCCCTCCCGTATCGTAGTTATCTACACGACGGGGAGTCAG
GCAACTATGGATGAACGAAATAGACAGATCGCTGAGATAGGTGCCTCACTGA
TTAAGCATTGGTAACTGTCAGACCAAGTTTACTCATATATACTTTAGATTGAT
TTAAAACTTCATTTTTAATTTAAAAGGATCTAGGTGAAGATCCTTTTTGATAA
TCTCATGACCAAAATCCCTTAACGTGAGTTTTCGTTCCACTGAGCGTCAGACC
CCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGG
ATCAAGAGCTACCAACTCTTTTTCCGAAGGTAACTGGCTTCAGCAGAGCGCA
GATACCAAATACTGTTCTTCTAGTGTAGCCGTAGTTAGGCCACCACTTCAAGA
ACTCTGTAGCACCGCCTACATACCTCGCTCTGCTAATCCTGTTACCAGTGGCT
GCTGCCAGTGGCGATAAGTCGTGTCTTACCGGGTTGGACTCAAGACGATAGTT
ACCGGATAAGGCGCAGCGGTCGGGCTGAACGGGGGGTTCGTGCACACAGCCC
AGCTTGGAGCGAACGACCTACACCGAACTGAGATACCTACAGCGTGAGCTAT
GAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACG
CCTGGTATCTTTATAGTCCTGTCGGGTTTCGCCACCTCTGACTTGAGCGTCGAT
TTTTGTGATGCTCGTCAGGGGGGCGGAGCCTATGGAAAAACGCCAGCAACGC
GGCCTTTTTACGGTTCCTGGCCTTTTGCTGGCCTTTTGCTCACATGTTCTTTCCT
GCGTTATCCCCTGATTCTGTGGATAACCGTATTACCGCCTTTGAGTGAGCTGA
TACCGCTCGCCGCAGCCGAACGACCGAGCGCAGCGAGTCAGTGAGCGAGGA
AGCGGAAGAGCGCCCAATACGCAAACCGCCTCTCCCCGCGCGTTGGCCGATT
CATTAATGCAGCTGGCACGACAGGTTTCCCGACTGGAAAGCGGGCAGTGAGC
GCAACGCAATTAATGTGAGTTAGCTCACTCATTAGGCACCCCAGGCTTTACAC
TTTATGCTTCCGGCTCGTATGTTGTGTGGAATTGTGAGCGGATAACAATTTCA
CACAGGAAACAGCTATGACCATGATTACGCCAAGCGCGCAATTAACCCTCAC
TAAAGGGAACAAAAGCTGGAGCTGCAAGCTTAATGTAGTCTTATGCAATACT
CTTGTAGTCTTGCAACATGGTAACGATGAGTTAGCAACATGCCTTACAAGGA
GAGAAAAAGCACCGTGCATGCCGATTGGTGGAAGTAAGGTGGTACGATCGTG
CCTTATTAGGAAGGCAACAGACGGGTCTGACATGGATTGGACGAACCACTGA
ATTGCCGCATTGCAGAGATATTGTATTTAAGTGCCTAGCTCGATACATAAACG
GGTCTCTCTGGTTAGACCAGATCTGAGCCTGGGAGCTCTCTGGCTAACTAGGG
AACCCACTGCTTAAGCCTCAATAAAGCTTGCCTTGAGTGCTTCAAGTAGTGTG
TGCCCGTCTGTTGTGTGACTCTGGTAACTAGAGATCCCTCAGACCCTTTTAGT
CAGTGTGGAAAATCTCTAGCAGTGGCGCCCGAACAGGGACTTGAAAGCGAAA
GGGAAACCAGAGGAGCTCTCTCGACGCAGGACTCGGCTTGCTGAAGCGCGCA
CGGCAAGAGGCGAGGGGCGGCGACTGGTGAGTACGCCAAAAATTTTGACTAG
CGGAGGCTAGAAGGAGAGAGATGGGTGCGAGAGCGTCAGTATTAAGCGGGG
GAGAATTAGATCGCGATGGGAAAAAATTCGGTTAAGGCCAGGGGGAAAGAA
AAAATATAAATTAAAACATATAGTATGGGCAAGCAGGGAGCTAGAACGATTC
GCAGTTAATCCTGGCCTGTTAGAAACATCAGAAGGCTGTAGACAAATACTGG
GACAGCTACAACCTCCCTTCAGACAGGATCAGAAGAACTTAGATCATTATA
TAATACAGTAGCAACCCTCTATTGTGTGCATCAAAGGATAGAGATAAAAGAC
ACCAAGGAAGCTTTAGACAAGATAGAGGAAGAGCAAAACAAAAGTAAGACC
ACCGCACAGCAAGCGGCCGCTGATCTTCAGACCTGGAGGAGGAGATATGAGG
GACAATTGGAGAAGTGAATTATATAAATATAAAGTAGTAAAAATTGAACCAT
TAGGAGTAGCACCCACCAAGGCAAAGAGAAGAGTGGTGCAGAGAGAAAAAA

-continued

```
GAGCAGTGGGAATAGGAGCTTTGTTCCTTGGGTTCTTGGGAGCAGCAGGAAG
CACTATGGGCGCAGCGTCAATGACGCTGACGGTACAGGCCAGACAATTATTG
TCTGGTATAGTGCAGCAGCAGAACAATTTGCTGAGGGCTATTGAGGCGCAAC
AGCATCGTTGCAACTCACAGTCTGGGGCATCAAGCAGCTCCAGGCAAGAAT
CCTGGCTGTGGAAAGATACCTAAAGGATCAACAGCTCCTGGGGATTGGGGT
TGCTCTGGAAAACTCATTTGCACCACTGCTGTGCCTTGGAATGCTAGTTGGAG
TAATAAATCTCTGGAACAGATTTGGAATCACACGACCTGGATGGAGTGGGAC
AGAGAAATTAACAATTACACAAGCTTAATACACTCCTTAATTGAAGAATCGC
AAAACCAGCAAGAAAAGAATGAACAAGAATTATTGGAATTAGATAAATGGG
CAAGTTTGTGGAATTGGTTTAACATAACAAATTGGCTGTGGTATATAAAATTA
TTCATAATGATAGTAGGAGGCTTGGTAGGTTTAAGAATAGTTTTTGCTGTACT
TTCTATAGTGAATAGAGTTAGGCAGGGATATTCACCATTATCGTTTCAGACCC
ACCTCCCAACCCCGAGGGGACCCGACAGGCCCGAAGGAATAGAAGAAGAAG
GTGGAGAGAGAGACAGAGACAGATCCATTCGATTAGTGAACGGATCTCGACG
GTATCGATTAGACTGTAGCCCAGGAATATGGCAGCTAGATTGTACACATTTAG
AAGGAAAAGTTATCTTGGTAGCAGTTCATGTAGCCAGTGGATATATAGAAGC
AGAAGTAATTCCAGCAGAGACAGGGCAAGAAACAGCATACTTCCTCTTAAAA
TTAGCAGGAAGATGGCCAGTAAAAACAGTACATACAGACAATGGCAGCAATT
TCACCAGTACTACAGTTAAGGCCGCCTGTTGGTGGGCGGGGATCAAGCAGGA
ATTTGGCATTCCCTACAATCCCCAAAGTCAAGGAGTAATAGAATCTATGAATA
AAGAATTAAAGAAAATTATAGGACAGGTAAGAGATCAGGCTGAACATCTTAA
GACAGCAGTACAAATGGCAGTATTCATCCACAATTTTAAAAGAAAAGGGGGG
ATTGGGGGGTACAGTGCAGGGGAAAGAATAGTAGACATAATAGCAACAGAC
ATACAAACTAAAGAATTACAAAAACAAATTACAAAAATTCAAAATTTTCGGG
TTTATTACAGGGACAGCAGAGATCCAGTTTGGCTGCATACGCGTCGTGAGGCT
CCGGTGCCCGTCAGTGGGCAGAGCGCACATCGCCCACAGTCCCCGAGAAGTT
GGGGGGAGGGGTCGGCAATTGAACCGGTGCCTAGAGAAGGTGGCGCGGGGT
AAACTGGGAAAGTGATGTCGTGTACTGGCTCCGCCTTTTTCCCGAGGGTGGGG
GAGAACCGTATATAAGTGCAGTAGTCGCCGTGAACGTTCTTTTTCGCAACGGG
TTTGCCGCCAGAACACAGGTAAGTGCCGTGTGTGGTTCCCGCGGGCCTGGCCT
CTTTACGGGTTATGGCCCTTGCGTGCCTTGAATTACTTCCACCTGGCTGCAGT
ACGTGATTCTTGATCCCGAGCTTCGGGTTGGAAGTGGGTGGGAGAGTTCGAG
GCCTTGCGCTTAAGGAGCCCCTTCGCCTCGTGCTTGAGTTGAGGCCTGGCCTG
GGGCGCTGGGGCCGCCGCGTGCGAATCTGGTGGCACCTTCGCGCCTGTCTCGCT
GCTTTCGATAAGTCTCTAGCCATTTAAAATTTTTGATGACCTGCTGCGACGCTT
TTTTTCTGGCAAGATAGTCTTGTAAATGCGGGCCAAGATCTGCACACTGGTAT
TTCGGTTTTTGGGGCCGCGGGCGGCGACGGGCCCGTGCGTCCCAGCGCACA
TGTTCGGCGAGGCGGGGCCTGCGAGCGCGGCCACCGAGAATCGGACGGGGGT
AGTCTCAAGCTGGCCGGCCTGCTCTGGTGCCTGGCCTCGCGCGCCGTGTATC
GCCCCGCCCTGGGCGGCAAGGCTGGCCCGGTCGGCACCAGTTGCGTGAGCGG
AAAGATGGCCGCTTCCCGGCCCTGCTGCAGGGAGCTCAAAATGGAGGACGCG
GCGCTCGGGAGAGCGGGCGGGTGAGTCACCCACACAAAGGAAAAGGGCCTT
TCCGTCCTCAGCCGTCGCTTCATGTGACTCCACTGAGTACCGGGCGCCGTCCA
GGCACCTCGATTAGTTCTCGTGCTTTTGGAGTACGTCGTCTTTAGGTTGGGGG
GAGGGGTTTTATGCGATGGAGTTTCCCCACACTGAGTGGGTGGAGACTGAAG
TTAGGCCAGCTTGGCACTTGATGTAATTCTCCTTGGAATTTGCCCTTTTTGAGT
TTGGATCTTGGTTCATTCTCAAGCCTCAGACAGTGGTTCAAAGTTTTTTCTTC
CATTTCAGGTGTCGTGAGCTAGCTCTAGAGCCAGCATGGCCTTACCAGTGACC
GCCTTGCTCCTGCCGCTGGCCTTGCTGCTCCACGCCGCCAGGCCGcaggtgcagctgc
aggagtctgggggaggcttggtgcagcctggggggtctctgagcctctcctgtacagcct
ctggattcacgttcagtagttactccatggcctgggtccgccaggctccagggaaggg
acccgaatgggtctcagggatttacccttctgatggtaagacaaggtatgca
gacttcgtgaagggccgattcagcatctccagagacaacgccaagaatatgttgtatc
tgcaaatgaacaacctggaacctgaggacacggccctatattactgtgcgagagg
tatcaccggattgggaccccggggccaggggacccaggtcaccgtctcctcagcg
gccgccactagtGAGTCTAAGTACGGCCCTCCCTGCCCTCCTTGCCCATACATCTGG
GCGCCCTTGGCCGGGACTTGTGGGGTCCTTCTCCTGTCACTGGTTATCACCCTT
TACTGCAAACGGGGCAGAAAGAAACTCCTGTATATATTCAAACAACCATTTA
TGAGACCAGTACAAACTACTCAAGAGGAAGATGGCTGTAGCTGCCGATTTCC
AGAAGAAGAAGAAGGAGGATGTGAACTGCTCGAGGGAAGCGGAGCTACTAA
CTTCAGCCTGCTGAAGCAGGCTGGAGACGTGGAGGAGAACCCTGGACCTCCT
AGGATGGCCTTACCAGTGACCGCCTTGCTCCTGCCGCTGGCCTTGCTGCTCCA
CGCCGCCAGGCCGGGATCCAGGTGCAGCTGCAGGAGTCTGGGGGAGGATTG
GTGCAGGCTGGGGGCTCTCTGAGACTCTCCTGTGCAGCCTCTGGATTCACGTT
TGGTAGTTATGTTATGGGCTGGTTCCGCCAGGCTCCAGGGAAGGAGCGTGAA
TTTGTGGCAAGTATTAGTACGAGTGGTGGCATAACATCTTATGCAGACTCCGT
GAAGGGCCGATTCACTGTCTCCAGAGACAACGCCAAGAATACGGTCTACTTA
CAAATGAACAGCCTGAAACCTGAGGACACGGCCGTTTATTACTGCGCACGAG
ATCTGACATACTATCGTACTGGTGGTAGGTTACCAGATAACGCTAATGGATAT
GCGTACTGGGGCCAGGGTACCCAGGTCACCGTCTCCTCAGCGGCCGCCACTA
GTTCCGGAACCACTACACCAGCGCCCAGACCACCTACCCCGGCTCCTACCATC
GCATCTCAGCCCTTGAGTCTTAGACCCGAGGCATGTCGGCCAGCGGCGGGGG
GCGCAGTGCACACGAGGGGGCTGGACTTCGCCTGTGATTACATCTGGGCGCC
CTTGGCCGGGACTTGTGGGGTCCTTCTCCTGTCACTGGTTATCACCCTTTACTG
CAGAGTGAAGTTCAGCAGGAGCGCAGACGCCCCCGCGTACAAGCAGGGCCA
GAACCAGCTCTATAACGAGCTCAATCTAGGACGAAGAGAGGAGTACGATGTT
TTGGACAAGAGACGTGGCCGGGACCCTGAGATGGGGGGAAAGCCGAGAAGG
AAGAACCCTCAGGAAGGCCTGTACAATGAACTGCAGAAAGATAAGATGGCG
GAGGCCTACAGTGAGATTGGGATGAAAGGCGAGCGCCGGAGGGGCAAGGGG
CACGATGGCCTTTACCAGGGTCTCAGTACAGCCACCAAGGACACCTACGACG
CCCTTCACATGCAGGCCCTGCCCCCTCGCTAAGTCGACAATCAACCTCTGGAT
```

-continued

TACAAAATTTGTGAAAGATTGACTGGTATTCTTAACTATGTTGCTCCTTTTACG
CTATGTGGATACGCTGCTTTAATGCCTTTGTATCATGCTATTGCTTCCCGTATG
GCTTTCATTTTCTCCTCCTTGTATAAATCCTGGTTGCTGTCTCTTTATGAGGAG
TTGTGGCCCGTTGTCAGGCAACGTGGCGTGGTGTGCACTGTGTTTGCTGACGC
AACCCCCACTGGTTGGGGCATTGCCACCACCTGTCAGCTCCTTTCCGGGACTT
TCGCTTTCCCCCTCCCTATTGCCACGGCGGAACTCATCGCCGCCTGCCTTGCC
CGCTGCTGGACAGGGGCTCGGCTGTTGGGCACTGACAATTCCGTGGTGTTGTC
GGGGAAGCTGACGTCCTTTCCTTGGCTGCTCGCCTGTGTTGCCACCTGGATTC
TGCGCGGGACGTCCTTCTGCTACGTCCCTTCGGCCCTCAATCCAGCGGACCTT
CCTTCCCGCGGCCTGCTGCCGGCTCTGCGGCCTCTTCCGCGCTCTTCGCCTTCGC
CCTCAGACGAGTCGGATCTCCCTTTGGGCCGCCTCCCCGCCTGGAATTCGAGC
TCGGTACCTTTAAGACCAATGACTTACAAGGCAGCTGTAGATCTTAGCCACTT
TTTAAAAGAAAAGGGGGGACTGGAAGGGCTAATTCACTCCCAACGAAGACA
AGATCTGCTTTTTGCTTGTACTGGGTCTCTCTGGTTAGACCAGATCTGAGCCTG
GGAGCTCTCTGGCTAACTAGGGAACCCACTGCTTAAGCCTCAATAAAGCTTGC
CTTGAGTGCTTCAAGTAGTGTGTGCCCGTCTGTTGTGTGACTCTGGTAACTAG
AGATCCCTCAGACCCTTTTAGTCAGTGTGGAAAATCTCTAGCAGTAGTAGTTC
ATGTCATCTTATTATTCAGTATTTATAACTTGCAAAGAAATGAATATCAGAGA
GTGAGAGGAACTTGTTTATTGCAGCTTATAATGGTTACAAATAAAGCAATAG
CATCACAAATTTCACAAATAAAGCATTTTTTTCACTGCATTCTAGTTGTGGTTT
GTCCAAACTCATCAATGTATCTTATCATGTCTGGCTCTAGCTATCCCGCCCCTA
ACTCCGCCCAGTTCCGCCCATTCTCCGCCCCATGGCTGACTAATTTTTTTTATT
TATGCAGAGGCCGAGGCCGCCTCGGCCTCTGAGCTATTCCAGAAGTAGTGAG
GAGGCTTTTTTGGAGGCCTAGCTAGGGACGTACCCAATTCGCCCTATAGTGAG
TCGTATTACGCGCGCTCACTGGCCGTCGTTTTACAACGTCGTGACTGGGAAAA
CCCTGGCGTTACCCAACTTAATCGCCTTGCAGCACATCCCCCTTTCGCCAGCT
GGCGTAATAGCGAAGAGGCCCGCACCGATCGCCCTTCCCAACAGTTGCGCAG
CCTGAATGGCGAATGGGACGCGCCCTGTAGCGGCGCATTAAGCGCGGCGGGT
GTGGTGGTTACGCGCAGCGTGACCGCTACACTTGCCAGCGCCCTAGCGCCCG
CTCCTTTCGCTTTCTTCCCTTCCTTTCTCGCCACGTTCGCCGGCTTTCCCCGTCA
AGCTCTAAATCGGGGGCTCCCTTTAGGGTTCCGATTTAGTGCTTTACGGCACC
TCGACCCCAAAAAACTTGATTAGGGTGATGGTTCACGTAGTGGGCCATCGCC
CTGATAGACGGTTTTTCGCCCTTTGACGTTGGAGTCCACGTTCTTTAATAGTG
GACTCTTGTTCCAAACTGGAACAACACTCAACCCTATCTCGGTCTATTCTTTTG
ATTTATAAGGGATTTTGCCGATTTCGGCCTATTGGTTAAAAAATGAGCTGATT
TAACAAAAATTTAACGCGAATTTTAACAAAATATTAACGCTTACAATTTAGGT
GGCACTTTTCGGGGAAATGTGCGCGGAACCCCTATTTGTTTATTTTTCTAAAT
ACATTCAAATATGTATCCGCTCATGAGACAATAACCCTGATAAATGCTTCAAT
AATATTGAAAAAGGAAGAGTATGAGTATTCAACATTTCCGTGTCGCCCTTATT
CCCTTTTTTGCGGCATTTTGCCTTCCTGTTTTTGCTCACCCAGAAACGCTGGTG
AAAGTAAAAGATGCTGAAGATCAGTTGG

BiCAR2 VHH32
                                                      (SEQ ID NO: 37)
GTGCACGAGTGGGTTACATCGAACTGGATCTCAACAGCGGTAAGATCCTTGA
GAGTTTTCGCCCCGAAGAACGTTTTCCAATGATGAGCACTTTTAAAGTTCTGC
TATGTGGCGCGGTATTATCCCGTATTGACGCCGGGCAAGAGCAACTCGGTCG
CCGCATACACTATTCTCAGAATGACTTGGTTGAGTACTCACCAGTCACAGAAA
AGCATCTTACGGATGGCATGACAGTAAGAGAATTATGCAGTGCTGCCATAAC
CATGAGTGATAACACTGCGGCCAACTTACTTCTGACAACGATCGGAGGACCG
AAGGAGCTAACCGCTTTTTTGCACAACATGGGGGATCATGTAACTCGCCTTGA
TCGTTGGGAACCGGAGCTGAATGAAGCCATACCAAACGACGAGCGTGACACC
ACGATGCCTGTAGCAATGGCAACAACGTTGCGCAAACTATTAACTGGCGAAC
TACTTACTCTAGCTTCCCGGCAACAATTAATAGACTGGATGGAGGCGGATAA
AGTTGCAGGACCACTTCTGCGCTCGGCCCTTCCGGCTGGCTGGTTTATTGCTG
ATAAATCTGGAGCCGGTGAGCGTGGGTCTCGCGGTATCATTGCAGCACTGGG
GCCAGATGGTAAGCCCTCCCGTATCGTAGTTATCTACACGACGGGGAGTCAG
GCAACTATGGATGAACGAAATAGACAGATCGCTGAGATAGGTGCCTCACTGA
TTAAGCATTGGTAACTGTCAGACCAAGTTTACTCATATATACTTTAGATTGAT
TTAAAACTTCATTTTTAATTTAAAAGGATCTAGGTGAAGATCCTTTTTGATAA
TCTCATGACCAAAATCCCTTAACGTGAGTTTTCGTTCCACTGAGCGTCAGACC
CCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGG
ATCAAGAGCTACCAACTCTTTTTCCGAAGGTAACTGGCTTCAGCAGAGCGCA
GATACCAAATACTGTTCTTCTAGTGTAGCCGTAGTTAGGCCACCACTTCAAGA
ACTCTGTAGCACCGCCTACATACCTCGCTCTGCTAATCCTGTTACCAGTGGCT
GCTGCCAGTGGCGATAAGTCGTGTCTTACCGGGTTGGACTCAAGACGATAGTT
ACCGGATAAGGCGCAGCGGTCGGGCTGAACGGGGGGTTCGTGCACACAGCCC
AGCTTGGAGCGAACGACCTACACCGAACTGAGATACCTACAGCGTGAGCTAT
GAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACG
CCTGGTATCTTTATAGTCCTGTCGGGTTTCGCCACCTCTGACTTGAGCGTCGAT
TTTTGTGATGCTCGTCAGGGGGCGGAGCCTATGGAAAAACGCCAGCAACGC
GGCCTTTTTACGGTTCCTGGCCTTTTGCTGGCCTTTTGCTCACATGTTCTTTCCT
GCGTTATCCCCTGATTCTGTGGATAACCGTATTACCGCCTTTGAGTGAGCTGA
TACCGCTCGCCGCAGCCGAACGACCGAGCGCAGCGAGTCAGTGAGCGAGGA
AGCGGAAGAGCGCCCAATACGCAAACCGCCTCTCCCCGCGCGTTGGCCGATT
CATTAATGCAGCTGGCACGACAGGTTTCCCGACTGGAAAGCGGGCAGTGAGC
GCAACGCAATTAATGTGAGTTAGCTCACTCATTAGGCACCCCAGGCTTTACAC
TTTATGCTTCCGGCTCGTATGTTGTGTGGAATTGTGAGCGGATAACAATTTCA
CACAGGAAACAGCTATGACCATGATTACGCCAAGCGCGCAATTAACCCTCAC

-continued

```
TAAAGGGAACAAAAGCTGGAGCTGCAAGCTTAATGTAGTCTTATGCAATACT
CTTGTAGTCTTGCAACATGGTAACGATGAGTTAGCAACATGCCTTACAAGGA
GAGAAAAAGCACCGTGCATGCCGATTGGTGGAAGTAAGGTGGTACGATCGTG
CCTTATTAGGAAGGCAACAGACGGGTCTGACATGGATTGGACGAACCACTGA
ATTGCCGCATTGCAGAGATATTGTATTTAAGTGCCTAGCTCGATACATAAACG
GGTCTCTCTGGTTAGACCAGATCTGAGCCTGGGAGCTCTCTGGCTAACTAGGG
AACCCACTGCTTAAGCCTCAATAAAGCTTGCCTTGAGTGCTTCAAGTAGTGTG
TGCCCGTCTGTTGTGTGACTCTGGTAACTAGAGATCCCTCAGACCCTTTTAGT
CAGTGTGGAAAATCTCTAGCAGTGGCGCCCGAACAGGGACTTGAAAGCGAAA
GGGAAACCAGAGGAGCTCTCTCGACGCAGGACTCGGCTTGCTGAAGCGCGCA
CGGCAAGAGGCGAGGGGCGGCGACTGGTGAGTACGCCAAAAATTTTGACTAG
CGGAGGCTAGAAGGAGAGAGATGGGTGCGAGAGCGTCAGTATTAAGCGGGG
GAGAATTAGATCGCGATGGGAAAAAATTCGGTTAAGGCCAGGGGGAAAGAA
AAAATATAAATTAAAACATATAGTATGGGCAAGCAGGGAGCTAGAACGATTC
GCAGTTAATCCTGGCCTGTTAGAAACATCAGAAGGCTGTAGACAAATACTGG
GACAGCTACAACCATCCCTTCAGACAGGATCAGAAGAACTTAGATCATTATA
TAATACAGTAGCAACCCTCTATTGTGTGCATCAAAGGATAGAGATAAAAGAC
ACCAAGGAAGCTTTAGACAAGATAGAGGAAGAGCAAAACAAAAGTAAGACC
ACCGCACAGCAAGCGGCCGCTGATCTTCAGACCTGGAGGAGGAGATATGAGG
GACAATTGGAGAAGTGAATTATATAAATATAAAGTAGTAAAAATTGAACCAT
TAGGAGTAGCACCCACCAAGGCAAAGAGAAGAGTGGTGCAGAGAGAAAAAA
GAGCAGTGGGAATAGGAGCTTTGTTCCTTGGGTTCTTGGGAGCAGCAGGAAG
CACTATGGGCGCAGCGTCAATGACGCTGACGGTACAGGCCAGACAATTATTG
TCTGGTATAGTGCAGCAGCAGAACAATTTGCTGAGGGCTATTGAGGCGCAAC
AGCATCTGTTGCAACTCACAGTCTGGGGCATCAAGCAGCTCCAGGCAAGAAT
CCTGGCTGTGGAAAGATACCTAAAGGATCAACAGCTCCTGGGGATTTGGGGT
TGCTCTGGAAAACTCATTTGCACCACTGCTGTGCCTTGGAATGCTAGTTGGAG
TAATAAATCTCTGGAACAGATTTGGAATCACACGACCTGGATGGAGTGGGAC
AGAGAAATTAACAATTACACAAGCTTAATACACTCCTTAATTGAAGAATCGC
AAAACCAGCAAGAAAAGAATGAACAAGAATTATTGGAATTAGATAAATGGG
CAAGTTTGTGGAATTGGTTTAACATAACAAATTGGCTGTGGTATATAAAATTA
TTCATAATGATAGTAGGAGGCTTGGTAGGTTTAAGAATAGTTTTTGCTGTACT
TTCTATAGTGAATAGAGTTAGGCAGGGATATTCACCATTATCGTTTCAGACCC
ACCTCCCAACCCCGAGGGGACCCGACAGGCCCGAAGGAATAGAAGAAGAAG
GTGGAGAGAGAGACAGAGACAGATCCATTCGATTAGTGAACGGATCTCGACG
GTATCGATTAGACTGTAGCCCAGGAATATGGCAGCTAGATTGTACACATTTAG
AAGGAAAAGTTATCTTGGTAGCAGTTCATGTAGCCAGTGGATATATAGAAGC
AGAAGTAATTCCAGCAGAGACAGGGCAAGAAACAGCATACTTCCTCTTAAAA
TTAGCAGGAAGATGGCCAGTAAAAACAGTACATACAGACAATGGCAGCAATT
TCACCAGTACTACAGTTAAGGCCGCCTGTTGGTGGGCGGGATCAAGCAGGA
ATTTGGCATTCCCTACAATCCCCAAAGTCAAGGAGTAATAGAATCTATGAATA
AAGAATTAAAGAAAATTATAGGACAGGTAAGAGATCAGGCTGAACATCTTAA
GACAGCAGTACAAATGGCAGTATTCATCCACAATTTTAAAAGAAAAGGGGGG
ATTGGGGGGTACAGTGCAGGGGAAAGAATAGTAGACATAATAGCAACAGAC
ATACAAACTAAAGAATTACAAAAACAAATTACAAAAATTCAAAATTTTCGGG
TTTATTACAGGGACAGCAGAGATCCAGTTTGGCTGCATACGCGTCGTGAGGCT
CCGGTGCCCGTCAGTGGGCAGAGCGCACATCGCCCACAGTCCCCGAGAAGTT
GGGGGGAGGGGTCGGCAATTGAACCGGTGCCTAGAGAAGGTGGCGCGGGGT
AAACTGGGAAAGTGATGTCGTGTACTGGCTCCGCCTTTTTCCCGAGGGTGGGG
GAGAACCGTATATAAGTGCAGTAGTCGCCGTGAACGTTCTTTTTCGCAACGGG
TTTGCCGCCAGAACACAGGTAAGTGCCGTGTGTGGTTCCCGCGGGCCTGGCCT
CTTTTACGGGTTATGGCCCTTGCGTGCCTTGAATTACTTCCACCTGGCTGCAGT
ACGTGATTCTTGATCCCGAGCTTCGGGTTGGAAGTGGGTGGGAGAGTTCGAG
GCCTTGCGCTTAAGGAGCCCCTTCGCCTCGTGCTTGAGTTGAGGCCTGGCCTG
GGCGCTGGGGCCGCCGCGTGCGAATCTGGTGGCACCTTCGCGCCTGTCTCGCT
GCTTTCGATAAGTCTCTAGCCATTTAAAATTTTTGATGACCTGCTGCGACGCTT
TTTTTCTGGCAAGATAGTCTTGTAAATGCGGGCCAAGATCTGCACACTGGTAT
TTCGGTTTTTGGGGCCGCGGGCGGCGACGGGCCCGTGCGTCCCAGCGCACA
TGTTCGGCGAGGCGGGGCCTGCGAGCGCGGCCACCGAGAATCGGACGGGGT
AGTCTCAAGCTGGCCGGCCTGCTCTGGTGCCTGGCCTCGCGCCGCCGTGTATC
GCCCCGCCCTGGGCGGCAAGGCTGGCCCGGTCGGCACCAGTTGCGTGAGCGG
AAAGATGGCCGCTTCCCGGCCCTGCTGCAGGGAGCTCAAAATGGAGGACGCG
GCGCTCGGGAGAGCGGGCGGGTGAGTCACCCACACAAAGGAAAAGGGCCTT
TCCGTCCTCAGCCGTCGCTTCATGTGACTCCACTGAGTACCGGGCGCCGTCCA
GGCACCTCGATTAGTTCTCGTGCTTTTGGAGTACGTCGTCTTTAGGTTGGGGG
GAGGGGTTTTATGCGATGGAGTTTCCCCACACTGAGTGGGTGGAGACTGAAG
TTAGGCCAGCTTGGCACTTGATGTAATTCTCCTTGGAATTTGCCCTTTTTGAGT
TTGGATCTTGGTTCATTCTCAAGCCTCAGACAGTGGTTCAAAGTTTTTTTCTTC
CATTTCAGGTGTCGTGAGCTAGCTCTAGAGCCAGCATGGCCTTACCAGTGACC
GCCTTGCTCCTGCCGCTGGCCTTGCTGCTCCACGCCGCCAGGCCGcaggtgcagctgc
aggagtctgggggaggcttggtgcagcctggggggtctctgagcctctcctgtacagcctct
ggattcacgttcagtagttactccatggcctgggtccgccaggctccagggaagggacc
cgaatgggtctcagggattttaccttctgatggtaagacaaggtatgca
gacttcgtgaagggccgattcagcatctccagagacaacgccaagaatatgttgtatctgcaaa
tgaacaacctggaacctgaggacacggccctatattactgtgcgagaggtatcaccgga
ttgggaccccggggccagggga accc ggtcaccgtctcctcagcg
gccgccactagtGAGTCTAAGTACGGCCCTCCCTGCCCTCCTTGCCCATACATCTGG
GCGCCCTTGGCCGGGACTTGTGGGGTCCTTCTCCTGTCACTGGTTATCACCCTT
TACTGCAAACGGGGCAGAAAGAAACTCCTGTATATATTCAAACAACCATTTA
TGAGACCAGTACAAACTACTCAAGAGGAAGATGGCTGTAGCTGCCGATTTCC
AGAAGAAGAAGAAGGAGGATGTGAACTGCTCGAGGGAAGCGGAGCTACTAA
```

-continued

```
CTTCAGCCTGCTGAAGCAGGCTGGAGACGTGGAGGAGAACCCTGGACCTCCT
AGGATGGCCTTACCAGTGACCGCCTTGCTCCTGCCGCTGGCCTTGCTGCTCCA
CGCCGCCAGGCCGGGATCCCAGGTGCAGCTGCAGGAGTCTGGAGGAGGCTTG
GTGCAGGCTGGGGGGTCTCTAAATCTCTCCTGTGCAGCCTCTGGAAGTTCCTT
CAGACTCTATACCGTCGGCTGGCACCGCCAGGCGCCAGGGAAGCAGCGCGAG
TTGGTCGCATGGATTAGTGGTGCGGGCAGCACAAACTATCATTCGTCCGTGAA
GGGCCGATTCACCATCTCCAGAGACAACGCCAAGAACACGGCACTCCTGCAA
ATGAACAACCTGGCACCTGAAGACACGGCCGTCTATTACTGTAATCTACTGA
ACTACTGGGGCCAGGGGACCCAGGTCACCGTCTCCTCAGCGGCCGCCACTAG
TTCCGGAACCACTACACCAGCGCCCAGACCACCTACCCCGGCTCCTACCATCG
CATCTCAGCCCTTGAGTCTTAGACCCGAGGCATGTCGGCCAGCGGCGGGGGG
CGCAGTGCACACGAGGGGGCTGGACTTCGCCTGTGATTACATCTGGGCGCCC
TTGGCCGGGACTTGTGGGGTCCTTCTCCTGTCACTGGTTATCACCCTTTACTGC
AGAGTGAAGTTCAGCAGGAGCGCAGACGCCCCCGCGTACAAGCAGGGCCAG
AACCAGCTCTATAACGAGCTCAATCTAGGACGAAGAGAGGAGTACGATGTTT
TGGACAAGAGACGTGGCCGGGACCCTGAGATGGGGGGAAAGCCGAGAAGGA
AGAACCCTCAGGAAGGCCTGTACAATGAACTGCAGAAAGATAAGATGGCGG
AGGCCTACAGTGGAGATTGGGATGAAAGGCGAGCGCCGGAGGGCAAGGGGC
ACGATGGCCTTTACCAGGGTCTCAGTACAGCCACCAAGGACACCTACGACGC
CCTTCACATGCAGGCCCTGCCCCCTCGCTAAGTCGACAATCAACCTCTGGATT
ACAAAATTTGTGAAAGATTGACTGGTATTCTTAACTATGTTGCTCCTTTTACG
CTATGTGGATACGCTGCTTTAATGCCTTTGTATCATGCTATTGCTTCCCGTATG
GCTTTCATTTTCTCCTCCTTGTATAAATCCTGGTTGCTGTCTCTTTATGAGGAG
TTGTGGCCCGTTGTCAGGCAACGTGGCGTGGTGTGCACTGTGTTTGCTGACGC
AACCCCCACTGGTTGGGGCATTGCCACCACCTGTCAGCTCCTTTCCGGGACTT
TCGCTTTCCCCCTCCCTATTGCCACGGCGGAACTCATCGCCGCCTGCCTTGCC
CGCTGCTGGACAGGGGCTCGGCTGTTGGGCACTGACAATTCCGTGGTGTTGTC
GGGGAAGCTGACGTCCTTTCCTTGGCTGCTCGCCTGTGTTGCCACCTGGATTC
TGCGCGGGACGTCCTTCTGCTACGTCCCTTCGGCCCTCAATCCAGCGGACCTT
CCTTCCCGCGGCCTGCTGCCGGCTCTGCGGCCTCTTCCGCGTCTTCGCCTTCGC
CCTCAGACGAGTCGGATCTCCCTTTGGGCCGCCTCCCCGCCTGGAATTCGAGC
TCGGTACCTTTAAGACCAATGACTTACAAGGCAGCTGTAGATCTTAGCCACTT
TTTAAAAGAAAAGGGGGGACTGGAAGGGCTAATTCACTCCCAACGAAGACA
AGATCTGCTTTTTGCTTGTACTGGGTCTCTCTGGTTAGACCAGATCTGAGCCTG
GGAGCTCTCTGGCTAACTAGGGAACCCACTGCTTAAGCCTCAATAAAGCTTGC
CTTGAGTGCTTCAAGTAGTGTGTGCCCGTCTGTTGTGTGACTCTGGTAACTAG
AGATCCCTCAGACCCTTTTAGTCAGTGTGGAAAATCTCTAGCAGTAGTAGTTC
ATGTCATCTTATTATTCAGTATTTATAACTTGCAAAGAAATGAATATCAGAGA
GTGAGAGGAACTTGTTTATTGCAGCTTATAATGGTTACAAATAAAGCAATAG
CATCACAAATTTCACAAATAAAGCATTTTTTTCACTGCATTCTAGTTGTGGTTT
GTCCAAACTCATCAATGTATCTTATCATGTCTGGCTCTAGCTATCCCGCCCCTA
ACTCCGCCCAGTTCCGCCCATTCTCCGCCCCATGGCTGACTAATTTTTTTATT
TATGCAGAGGCCGAGGCCGCCTCGGCCTCTGAGCTATTCCAGAAGTAGTGAG
GAGGCTTTTTTGGAGGCCTAGCTAGGGACGTACCCAATTCGCCCTATAGTGAG
TCGTATTACGCGCGCTCACTGCCGTCGTTTTACAACGTCGTGACTGGGAAAA
CCCTGGCGTTACCCAACTTAATCGCCTTGCAGCACATCCCCCTTTCGCCAGCT
GGCGTAATAGCGAAGAGGCCCGCACCGATCGCCCTTCCCAACAGTTGCGCAG
CCTGAATGGCGAATGGGACGCGCCCTGTAGCGGCGCATTAAGCGCGGCGGGT
GTGGTGGTTACGCGCAGCGTGACCGCTACACTTGCCAGCGCCCTAGCGCCCG
CTCCTTTCGCTTTCTTCCCTTCCTTTCTCGCCACGTTCGCCGGCTTTCCCCGTCA
AGCTCTAAATCGGGGGCTCCCTTTAGGGTTCCGATTTAGTGCTTTACGGCACC
TCGACCCCAAAAAACTTGATTAGGGTGATGGTTCACGTAGTGGGCCATCGCC
CTGATAGACGGTTTTTCGCCCTTTGACGTTGGAGTCCACGTTCTTTAATAGTG
GACTCTTGTTCCAAACTGGAACAACACTCAACCCTATCTCGGTCTATTCTTTTG
ATTTATAAGGGATTTTGCCGATTTCGGCCTATTGGTTAAAAAATGGCTGATT
TAACAAAAATTTAACGCGAATTTTAACAAAATATTAACGCTTACAATTTAGGT
GGCACTTTTCGGGGAAATGTGCGCGGAACCCCTATTTGTTTATTTTTCTAAAT
ACATTCAAATATGTATCCGCTCATGAGACAATAACCCTGATAAATGCTTCAAT
AATATTGAAAAAGGAAGAGTATGAGTATTCAACATTTCCGTGTCGCCCTTATT
CCCTTTTTTGCGGCATTTTGCCTTCCTGTTTTTGCTCACCCAGAAACGCTGGTG
AAAGTAAAAGATGCTGAAGATCAGTTGG
```

BiCAR2 VHH33

(SEQ ID NO: 38)

```
GTGCACGAGTGGGTTACATCGAACTGGATCTCAACAGCGGTAAGATCCTTGA
GAGTTTTCGCCCCGAAGAACGTTTTCCAATGATGAGCACTTTTAAAGTTCTGC
TATGTGGCGCGGTATTATCCCGTATTGACGCCGGGCAAGAGCAACTCGGTCG
CCGCATACACTATTCTCAGAATGACTTGGTTGAGTACTCACCAGTCACAGAAA
AGCATCTTACGGATGGCATGACAGTAAGAGAATTATGCAGTGCTGCCATAAC
CATGAGTGATAACACTGCGGCCAACTTACTTCTGACAACGATCGGAGGACCG
AAGGAGCTAACCGCTTTTTTGCACAACATGGGGGATCATGTAACTCGCCTTGA
TCGTTGGGAACCGGAGCTGAATGAAGCCATACCAAACGACGAGCGTGACACC
ACGATGCCTGTAGCAATGGCAACAACGTTGCGCAAACTATTAACTGGCGAAC
TACTTACTCTAGCTTCCCGGCAACAATTAATAGACTGGATGGAGGCGGATAA
AGTTGCAGGACCACTTCTGCGCTCGGCCCTTCCGGCTGGCTGGTTTATTGCTG
ATAAATCTGGAGCCGGTGAGCGTGGGTCTCGCGGTATCATTGCAGCACTGGG
GCCAGATGGTAAGCCCTCCCGTATCGTAGTTATCTACACGACGGGGAGTCAG
GCAACTATGGATGAACGAAATAGACAGATCGCTGAGATAGGTGCCTCACTGA
TTAAGCATTGGTAACTGTCAGACCAAGTTTACTCATATATACTTTAGATTGAT
TTAAAACTTCATTTTTAATTTAAAAGGATCTAGGTGAAGATCCTTTTTGATAA
TCTCATGACCAAAATCCCTTAACGTGAGTTTTCGTTCCACTGAGCGTCAGACC
```

-continued

```
CCGTAGAAAAGATCAAAGGATCTTCTTGAGATCCTTTTTTCTGCGCGTAATC
TGCTGCTTGCAAACAAAAAAACCACCGCTACCAGCGGTGGTTTGTTTGCCGG
ATCAAGAGCTACCAACTCTTTTTCCGAAGGTAACTGGCTTCAGCAGAGCGCA
GATACCAAATACTGTTCTTCTAGTGTAGCCGTAGTTAGGCCACCACTTCAAGA
ACTCTGTAGCACCGCCTACATACCTCGCTCTGCTAATCCTGTTACCAGTGGCT
GCTGCCAGTGGCGATAAGTCGTGTCTTACCGGGTTGGACTCAAGACGATAGTT
ACCGGATAAGGCGCAGCGGTCGGGCTGAACGGGGGGTTCGTGCACACAGCCC
AGCTTGGAGCGAACGACCTACACCGAACTGAGATACCTACAGCGTGAGCTAT
GAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACG
CCTGGTATCTTTATAGTCCTGTCGGGTTTCGCCACCTCTGACTTGAGCGTCGAT
TTTTGTGATGCTCGTCAGGGGGCGGAGCCTATGGAAAAACGCCAGCAACGC
GGCCTTTTTACGGTTCCTGGCCTTTTGCTGGCCTTTTGCTCACATGTTCTTTCCT
GCGTTATCCCCTGATTCTGTGGATAACCGTATTACCGCCTTTGAGTGAGCTGA
TACCGCTCGCCGCAGCCGAACGACCGAGCGCAGCGAGTCAGTGAGCGAGGA
AGCGGAAGAGCGCCCAATACGCAAACCGCCTCTCCCCGCGCGTTGGCCGATT
CATTAATGCAGCTGGCACGACAGGTTTCCCGACTGGAAAGCGGGCAGTGAGC
GCAACGCAATTAATGTGAGTTAGCTCACTCATTAGGCACCCCAGGCTTTACAC
TTTATGCTTCCGGCTCGTATGTTGTGTGGAATTGTGAGCGGATAACAATTTCA
CACAGGAAACAGCTATGACCATGATTACGCCAAGCGCGCAATTAACCCTCAC
TAAAGGGAACAAAAGCTGGAGCTGCAAGCTTAATGTAGTCTTATGCAATACT
CTTGTAGTCTTGCAACATGGTAACGATGAGTTAGCAACATGCCTTACAAGGA
GAGAAAAAGCACCGTGCATGCCGATTGGTGGAAGTAAGGTGGTACGATCGTG
CCTTATTAGGAAGGCAACAGACGGGTCTGACATGGATTGGACGAACCACTGA
ATTGCCGCATTGCAGAGATATTGTATTTAAGTGCCTAGCTCGATACATAAACG
GGTCTCTCTGGTTAGACCAGATCTGAGCCTGGGAGCTCTCTGGCTAACTAGGG
AACCCACTGCTTAAGCCTCAATAAAGCTTGCCTTGAGTGCTTCAAGTAGTGTG
TGCCCGTCTGTTGTGTGACTCTGGTAACTAGAGATCCCTCAGACCCTTTTAGT
CAGTGTGGAAAATCTCTAGCAGTGGCGCCCGAACAGGGACTTGAAAGCGAAA
GGGAAACCAGAGGAGCTCTCTCGACGCAGGACTCGGCTTGCTGAAGCGCGCA
CGGCAAGAGGCGAGGGGCGGCGACTGGTGAGTACGCCAAAAATTTTGACTAG
CGGAGGCTAGAAGGAGAGAGATGGGTGCGAGAGCGTCAGTATTAAGCGGGG
GAGAATTAGATCGCGATGGGAAAAAATTCGGTTAAGGCCAGGGGGAAAGAA
AAAATATAAATTAAAACATATAGTATGGGCAAGCAGGGAGCTAGAACGATTC
GCAGTTAATCCTGGCCTGTTAGAAACATCAGAAGGCTGTAGACAAATACTGG
GACAGCTACAACCATCCCTTCAGACAGGATCAGAAGAACTTAGATCATTATA
TAATACAGTAGCAACCCTCTATTGTGTGCATCAAAGGATAGAGATAAAAGAC
ACCAAGGAAGCTTTAGACAAGATAGAGGAAGAGCAAAACAAAAGTAAGACC
ACCGCACAGCAAGCGGCCGCTGATCTTCAGACCTGGAGGAGGAGATATGAGG
GACAATTGGAGAAGTGAATTATATAAATATAAAGTAGTAAAAATTGAACCAT
TAGGAGTAGCACCCACCAAGGCAAAGAGAAGAGTGGTGCAGAGAGAAAAAA
GAGCAGTGGGAATAGGAGCTTTGTTCCTTGGGTTCTTGGGAGCAGCAGGAAG
CACTATGGGCGCAGCGTCAATGACGCTGACGGTACAGGCCAGACAATTATTG
TCTGGTATAGTGCAGCAGCAGAACAATTTGCTGAGGGCTATTGAGGCGCAAC
AGCATCTGTTGCAACTCACAGTCTGGGGCATCAAGCAGCTCCAGGCAAGAAT
CCTGGCTGTGGAAAGATACCTAAAGGATCAACAGCTCCTGGGGATTTGGGGT
TGCTCTGGAAAACTCATTTGCACCACTGCTGTGCCTTGGAATGCTAGTTGGAG
TAATAAATCTCTGGAACAGATTTGGAATCACACGACCTGGATGGAGTGGGAC
AGAGAAATTAACAATTACACAAGCTTAATACACTCCTTAATTGAAGAATCGC
AAAACCAGCAAGAAAAGAATGAACAAGAATTATTGGAATTAGATAAATGGG
CAAGTTTGTGGAATTGGTTTAACATAACAAATTGGCTGTGGTATATAAAATTA
TTCATAATGATAGTAGGAGGCTTGGTAGGTTTAAGAATAGTTTTTGCTGTACT
TTCTATAGTGAATAGAGTTAGGCAGGGATATTCACCATTATCGTTTCAGACCC
ACCTCCCAACCCCGAGGGGACCCGACAGGCCCGAAGGAATAGAAGAAGAAG
GTGGAGAGAGAGACAGAGACAGATCCATTCGATTAGTGAACGGATCTCGACG
GTATCGATTAGACTGTAGCCCAGGAATATGGCAGCTAGATTGTACACATTTAG
AAGGAAAAGTTATCTTGGTAGCAGTTCATGTAGCCAGTGGATATATAGAAGC
AGAAGTAATTCCAGCAGAGACAGGGCAAGAAACAGCATACTTCCTCTTAAAA
TTAGCAGGAAGATGGCCAGTAAAAACAGTACATACAGACAATGGCAGCAATT
TCACCAGTACTACAGTTAAGGCCGCCTGTTGGTGGGCGGGGATCAAGCAGGA
ATTTGGCATTCCCTACAATCCCCAAAGTCAAGGAGTAATAGAATCTATGAATA
AAGAATTAAAGAAAATTATAGGACAGGTAAGAGATCAGGCTGAACATCTTAA
GACAGCAGTACAAATGGCAGTATTCATCCACAATTTTAAAAGAAAAGGGGGG
ATTGGGGGGTACAGTGCAGGGGAAAGAATAGTAGACATAATAGCAACAGAC
ATACAAACTAAAGAATTACAAAAACAAATTACAAAAATTCAAAATTTTCGGG
TTTATTACAGGGACAGCAGAGATCCAGTTTGGCTGCATACGCGTCGTGAGGCT
CCGGTGCCCGTCAGTGGGCAGAGCGCACATCGCCCACAGTCCCCGAGAAGTT
GGGGGGAGGGGTCGGCAATTGAACCGGTGCCTAGAGAAGGTGGCGCGGGGT
AAACTGGGAAAGTGATGTCGTGTACTGGCTCCGCCTTTTTCCCGAGGGTGGGG
GAGAACCGTATATAAGTGCAGTAGTCGCCGTGAACGTTCTTTTTCGCAACGGG
TTTGCCGCCAGAACACAGGTAAGTGCCGTGTGTGGTTCCCGCGGGCCTGGCCT
CTTTACGGGTTATGGCCCTTGCGTGCCTTGAATTACTTCCACCTGGCTGCAGT
ACGTGATTCTTGATCCCGAGCTTCGGGTTGGAAGTGGGTGGGAGAGTTCGAG
GCCTTGCGCTTAAGGAGCCCCTTCGCCTCGTGCTTGAGTTGAGGCCTGGCCTG
GGCGCTGGGGCCGCCGCGTGCGAATCTGGTGGCACCTTCGCGCCTGTCTCGCT
GCTTTCGATAAGTCTCTAGCCATTTAAAATTTTGATGACCTGCTGCGACGCTT
TTTTTCTGGCAAGATAGTCTTGTAAATGCGGGCCAAGATCTGCACACTGGTAT
TTCGGTTTTTGGGGCCGCGGGCGGCGACGGGCCCGTGCGTCCCAGCGCACA
TGTTCGGCGAGGCGGGCCTGCGAGCGCGGCCACCGAGAATCGGACGGGGGT
AGTCTCAAGCTGGCCGGCCTGCTCTGGTGCCTGGCCTCGCGCCGCCGTGTATC
GCCCCGCCCTGGGCGGCAAGGCTGGCCCGGTCGGCACCAGTTGCGTGAGCGG
```

-continued

```
AAAGATGGCCGCTTCCCGGCCCTGCTGCAGGGAGCTCAAAATGGAGGACGCG
GCGCTCGGGAGAGCGGGCGGGTGAGTCACCCACACAAAGGAAAAGGGCCTT
TCCGTCCTCAGCCGTCGCTTCATGTGACTCCACTGAGTACCGGGCGCCGTCCA
GGCACCTCGATTAGTTCTCGTGCTTTTGGAGTACGTCGTCTTTAGGTTGGGGG
GAGGGGTTTTATGCGATGGAGTTTCCCCACACTGAGTGGGTGGAGACTGAAG
TTAGGCCAGCTTGGCACTTGATGTAATTCTCCTTGGAATTTGCCCTTTTTGAGT
TTGGATCTTGGTTCATTCTCAAGCCTCAGACAGTGGTTCAAAGTTTTTTCTTC
CATTTCAGGTGTCGTGAGCTAGCTCTAGAGCCAGCATGGCCTTACCAGTGACC
GCCTTGCTCCTGCCGCTGGCCTTGCTGCTCCACGCCGCCAGGCCGcaggtgcagctgc
aggagtctgggggaggcttggtgcagcctgggggtctctgagcctctcctgtacagcctct
ggattcacgttcagtagttactccatggcctgggtccgccaggctccagggaagggacccg
aatgggtctcagggatttacccttctgatggtaagacaaggtatgcagacttcgtgaagg
gccgattcagcatctccagagacaacgccaagaatatgttgtatctgcaaatgaaca
acctggaacctgaggacacggccctatattactgtgcgagaggtatcaccgga
ttgggacccgggccaggggacccaggtcaccgtctcctcagcg
gccgccactagtGAGTCTAAGTACGGCCCTCCCTGCCCTCCTTGCCCATACATCTGG
GCGCCCTTGGCCGGACTTGTGGGGTCCTTCTCCTGTCACTGGTTATCACCCTT
TACTGCAAACGGGGCAGAAAGAAACTCCTGTATATATTCAACAACCATTTA
TGAGACCAGTACAAACTACTCAAGAGGAAGATGGCTGTAGCTGCCGATTTCC
AGAAGAAGAAGAAGGAGGATGTGAACTGCTCGAGGGAAGCGGAGCTACTAA
CTTCAGCCTGCTGAAGCAGGCTGGAGACGTGGAGGAGAACCCTGGACCTCCT
AGGATGGCCTTACCAGTGACCGCCTTGCTCCTGCCGCTGGCCTTGCTGCTCCA
CGCCGCCAGGCCGGGATCCCAGGTGCAGCTGCAGGAGTCTGGGGGAGGCTTG
GTGCAGCCTGGGGGGTCTCTGAGACTCTCCTGTGCAGTCTCTGGACTCACGCC
GGATGCTTATGTCATGGGCTGGTTCCGCCAGGCCCCAGGGAAGGAGCGCGAG
GGGGTCTCATGTATTAGTCCTAGTGGTGGTACTACAAGCTATCCAGACTCCGT
GAAGGGCCGATTCACCATCTCCAGAGACAATGCCAAGAACACGGTGTACCTG
CAAATGAACAGCCTGAAACCTGAGGACACGGGCGTTTATTACTGTGCGGCAG
TTGCGGGCCGCTGGTGTGACTACGGCATGAACTACTACGGCAAAGGGACCCA
GGTCACCGTCTCCTCAGCGGCCGCCACTAGTTCCGGAACCACTACACCAGCG
CCCAGACCACCTACCCCGGCTCCTACCATCGCATCTCAGCCCTTGAGTCTTAG
ACCCGAGGCATGTCGGCCAGCGGCGGGGGCGCAGTGCACACGAGGGGGCT
GGACTTCGCCTGTGATTACATCTGGGCGCCCTTGGCCGGGACTTGTGGGGTCC
TTCTCCTGTCACTGGTTATCACCCTTTACTGCAGAGTGAAGTTCAGCAGGAGC
GCAGACGCCCCCGCGTACAAGCAGGGCCAGAACCAGCTCTATAACGAGCTCA
ATCTAGGACGAAGAGAGGAGTACGATGTTTTGGACAAGAGACGTGGCCGGG
ACCCTGAGATGGGGGGAAAGCCGAGAAGGAAGAACCCTCAGGAAGGCCTGT
ACAATGAACTGCAGAAAGATAAGATGGCGGAGGCCTACAGTGAGATTGGGA
TGAAAGGCGAGCGCCGGAGGGGCAAGGGGCACGATGGCCTTTACCAGGGTCT
CAGTACAGCCACCAAGGACACCTACGACGCCCTTCACATGCAGGCCCTGCCC
CCTCGCTAAGTCGACAATCAACCTCTGGATTACAAAATTTGTGAAAGATTGAC
TGGTATTCTTAACTATGTTGCTCCTTTTACGCTATGTGGATACGCTGCTTTAAT
GCCTTTGTATCATGCTATTGCTTCCCGTATGGCTTTCATTTTCTCCTCCTTGTAT
AAATCCTGGTTGCTGTCTCTTTATGAGGAGTTGTGGCCCGTTGTCAGGCAACG
TGGCGTGGTGTGCACTGTGTTTGCTGACGCAACCCCCACTGGTTGGGGCATTG
CCACCACCTGTCAGCTCCTTTCCGGGACTTTCGCTTTCCCCCTCCCTATTGCCA
CGGCGGAACTCATCGCCGCCTGCCTTGCCCGCTGCTGGACAGGGGCTCGGCT
GTTGGGCACTGACAATTCCGTGGTGTTGTCGGGGAAGCTGACGTCCTTTCCTT
GGCTGCTCGCCTGTGTTGCCACCTGGATTCTGCGCGGGACGTCCTTCTGCTAC
GTCCCTTCGGCCCTCAATCCAGCGGACCTTCCTTCCCGCGGCCTGCTGCCGGC
TCTGCGGCCTCTTCCGCGTCTTCGCCTTCGCCCTCAGACGAGTCGGATCTCCT
TTGGGCCGCCTCCCCGCCTGGAATTCGAGCTCGGTACCTTTAAGACCAATGAC
TTACAAGGCAGCTGTAGATCTTAGCCACTTTTTAAAAGAAAAGGGGGGACTG
GAAGGGCTAATTCACTCCCAACGAAGACAAGATCTGCTTTTTGCTTGTACTGG
GTCTCTCTGGTTAGACCAGATCTGAGCCTGGGAGCTCTCTGGCTAACTAGGGA
ACCCACTGCTTAAGCCTCAATAAAGCTTGCCTTGAGTGCTTCAAGTAGTGTGT
GCCCGTCTGTTGTGTGACTCTGGTAACTAGAGATCCCTCAGACCCTTTTAGTC
AGTGTGGAAAATCTCTAGCAGTAGTAGTTCATGTCATCTTATTATTCAGTATT
TATAACTTGCAAAGAAATGAATATCAGAGAGTGAGAGGAACTTGTTTATTGC
AGCTTATAATGGTTACAAATAAAGCAATAGCATCACAAATTTCACAAATAAA
GCATTTTTTCACTGCATTCTAGTTGTGGTTTGTCCAAACTCATCAATGTATCT
TATCATGTCTGGCTCTAGCTATCCCGCCCCTAACTCCGCCCAGTTCCGCCCATT
CTCCGCCCCATGGCTGACTAATTTTTTTATTTATGCAGAGGCCGAGGCCGCC
TCGGCCTCTGAGCTATTCCAGAAGTAGTGAGGAGGCTTTTTTGGAGGCCTAGC
TAGGGACGTACCCAATTCGCCCTATAGTGAGTCGTATTACGCGCGCTCACTGG
CCGTCGTTTTACAACGTCGTGACTGGGAAAACCCTGGCGTTACCCAACTTAAT
CGCCTTGCAGCACATCCCCCTTTCGCCAGCTGGCGTAATAGCGAAGAGGCCC
GCACCGATCGCCCTTCCCAACAGTTGCGCAGCCTGAATGGCGAATGGGACGC
GCCCTGTAGCGGCGCATTAAGCGCGGCGGGTGTGGTGGTTACGCGCAGCGTG
ACCGCTACACTTGCCAGCGCCCTAGCGCCCGCTCCTTTCGCTTTCTTCCCTTCC
TTTCTCGCCACGTTCGCCGGCTTTCCCCGTCAAGCTCTAAATCGGGGCTCCC
TTTAGGGTTCCGATTTAGTGCTTTACGGCACCTCGACCCCAAAAAACTTGATT
AGGGTGATGGTTCACGTAGTGGGCCATCGCCCTGATAGACGGTTTTTCGCCCT
TTGACGTTGGAGTCCACGTTCTTTAATAGTGGACTCTTGTTCCAAACTGGAAC
AACACTCAACCCTATCTCGGTCTATTCTTTTGATTTATAAGGGATTTTGCCGAT
TTCGGCCTATTGGTTAAAAAATGAGCTGATTTAACAAAAATTTAACGCGAATT
TTAACAAAATATTAACGCTTACAATTTAGGTGGCACTTTTCGGGGAAATGTGC
GCGGAACCCCTATTTGTTTATTTTTCTAAATACATTCAAATATGTATCCGCTCA
```

-continued
```
TGAGACAATAACCCTGATAAATGCTTCAATAATATTGAAAAAGGAAGAGTAT
GAGTATTCAACATTTCCGTGTCGCCCTTATTCCCTTTTTTGCGGCATTTTGCCT
TCCTGTTTTTGCTCACCCAGAAACGCTGGTGAAAGTAAAAGATGCTGAAGATC
AGTTGG
```

BiCAR2 VHH38

(SEQ ID NO: 39)

```
GTGCACGAGTGGGTTACATCGAACTGGATCTCAACAGCGGTAAGATCCTTGA
GAGTTTTCGCCCCGAAGAACGTTTTCCAATGATGAGCACTTTTAAAGTTCTGC
TATGTGGCGCGGTATTATCCCGTATTGACGCCGGGCAAGAGCAACTCGGTCG
CCGCATACACTATTCTCAGAATGACTTGGTTGAGTACTCACCAGTCACAGAAA
AGCATCTTACGGATGGCATGACAGTAAGAGAATTATGCAGTGCTGCCATAAC
CATGAGTGATAACACTGCGGCCAACTTACTTCTGACAACGATCGGAGGACCG
AAGGAGCTAACCGCTTTTTTGCACAACATGGGGGATCATGTAACTCGCCTTGA
TCGTTGGGAACCGGAGCTGAATGAAGCCATACCCAAACGACGAGCGTGACACC
ACGATGCCTGTAGCAATGGCAACAACGTTGCGCAAACTATTAACTGGCGAAC
TACTTACTCTAGCTTCCCGGCAACAATTAATAGACTGGATGGAGGCGGATAA
AGTTGCAGGACCACTTCTGCGCTCGGCCCTTCCGGCTGGCTGGTTTATTGCTG
ATAAATCTGGAGCCGGTGAGCGTGGGTCTCGCGGTATCATTGCAGCACTGGG
GCCAGATGGTAAGCCCTCCCGTATCGTAGTTATCTACACGACGGGGAGTCAG
GCAACTATGGATGAACGAAATAGACAGATCGCTGAGATAGGTGCCTCACTGA
TTAAGCATTGGTAACTGTCAGACCAAGTTTACTCATATATACTTTAGATTGAT
TTAAAACTTCATTTTTAATTTAAAAGGATCTAGGTGAAGATCCTTTTTGATAA
TCTCATGACCAAAATCCCTTAACGTGAGTTTTCGTTCCACTGAGCGTCAGACC
CCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGG
ATCAAGAGCTACCAACTCTTTTTCCGAAGGTAACTGGCTTCAGCAGAGCGCA
GATACCAAATACTGTTCTTCTAGTGTAGCCGTAGTTAGGCCACCACTTCAAGA
ACTCTGTAGCACCGCCTACATACCTCGCTCTGCTAATCCTGTTACCAGTGGCT
GCTGCCAGTGGCGATAAGTCGTGTCTTACCGGGTTGGACTCAAGACGATAGTT
ACCGGATAAGGCGCAGCGGTCGGGCTGAACGGGGGGTTCGTGCACACAGCCC
AGCTTGGAGCGAACGACCTACACCGAACTGAGATACCTACAGCGTGAGCTAT
GAGAAAGCGCCACGCTTCCCGAAGGGAGAAAGGCGGACAGGTATCCGGTAA
GCGGCAGGGTCGGAACAGGAGAGCGCACGAGGGAGCTTCCAGGGGGAAACG
CCTGGTATCTTTATAGTCCTGTCGGGTTTCGCCACCTCTGACTTGAGCGTCGAT
TTTTGTGATGCTCGTCAGGGGGCGGAGCCTATGGAAAAACGCCAGCAACGC
GGCCTTTTTACGGTTCCTGGCCTTTTGCTGGCCTTTTGCTCACATGTTCTTTCCT
GCGTTATCCCCTGATTCTGTGGATAACCGTATTACCGCCTTTGAGTGAGCTGA
TACCGCTCGCCGCAGCCGAACGACCGAGCGCAGCGAGTCAGTGAGCGAGGA
AGCGGAAGAGCGCCCAATACGCAAACCGCCTCTCCCCGCGCGTTGGCCGATT
CATTAATGCAGCTGGCACGACAGGTTTCCCGACTGGAAAGCGGGCAGTGAGC
GCAACGCAATTAATGTGAGTTAGCTCACTCATTAGGCACCCCAGGCTTTACAC
TTTATGCTTCCGGCTCGTATGTTGTGTGGAATTGTGAGCGGATAACAATTTCA
CACAGGAAACAGCTATGACCATGATTACGCCAAGCGCGCAATTAACCCTCAC
TAAAGGGAACAAAAGCTGGAGCTGCAAGCTTAATGTAGTCTTATGCAATACT
CTTGTAGTCTTGCAACATGGTAACGATGAGTTAGCAACATGCCTTACAAGGA
GAGAAAAAGCACCGTGCATGCCGATTGGTGGAAGTAAGGTGGTACGATCGTG
CCTTATTAGGAAGGCAACAGACGGGTCTGACATGGATTGGACGAACCACTGA
ATTGCCGCATTGCAGAGATATTGTATTTAAGTGCCTAGCTCGATACATAAACG
GGTCTCTCTGGTTAGACCAGATCTGAGCCTGGGAGCTCTCTGGCTAACTAGGG
AACCCACTGCTTAAGCCTCAATAAAGCTTGCCTTGAGTGCTTCAAGTAGTGTG
TGCCCGTCTGTTGTGTGACTCTGGTAACTAGAGATCCCTCAGACCCTTTTAGT
CAGTGTGGAAAATCTCTAGCAGTGGCGCCCGAACAGGGACTTGAAAGCGAAA
GGGAAACCAGAGGAGCTCTCTCGACGCAGGACTCGGCTTGCTGAAGCGCGCA
CGGCAAGAGGCGAGGGGCGGCGACTGGTGAGTACGCCAAAAATTTTGACTAG
CGGAGGCTAGAAGGAGAGAGATGGGTGCGAGAGCGTCAGTATTAAGCGGGG
GAGAATTAGATCGCGATGGGAAAAAATTCGGTTAAGGCCAGGGGGAAAGAA
AAAATATAAATTAAAACATATAGTATGGGCAAGCAGGGAGCTAGAACGATTC
GCAGTTAATCCTGGCCTGTTAGAAACATCAGAAGGCTGTAGACAAATACTGG
GACAGCTACAACCATCCCTTCAGACAGGATCAGAAGAACTTAGATCATTATA
TAATACAGTAGCAACCCTCTATTGTGTGCATCAAAGGATAGAGATAAAAGAC
ACCAAGGAAGCTTTAGACAAGATAGAGGAAGAGCAAAACAAAAGTAAGACC
ACCGCACAGCAAGCGGCCGCTGATCTTCAGACCTGGAGGAGGAGATATGAGG
GACAATTGGAGAAGTGAATTATATAAATATAAAGTAGTAAAAATTGAACCAT
TAGGAGTAGCACCCACCAAGGCAAAGAGAAGAGTGGTGCAGAGAGAAAAA
GAGCAGTGGGAATAGGAGCTTTGTTCCTTGGGTTCTTGGGAGCAGCAGGAAG
CACTATGGGCGCAGCGTCAATGACGCTGACGGTACAGGCCAGACAATTATTG
TCTGGTATAGTGCAGCAGCAGAACAATTTGCTGAGGGCTATTGAGGCGCAAC
AGCATCTGTTGCAACTCACAGTCTGGGGCATCAAGCAGCTCCAGGCAAGAAT
CCTGGCTGTGGAAAGATACCTAAAGGATCAACAGCTCCTGGGGATTTGGGGT
TGCTCTGGAAAACTCATTTGCACCACTGCTGTGCCTTGGAATGCTAGTTGGAG
TAATAAATCTCTGGAACAGATTTGGAATCACACGACCTGATGGAGTGGGAC
AGAGAAATTAACAATTACACAAGCTTAATACACTCCTTAATTGAAGAATCGC
AAAACCAGCAAGAAAAGAATGAACAAGAATTATTGGAATTAGATAAATGGG
CAAGTTTGTGGAATTGGTTTAACATAACAAATTGGCTGTGGTATATAAAATTA
TTCATAATGATAGTAGGAGGCTTGGTAGGTTTAAGAATAGTTTTTGCTGTACT
TTCTATAGTGAATAGAGTTAGGCAGGGATATTCACCATTATCGTTTCAGACCC
ACCTCCCAACCCCGAGGGGACCCGACAGGCCCGAAGGAATAGAAGAAGAAG
GTGGAGAGAGAGACAGAGACAGATCCATTCGATTAGTGAACGGATCTCGACG
GTATCGATTAGACTGTAGCCCAGGAATATGGCAGCTAGATTGTACACATTTAG
AAGGAAAAGTTATCTTGGTAGCAGTTCATGTAGCCAGTGGATATATAGAAGC
```

-continued

```
AGAAGTAATTCCAGCAGAGACAGGGCAAGAAACAGCATACTTCCTCTTAAAA
TTAGCAGGAAGATGGCCAGTAAAAACAGTACATACAGACAATGGCAGCAATT
TCACCAGTACTACAGTTAAGGCCGCCTGTTGGTGGGCGGGGATCAAGCAGGA
ATTTGGCATTCCCTACAATCCCCAAAGTCAAGGAGTAATAGAATCTATGAATA
AAGAATTAAAGAAAATTATAGGACAGGTAAGAGATCAGGCTGAACATCTTAA
GACAGCAGTACAAATGGCAGTATTCATCCACAATTTTAAAAGAAAAGGGGGG
ATTGGGGGGTACAGTGCAGGGGAAAGAATAGTAGACATAATAGCAACAGAC
ATACAAACTAAAGAATTACAAAAACAAATTACAAAAATTCAAAATTTTCGGG
TTTATTACAGGGACAGCAGAGATCCAGTTTGGCTGCATACGCGTCGTGAGGCT
CCGGTGCCCGTCAGTGGGCAGAGCGCACATCGCCCACAGTCCCCGAGAAGTT
GGGGGGAGGGGTCGGCAATTGAACCGGTGCCTAGAGAAGGTGGCGCGGGGT
AAACTGGGAAAGTGATGTCGTGTACTGGCTCCGCCTTTTTCCCGAGGGTGGGG
GAGAACCGTATATAAGTGCAGTAGTCGCCGTGAACGTTCTTTTTCGCAACGGG
TTTGCCGCCAGAACACAGGTAAGTGCCGTGTGTGGTTCCCGCGGGCCTGGCCT
CTTTTACGGGTTATGGCCCTTGCGTGCCTTGAATTACTTCCACCTGGCTGCAGT
ACGTGATTCTTGATCCCGAGCTTCGGGTTGGAAGTGGGTGGGAGAGTTCGAG
GCCTTGCGCTTAAGGAGCCCCTTCGCCTCGTGCTTGAGTTGAGGCCTGGCCTG
GGCGCTGGGGCCGCCGCGTGCGAATCTGGTGGCACCTTCGCGCCTGTCTCGCT
GCTTTCGATAAGTCTCTAGCCATTTAAAATTTTTGATGACCTGCTGCGACGCTT
TTTTTCTGGCAAGATAGTCTTGTAAATGCGGGCCAAGATCTGCACACTGGTAT
TTCGGTTTTTGGGGCCGCGGGCGGCGACGGGGCCCGTGCGTCCCAGCGCACA
TGTTCGGCGAGGCGGGGCCTGCGAGCGCGGCCACCGAGAATCGGACGGGGGT
AGTCTCAAGCTGGCCGGCCTGCTCTGGTGCCTGGCCTCGCGCCGCCGTGTATC
GCCCCGCCCTGGGCGGCAAGGCTGGCCCGGTCGGCACCAGTTGCGTGAGCGG
AAAGATGGCCGCTTCCCGGCCCTGCTGCAGGGAGCTCAAAATGGAGGACGCG
GCGCTCGGGAGAGCGGGCGGGTGAGTCACCCACACAAAGGAAAAGGGCCTT
TCCGTCCTCAGCCGTCGCTTCATGTGACTCCACTGAGTACCGGGCGCCGTCCA
GGCACCTCGATTAGTTCTCGTGCTTTTGGAGTACGTCGTCTTTAGGTTGGGGG
GAGGGGTTTTATGCGATGGAGTTTCCCCACACTGAGTGGGTGGAGACTGAAG
TTAGGCCAGCTTGGCACTTGATGTAATTCTCCTTGGAATTTGCCCTTTTTGAGT
TTGGATCTTGGTTCATTCTCAAGCCTCAGACAGTGGTTCAAAGTTTTTTTCTTC
CATTTCAGGTGTCGTGAGCTAGCTCTAGAGCCAGCATGGCCTTACCAGTGACC
GCCTTGCTCCTGCCGCTGGCCTTGCTGCTCCACGCCGCCAGGCCGcaggtgcagctgc
aggagtctgggggaggcttggtgcagcctggggggtctctgagcctctcctgtacagcc
tctggattcacgttcagtagttactccatggcctgggtcgtccaggggaaggg
acccgaatgggtctcagggatttacccttctgatggtaagcaaggtatgca
gacttcgtgaagggccgattcagcatctccagagacaacgccaagaatatgttgtatct
gcaaatgaacaacctggaacctgaggacacggccctatattactgtgcgag
aggtatcaccggattgggacccgggggccaggggacccaggtcaccgtctcctcagcg
gccgccactagtGAGTCTAAGTACGGCCCTCCCTGCCCTCCTTGCCCATACATCTGG
GCGCCCTTGGCCGGGACTTGTGGGGTCCTTCTCCTGTCACTGGTTATCACCCTT
TACTGCAAACGGGGCAGAAAGAAACTCCTGTATATATTCAAACAACCATTTA
TGAGACCAGTACAAACTACTCAAGAGGAAGATGGCTGTAGCTGCCGATTTCC
AGAAGAAGAAGAAGGAGGATGTGAACTGCTGCAGGGAAGCGGAGCTACTAA
CTTCAGCCTGCTGAAGCAGGCTGGAGACGTGGAGGAGAACCCTGGACCTCCT
AGGATGGCCTTACCAGTGACCGCCTTGCTCCTGCCGCTGGCCTTGCTGCTCCA
CGCCGCCAGGCCGGGATCCCAGGTGCAGCTGCAGGAGTCTGGGGGAGGTTTG
GTGCAGGCTGGGGACTCTCTGAGACTCTCCTGTGCAGTCGGACGCACGTTCAG
TGCGTCAACCTTGGGCTGGTTCCGCCAGTCTCCAGGGAAGGAGCGTGAGTTTG
TCGCAGCGATTAGTTGGTGGCGTGGTGAGGCATACTATGGGGACTCCGTGAA
GGGCCGATTCACCATCTCCAGAGACAACACCAAGACAACGATCAATCTGCAA
ATGAATAGCCTGAAACCTGAGGACACGGCCGTTTATTACTGTGCACGAGCCC
AATTTGATGGCGCGACACGGGCAGATGACTATGACAACTGGGGTCAGGGGAC
CCAGGTCACCGTCTCCTCAGCGGCCGCCACTAGTTCCGGAACCACTACACCA
GCGCCCAGACCACCTACCCCGGCTCCTACCATCGCATCTCAGCCCTTGAGTCT
TAGACCCGAGGCATGTCGGCCAGCGGCGGGGGCGCAGTGCACACGAGGGG
GCTGGACTTCGCCTGTGATTACATCTGGGCGCCCTTGGCCGGGACTTGTGGGG
TCCTTCTCCTGTCACTGGTTATCACCCTTTACTGCAGAGTGAAGTTCAGCAGG
AGCGCAGACGCCCCGCGTACAAGCAGGGCCAGAACCAGCTCTATAACGAGC
TCAATCTAGGACGAAGAGAGGAGTACGATGTTTTGGACAAGAGACGTGGCCG
GGACCCTGAGATGGGGGGAAAGCCGAGAAGGAAGAACCCTCAGGAAGGCCT
GTACAATGAACTGCAGAAAGATAAGATGGCGGAGGCCTACAGTGAGATTGG
GATGAAAGGCGAGCGCCGGAGGGGCAAGGGGCACGATGGCCTTTACCAGGG
TCTCAGTACAGCCACCAAGGACACCTACGACGCCCTTCACATGCAGGCCCTG
CCCCCTCGCTAAGTCGACAATCAACCTCTGGATTACAAAATTTGTGAAAGATT
GACTGGTATTCTTAACTATGTTGCTCCTTTTACGCTATGTGGATACGCTGCTTT
AATGCCTTTGTATCATGCTATTGCTTCCCGTATGGCTTTCATTTTCTCCTCCTTG
TATAAATCCTGGTTGCTGTCTCTTTATGAGGAGTTGTGGCCCGTTGTCAGGCA
ACGTGGCGTGGTGTGCACTGTGTTTGCTGACGCAACCCCCACTGGTTGGGGCA
TTGCCACCACCTGTCAGCTCCTTTCCGGGACTTTCGCTTTCCCCCTCCCTATTG
CCACGGCGGAACTCATCGCCGCCTGCCTTGCCCGCTGCTGGACAGGGGCTCG
GCTGTTGGGCACTGACAATTCCGTGGTGTTGTCGGGGAAGCTGACGTCCTTTC
CTTGGCTGCTCGCCTGTGTTGCCACCTGGATTCTGCGCGGGACGTCCTTCTGCT
ACGTCCCTTCGGCCCTCAATCCAGCGGACCTTCCTTCCCGCGGCCTGCTGCCG
GCTCTGCGGCCTCTTCCGCGTCTTCGCCTTCGCCCTCAGACGAGTCGGATCTC
CCTTTGGGCCGCCTCCCCGCCTGGAATTCGAGCTCGGTACCTTTAAGACCAAT
GACTTACAAGGCAGCTGTAGATCTTAGCCACTTTTTAAAAGAAAAGGGGGGA
CTGGAAGGGCTAATTCACTCCCAACGAAGACAAGATCTGCTTTTTGCTTGTAC
TGGGTCTCTCTGGTTAGACCAGATCTGAGCCTGGGAGCTCTCTGGCTAACTAG
GGAACCCACTGCTTAAGCCTCAATAAAGCTTGCCTTGAGTGCTTCAAGTAGTG
TGTGCCCGTCTGTTGTGTGACTCTGGTAACTAGAGATCCCTCAGACCCTTTTA
```

-continued
```
GTCAGTGTGGAAAATCTCTAGCAGTAGTAGTTCATGTCATCTTATTATTCAGT
ATTTATAACTTGCAAAGAAATGAATATCAGAGAGTGAGAGGAACTTGTTTAT
TGCAGCTTATAATGGTTACAAATAAAGCAATAGCATCACAAATTTCACAAAT
AAAGCATTTTTTCACTGCATTCTAGTTGTGGTTTGTCCAAACTCATCAATGTA
TCTTATCATGTCTGGCTCTAGCTATCCCGCCCCTAACTCCGCCCAGTTCCGCC
ATTCTCCGCCCCATGGCTGACTAATTTTTTTTATTTATGCAGAGGCCGAGGCC
GCCTCGGCCTCTGAGCTATTCCAGAAGTAGTGAGGAGGCTTTTTTGGAGGCCT
AGCTAGGGACGTACCCAATTCGCCCTATAGTGAGTCGTATTACGCGCGCTCAC
TGGCCGTCGTTTTACAACGTCGTGACTGGGAAAACCCTGGCGTTACCCAACTT
AATCGCCTTGCAGCACATCCCCCTTTCGCCAGCTGGCGTAATAGCGAAGAGG
CCCGCACCGATCGCCCTTCCCAACAGTTGCGCAGCCTGAATGGCGAATGGGA
CGCGCCCTGTAGCGGCGCATTAAGCGCGGCGGGTGTGGTGGTTACGCGCAGC
GTGACCGCTACACTTGCCAGCGCCCTAGCGCCCGCTCCTTTCGCTTTCTTCCCT
TCCTTTCTCGCCACGTTCGCCGGCTTTCCCCGTCAAGCTCTAAATCGGGGGCT
CCCTTTAGGGTTCCGATTTAGTGCTTTACGGCACCTCGACCCCAAAAACTTG
ATTAGGGTGATGGTTCACGTAGTGGGCCATCGCCCTGATAGACGGTTTTTCGC
CCTTTGACGTTGGAGTCCACGTTCTTTAATAGTGGACTCTTGTTCCAAACTGG
AACAACACTCAACCCTATCTCGGTCTATTCTTTTGATTTATAAGGGATTTTGCC
GATTTCGGCCTATTGGTTAAAAAATGAGCTGATTTAACAAAAATTTAACGCGA
ATTTTAACAAAATATTAACGCTTACAATTTAGGTGGCACTTTTCGGGGAAATG
TGCGCGGAACCCCTATTTGTTTATTTTTCTAAATACATTCAAATATGTATCCGC
TCATGAGACAATAACCCTGATAAATGCTTCAATAATATTGAAAAAGGAAGAG
TATGAGTATTCAACATTTCCGTGTCGCCCTTATTCCCTTTTTTGCGGCATTTTG
CCTTCCTGTTTTTGCTCACCCAGAAACGCTGGTGAAAGTAAAAGATGCTGAAG
ATCAGTTGG
```

Antibodies and Nanobodies

In certain aspects, the invention provides anti-TIM3 antibodies and nanobodies. In certain embodiments, the antibody or nanobody comprises an amino acid sequence at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any of the amino acid sequences set forth in SEQ ID NO: 20, 22, 24, 26, 28, 30, and 32. In certain embodiments, the antibody or nanobody is encoded by a nucleotide sequence at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to any of the nucleotide sequences set forth in SEQ ID NO: 19, 21, 23, 25, 27, 29, and 31.

Modified Immune Cells

The present invention provides modified immune cells or precursors thereof (e.g., T cells) comprising chimeric antigen receptors (CARs) or bispecific CARs capable of binding TIM-3. Also provided are modified immune cells or precursors thereof (e.g., T cells) comprising bispecific CARs capable of binding TIM-3 and CD13. The invention includes modified immune cells or precursors thereof comprising any of the CARs or bispecific CARs disclosed herein. The invention also includes modified immune cells or precursors thereof comprising any of the nucleic acids disclosed herein or any of the vectors disclosed herein.

In certain embodiments, the modified cell is a modified immune cell. In certain embodiments, the modified cell is a modified T cell. In certain embodiments, the modified cell is an autologous cell. In certain embodiments, the modified cell is an autologous cell obtained from a human subject.

Methods of Treatment

The modified cells (e.g., CAR T cells) described herein, may be included in a composition for immunotherapy. The composition may include a pharmaceutical composition and further include a pharmaceutically acceptable carrier. A therapeutically effective amount of the pharmaceutical composition comprising the modified T cells may be administered.

In one aspect, the invention includes a method for adoptive cell transfer therapy comprising administering to a subject in need thereof a modified T cell of the present invention. In another aspect, the invention includes a method of treating a disease or condition in a subject comprising administering to a subject in need thereof a population of modified T cells. In certain embodiments, the disease to be treated is cancer. In certain embodiments, the cancer is acute myeloid leukemia (AML).

Methods for administration of immune cells for adoptive cell therapy are known in the art and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8 (10): 577-85). See, e.g., Themeli et al. (2013) Nat Biotechnol. 31 (10): 928-933; Tsukahara et al. (2013) Biochem Biophys Res Commun 438 (1): 84-9; Davila et al. (2013) PLOS ONE 8 (4): e61338. In some embodiments, the cell therapy, e.g., adoptive T cell therapy is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject has been treated with a therapeutic agent targeting the disease or condition, e.g. the tumor, prior to administration of the cells or composition containing the cells. In some aspects, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse. In some aspects, the subject has not received prior treatment with another therapeutic agent.

The modified immune cells of the present invention can be administered to an animal, preferably a mammal, even more preferably a human, to treat a cancer (e.g. AML). In addition, the cells of the present invention can be used for the treatment of any condition related to a cancer, especially a cell-mediated immune response against a tumor cell(s), where it is desirable to treat or alleviate the disease. The types of cancers to be treated with the modified cells or pharmaceutical compositions of the invention include, acute myeoloid leukemia, chronic myeloid leukemia, pancreatic neuroenodocrine tumor (PNETs), gastrointestinal NETs, and lung and prostate cancer NETs, carcinoma, blastoma, and sarcoma, and certain leukemia or lymphoid malignancies, benign and malignant tumors, and malignancies e.g., sarcomas, carcinomas, and melanomas. Other exemplary cancers include but are not limited breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. The cancers may be non-solid tumors (such as hematological tumors) or solid tumors. Adult tumors/cancers and pediatric tumors/cancers are also included. In one embodiment, the cancer is a solid tumor or a hematological tumor. In one embodiment, the cancer is a carcinoma. In one embodiment, the cancer is a sarcoma. In one embodiment, the cancer is a leukemia. In one embodiment the cancer is a solid tumor. In one embodiment, the cancer is ovarian cancer. In one embodiment, the cancer is endometrial cancer. In one embodiment, the cancer is AML.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, ovarian cancer, endometrial cancer, uterine sarcoma, cervical carcinoma, breast cancer, lung cancer, prostate cancer, ocular melanoma, and any MISIIR-expressing tumor.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

In certain exemplary embodiments, the modified immune cells of the invention are used to treat a myeloma, or a condition related to myeloma. Examples of myeloma or conditions related thereto include, without limitation, light chain myeloma, non-secretory myeloma, monoclonal gamopathy of undertermined significance (MGUS), plasmacytoma (e.g., solitary, multiple solitary, extramedullary plasmacytoma), amyloidosis, and multiple myeloma. In one embodiment, a method of the present disclosure is used to treat multiple myeloma. In one embodiment, a method of the present disclosure is used to treat refractory myeloma. In one embodiment, a method of the present disclosure is used to treat relapsed myeloma.

In certain exemplary embodiments, the modified immune cells of the invention are used to treat a melanoma, or a condition related to melanoma. Examples of melanoma or conditions related thereto include, without limitation, superficial spreading melanoma, nodular melanoma, lentigo maligna melanoma, acral lentiginous melanoma, amelanotic melanoma, or melanoma of the skin (e.g., cutaneous, eye, vulva, vagina, rectum melanoma). In one embodiment, a method of the present disclosure is used to treat cutaneous melanoma. In one embodiment, a method of the present disclosure is used to treat refractory melanoma. In one embodiment, a method of the present disclosure is used to treat relapsed melanoma.

In yet other exemplary embodiments, the modified immune cells of the invention are used to treat a sarcoma, or a condition related to sarcoma. Examples of sarcoma or conditions related thereto include, without limitation, angiosarcoma, chondrosarcoma, Ewing's sarcoma, fibrosarcoma, gastrointestinal stromal tumor, leiomyosarcoma, liposarcoma, malignant peripheral nerve sheath tumor, osteosarcoma, pleomorphic sarcoma, rhabdomyosarcoma, and synovial sarcoma. In one embodiment, a method of the present disclosure is used to treat synovial sarcoma. In one embodiment, a method of the present disclosure is used to treat liposarcoma such as myxoid/round cell liposarcoma, differentiated/dedifferentiated liposarcoma, and pleomorphic liposarcoma. In one embodiment, a method of the present disclosure is used to treat myxoid/round cell liposarcoma. In one embodiment, a method of the present disclosure is used to treat a refractory sarcoma. In one embodiment, a method of the present disclosure is used to treat a relapsed sarcoma.

The cells of the invention to be administered may be autologous, with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as CD8$^+$ and CD4$^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as CD4$^+$ to CD8$^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or subtype, or minimum number of cells of the population or sub-type per unit of body weight. Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of CD4$^+$ to CD8$^+$ cells, and/or is based on a desired fixed or minimum dose of CD4$^+$ and/or CD8$^+$ cells.

In certain embodiments, the cells, or individual populations of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $1\times10^5$ cells/kg to about $1\times10^{11}$ cells/kg $10^4$ and at or about $10^{11}$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^6$ T cells/kg body weight, for example, at or about $1\times10^5$ T cells/kg, $1.5\times10^5$ T cells/kg, $2\times10^5$ T cells/kg, or $1\times10^6$ T cells/kg body weight. In other exemplary embodiments, a suitable dosage range of modified cells for use in a method of the present disclosure includes, without limitation, from about $1\times10^5$ cells/kg to about $1\times10^6$ cells/kg, from about $1\times10^6$ cells/kg to about $1\times10^7$ cells/kg, from about $1\times10^7$ cells/kg about $1\times10^8$ cells/kg, from about $1\times10^8$ cells/kg about $1\times10^9$ cells/kg, from about $1\times10^9$ cells/kg about $1\times10^{10}$ cells/kg, from about $1\times10^{10}$ cells/kg about $1\times10^{11}$ cells/kg. In an exemplary embodiment, a suitable dosage for use in a method of the present disclosure is about $1\times10^8$ cells/kg. In an exemplary embodiment, a suitable dosage for use in a method of the present disclosure is about $1\times10^7$ cells/kg. In other embodiments, a suitable dosage is from about $1\times10^7$ total cells to about $5\times10^7$ total cells. In some embodiments, a suitable dosage is from about $1\times10^8$ total cells to about $5\times10^8$ total cells. In some embodiments, a suitable dosage is from about $1.4\times10^7$ total cells to about $1.1\times10^9$ total cells. In an exemplary embodiment, a suitable dosage for use in a method of the present disclosure is about $7\times10^9$ total cells.

In some embodiments, the cells are administered at or within a certain range of error of between at or about $10^4$ and at or about $10^9$ CD4$^+$ and/or CD8$^+$ cells/kilograms (kg) body weight, such as between $10^5$ and $10^6$ CD4$^+$ and/or CD8$^+$ cells/kg body weight, for example, at or about $1\times10^5$ CD4$^+$ and/or CD8$^+$ cells/kg, $1.5\times10^5$ CD4$^+$ and/or CD8$^+$ cells/kg, $2\times10^5$ CD4$^+$ and/or CD8$^+$ cells/kg, or $1\times10^6$ CD4$^+$ and/or CD8$^+$ cells/kg body weight. In some embodiments, the cells are administered at or within a certain range of error of, greater than, and/or at least about $1\times10^6$, about $2.5\times10^6$, about $5\times10^6$, about $7.5\times10^6$, or about $9\times10^6$ CD4$^+$ cells, and/or at least about $1\times10^6$, about $2.5\times10^6$, about $5\times10^6$, about $7.5\times10^6$, or about $9\times10^6$ CD8$^+$ cells, and/or at least about $1\times10^6$, about $2.5\times10^6$, about $5\times10^6$, about $7.5\times10^6$, or about $9\times10^6$ T cells. In some embodiments, the cells are administered at or within a certain range of error of between about $10^8$ and $10^{12}$ or between about $10^{10}$ and $10^{11}$ T cells, between about $10^8$ and $10^{12}$ or between about $10^{10}$ and $10^{11}$ CD4$^+$ cells, and/or between about $10^8$ and $10^{12}$ or between about $10^{10}$ and $10^{11}$ CD8$^+$ cells.

In some embodiments, the cells are administered at or within a tolerated range of a desired output ratio of multiple cell populations or sub-types, such as CD4$^+$ and CD8$^+$ cells or sub-types. In some aspects, the desired ratio can be a specific ratio or can be a range of ratios, for example, in some embodiments, the desired ratio (e.g., ratio of CD4$^+$ to CD8$^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9: 1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, a dose of modified cells is administered to a subject in need thereof, in a single dose or multiple doses. In some embodiments, a dose of modified cells is administered in multiple doses, e.g., once a week or every 7 days, once every 2 weeks or every 14 days, once every 3 weeks or every 21 days, once every 4 weeks or every 28 days. In an exemplary embodiment, a single dose of modified cells is administered to a subject in need thereof. In an exemplary embodiment, a single dose of modified cells is administered to a subject in need thereof by rapid intravenous infusion.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

In certain embodiments, the modified cells of the invention (e.g., a modified cell comprising a CAR) may be administered to a subject in combination with an immune checkpoint antibody (e.g., an anti-PD1, anti-CTLA-4, or anti-PDL1 antibody). For example, the modified cell may be administered in combination with an antibody or antibody fragment targeting, for example, PD-1 (programmed death 1 protein). Examples of anti-PD-1 antibodies include, but are not limited to, pembrolizumab (KEYTRUDA®, formerly lambrolizumab, also known as MK-3475), and nivolumab (BMS-936558, MDX-1106, ONO-4538, OPDIVA®) or an antigen-binding fragment thereof. In certain embodiments, the modified cell may be administered in combination with an anti-PD-L1 antibody or antigen-binding fragment thereof. Examples of anti-PD-L1 antibodies include, but are not limited to, BMS-936559, MPDL3280A (TECENTRIQ®, Atezolizumab), and MEDI4736 (Durvalumab, Imfinzi). In certain embodiments, the modified cell may be administered in combination with an anti-CTLA-4 antibody or antigen-binding fragment thereof. An example of an anti-CTLA-4 antibody includes, but is not limited to, Ipilimumab (trade name Yervoy). Other types of immune checkpoint modulators may also be used including, but not limited to, small molecules, siRNA, miRNA, and CRISPR systems. Immune checkpoint modulators may be administered before, after, or concurrently with the modified cell comprising the CAR. In certain embodiments, combination treatment comprising an immune checkpoint modulator may increase the therapeutic efficacy of a therapy comprising a modified cell of the present invention.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32 (7): 689-702 (2009), and Herman et al. J. Immunological Methods, 285 (1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

In certain embodiments, the subject is provided a secondary treatment. Secondary treatments include but are not limited to chemotherapy, radiation, surgery, and medications.

In some embodiments, the subject can be administered a conditioning therapy prior to CAR T cell therapy. In some embodiments, the conditioning therapy comprises administering an effective amount of cyclophosphamide to the subject. In some embodiments, the conditioning therapy comprises administering an effective amount of fludarabine to the subject. In preferred embodiments, the conditioning therapy comprises administering an effective amount of a combination of cyclophosphamide and fludarabine to the subject. Administration of a conditioning therapy prior to CAR T cell therapy may increase the efficacy of the CAR T cell therapy. Methods of conditioning patients for T cell therapy are described in U.S. Pat. No. 9,855,298, which is incorporated herein by reference in its entirety.

In some embodiments, a specific dosage regimen of the present disclosure includes a lymphodepletion step prior to the administration of the modified T cells. In an exemplary embodiment, the lymphodepletion step includes administration of cyclophosphamide and/or fludarabine.

In some embodiments, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day). In an exemplary embodiment, the dose of cyclophosphamide is about 300 mg/m$^2$/day. In some embodiments, the lymphodepletion step includes administration of fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the dose of fludarabine is about 30 mg/m$^2$/day.

In some embodiment, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, the lymphodepletion step includes administration of cyclophosphamide at a dose of about 300 mg/m$^2$/day, and fludarabine at a dose of about 30 mg/m$^2$/day.

In an exemplary embodiment, the dosing of cyclophosphamide is 300 mg/m$^2$/day over three days, and the dosing of fludarabine is 30 mg/m$^2$/day over three days.

Dosing of lymphodepletion chemotherapy may be scheduled on Days −6 to −4 (with a −1 day window, i.e., dosing on Days −7 to −5) relative to T cell (e.g., CAR-T.) infusion on Day 0.

In an exemplary embodiment, for a subject having cancer, the subject receives lymphodepleting chemotherapy including 300 mg/m$^2$ of cyclophosphamide by intravenous infusion 3 days prior to administration of the modified T cells. In an exemplary embodiment, for a subject having cancer, the subject receives lymphodepleting chemotherapy including 300 mg/m$^2$ of cyclophosphamide by intravenous infusion for 3 days prior to administration of the modified T cells.

In an exemplary embodiment, for a subject having cancer, the subject receives lymphodepleting chemotherapy including fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having cancer, the subject receives lymphodepleting chemotherapy including fludarabine at a dose of 30 mg/m$^2$ for 3 days.

In an exemplary embodiment, for a subject having cancer, the subject receives lymphodepleting chemotherapy including cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day), and fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m$^2$/day). In an exemplary embodiment, for a subject having cancer, the subject receives lymphodepleting chemotherapy including cyclophosphamide at a dose of about 300 mg/m$^2$/day, and fludarabine at a dose of 30 mg/m$^2$ for 3 days.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

It is known in the art that one of the adverse effects following infusion of CAR T cells is the onset of immune activation, known as cytokine release syndrome (CRS). CRS is immune activation resulting in elevated inflammatory cytokines. CRS is a known on-target toxicity, development of which likely correlates with efficacy. Clinical and laboratory measures range from mild CRS (constitutional symptoms and/or grade-2 organ toxicity) to severe CRS (sCRS; grade ≥3 organ toxicity, aggressive clinical intervention, and/or potentially life threatening). Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. One CRS signature is elevation of cytokines including IL-6 (severe elevation), IFN-gamma, TNF-alpha (moderate), and IL-2 (mild). Elevations in clinically available markers of inflammation including ferritin and C-reactive protein (CRP) have also been observed to correlate with the CRS syndrome. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, the invention provides for, following the diagnosis of CRS, appropriate CRS management strategies to mitigate the physiological symptoms of uncontrolled inflammation without dampening the antitumor efficacy of the engineered cells (e.g., CAR T cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

CRS is generally managed based on the severity of the observed syndrome and interventions are tailored as such. CRS management decisions may be based upon clinical signs and symptoms and response to interventions, not solely on laboratory values alone.

Mild to moderate cases generally are treated with symptom management with fluid therapy, non-steroidal anti-inflammatory drug (NSAID) and antihistamines as needed for adequate symptom relief. More severe cases include patients with any degree of hemodynamic instability; with any hemodynamic instability, the administration of tocilizumab is recommended. The first-line management of CRS may be tocilizumab, in some embodiments, at the labeled dose of 8 mg/kg IV over 60 minutes (not to exceed 800 mg/dose); tocilizumab can be repeated Q8 hours. If suboptimal response to the first dose of tocilizumab, additional doses of tocilizumab may be considered. Tocilizumab can be administered alone or in combination with corticosteroid therapy. Patients with continued or progressive CRS symptoms, inadequate clinical improvement in 12-18 hours or poor response to tocilizumab, may be treated with high-dose corticosteroid therapy, generally hydrocortisone 100 mg IV or methylprednisolone 1-2 mg/kg. In patients with more severe hemodynamic instability or more severe respiratory symptoms, patients may be administered high-dose corticosteroid therapy early in the course of the CRS. CRS management guidance may be based on published standards (Lee et al. (2019) Biol Blood Marrow Transplant, doi.org/10.1016/j.bbmt.2018.12.758; Neelapu et al. (2018) Nat Rev Clin Oncology, 15:47; Teachey et al. (2016) Cancer Discov, 6 (6): 664-679).

Features consistent with Macrophage Activation Syndrome (MAS) or Hemophagocytic lymphohistiocytosis (HLH) have been observed in patients treated with CAR-T therapy (Henter, 2007), coincident with clinical manifestations of the CRS. MAS appears to be a reaction to immune activation that occurs from the CRS, and should therefore be considered a manifestation of CRS. MAS is similar to HLH (also a reaction to immune stimulation). The clinical syndrome of MAS is characterized by high grade non-remitting fever, cytopenias affecting at least two of three lineages, and hepatosplenomegaly. It is associated with high serum ferritin, soluble interleukin-2 receptor, and triglycerides, and a decrease of circulating natural killer (NK) activity.

In one aspect, the invention includes a method of treating cancer in a subject in need thereof, comprising administering to the subject any one of the modified immune or precursor cells disclosed herein. Yet another aspect of the invention includes a method of treating cancer in a subject in need thereof, comprising administering to the subject a modified immune or precursor cell generated by any one of the methods disclosed herein.

In one aspect, the invention includes a method for treating cancer in a subject in need thereof. The method comprises administering to the subject a modified T cell or precursor thereof comprising a bispecific CAR comprising a first antigen binding domain comprising a nanobody capable of binding CD13, a first intracellular domain, a second antigen binding domain capable of binding TIM-3, a transmembrane domain, and a second intracellular domain.

In another embodiment, the method comprises administering to the subject a modified T cell or precursor thereof comprising a bispecific CAR comprising a first antigen binding domain comprising Nb157, a first intracellular domain comprising CD3 zeta, a second antigen binding domain capable of binding TIM-3, a CD28 transmembrane domain, and a second intracellular domain comprising 4-1BB.

In anther aspect, the invention includes a method of treating cancer in a subject in need thereof comprising administering to the subject a modified T cell or precursor thereof comprising an inducible bispecific CAR comprising a first antigen binding domain capable of binding Peptide-Neo-Epitope (PNE), a first transmembrane domain, a first intracellular domain, a second antigen binding domain capable of binding TIM-3, a transmembrane domain, and a second intracellular domain.

In another embodiment, the method comprises administering to the subject a modified T cell or precursor thereof comprising an inducible bispecific CAR comprising a first antigen binding domain capable of binding Peptide-Neo-Epitope (PNE), a first transmembrane domain, a first intracellular domain comprising CD3 zeta, a second antigen binding domain capable of binding TIM-3, a CD28 transmembrane domain, and a second intracellular domain comprising 4-1BB.

The method may further comprise administering, along with the inducible bispecific CAR, a nanobody fused to PNE. In certain embodiments, the nanobody is specific for CD13. In certain embodiments, the nanobody is Nb157 and may comprise the amino acid sequence set forth in SEQ ID NO: 1.

In certain embodiments, the T cell is a human cell. In certain embodiments, the T cell is autologous.

Vectors

A vector may be used to introduce the CAR into a T cell as described elsewhere herein. In certain aspects, the invention includes vectors comprising nucleic acid sequences encoding a CAR. The vector can comprise a plasmid vector, viral vector, retrotransposon (e.g. piggyback, sleeping beauty), site directed insertion vector (e.g. CRISPR, Zn finger nucleases, TALEN), suicide expression vector, lentiviral vector, RNA vector, or other known vector in the art.

The production of any of the molecules described herein can be verified by sequencing. Expression of the full length proteins may be verified using immunoblot, immunohistochemistry, flow cytometry or other technology well known and available in the art.

The present invention also provides a vector in which DNA of the present invention is inserted. Vectors, including those derived from retroviruses such as lentivirus, are suitable tools to achieve long-term gene transfer since they allow long-term, stable integration of a transgene and its propagation in daughter cells. Lentiviral vectors have the added advantage over vectors derived from onco-retroviruses, such as murine leukemia viruses, in that they can transduce non-proliferating cells, such as hepatocytes. They also have the added advantage of resulting in low immunogenicity in the subject into which they are introduced.

The expression of natural or synthetic nucleic acids is typically achieved by operably linking a nucleic acid or portions thereof to a promoter, and incorporating the construct into an expression vector. The vector is one generally capable of replication in a mammalian cell, and/or also capable of integration into the cellular genome of the mammal. Typical vectors contain transcription and translation terminators, initiation sequences, and promoters useful for regulation of the expression of the desired nucleic acid sequence.

The nucleic acid can be cloned into any number of different types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

The expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the EF-1 alpha promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479:79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Introduction of Nucleic Acids

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12 (8): 861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Chol") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5:505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Moreover, the nucleic acids may be introduced by any means, such as transducing the expanded T cells, transfecting the expanded T cells, and electroporating the expanded T cells. One nucleic acid may be introduced by one method and another nucleic acid may be introduced into the T cell by a different method.

RNA

In one embodiment, the nucleic acids introduced into the T cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a chimeric membrane protein. By way of example, the template encodes an antibody, a fragment of an antibody or a portion of an antibody. By way of another example, the template comprises an extracellular domain comprising a single chain variable domain of an antibody, such as anti-CD3, and an intracellular domain of a co-stimulatory molecule. In one embodiment, the template for the RNA chimeric membrane protein encodes a chimeric membrane protein comprising an extracellular domain comprising an antigen binding domain derived from an antibody to a co-stimulatory molecule, and an intracellular domain derived from a portion of an intracellular domain of CD28 and 4-1BB.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the RNA is electroporated into the cells, such as in vitro transcribed RNA.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171, 264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993, 434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

In certain embodiments, a source of T cells is obtained from a subject. Non-limiting examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, umbilical cord, and tumors. In certain embodiments, any number of T cell lines available in the art, may be used. In certain embodiments, T cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

In certain embodiments, T regulatory cells (Tregs) can be isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. Methods for isolating Tregs are described in U.S. Pat. Nos. 7,754,482, 8,722,400, and 9,555,105, and U.S. patent application Ser. No. 13/639,927, contents of which are incorporated herein in their entirety.

Expansion of T Cells

In certain embodiments, the T cells disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more by culturing the electroporated population. In one embodiment, human T regulatory cells are expanded via anti-CD3 antibody coated KT64.86 artificial antigen presenting cells (aAPCs). Methods for expanding and activating T cells can be found in U.S. Pat. Nos. 7,754,482, 8,722,400, and 9,555,105, contents of which are incorporated herein in their entirety.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

Pharmaceutical Compositions

Pharmaceutical compositions of the present invention may comprise the modified T cell as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

The cells of the invention to be administered may be autologous, allogeneic or xenogeneic with respect to the subject undergoing therapy.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

It can generally be stated that a pharmaceutical composition comprising the modified T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

The administration of the modified T cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Materials and Methods used in the performance of the experiments disclosed herein are now described.

Nb phage library construction from THP-1 cell-immunized llama: A llama was immunized with $2 \times 10^7$ THP-1 cells (Caprologics, Hardwick, MA) once a month for 3 months. Peripheral blood mononuclear cell isolation, RNA extraction, and complementary DNA (cDNA) synthesis were performed as previously described (Zhang et al., *J Immunol.* 2016; 196 (4): 1591-1603).

Animals and in vivo models: All laboratory mice were maintained on a 12 hr light-dark cycle. NOD/Shi-scid/IL-2Rγnull (NSG) mice, 8-12 weeks old, were obtained from Jackson Laboratories. NSG mice were inoculated with $1 \times 10^7$ cells of THP-1 or HL60 subcutaneously, or with $0.5 \times 10^7$ cells of K562 subcutaneously. When tumor volume reached 100 mm³ about 12 days after xenograft, Nb CAR T cells or untransduced (UTD) human T cells ($1 \times 10^7$ cells) were administrated via tail vein. Mice and tumors were monitored every other day. Tumor dimensions were measured with Vernier calipers and tumor volume was calculated as ½ larger diameter×(smaller diameter).

NSG mice were conditioned by Busulfex (30 mg/kg) 24 hrs prior to tail injection with $2 \times 10^7$ of patient-derived AML cells. Two weeks later CAR or UTD T cells were transduced into the mice. The recipient mice were sacrificed at the experimental end point based on the protocol, and the long bones (femurs), spleens and livers were collected for histological analysis by H & E staining. Mice were sacrificed according to protocol when moribund or upon the development of hind-limb paralysis.

Statistical analysis: Microsoft Excel and GraphPad Prism software was used for statistical analysis. Student's t test was used to determine the significance of the results unless otherwise indicated. Kaplan-Meier statistical analysis was performed using the log rank test. In the figures, asterisks denote statistically significant p values (*, p<0.05, , p<0.01, *p<0.001), and "ns" indicates lack of statistical significance (p>0.05).

Cell Lines, Cell Culture, Plasmids and Antibodies: The THP-1, Jurkat, K562, HL60, U937, MV4-11, NB4 and SKOV3 cell lines were obtained from the ATCC and maintained in RPMI1640 with 10% FBS and 1% penicillin/streptomycin (R10 medium) and maintained at 37° C. and 5% $CO_2$. HEK293T cells were obtained from ATCC and cultured in DMEM supplemented with 10% fetal bovine serum (FBS). NET NT-3 cell line was cultured in RPMI medium supplemented with 10% FBS, penicillin/streptomycin, HEPES, EGF (20 ng/mL), and FGF2 (10 ng/mL). Deidentified Patient derived AML cells were obtained from the University of Pennsylvania Stem Cell and Xenograft Core facility, and maintained in the R10 medium. Normal donor total T cells were obtained from the Human Immunology Core at University of Pennsylvania, and maintained in the R10 medium.

pComb3XSS was a gift from Carlos Barbas (Addgene plasmid #63890). pHIV-EGFP was a gift from Bryan Welm & Zena Werb (Addgene plasmid #21373). lentiCRISPR v2 was a gift from Feng Zhang (Addgene plasmid #52961). Human membrane protein cDNA library were provided by High-throughput Screen Core at University of Pennsylvania.

In vitro analysis of T cell function: For T-cell transduction, HEK293T cells were co-transfected with lenti-vector plasmid, psPAX2 and VSV-G plasmid DNA to produce the lentivirus 48 h after transfection. Normal donor T cells were positively selected from leukapheresis packs using anti-CD4 and CD8 microbeads (Miltenyi), expanded in vitro with anti-CD3/CD28 beads (Invitrogen) for up to 12 days. Total T cells were transduced with lentiviraus 24 hours after activation. The resulting virus from the supernatant were concentrated via untracentrifuation at 25,000 g for 2.5 h at 4° C.

Killing assays were performed as previously described (Cao, L. F. et al. (2010) Cytometry A 77, 534-545). In brief, target cells were labeled by anti-CD33 (BD) for detecting cell number with flow cytometry analysis or labeled by CellTrace Far Red for tracing cell division. Target cells were incubated with effector T cells for 16 hrs at a series of ratios. Cells were then harvested, washed, and stained by Propidium Iodide prior to flow cytometry analysis. Quantification was calculated by either Countbright beads or volume.

To detect cytokine secretion, effector and target cells were incubated at a 1:1 ratio in R10 medium for 16 hrs as indicated. Supernatant was analyzed using Human TNF-alpha or IFN-gamma DuoSet ELISA kits according to the manufacturer's instructions (R&D System).

To detect cell degranulation, activated and Nb CAR transduced or untransduced T cells ($1\times10^5$ cells) were co-cultured with THP-1 or K526 cells at a 1:1 ratio in 96-well plates for 4 hrs, in the presence of APC-conjugated anti-CD107a antibody, followed by washing and flow cytometry analysis.

To monitor cell proliferation assay, T cells were labeled by CellTrace™ Far Red Cell Proliferation Kit (Invitrogen) according to the manufacturer's instructions. The reaction was quenched with R10 medium, and the cells were washed twice. T cells were incubated at a 1:1 ratio with heat-inactivated target cells for 96 hrs.

Switchable CAR (sCAR) T system: Anti-PNE single chain variable fragment (scFv) (Zahnd C, et al. (2004) *J Biol Chem*. April 30; 279 (18): 18870-7) was custom synthesized by GeneArt (Rodgers, D. T. et al. (2016) *Proceedings of the National Academy of Sciences of the United States of America* 113, E459-468), followed by insertion into pHIV-41BB-CD3z vector. sCAR lentivirus was packaged and used to transduce human T cells. sCAR expression was detected by flow cytometry and western blot. Nb157 with C-terminal PNE (Nb157-C-PNE) or with N-terminal PNE (Nb157-N-PNE) were constructed by molecular cloning, followed by prokaryotic expression and purification via Ni-NTA affinity (QIAGEN) in TOP10 (Invitrogen) induced by isopropyl-β-d-thiogalactoside (IPTG).

The Results the experiments disclosed herein are now described.

Example 1: Anti-TIM-3 CAR

An anti-TIM-3 CAR comprised of an anti-TIM-3-scFv, an IgG4 hinge, a CD28 transmembrane domain, and 4-1BB and CD3z intracellular domains, was generated herein (FIG. 1C). TIM-3 was expressed on NB4-TIM-3 cell lines, as measured by Western Blot (FIG. 1A). NB4 or NB4-TIM-3 cells were incubated with anti-TIM-3-scFv-CAR T cells overnight and cytotoxicity was measured by flow cytometry analysis (FIG. 1B). Untransduced (UTD) T cells were used as a negative control. The data showed that anti-TIM3 CAR T cells specifically killed TIM-3-expressing myeloid leukemia cells. (FIG. 1D).

Example 2: Bispecific Split TIM-3&CD13 CAR

A bispecific split CAR was generated herein that specifically kills tumor cells expressing TIM-3 and CD13 (FIG. 2). The CAR was comprised of a nanobody specific for CD13 (Nb157), a CD3zeta domain, a P2A linker, an anti-TIM3-scFv, a CD28 transmembrane domain, and a 4-1BB intracellular domain. Bispecific split CAR T cells targeting CD13 and TIM-3 or control UTD T cells were injected into NSG mice transplanted with either NB4 cells or NB4-TIM3, and monitored for tumor growth. The results demonstraed that the bispecific split CAR (BissCAR) T cells eradicated the NB4-TIM3 tumors expressing both CD13 and TIM-3, but not the NB4 tumors that only express CD13.

Example 3: Inducible, Bispecific TIM-3&CD13 CAR

Figure 3C:
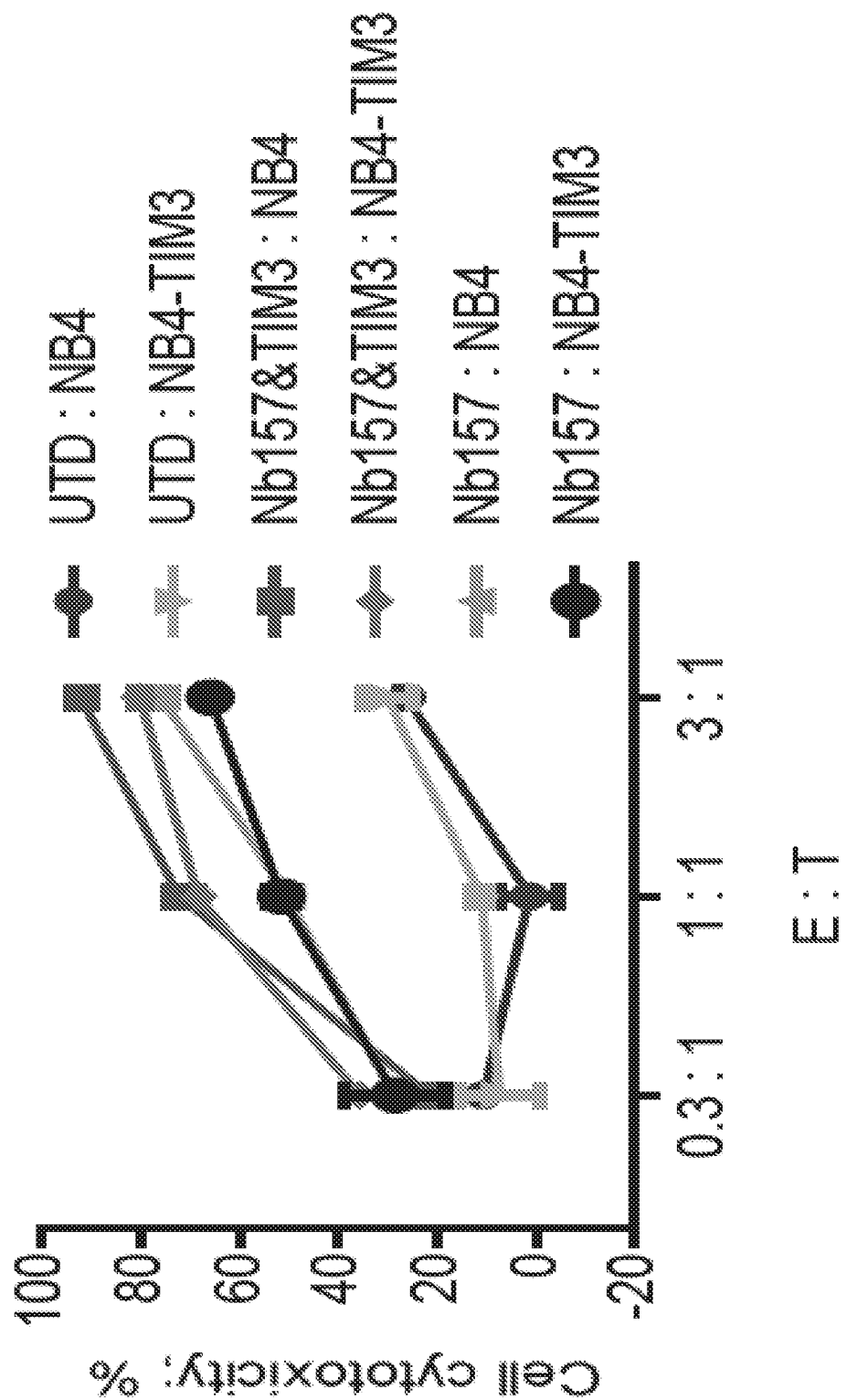
Figure 4A:
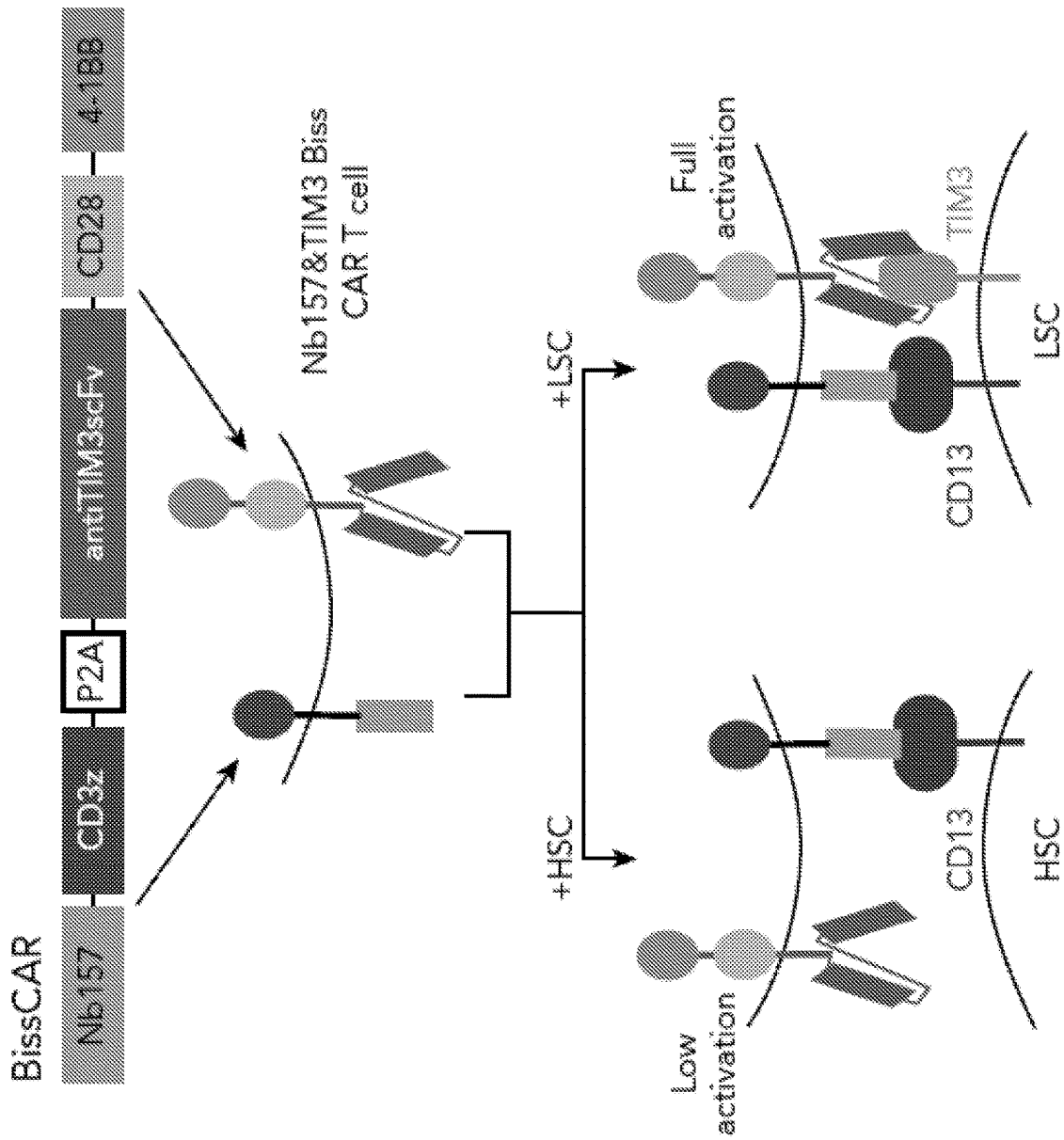
FIGS. 4A-4B illustrate combinatorial bispecific and split CARs targeting both CD13 and TIM-3. Bispecific and split CAR (BissCAR) T cells more potently kill leukemic stem cells (LSCs), which express both TIM3 and CD13, but spare normal HSCs, which express CD13, but not TIM3.
Figure 4B:
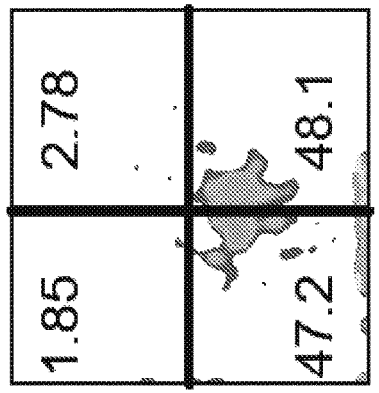
Figure 4B:
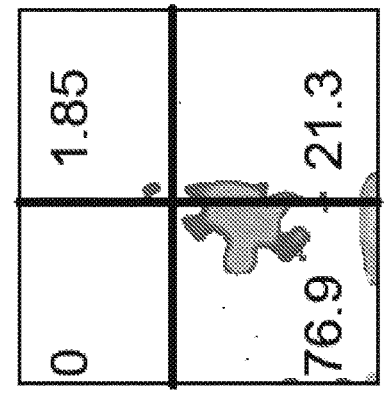
Figure 4B:
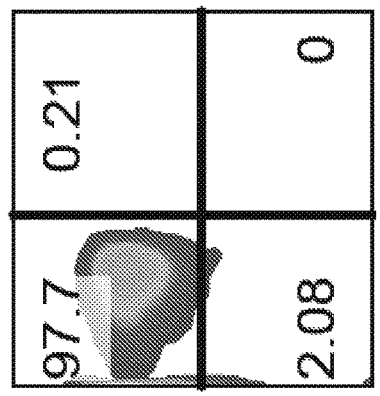
Figure 4B:
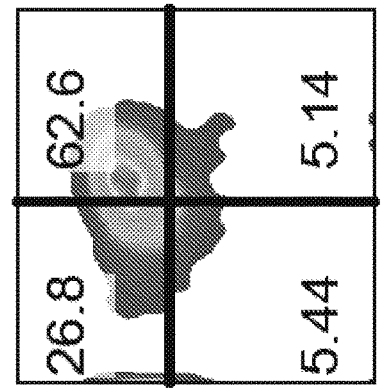

An inducible bispecific CAR was generated herein that specifically kills AML leukemic stem cells (LSCs) that express both TIM-3 and CD13 (FIG. 4B). Two CARs were linked by the P2A construct. The first CAR comprised an anti-TIM-3-scFv, a CD28 hinge, a CD28 transmembrane domain, and CD28 and 4-1BB intracellular domains. The second, switchable CAR (sCAR) was comprised of an anti-PNE-scFv, an IgG4 hinge, a CD8 transmembrane domain, and a CD3zeta intracellular domain (FIG. 3A). T cells expressing the bispecific CAR were incubated with human AML LSCs, which expressed both TIM-3 and CD13 (FIG. 3B). In the absence of Nb157-PNE, the sCAR bound the LSC by TIM-3 recognition, but didn't exhibit cytotoxicity (FIG. 3C). In the presence of the Nb157-PNE switch, the T cell fully activated and killed the LSC targets (FIG. 3C).

Example 4: Bispecific CARs of Nb157 and Anti-TIM3 Eradicate AML In Vivo in a Safer Manner CAR T therapy may cause serious cytokine release syndrome and other on-target/off-tumor side effects. To reduce this risk, as well as further attenuate the potential side effects of targeting moderately expressed CD13 in non-AML cells with low CD13 expression, such as hematopoietic stem cells, a logic-gated and controllable system to manipulate the antitumor activity of Nb157 CAR T cells to AML was developed. TIM3, an immune suppressing receptor, is highly expressed on the majority of human AML leukemia stem cells (LSCs), but not on human HSCs. To overcome the challenge that Nb157 CAR T cells kill both AML cells and HSCs, a combinational bispecific CAR T system was designed to specifically kill AML LSC that commonly express both TIM3 and CD13 (FIG. 4A), which effectively kills CD13+TIM3+ LSC cells, yet spares normal cells that only have CD13 expression.

To prove that the bispecific CAR T cells could eradicate LSCs but spare HSCs, a NB4 and NB4-TIM3 cell model was first constructed, which mimicked HSCs (CD13+ TIM3−) and LSCs (CD13+TIM3+) (FIG. 1B). A TIM3 CAR T cell was constructed with a published anti-TIM3 antibody (U.S. Pat. No. 9,605,070B2), followed by a linker, a transmembrane domain (TM), 4-1BB domain, and CD3 zeta domain (FIG. 1C). An in vitro killing experiment showed that the TIM3 CAR T cell exhibited potent and specific cytotoxicity against NB4-TIM3 cells, but ignored the NB4 cells as UTD T cells (FIG. 1D).

An Nb157&TIM3 combinational bispecific CAR was generated (FIGS. 3A and 4A), wherein the Nb157 recognizes CD13 activated CD3z signaling, and the antiTIM3scFv recognizes TIM3 transduced CD28 and 4-1BB co-stimulatory signaling. To overcome the challenge that Nb157 CAR T cells may kill both AML and HSCs, the Nb157&TIM3 CAR was transduced into human primary T cells by lentivirus, and the resulting T cells were used for flow cytometry to detect expression of both Nb157 (using a rabbit anti-llama VHH) and TIM3 (using an anti-mouse scFv). The results showed that both CARs were co-expressed on the surface of the transduced CAR T cells simultaneously (FIG. 3B). An in vitro killing assays showed Nb157&TIM3 CAR T cells showed potent toxicity against both NB4 and NB4-TIM3 cells. The CD3zeta cytotoxicity signaling was elicited by CD13 recognition, which is commonly expressed on leukemia cells (FIG. 3C). In the in vivo tumor killing assay, Nb157&TIM3 CAR T cells suppressed NB4 tumor growth (FIG. 5A), but eradicated the NB4-TIM3 tumor (FIG. 5B), which confirmed that the combination of bispecific and split CAR was needed to completely regress the tumor while sparing the single-antigen-expressing normal cells. Meanwhile, the Nb157&TIM3 CAR T cells in the NB4-TIM3 tumor mice proliferated one-fold more than in the NB4 tumor mice (FIG. 6), which also supported that in vivo tumor eradication requires sustainability and enhanced activity of the T cells.

The combinational bispecific CAR system was tested to determining if it could suppress primary AML cells from patients. Patient-derived AML cells were injected into NSG mice to induce leukemia, as determined by detection of the human CD33+ AML cells in the peripheral blood of the recipient mice (FIG. 7A). The leukemic mice were treated with Nb157&TIM3 CAR or UTD T cells two weeks after leukemia injection (FIG. 7A). The appearance of CD33+ AML cells or CD3+ T cells in peripheral blood were monitored by flow cytometry analysis weekly (FIGS. 7A-7C). The results indicated that peripheral blood AML cells, following the first week of injection, gradually decreased in the Nb157&TIM3 CAR T group (FIG. 7B), consistent with heavy leukemia infiltration in the spleen in later stage. Notably, treatment with Nb157&TIM3 CAR, but not UTD T cells, increased the number of peripheral T cells one week after the T cell injection, reflecting the quick activation and proliferation of the CAR T cells to kill the AML cells (FIG. 7C). Consistent with this observation, Kaplan Maier analysis showed that treatment with Nb157&TIM3 CAR T cells significantly prolonged survival compared to mice treated with UTD T cells (FIG. 7D). Therefore, the results demonstrated that the Nb157&TIM3 CAR T cells targeting both CD13 and TIM3 can effectively eradicate the double-positive patient-derived AML cells in a clinically relevant model.

Figure 7E:
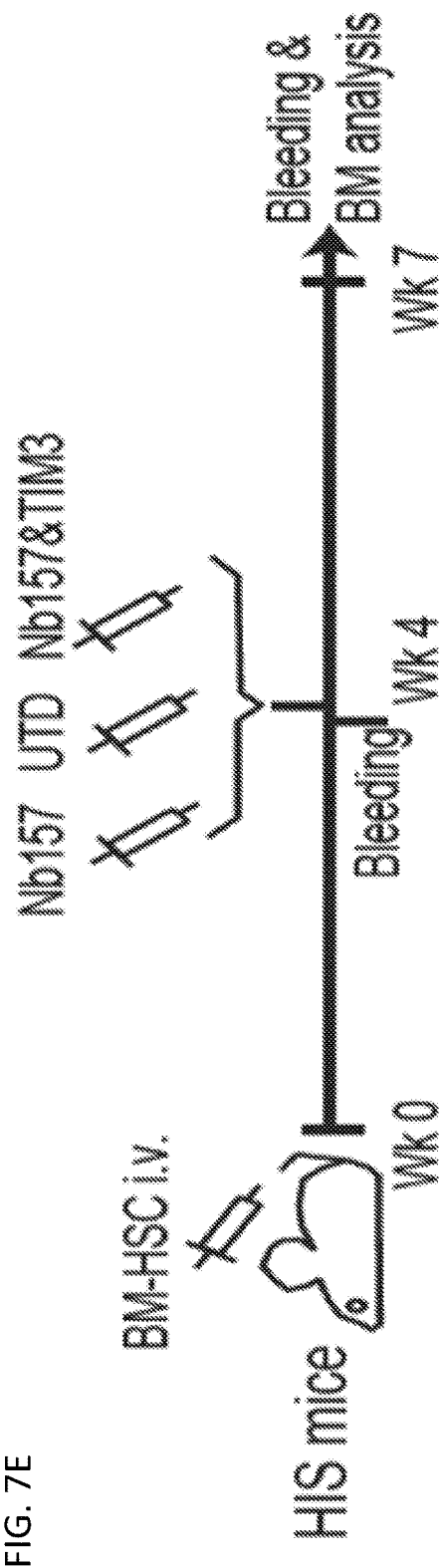
Figure 7F:
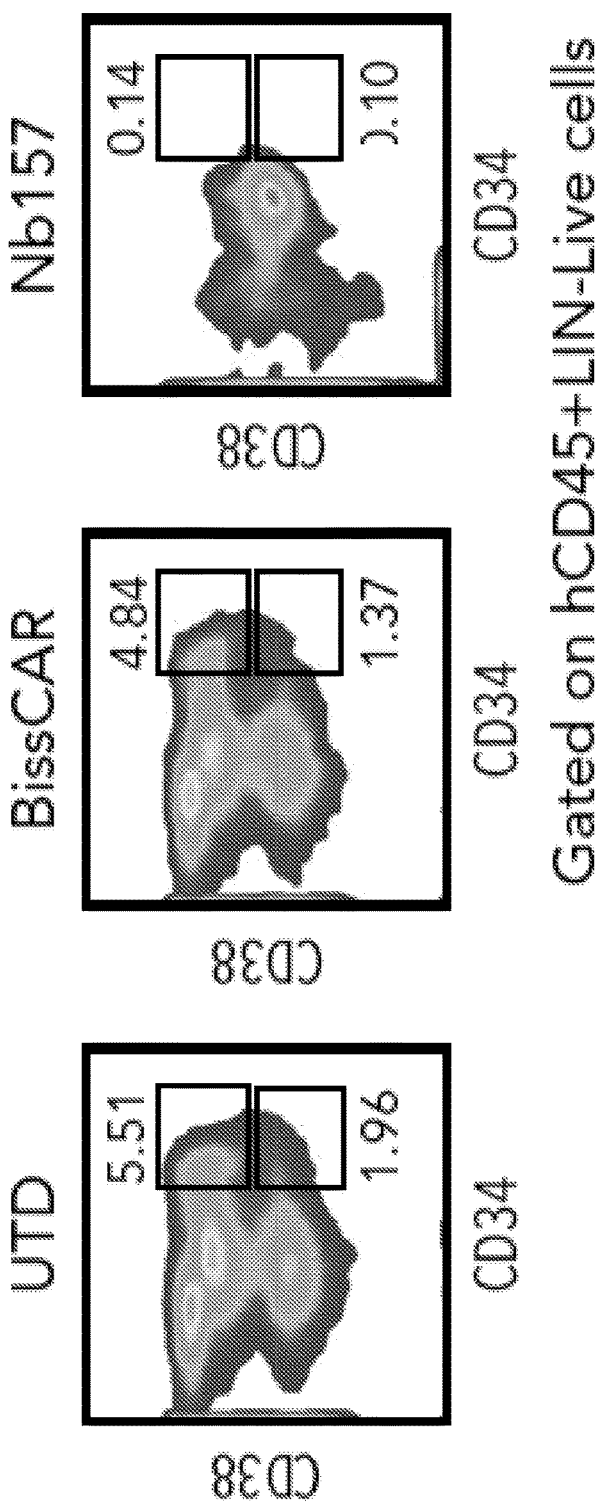
Figure 7H:
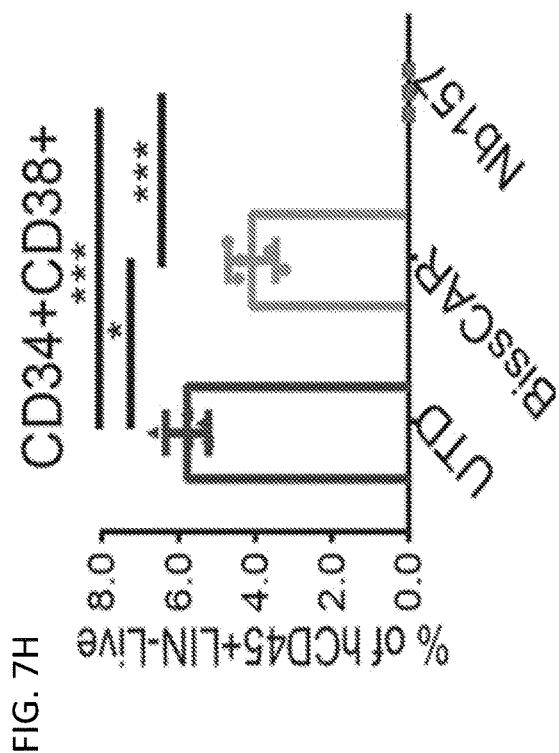

The impact of Nb157&TIM3 CAR T cells on normal hematopoiesis was investigated. Humanized immune system mice (HIS mice) were employed to assess hematopoietic toxicity of Nb157&TIM3 CAR T cells (FIG. 7E). NSG mice were conditioned by busulfan and engrafted with bone marrow CD34+ cells from normal adult donors, followed by treatment with Nb157&TIM3 CAR, Nb157 CAR, or UTD T cells four weeks later. Mice were bled before and after T cell treatment to confirm the engraftment and analyze the peripheral constitution of the mice. Bone marrow from the mice was collected for analysis three weeks after treatment (FIG. 7E). Based on CD13 expression on normal HSCs, analysis of the bone marrow three weeks after treatment showed near disappearance of both CD34+CD38− hematopoietic stem cells and CD34+CD38+ myeloid progenitors in the conventional Nb157 CAR group (FIGS. 87F-7H). However, the Nb157&TIM3 bispecific CARs showed ameliorated disruption in normal HSCs (FIGS. 7E-7F). Therefore, these results demonstrated that the Nb157&TIM3 CAR T cells effectively and safely eradicated patient-derived AML cells in the clinically relevant model.

Example 5: Combinatory Bispecific and Split CAR T Cells Targeting CD13 and TIMS Redirect T Cells to Eradicate AML Xenografts and AML PDXs In Vivo Because CAR T-cell therapy may cause on-target/off-tumor side effects, it is ideal to reduce the toxicity by increasing the specificity with multiple tumor markers. In this regard, novel bispecific CAR T cells were developed to synergistically kill the experimental tumor models by targeting >1 tumor-associated antigen (TAA).

One other potential TAA, TIM3, an immune-suppressing receptor, is highly expressed in the majority of human AML LSCs, but not in HSCs. A combinatory bispecific and split CAR (BissCAR) T-cell system was developed to effectively kill CD13$^+$TIM3$^+$ LSCs, while maintaining a reduced impact on normal cells that only express CD13 (FIG. 4A). TIM3 expression was extremely low in normal donor bone marrow but high in the LSC subset (CD34$^+$CD38$^-$CD90$^-$) (FIG. 4B, upper panels). In contrast, a high percentage of TIM3 and CD13 double-positive cells was detected in the LSC-enriched population (CD34$^+$CD38$^-$) from PD AML cells but not normal donor bone marrow (FIG. 4B), indicating the high coexpression of CD13 and TIM3 in LSGs.

NB4 (CD13$^+$TIM3$^-$) and NB4-TIM3 (CD13'TIM3$^+$) cell lines were generated to mimic the HSG and LSC models (FIG. 1A-1B). Next, a conventional TIM3-BBz CAR was generated (FIG. 1C), which guided the T cells to kill NB4-TIM3 cells potently and specifically in vitro and suppressed NB4-TIM3 tumor growth in vivo (FIG. 1D).

Next, the BissCAR was constructed, in which Nb157 recognizing CD13 was linked to CD3z and anti-TIMS scFv recognizing TIM3 was linked to CD28 and 4-1BB costimulatory domains (FIG. 2; FIG. 4A). The resulting BissCAR expression on the T cells was verified by flow cytometry (FIG. 3B). An in vitro killing assay showed that BissCAR T cells killed NB4 and NB4-TIM3 cells, because the CD13 recognition elicited CD3z signaling to induce target death in vitro (FIG. 3C).

Figure 5A:
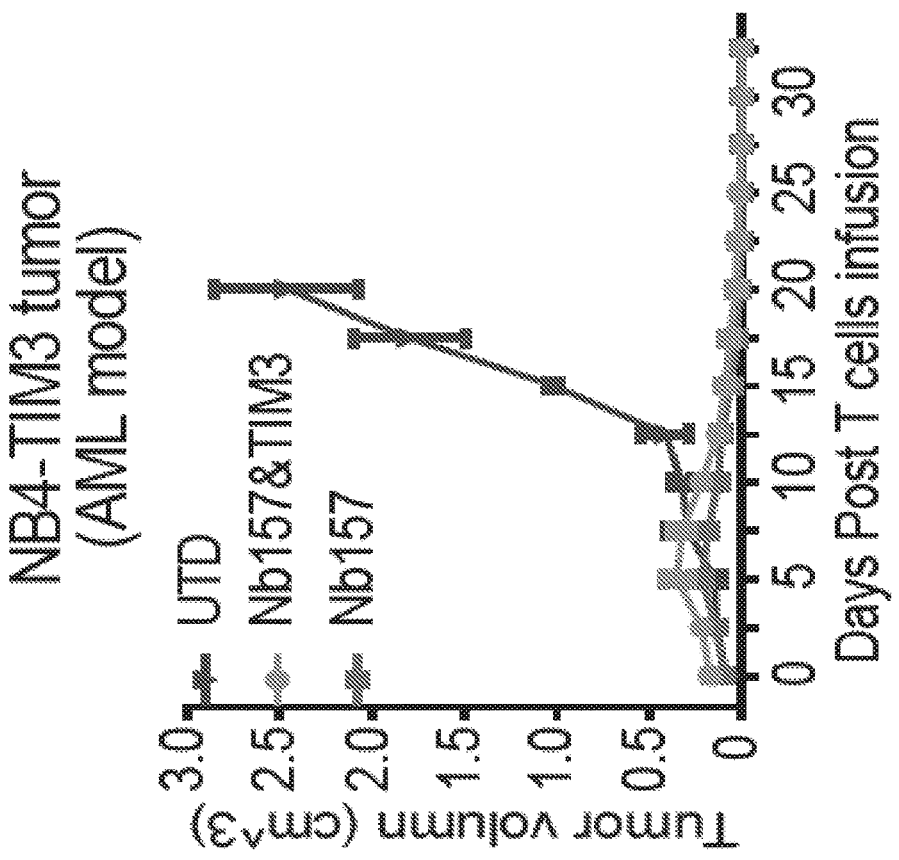
FIGS. 5A-5B show data from experiments wherein ten million NB4 or NB4-TIM3 cells were transplanted into NSG mice subcutaneously to form 100 mm³ tumors. Three million Nb157&TIM3 combinational BissCAR T cells, conventional Nb157 CAR T cells, or UTD T cells were injected intravenously into NSG mice separately. The engraftment volume was monitored by measuring the length and width of the tumor every other day (n=4).
Figure 5B:
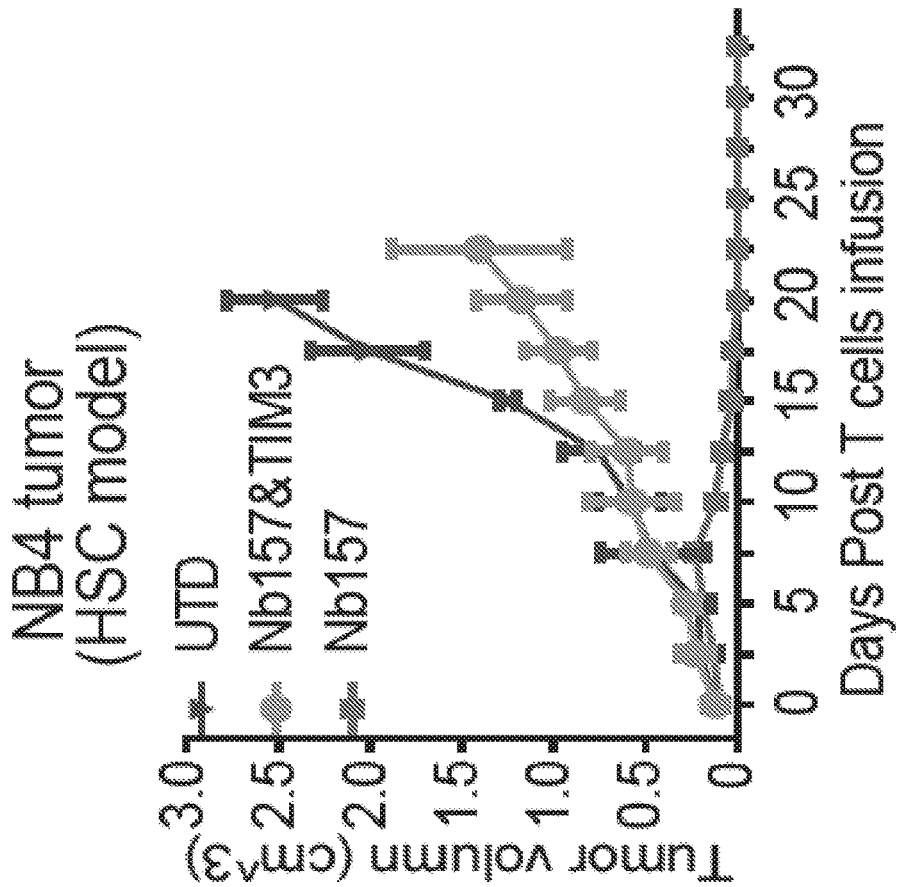
Figure 6:
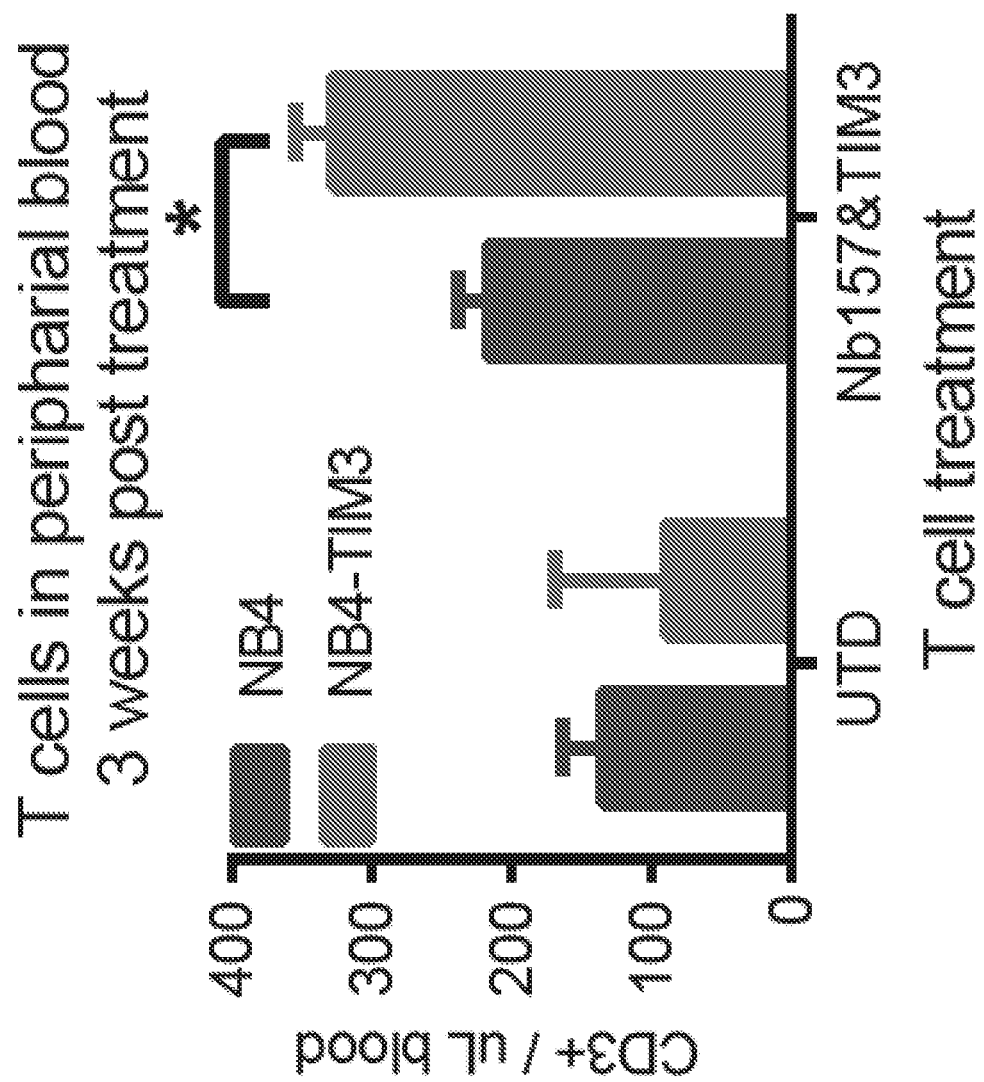
FIG. 6 illustrates the human T cells in peripheral blood of NSG mice bearing either NB4 or NB4-TIM3 tumors following treatment with the indicated control (UTD) or the indicated CAR T cells. Three weeks after mice with NB4 or NB4-TIM3 tumors were treated with the BissCAR (Nb157 &TIM3) T cells or UTD T cells, human T cell (CD3+) numbers in mouse peripheral blood were analyzed by flow cytometry and quantified using CountBright counting beads (n=3). *P<0.05, Student t test.

In the NB4 xenograft models, BissCAR T cells only moderately suppressed tumor growth compared with complete elimination when using Nb157 CAR T-cell treatment (FIG. 5A). However, BissCAR T cells could eradicate the NB4-TIM3 tumor as potently as Nb157 CAR T cells (FIG. 5B). These results indicate that BissCAR T cells are capable of completely shrinking the tumor expressing GDIS and TIMS, but they spared the cells expressing only CD13. Consistently, BissCAR T-cell number in peripheral blood in NB4-TIM3 tumor-bearing mice was significantly higher than in NB4 tumor-bearing mice (FIG. 6).

It was explored whether BissCAR T cells could suppress RD AML cells. To this end, RD AML cells were transplanted into NSG mice to induce leukemia, followed by treatment with BissCAR or UTD T cells 2 weeks later (FIG. 7A). The appearance of CD33$^+$ AML cells or CD3$^+$ T cells in peripheral blood was monitored weekly (FIGS. 7B-7C). The results indicated that, following the first week of injection, peripheral blood AML cells gradually decreased in the BissCAR T-cell group (FIG. 7B), consistent with heavy leukemic infiltration in the spleen in the later stage. Notably, treatment with BissCAR T cells, but not with UTD T cells, increased peripheral T-cell number 1 week after the T-cell injection, reflecting the quick activation and proliferation of CAR T cells to kill AML cells (FIG. 7C). Consistently, BissCAR T-cell treatment significantly prolonged survival of the mice compared with the UTD T-cell group (FIG. 7D). It has been reported that various immune-suppressing factors weaken the immunotherapy for AML, such as the PD-1, TIM3 immune checkpoint molecules, and regulatory T cells (Tregs). BissCAR T cells and UTD T cells have similar low PD-1 and TIMS expression in the mouse spleen; however, the PD-1/TIM3 levels were not correlated with resistance to CAR T cells, because CAR T cells eradicated AML in the xenograft and PDX models. T-cell suppression from Tregs was not observed, because of the robust elimination of the leukemia. Therefore, the results demonstrate that BissCART cells can effectively eradicate the double-positive PD AML cells in this clinically relevant model.

Figure 7G:
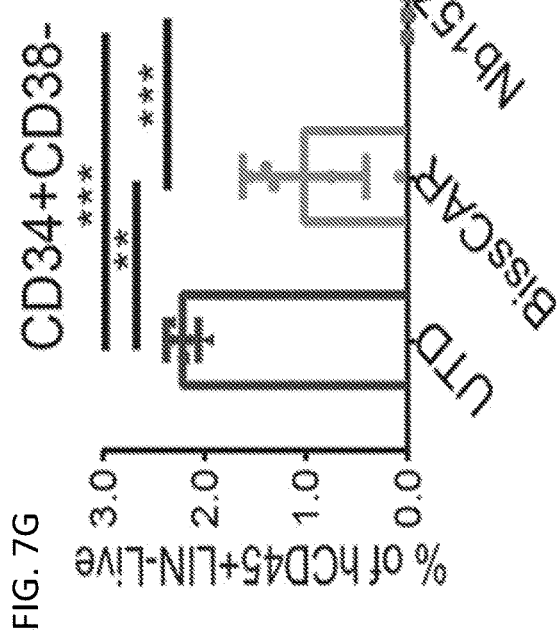
Figure 7I:
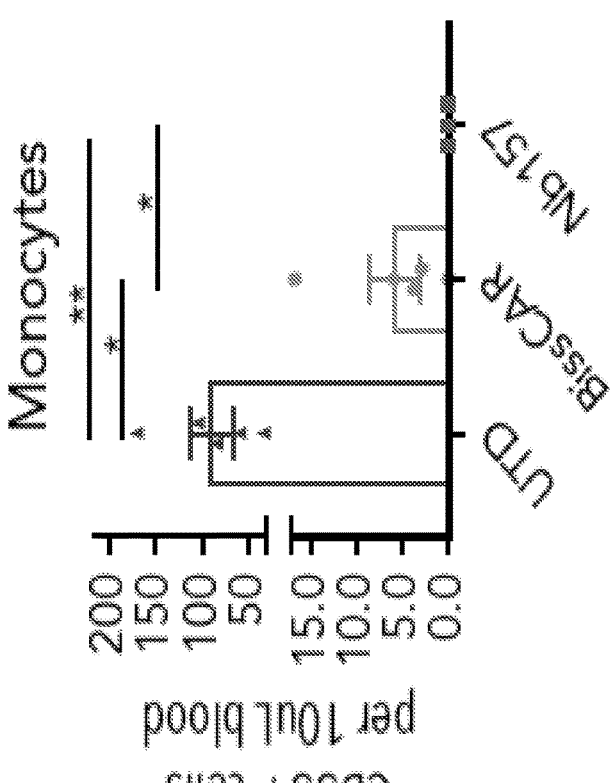
FIG. 7I shows monocytes (human $CD45^+$ CD33$^+$) from peripheral blood of HIS mice were analyzed by flow cytometry 3 weeks after the initial treatment; cell number and blood volume were quantified using CountBright counting beads.

Example 6: Combinatory BissCAR T Cells Targeting CD13 and TIMS have Reduced Toxicity to HSCs In Vivo The impact of BissCAR T cells on normal human HSCs was also investigated. Humanized immune system (HIS) mice were used to assess hematopoietic toxicity of BissCAR T cells (FIG. 7E). NSG mice were conditioned with busulfan and engrafted with bone marrow CD34$^+$ cells from a normal adult donor, followed by treatment with BissCAR, Nb157 CAR, or UTD T cells 4 weeks later. Bone marrow from these mice was collected for analysis 3 weeks after treatment. Nb1 57 CART cells almost completely depleted CD34$^+$CD38$^-$ HSCs, CD34$^+$CD38$^+$ myeloid progenitors, and peripheral monocytes (FIGS. 7F-7I). Notably, BissCAR T cells significantly reduced the toxicity to HSCs, retaining ~50% of the human HSC-enriched population and the myeloid progenitors of normal control mice (FIGS. 7F-7H). Moreover, BissCAR T cells significantly reduced the monocytes in peripheral blood and allowed the protection of part of the monocytes in peripheral blood in BissCAR T-cell-injected mice compared with Nb157 CAR T-cell-injected mice (FIG. 7I).

Together, these results indicate that BissCAR T cells effectively eradicate RD AML cells (FIGS. 7B-7D) and have much reduced toxicity to sensitive human HSCs (FIGS. 7F-7I), suggesting BissCART cells as a valuable approach to treat human AML with reduced and tolerable hematopoietic toxicity.

Example 7: Generation of Unique Individual Anti-TIM3 VHHs

Figure 9:
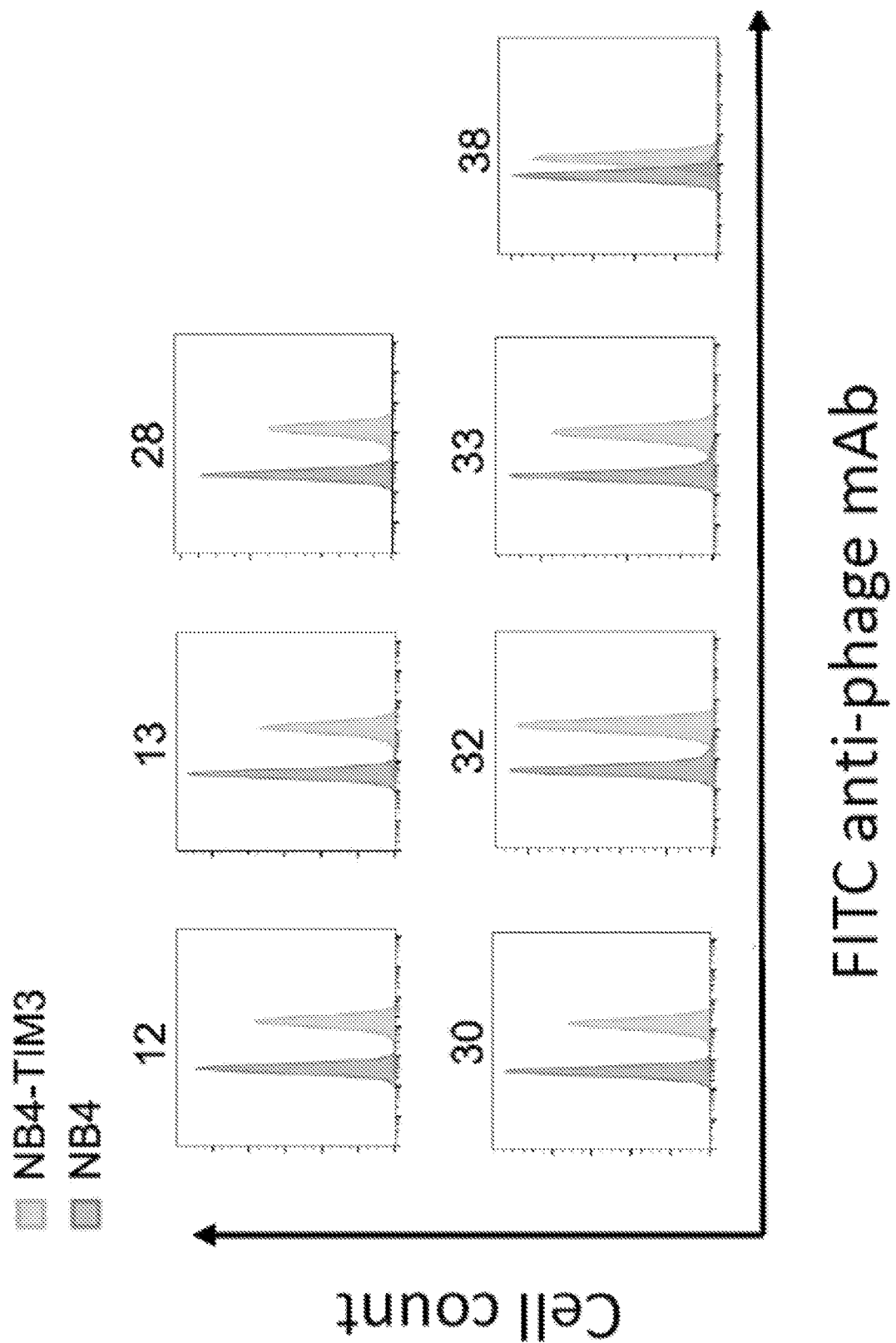
FIG. 9 illustrates identification of unique individual anti-TIM3 VHHs analyzed by flow cytometry. Isolation of individual VHH phage clones from library following TIM3-negative and positive NB4 screening.

Multiple novel VHHs targeting human TIM-3 were generated herein. Briefly, 3 llamas were immunized with purified human TIM-3 protein 4 times (Caprologics, Hardwick, MA). Peripheral blood mononuclear cells (PBMCs) were isolated, RNA extracted and cDNA synthesis performed as previously described (He et al., Blood. 2020; 135 (10): 713-723). Nanobody encoding fragments were amplified from llama PBMC cDNA with PCR primers, and then cloned into phage display vector pCOMB3X as previously described (He et al., Blood. 2020; 135 (10): 713-723). The resulting phage library was generated by infection with VCSM13 helper phage and PEG-precipitated from the bacterial supernatant in preparation for cell-surface selection, followed by panning on control NB4 cells and NB4 cells-expressing human TIM-3, using procedures as previous described (He et al., Blood. 2020; 135 (10): 713-723). Among multiple clones selected, three phage clones, i.e. VHH30, 32, and 33 showed specific binding to NB4-expressing human TIM-3, but not the TIM-3 negative NB4 cells (FIG. 9).

Example 8: Sequences of the Isolated VHHs Targeting Human TIM-3 Protein

To generate VHHs targeting human TIM-3, human recombinant extracellular TIM-3 purified from HEK293 cells was used to immununize llamas, and the resulting VHH phage display libraries were constructed. The phage VHH clones targeting TIM-3 were screened by panning through TIM-3 expressing NB4 cells. The positive clones specifically binding to TIM-3 expressing NB4 cells were isolated. DNA encoding each of the VHHs, including VHH30, 32, and 33, were sequenced. The sequences were consistent with the predicted sequences for VHHs. Each of the VHHs, with both nucleotide and amino acid sequences, are listed below.

Sequences of Isolated VHHs Targeting Human TIM-3 Protein:

```
Anti-TIM3 VHH12 nucleotide sequence
(SEQ ID NO: 19):
CAGGTGCAGCTGCAGGAGTCTGGAGGAGGATTGGTGCAGACTGGGGACT

CTCTGAGACTCTCCTGTGTAGTCTCTGGAGGCACCTTCAGAAACTATGT

TATGGGCTGGTTCCGCCAGGCTCCAGGGAAGGAGCGTGAGTTTGTGTCT

GCTATGAACTGGAGTGGCGGCATCACAGTCTATGCAGACTCCGTGAAGG

GCCGATTCACCATCTCCAGAGACAACGCCAAGAACGCGGTGTATCTGCA

AATGGGCAGCCTGAAACCTGGCGACACGGCCGTTTATTACTGTGCAGCT

GCTGCAATCGATGGTGGAACCGTCAGAAGCATTAACAGTTATGCCTACT

GGGGCCAGGGGACCCAGGTCACCGTCTCCTCAGCGGCCGCCACTAGT

Anti-TIM3 VHH12 amino acid sequence
(SEQ ID NO: 20):
QVQLQESGGGLVQTGDSLRLSCVVSGGTFRNYVMGWFRQAPGKEREFVS

AMNWSGGITVYADSVKGRFTISRDNAKNAVYLQMGSLKPGDTAVYYCAA

AAIDGGTVRSINSYAYWGQGTQVTVSSAAATS
```

Anti-TIM3 VHH13 nucleotide sequence
(SEQ ID NO: 21):
CAGGTGCAGCTGCAGGAGTCTGGAGGAGGATTGGTGCAGGCTGGGGGCT

CTCTGAGCCTCTCCTGTGCAGCCTCTGGACGCACCTTCAAGAACTATCT

CATGGCCTGGTTCCGCCAGACTCCAGGGAAGGAGCGTGAGTTTGTGCA

GCTATTACTCAGCTTGGTACTAGATCATTAAATGAAGACTTCGTGAAGG

GCCGATTCACCATCTCCAGGGACAACGCCAAGAACACGGTGTATCTGCA

AATGAACGACCTGAAAACTGACGACACGGGCGTTTATTCTTGTGCAGCA

AGCCTACAGAGTGGGGGTCACTACGGTACGCGAAGTATGACTATTGGG

GCCAGGGGACCCAGGTCACCGTCTCCTCAGCGGCCGCCACTAGT

Anti-TIM3 VHH13 amino acid sequence
(SEQ ID NO: 22):
QVQLQESGGGLVQAGGSLSLSCAASGRTFKNYLMAWFRQTPGKEREFVA

AITQLGTRSLNEDFVKGRFTISRDNAKNTVYLQMNDLKTDDTGVYSCAA

SLQSGGSLRYAKYDYWGQGTQVTVSSAAATS

Anti-TIM3 VHH28 nucleotide sequence
(SEQ ID NO: 23):
CAGGTGCAGCTGCAGGAGTCTGGGGGAGGATTGGTGCAGGCTGGGGGCT

CTCTGAGACTCTCCTGTGCAGCCTCTGAAGGCACCGTCAGCACCTACAC

CATGGCCTGGTTCCGCCAGGCTCCAGGGAAGGAGCGTGAGTTTGTAGCC

AGGATTACTGGTGTTAGTACGGCTGTGAAGGGCCGGTTCACCTTCTCCA

GAGACGAGCCCAAAAACACAGTGTATCTGCAAATGAACAGCCTGAAACC

TGAGGACACGGCCGTCTATTACTGCGCGGCACACTATTTGGGTGGTCGT

CCAGATATGCCGACTCAGTATCAATACTTGGGCCAGGGGACCCAGGTCA

CCGTCTCCTCAGCGGCCGCCACTAGT

Anti-TIM3 VHH28 amino acid sequence
(SEQ ID NO: 24):
QVQLQESGGGLVQAGGSLRLSCAASEGTVSTYTMAWFRQAPGKEREFVA

RITGVSTAVKGRFTFSRDEPKNTVYLQMNSLKPEDTAVYYCAAHYLGGR

PDMPTQYQYLGQGTQVTVSSAAATS

Anti-TIM3 VHH30 nucleotide sequence
(SEQ ID NO: 25):
CAGGTGCAGCTGCAGGAGTCTGGGGGAGGATTGGTGCAGGCTGGGGGCT

CTCTGAGACTCTCCTGTGCAGCCTCTGGATTCACGTTTGGTAGTTATGT

TATGGGCTGGTTCCGCCAGGCTCCAGGGAAGGAGCGTGAATTTGTGGCA

AGTATTAGTACGAGTGGTGGCATAACATCTTATGCAGACTCCGTGAAGG

GCCGATTCACTGTCTCCAGAGACAACGCCAAGAATACGGTCTACTTACA

AATGAACAGCCTGAAACCTGAGGACACGGCCGTTTATTACTGCGCACGA

GATCTGACATACTATCGTACTGGTGGTAGGTTACCAGATAACGCTAATG

GATATGCGTACTGGGGCCAGGGTACCCAGGTCACCGTCTCCTCAGCGGC

CGCCACTAGT

Anti-TIM3 VHH30 amino acid sequence
(SEQ ID NO: 26):
QVQLQESGGGLVQAGGSLRLSCAASGFTFGSYVMGWFRQAPGKEREFVA

SISTSGGITSYADSVKGRFTVSRDNAKNTVYLQMNSLKPEDTAVYYCAR

DLTYYRTGGRLPDNANGYAYWGQGTQVTVSSAAATS

Anti-TIM3 VHH32 nucleotide sequence
(SEQ ID NO: 27):
CAGGTGCAGCTGCAGGAGTCTGGAGGAGGCTTGGTGCAGGCTGGGGGGT

CTCTAAATCTCTCCTGTGCAGCCTCTGGAAGTTCCTTCAGACTCTATAC

CGTCGGCTGGCACCGCCAGGCGCCAGGGAAGCAGCGCGAGTTGGTCGCA

TGGATTAGTGGTGCGGGCAGCACAAACTATCATTCGTCCGTGAAGGGCC

GATTCACCATCTCCAGAGACAACGCCAAGAACACGGCACTCCTGCAAAT

GAACAACCTGGCACCTGAAGACACGGCCGTCTATTACTGTAATCTACTG

AACTACTGGGGCCAGGGGACCCAGGTCACCGTCTCCTCAGCGGCCGCCA

CTAGT

Anti-TIM3 VHH32 amino acid sequence
(SEQ ID NO: 28):
QVQLQESGGGLVQAGGSLNLSCAASGSSFRLYTVGWHRQAPGKQRELVA

WISGAGSTNYHSSVKGRFTISRDNAKNTALLQMNNLAPEDTAVYYCNLL

NYWGQGTQVTVSSAAATS

Anti-TIM3 VHH33 nucleotide sequence
(SEQ ID NO: 29):
CAGGTGCAGCTGCAGGAGTCTGGGGGAGGCTTGGTGCAGCCTGGGGGGT

CTCTGAGACTCTCCTGTGCAGTCTCTGGACTCACGCCGGATGCTTATGT

CATGGGCTGGTTCCGCCAGGCCCCAGGGAAGGAGCGCGAGGGGGTCTCA

TGTATTAGTCCTAGTGGTGGTACTACAAGCTATCCAGACTCCGTGAAGG

GCCGATTCACCATCTCCAGAGACAATGCCAAGAACACGGTGTACCTGCA

AATGAACAGCCTGAAACCTGAGGACACGGGCGTTTATTACTGTGCGGCA

GTTGCGGGCCGCTGGTGTGACTACGGCATGAACTACTACGGCAAAGGGA

CCCAGGTCACCGTCTCCTCAGCGGCCGCCACTAGT

Anti-TIM3 VHH33 amino acid sequence
(SEQ ID NO: 30):
QVQLQESGGGLVQPGGSLRLSCAVSGLTPDAYVMGWFRQAPGKEREGVS

CISPSGGTTSYPDSVKGRFTISRDNAKNTVYLQMNSLKPEDTGVYYCAA

VAGRWCDYGMNYYGKGTQVTVSSAAATS

Anti-TIM3 VHH38 nucleotide sequence
(SEQ ID NO: 31):
CAGGTGCAGCTGCAGGAGTCTGGGGGAGGTTTGGTGCAGGCTGGGGACT

CTCTGAGACTCTCCTGTGCAGTCGGACGCACGTTCAGTGCGTCAACCTT

GGGCTGGTTCCGCCAGTCTCCAGGGAAGGAGCGTGAGTTTGTCGCAGCG

ATTAGTTGGTGGCGTGGTGAGGCATACTATGGGGACTCCGTGAAGGGCC

GATTCACCATCTCCAGAGACAACACCAAGACAACGATCAATCTGCAAAT

GAATAGCCTGAAACCTGAGGACACGGCCGTTTATTACTGTGCACGAGCC

CAATTTGATGGCGCGACACGGGCAGATGACTATGACAACTGGGGTCAGG

GGACCCAGGTCACCGTCTCCTCAGCGGCCGCCACTAGT

Anti-TIM3 VHH38 amino acid sequence
(SEQ ID NO: 32):
QVQLQESGGGLVQAGDSLRLSCAVGRTFSASTLGWFRQSPGKEREFVAA

ISWWRGEAYYGDSVKGRFTISRDNTKTTINLQMNSLKPEDTAVYYCARA

QFDGATRADDYDNWGQGTQVTVSSAAATS

Figure 10A:
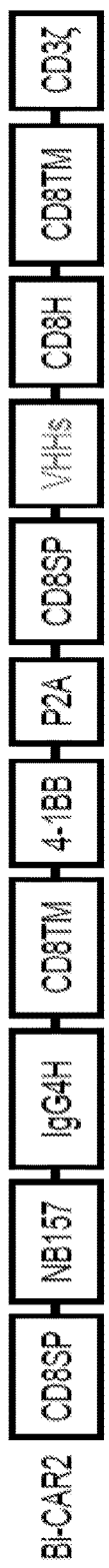
FIGS. 10A-10B illustrate bispecific CAR comprising anti-TIM3 VHHs.
Figure 10B:
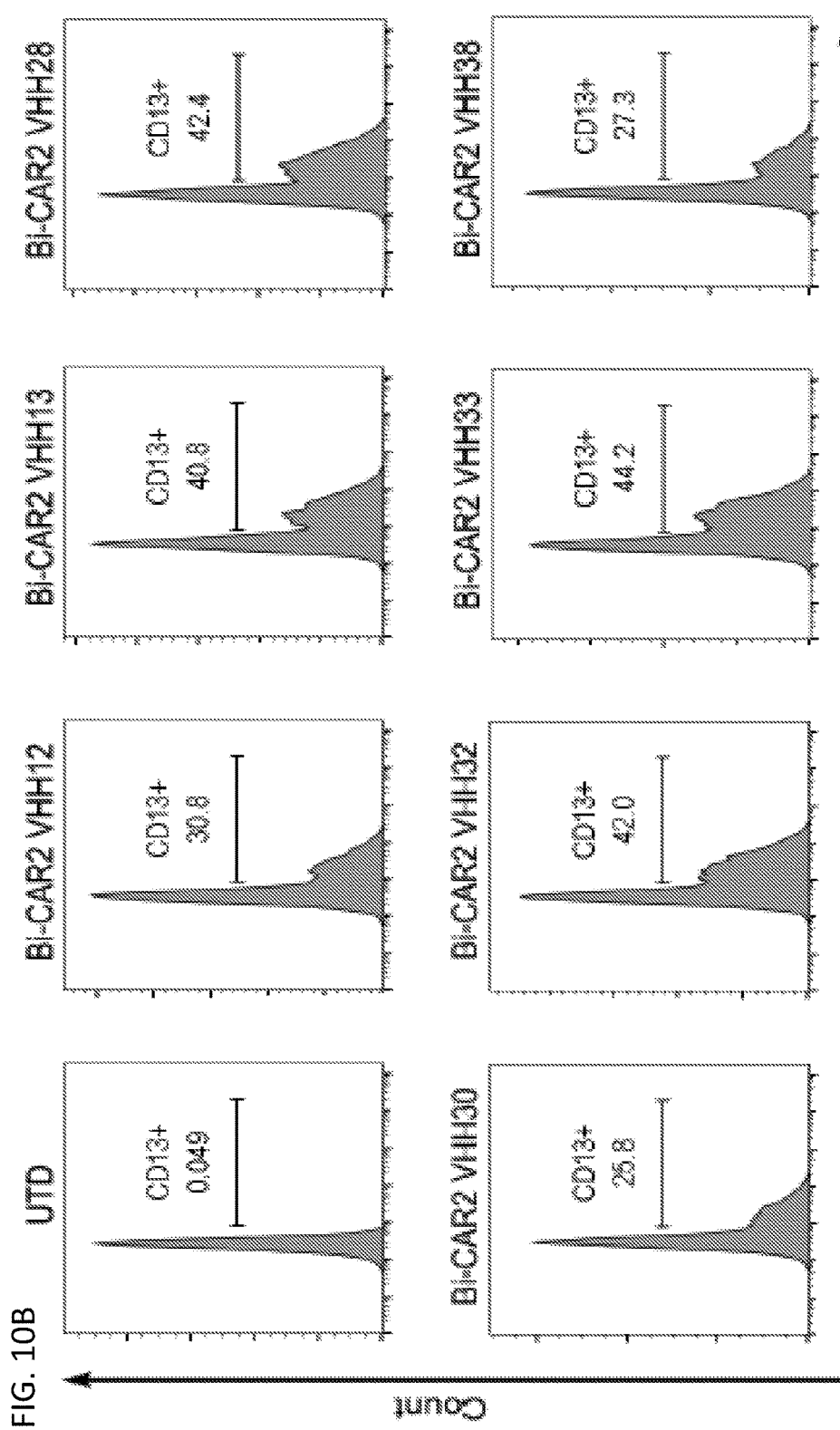
Figure 10C:
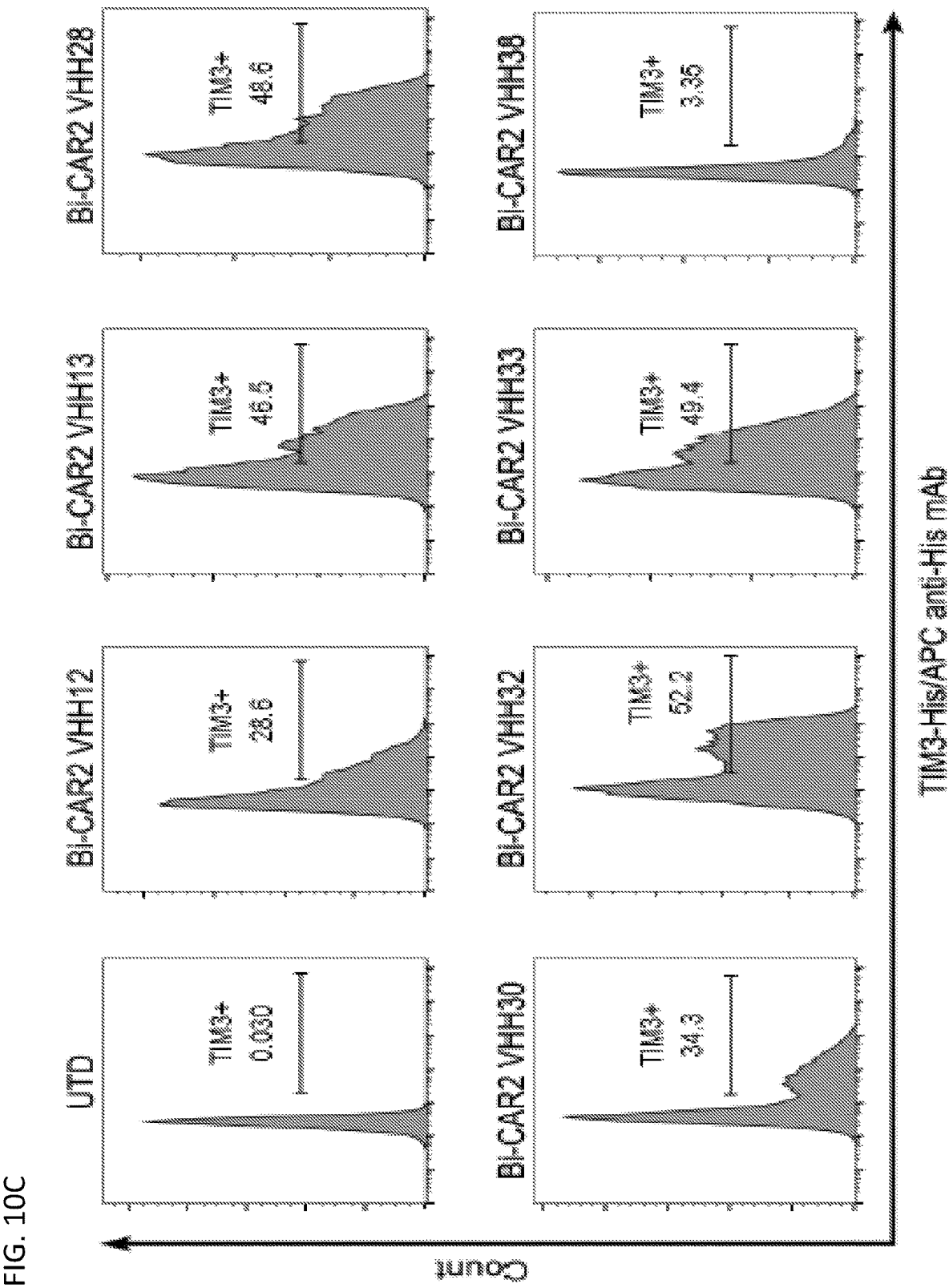

Example 9: Generation of CD13/TIM-3 VHH Bi-CARs Using Newly Generated Anti-TIM3 VHHs, and Evaluation of the biCARs on Primary Human T Cells To generate more choices and better CD13-TIM-3 biCARs, each of the three new VHHs targeting TIM-3 were cloned downstream of the 2A sequence, as shown in FIG. 10A. The resulting constructs were packaged into lentiviruses, which were transduced to human primary T cells. Flow cytometry analysis showed that transduction of T cells with each of the biCARs resulted in expression of the CARs on the T cell surface that bind both CD13 protein antigen (FIG. 10B) and TIM-3 (FIG. 10C). Sequences for each of the Bi-CARs, i.e. Bi-CAR2 VHH12 (SEQ ID NO: 33), VHH13 (SEQ ID NO: 34), VHH28 (SEQ ID NO: 35), VHH30 (SEQ ID NO: 36), VHH32 (SEQ ID NO: 37), VHH33 (SEQ ID NO: 38), and VHH38 (SEQ ID NO: 39) are provided herein. Together, these results demonstrated that each of the biCARs are expressed on the T cell surface, and are functionally capable of binding both targets, CD13 and TIM-3.

Figure 11A:
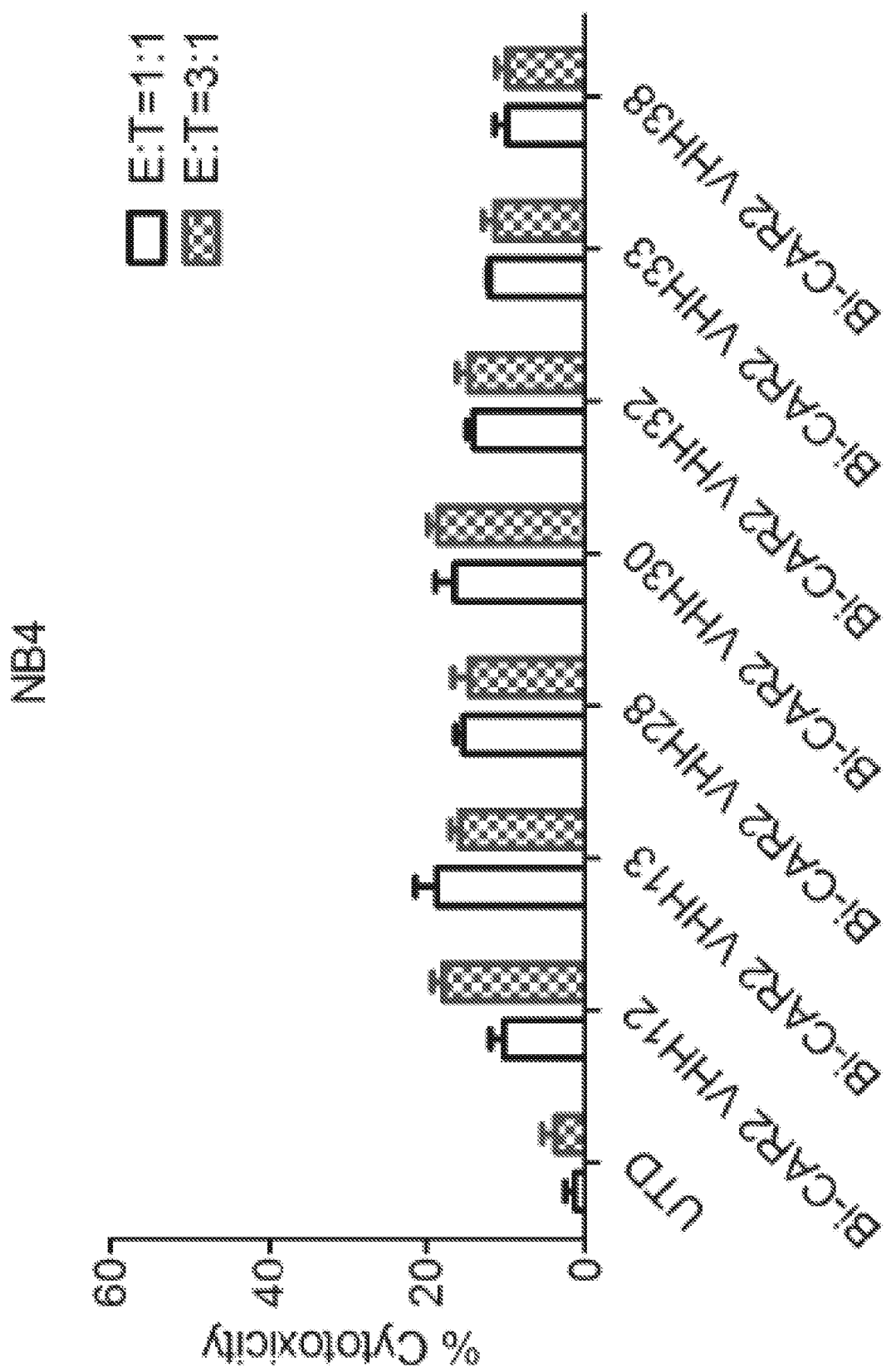
FIGS. 11A-11B illustrate the killing effects of bispecific CARs against NB4 (FIG. 11A) and NB4-TIM3 (FIG. 11B) cells.
Figure 11B:
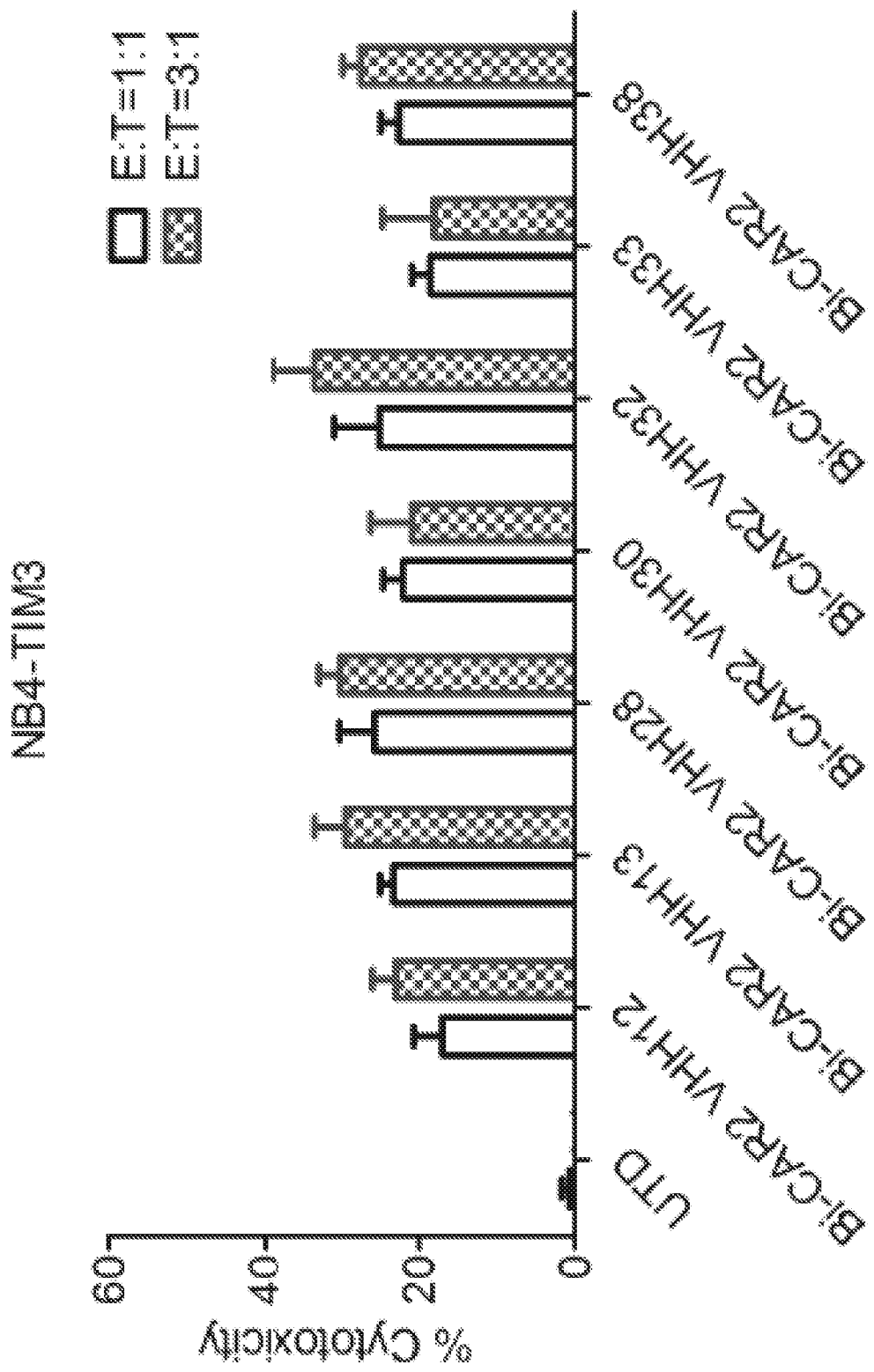
Figure 11A:
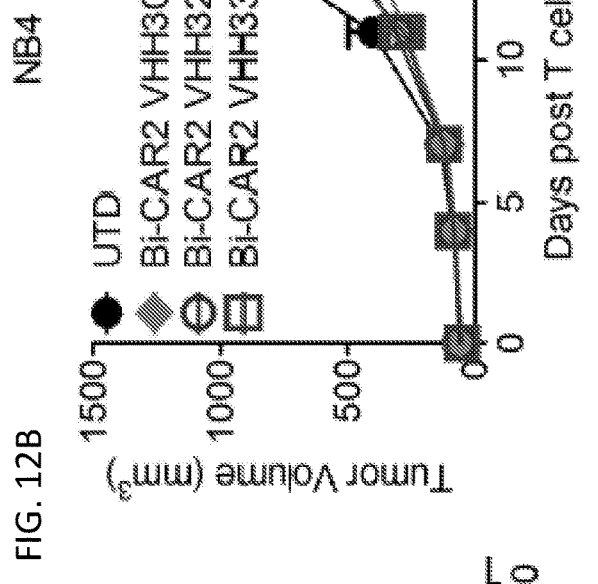
Figure 12B:
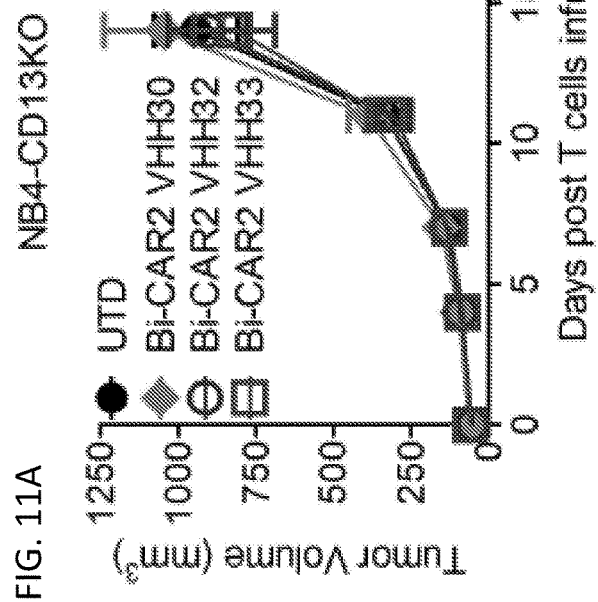
Figure 12C:
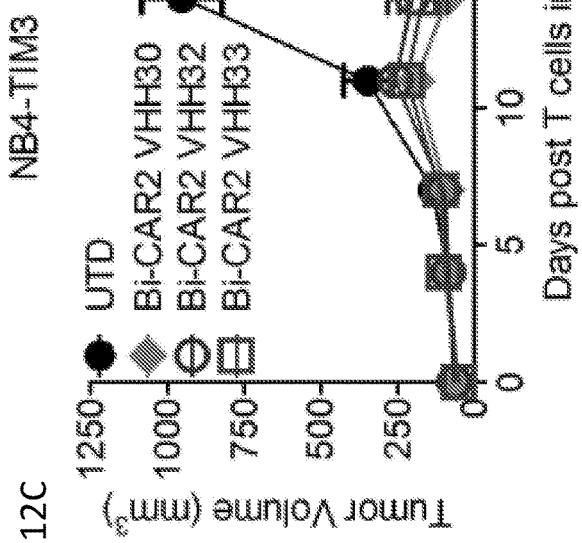
Figure 12D:
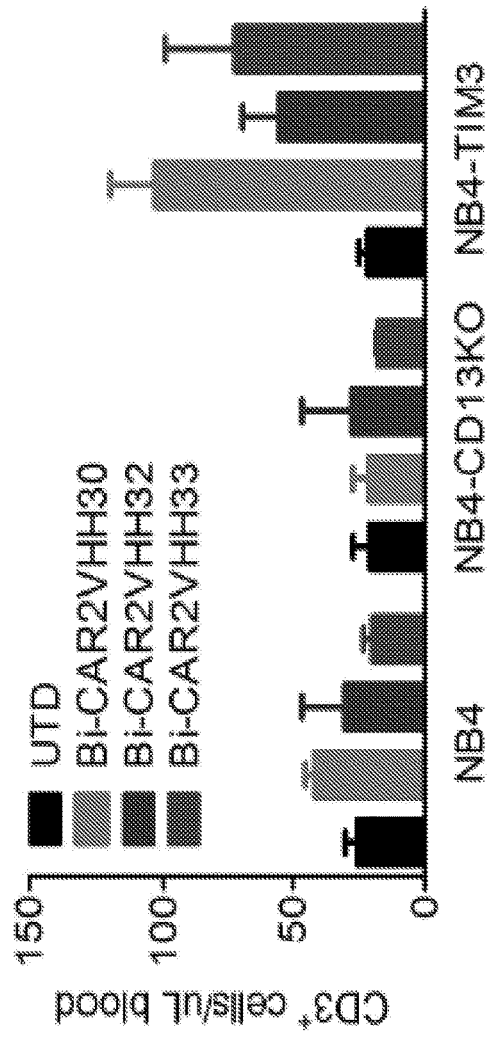
Figure 12E:
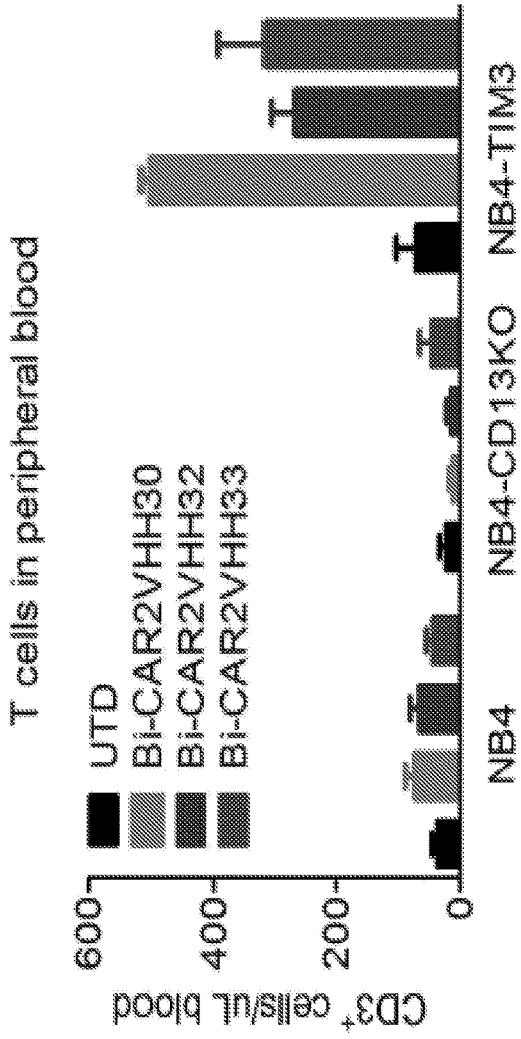

The bispecific CARs demonstrated in vitro killing against NB4 (FIG. 11A) and NB4-TIM3 (FIG. 11B) cells.

The various bispecific CARTs were also capable of suppressing tumors in vivo (FIGS. 12A-12E). The anti-tumor effects of bispecific CAR T cells against NB4-CD13KO (FIG. 12A), NB4 (FIG. 12B) and NB4-TIM3 (FIG. 12C) tumors were evaluated. Various NB4 cells were injected subcutaneously into each flank of a NSG mice (n=3), and the indicated CARTs ($5*10^6$) were injected into each mouse via tail vein at 7 days after tumor cell injection. The number of human T cells in peripheral blood of mice bearing NB4-CD13KO, NB4 and NB4-TIM3 tumors was measured by flow cytometry 7 days (FIG. 12D) and 14 days (FIG. 12E) after T cell infusion.

Figure 13A:
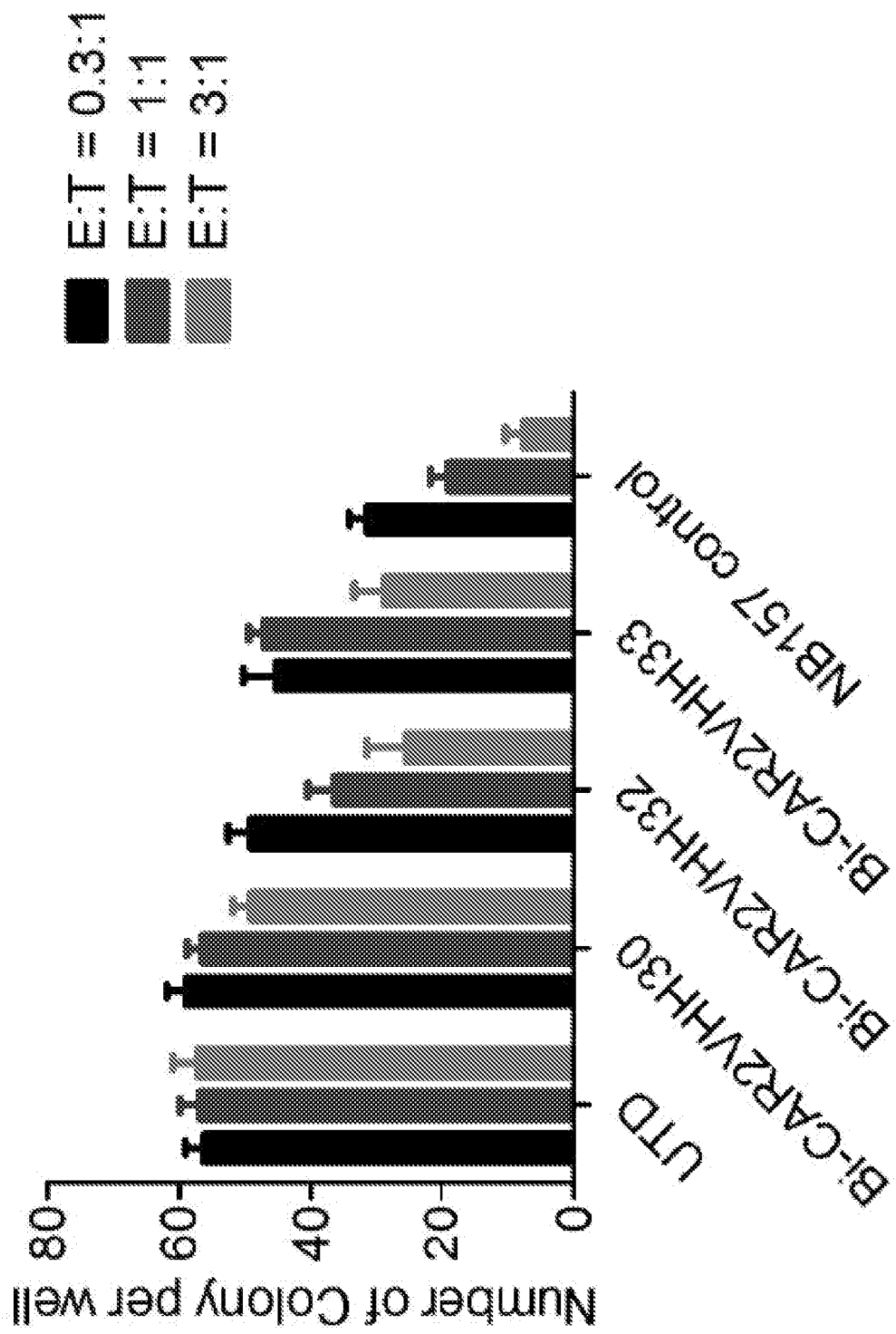
FIGS. 13A-13B illustrate data evaluating the potential toxicity of the bispecific CAR T cells against human bone marrow CD34+ cells. BM CD34+ cells (5000 per well) were co-cultured with the indicated T cells (0.3:1, 1:1, 3:1) for 4 hours. Cells were transferred into 12-well plates and cultured in MethoCult™ H4435 Enriched medium. Two weeks later, the number of clones was measured.
Figure 13B:
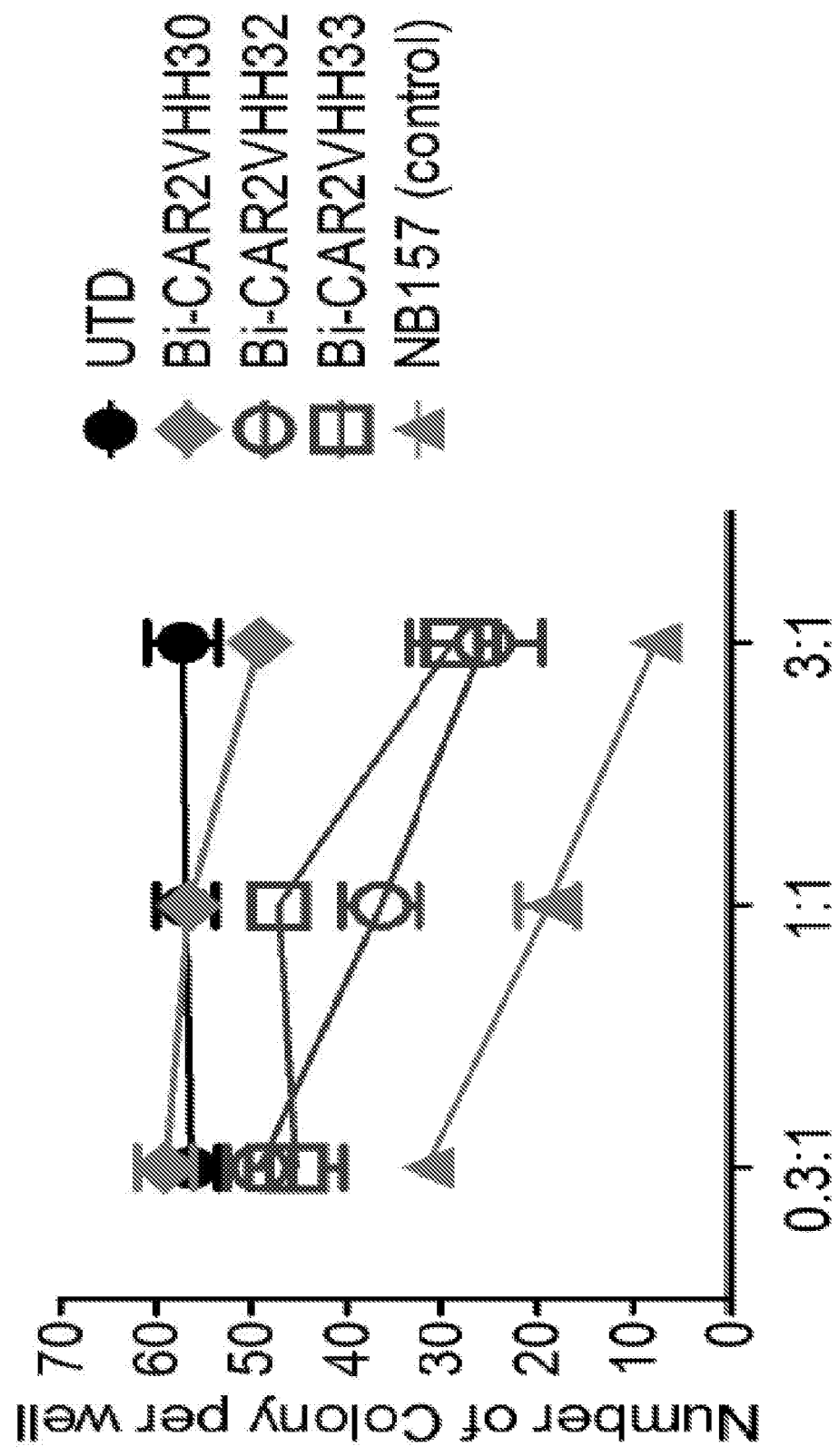

The potential toxicity of the bispecific CAR T cells against human bone marrow CD34+ cells was evaluated (FIGS. 13A-13B). BM CD34+ cells (5000 per well) were co-cultured with the indicated T cells (0.3:1, 1:1, 3:1) for 4 hours. Cells were transferred into 12-well plates and cultured in MethoCult™ H4435 Enriched medium. Two weeks later, the number of clones was measured. FIG. 13A shows the number of colonies from control (UTD) or the bispecific CART treated plates. FIG. 13B is a linear graph comparing the dose-dependent effect of the CARTs based on colony number. Overall, the results demonstrated that generation of multiple TIM-3 VHHs allowed construction of CD13-TIM3 biCARs that express the split CAR components to specifically target CD13-TIM-3 dual positive cancer cells, yet reduce the toxicity to normal cells with single target.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

---

What is claimed is:

1. A bispecific chimeric antigen receptor (CAR) comprising a first antigen binding domain capable of binding CD13, a first intracellular domain, a second antigen binding domain capable of binding TIM-3, a transmembrane domain, and a second intracellular domain, wherein the first antigen binding domain comprises the amino acid sequence set forth in SEQ ID NO: 1.

2. The bispecific CAR of claim 1, wherein the first and/or second antigen binding domain is selected from the group consisting of an antibody, a nanobody, a Fab, and an scFv.

3. The bispecific CAR of claim 1, wherein the second antigen binding domain comprises the amino acid sequence set forth in SEQ ID NO: 6.

4. The bispecific CAR of claim 1, wherein the second antigen binding domain comprises an amino acid sequence selected from the group consisting of SEQ ID NO: 20, 22, 24, 26, 28, 30, and 32.

5. The bispecific CAR of claim 1, wherein the second antigen binding domain is encoded by a nucleotide sequence selected from the group consisting of SEQ ID NO: 19, 21, 23, 25, 27, 29, and 31.

6. The bispecific CAR of claim 1, wherein the transmembrane domain comprises CD28.

7. The bispecific CAR of claim 1, wherein the first intracellular domain is selected from the group consisting of 4-1BB, CD28, and CD3 zeta.

8. The bispecific CAR of claim 1, wherein the second intracellular domain is selected from the group consisting of 4-1BB, CD28, and CD3 zeta.

9. The bispecific CAR of claim 1, wherein the bispecific CAR further comprises a hinge domain selected from the group consisting of a CD8 hinge, an IgG3s hinge, and an IgG4m hinge.

10. The bispecific CAR of claim 1, wherein the bispecific CAR is encoded by a nucleotide sequence selected from the group consisting of SEQ ID NOs: 33-39.

11. A modified T cell or precursor thereof, comprising the bispecific CAR of claim 1.

12. The cell of claim 11, wherein the T cell is autologous.

13. A nucleic acid encoding the bispecific CAR of claim 1.

14. A method for treating cancer in a subject in need thereof, the method comprising administering to the subject a modified T cell or precursor thereof comprising the bispecific CAR of claim 1.

15. The method of claim 14, wherein the cancer is acute myeloid leukemia (AML).

* * * * *

SEQUENCE LISTING

```
<160> NUMBER OF SEQ ID NOS: 40

<210> SEQ ID NO 1
<211> LENGTH: 123
<212> TYPE: PRT
<213> ORGANISM: Artificial Sequence
<220> FEATURE:
<223> OTHER INFORMATION: VHH157

<400> SEQUENCE: 1

Ala Ala Gln Ala Ala Gln Val Gln Leu Gln Glu Ser Gly Gly Gly Leu
1               5                   10                  15

Val Gln Pro Gly Gly Ser Leu Ser Leu Ser Cys Thr Ala Ser Gly Phe
            20                  25                  30

Thr Phe Ser Ser Tyr Ser Met Ala Trp Val Arg Gln Ala Pro Gly Lys
        35                  40                  45

Gly Pro Glu Trp Val Ser Gly Ile Tyr Pro Ser Asp Gly Lys Thr Arg
    50                  55                  60

Tyr Ala Asp Phe Val Lys Gly Arg Phe Ser Ile Ser Arg Asp Asn Ala
65                  70                  75                  80

Lys Asn Met Leu Tyr Leu Gln Met Asn Asn Leu Glu Pro Glu Asp Thr
                85                  90                  95

Ala Leu Tyr Tyr Cys Ala Arg Gly Ile Thr Gly Leu Gly Pro Arg Gly
            100                 105                 110

Gln Gly Thr Gln Val Thr Val Ser Ser Ala Ala
        115                 120
```

<210> SEQ ID NO 2
<211> LENGTH: 363
<212> TYPE: DNA
<213> ORGANISM: Artificial Sequence
<220> FEATURE:
<223> OTHER INFORMATION: VHH157

<400> SEQUENCE: 2

```
gcggcccagg tgcagctgca ggagtctggg ggaggcttgg tgcagcctgg ggggtctctg      60
agcctctcct gtacagcctc tggattcacg ttcagtagtt actccatggc ctgggtccgc     120
caggctccag ggaagggacc cgaatgggtc tcagggattt accccttctga tggtaagaca     180
aggtatgcag acttcgtgaa gggccgattc agcatctcca gagacaacgc caagaatatg     240
ttgtatctgc aaatgaacaa cctggaacct gaggacacgg ccctatatta ctgtgcgaga     300
ggtatcaccg gattgggacc ccggggccag gggacccagg tcaccgtctc ctcagcggcc     360
gcc                                                                    363
```

<210> SEQ ID NO 3
<211> LENGTH: 5
<212> TYPE: PRT
<213> ORGANISM: Artificial Sequence
<220> FEATURE:
<223> OTHER INFORMATION: VHH157 CDR1

<400> SEQUENCE: 3

Ser Tyr Ser Met Ala
1               5

<210> SEQ ID NO 4
<211> LENGTH: 18
<212> TYPE: PRT
<213> ORGANISM: Artificial Sequence
<220> FEATURE:
<223> OTHER INFORMATION: VHH157 CDR2

<400> SEQUENCE: 4

Gly Ile Tyr Pro Ser Asp Gly Lys Thr Arg Tyr Ala Asp Phe Val Lys
1               5                   10                  15

Gly Arg

<210> SEQ ID NO 5
<211> LENGTH: 9
<212> TYPE: PRT
<213> ORGANISM: Artificial Sequence
<220> FEATURE:
<223> OTHER INFORMATION: VHH157 CDR3

<400> SEQUENCE: 5

Ala Arg Gly Ile Thr Gly Leu Gly Pro
1               5

<210> SEQ ID NO 6
<211> LENGTH: 249
<212> TYPE: PRT
<213> ORGANISM: Artificial Sequence
<220> FEATURE:
<223> OTHER INFORMATION: TIM3 scFv

<400> SEQUENCE: 6

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr

```
                     20                  25                  30
Asn Met His Trp Ile Lys Gln Thr Pro Gly Gln Gly Leu Glu Trp Ile
             35                  40                  45

Gly Asp Ile Tyr Pro Gly Asn Gly Asp Thr Ser Tyr Asn Gln Lys Phe
         50                  55                  60

Lys Gly Lys Ala Thr Leu Thr Ala Asp Lys Ser Ser Thr Val Tyr
 65                  70                  75                  80

Met Gln Leu Ser Ser Leu Thr Ser Glu Asp Ser Ala Val Tyr Tyr Cys
                 85                  90                  95

Ala Arg Val Gly Gly Ala Phe Pro Met Asp Tyr Trp Gly Gln Gly Thr
             100                 105                 110

Ser Val Thr Val Ser Ser Gly Gly Gly Gly Ser Gly Gly Gly Gly Ser
             115                 120                 125

Gly Gly Gly Gly Ser Gly Gly Gly Ser Asp Ile Val Leu Thr Gln
         130                 135                 140

Ser Pro Ala Ser Leu Ala Val Ser Leu Gly Gln Arg Ala Thr Ile Ser
145                 150                 155                 160

Cys Arg Ala Ser Glu Ser Val Glu Tyr Tyr Gly Thr Ser Leu Met Gln
                 165                 170                 175

Trp Tyr Gln Gln Lys Pro Gly Gln Pro Pro Lys Leu Leu Ile Tyr Ala
             180                 185                 190

Ala Ser Asn Val Glu Ser Gly Val Pro Ala Arg Phe Ser Gly Ser Gly
             195                 200                 205

Ser Gly Thr Asp Phe Ser Leu Asn Ile His Pro Val Glu Glu Asp Asp
         210                 215                 220

Ile Ala Ile Tyr Phe Cys Gln Gln Ser Arg Lys Asp Pro Ser Thr Phe
225                 230                 235                 240

Gly Gly Gly Thr Lys Leu Glu Ile Lys
                 245

<210> SEQ ID NO 7
<211> LENGTH: 747
<212> TYPE: DNA
<213> ORGANISM: Artificial Sequence
<220> FEATURE:
<223> OTHER INFORMATION: TIM3 scFv

<400> SEQUENCE: 7
caggtgcaac tgcagcagcc tggggctgag ctggtgaagc tggggcctc   agtgaagatg      60 tcctgcaagg cttctggcta cacatttacc agttacaata tgcactggat aaagcagaca     120
cctggacagg gcctggaatg gattggagat atttatccag gaaatggtga cttcctac      180 aatcagaaat tcaaaggcaa ggccacattg actgcagaca atcctccag cacagtctac     240 atgcagctca gcagcctgac atctgaggac tctgcggtct attactgtgc aagagtgggg     300
ggtgcctttc ctatggacta ctggggtcaa ggaacctcag tcaccgtctc ctcaggaggc     360
ggaggatctg gcggcggagg aagtggcgga ggggatcag ggggaggcgg atctgacatt     420
gtgctcaccc aatctccagc ttctttggct gtgtctctag gcagagagc caccatctcc     480 tgcagagcca gtgaaagtgt tgaatattat ggcacaagtt taatgcagtg gtaccaacag     540
aaaccaggac agccacccaa actcctcatc tatgctgcat ccaacgtaga atctggggtc     600
cctgccaggt ttagtggcag tgggtctggg acagacttca gcctcaacat ccatcctgtg     660
gaggaggatg atattgcaat atatttctgt cagcaaagta ggaaggatcc ttcgacgttc     720
ggtggaggca ccaagctgga gatcaaa                                         747
```

```
<210> SEQ ID NO 8
<211> LENGTH: 10
<212> TYPE: PRT
<213> ORGANISM: Artificial Sequence
<220> FEATURE:
<223> OTHER INFORMATION: TIM3 CDR1

<400> SEQUENCE: 8

Gly Tyr Thr Phe Thr Ser Tyr Asn Met His
1               5                   10

<210> SEQ ID NO 9
<211> LENGTH: 17
<212> TYPE: PRT
<213> ORGANISM: Artificial Sequence
<220> FEATURE:
<223> OTHER INFORMATION: TIM3 CDR2

<400> SEQUENCE: 9

Asp Ile Tyr Pro Gly Asn Gly Asp Thr Ser Tyr Asn Gln Lys Phe Lys
1               5                   10                  15

Gly

<210> SEQ ID NO 10
<211> LENGTH: 9
<212> TYPE: PRT
<213> ORGANISM: Artificial Sequence
<220> FEATURE:
<223> OTHER INFORMATION: TIM3 CDR3

<400> SEQUENCE: 10

Val Gly Gly Ala Phe Pro Met Asp Tyr
1               5

<210> SEQ ID NO 11
<211> LENGTH: 248
<212> TYPE: PRT
<213> ORGANISM: Artificial Sequence
<220> FEATURE:
<223> OTHER INFORMATION: PNE scFv

<400> SEQUENCE: 11

His Ala Ala Arg Pro Asp Ala Val Val Thr Gln Glu Ser Ala Leu Thr
1               5                   10                  15

Ser Ser Pro Gly Glu Thr Val Thr Leu Thr Cys Arg Ser Ser Thr Gly
                20                  25                  30

Ala Val Thr Thr Ser Asn Tyr Ala Ser Trp Val Gln Glu Lys Pro Asp
            35                  40                  45

His Leu Phe Thr Gly Leu Ile Gly Gly Thr Asn Asn Arg Ala Pro Gly
        50                  55                  60

Val Pro Ala Arg Phe Ser Gly Ser Leu Ile Gly Asp Lys Ala Ala Leu
65                  70                  75                  80

Thr Ile Thr Gly Ala Gln Thr Glu Asp Glu Ala Ile Tyr Phe Cys Val
                85                  90                  95

Leu Trp Tyr Ser Asp His Trp Val Phe Gly Gly Gly Thr Lys Leu Thr
                100                 105                 110

Val Leu Gly Gly Gly Gly Ser Gly Gly Gly Ser Gly Gly Gly
            115                 120                 125

Gly Ser Gly Gly Gly Gly Ser Asp Val Gln Leu Gln Glu Ser Gly Pro
        130                 135                 140
```

```
Gly Leu Val Ala Pro Ser Gln Ser Leu Ser Ile Thr Cys Thr Val Ser
145                 150                 155                 160

Gly Phe Leu Leu Thr Asp Tyr Gly Val Asn Trp Val Arg Gln Ser Pro
                165                 170                 175

Gly Lys Gly Leu Glu Trp Leu Gly Val Ile Trp Gly Asp Gly Ile Thr
            180                 185                 190

Asp Tyr Asn Ser Ala Leu Lys Ser Arg Leu Ser Val Thr Lys Asp Asn
            195                 200                 205

Ser Lys Ser Gln Val Phe Leu Lys Met Asn Ser Leu Gln Ser Gly Asp
        210                 215                 220

Ser Ala Arg Tyr Tyr Cys Val Thr Gly Leu Phe Asp Tyr Trp Gly Gln
225                 230                 235                 240

Gly Thr Thr Leu Thr Val Ser Ser
                245
```

```
<210> SEQ ID NO 12
<211> LENGTH: 744
<212> TYPE: DNA
<213> ORGANISM: Artificial Sequence
<220> FEATURE:
<223> OTHER INFORMATION: PNE scFv

<400> SEQUENCE: 12
catgccgcta gacctgatgc cgtcgtgacc caggaaagcg ccctgacaag cagccctggc      60
gagacagtga ccctgacctg cagatctagc acaggcgccg tgaccaccag caactacgcc     120
agctgggtgc aggaaaagcc cgaccacctg ttcaccggcc tgatcggcgg caccaacaat     180
agagcacctg gcgtgcccgc cagattcagc ggctctctga tcggagataa ggccgccctg     240
accatcactg gcgcccagac agaggacgag gccatctact tttgcgtgct gtggtacagc     300
gaccactggg tgttcggcgg aggcaccaag ctgacagtgc tgggcggagg cggaggatct     360
ggcggcggag gaagtggcgg aggggatca gggggaggcg atctgatgt gcagctgcag     420
gaatctggcc caggactggt ggcccctagc cagagcctga gcatcacctg taccgtgtcc     480
ggcttcctgc tgaccgacta cggcgtgaac tgggtgcgcc agtctcctgg caagggcctg     540
gaatggctgg gagtgatctg gggcgacgga atcaccgact acaactccgc cctgaagtcc     600
cggctgagcg tgaccaagga caacagcaag agccaggtgt tcctgaagat gaacagcctg     660
cagagcggca cagcgcccg gtactattgt gtgaccggcc tgttcgacta ctggggccag     720
ggcacaaccc tgaccgtgtc tagc                                             744
```

```
<210> SEQ ID NO 13
<211> LENGTH: 477
<212> TYPE: PRT
<213> ORGANISM: Artificial Sequence
<220> FEATURE:
<223> OTHER INFORMATION: TIM3 CAR

<400> SEQUENCE: 13

Met Ala Leu Pro Val Thr Ala Leu Leu Leu Pro Leu Ala Leu Leu Leu
1               5                   10                  15

His Ala Ala Arg Pro Gly Ser Ala Ala Gln Ala Gln Val Gln Leu
            20                  25                  30

Gln Gln Pro Gly Ala Glu Leu Val Lys Pro Gly Ala Ser Val Lys Met
        35                  40                  45

Ser Cys Lys Ala Ser Gly Tyr Thr Phe Thr Ser Tyr Asn Met His Trp
    50                  55                  60
```

```
Ile Lys Gln Thr Pro Gly Gln Gly Leu Glu Trp Ile Gly Asp Ile Tyr
 65                  70                  75                  80

Pro Gly Asn Gly Asp Thr Ser Tyr Asn Gln Lys Phe Lys Gly Lys Ala
                 85                  90                  95

Thr Leu Thr Ala Asp Lys Ser Ser Thr Val Tyr Met Gln Leu Ser
            100                 105                 110

Ser Leu Thr Ser Glu Asp Ser Ala Val Tyr Tyr Cys Ala Arg Val Gly
        115                 120                 125

Gly Ala Phe Pro Met Asp Tyr Trp Gly Gln Gly Thr Ser Val Thr Val
    130                 135                 140

Ser Ser Gly Gly Gly Ser Gly Gly Gly Ser Gly Gly Gly Gly
145                 150                 155                 160

Ser Gly Gly Gly Ser Asp Ile Val Leu Thr Gln Ser Pro Ala Ser
                165                 170                 175

Leu Ala Val Ser Leu Gly Gln Arg Ala Thr Ile Ser Cys Arg Ala Ser
            180                 185                 190

Glu Ser Val Glu Tyr Tyr Gly Thr Ser Leu Met Gln Trp Tyr Gln Gln
        195                 200                 205

Lys Pro Gly Gln Pro Pro Lys Leu Leu Ile Tyr Ala Ala Ser Asn Val
    210                 215                 220

Glu Ser Gly Val Pro Ala Arg Phe Ser Gly Ser Gly Ser Gly Thr Asp
225                 230                 235                 240

Phe Ser Leu Asn Ile His Pro Val Glu Glu Asp Asp Ile Ala Ile Tyr
                245                 250                 255

Phe Cys Gln Gln Ser Arg Lys Asp Pro Ser Thr Phe Gly Gly Gly Thr
            260                 265                 270

Lys Leu Glu Ile Lys His Met Gly Gln Ala Gly Gln Ser Gly Glu Ser
        275                 280                 285

Lys Tyr Gly Pro Pro Cys Pro Pro Cys Pro Ala Ser Tyr Ile Trp Ala
    290                 295                 300

Pro Leu Ala Gly Thr Cys Gly Val Leu Leu Ser Leu Val Ile Thr
305                 310                 315                 320

Leu Tyr Cys Lys Arg Gly Arg Lys Lys Leu Leu Tyr Ile Phe Lys Gln
                325                 330                 335

Pro Phe Met Arg Pro Val Gln Thr Thr Gln Glu Glu Asp Gly Cys Ser
            340                 345                 350

Cys Arg Phe Pro Glu Glu Glu Glu Gly Gly Cys Glu Leu Arg Val Lys
        355                 360                 365

Phe Ser Arg Ser Ala Asp Ala Pro Ala Tyr Lys Gln Gly Gln Asn Gln
    370                 375                 380

Leu Tyr Asn Glu Leu Asn Leu Gly Arg Arg Glu Glu Tyr Asp Val Leu
385                 390                 395                 400

Asp Lys Arg Arg Gly Arg Asp Pro Glu Met Gly Gly Lys Pro Arg Arg
                405                 410                 415

Lys Asn Pro Gln Glu Gly Leu Tyr Asn Glu Leu Gln Lys Asp Lys Met
            420                 425                 430

Ala Glu Ala Tyr Ser Glu Ile Gly Met Lys Gly Glu Arg Arg Arg Gly
        435                 440                 445

Lys Gly His Asp Gly Leu Tyr Gln Gly Leu Ser Thr Ala Thr Lys Asp
    450                 455                 460

Thr Tyr Asp Ala Leu His Met Gln Ala Leu Pro Pro Arg
465                 470                 475
```

<210> SEQ ID NO 14
<211> LENGTH: 1434
<212> TYPE: DNA
<213> ORGANISM: Artificial Sequence
<220> FEATURE:
<223> OTHER INFORMATION: TIM3 CAR

<400> SEQUENCE: 14

```
atggccttac cagtgaccgc cttgctcctg ccgctggcct tgctgctcca cgccgccagg      60
ccgggatccg cggcccaggc ggcccaggtg caactgcagc agcctggggc tgagctggtg     120
aagcctgggg cctcagtgaa gatgtcctgc aaggcttctg gctacacatt taccagttac     180
aatatgcact ggataaagca gacacctgga cagggcctgg aatggattgg agatatttat     240
ccaggaaatg gtgatacttc ctacaatcag aaattcaaag gcaaggccac attgactgca     300
gacaaatcct ccagcacagt ctacatgcag ctcagcagcc tgacatctga ggactctgcg     360
gtctattact gtgcaagagt gggggggtgcc tttcctatgg actactgggg tcaaggaacc     420
tcagtcaccg tctcctcagg aggcggagga tctggcggcg aggaagtgg cggagggga     480
tcaggggag gcggatctga cattgtgctc acccaatctc cagcttcttt ggctgtgtct     540
ctagggcaga gagccaccat ctcctgcaga gccagtgaaa gtgttgaata ttatggcaca     600
agtttaatgc agtggtacca acagaaacca ggacagccac ccaaactcct catctatgct     660
gcatccaacg tagaatctgg ggtccctgcc aggtttagtg gcagtgggtc tgggacagac     720
ttcagcctca acatccatcc tgtggaggag gatgatattg caatatattt ctgtcagcaa     780
agtaggaagg atccttcgac gttcggtgga ggcaccaagc tggagatcaa acatatgggc     840
caggccggcc agtccggaga gagcaagtac ggccctccct gccccccttg ccctgctagc     900
tacatctggg cgcccttggc cgggacttgt ggggtccttc cctgtcact ggttatcacc     960
ctttactgca acgggcag aagaaactc ctgtatatat caaacaacc atttatgaga    1020
ccagtacaaa ctactcaaga ggaagatggc tgtagctgcc gatttccaga agaagaagaa    1080
ggaggatgtg aactgagagt gaagttcagc aggagcgcag acgccccgc gtacaagcag    1140
ggccagaacc agctctataa cgagctcaat ctaggacgaa gagaggagta cgatgttttg    1200
gacaagagac gtggccggga ccctgagatg gggggaaagc cgagaaggaa gaaccctcag    1260
gaaggcctgt acaatgaact gcagaaagat aagatggcgg aggcctacag tgagattggg    1320
atgaaaggcg agcgccggag gggcaagggg cacgatggcc tttaccaggg tctcagtaca    1380
gccaccaagg acacctacga cgcccttcac atgcaggccc tgccccctcg ctaa          1434
```

<210> SEQ ID NO 15
<211> LENGTH: 733
<212> TYPE: PRT
<213> ORGANISM: Artificial Sequence
<220> FEATURE:
<223> OTHER INFORMATION: TIM3 CD13 biCAR

<400> SEQUENCE: 15

Met Ala Leu Pro Val Thr Ala Leu Leu Leu Pro Leu Ala Leu Leu Leu
1               5                   10                  15

His Ala Ala Arg Pro Gly Ser Ala Ala Gln Ala Gln Val Gln Leu
            20                  25                  30

Gln Glu Ser Gly Gly Gly Leu Val Gln Pro Gly Gly Ser Leu Ser Leu
        35                  40                  45

Ser Cys Thr Ala Ser Gly Phe Thr Phe Ser Ser Tyr Ser Met Ala Trp
    50                  55                  60

-continued

```
Val Arg Gln Ala Pro Gly Lys Gly Pro Glu Trp Val Ser Gly Ile Tyr
 65                  70                  75                  80

Pro Ser Asp Gly Lys Thr Arg Tyr Ala Asp Phe Val Lys Gly Arg Phe
                 85                  90                  95

Ser Ile Ser Arg Asp Asn Ala Lys Asn Met Leu Tyr Leu Gln Met Asn
            100                 105                 110

Asn Leu Glu Pro Glu Asp Thr Ala Leu Tyr Tyr Cys Ala Arg Gly Ile
        115                 120                 125

Thr Gly Leu Gly Pro Arg Gly Gln Gly Thr Gln Val Thr Val Ser Ser
    130                 135                 140

Ala Ala Ala Thr Ser Gly Gln Thr Val Ser Ser Glu Ser Lys Tyr Gly
145                 150                 155                 160

Pro Pro Cys Pro Pro Cys Pro Tyr Ile Trp Ala Pro Leu Ala Gly Thr
                165                 170                 175

Cys Gly Val Leu Leu Leu Ser Leu Val Ile Thr Leu Tyr Cys Arg Val
            180                 185                 190

Lys Phe Ser Arg Ser Ala Asp Ala Pro Ala Tyr Lys Gln Gly Gln Asn
        195                 200                 205

Gln Leu Tyr Asn Glu Leu Asn Leu Gly Arg Arg Glu Glu Tyr Asp Val
    210                 215                 220

Leu Asp Lys Arg Arg Gly Arg Asp Pro Glu Met Gly Gly Lys Pro Arg
225                 230                 235                 240

Arg Lys Asn Pro Gln Glu Gly Leu Tyr Asn Glu Leu Gln Lys Asp Lys
                245                 250                 255

Met Ala Glu Ala Tyr Ser Glu Ile Gly Met Lys Gly Glu Arg Arg Arg
            260                 265                 270

Gly Lys Gly His Asp Gly Leu Tyr Gln Gly Leu Ser Thr Ala Thr Lys
        275                 280                 285

Asp Thr Tyr Asp Ala Leu His Met Gln Ala Leu Pro Pro Arg Leu Glu
    290                 295                 300

Gly Ser Gly Ala Thr Asn Phe Ser Leu Leu Lys Gln Ala Gly Asp Val
305                 310                 315                 320

Glu Glu Asn Pro Gly Pro Pro Arg Met Ala Leu Pro Val Thr Ala Leu
                325                 330                 335

Leu Leu Pro Leu Ala Leu Leu Leu His Ala Ala Arg Pro Gly Ser Ala
            340                 345                 350

Ala Gln Ala Ala Gln Val Gln Leu Gln Gln Pro Gly Ala Glu Leu Val
        355                 360                 365

Lys Pro Gly Ala Ser Val Lys Met Ser Cys Lys Ala Ser Gly Tyr Thr
    370                 375                 380

Phe Thr Ser Tyr Asn Met His Trp Ile Lys Gln Thr Pro Gly Gln Gly
385                 390                 395                 400

Leu Glu Trp Ile Gly Asp Ile Tyr Pro Gly Asn Gly Asp Thr Ser Tyr
                405                 410                 415

Asn Gln Lys Phe Lys Gly Lys Ala Thr Leu Thr Ala Asp Lys Ser Ser
            420                 425                 430

Ser Thr Val Tyr Met Gln Leu Ser Ser Leu Thr Ser Glu Asp Ser Ala
        435                 440                 445

Val Tyr Tyr Cys Ala Arg Val Gly Ala Phe Pro Met Asp Tyr Trp
    450                 455                 460

Gly Gln Gly Thr Ser Val Thr Val Ser Ser Gly Gly Gly Gly Ser Gly
465                 470                 475                 480

Gly Gly Gly Ser Gly Gly Gly Gly Ser Gly Gly Gly Gly Ser Asp Ile
```

```
                485                 490                 495
Val Leu Thr Gln Ser Pro Ala Ser Leu Ala Val Ser Leu Gly Gln Arg
                500                 505                 510

Ala Thr Ile Ser Cys Arg Ala Ser Glu Ser Val Glu Tyr Tyr Gly Thr
                515                 520                 525

Ser Leu Met Gln Trp Tyr Gln Gln Lys Pro Gly Gln Pro Pro Lys Leu
            530                 535                 540

Leu Ile Tyr Ala Ala Ser Asn Val Glu Ser Gly Val Pro Ala Arg Phe
545                 550                 555                 560

Ser Gly Ser Gly Ser Gly Thr Asp Phe Ser Leu Asn Ile His Pro Val
                565                 570                 575

Glu Glu Asp Asp Ile Ala Ile Tyr Phe Cys Gln Gln Ser Arg Lys Asp
            580                 585                 590

Pro Ser Thr Phe Gly Gly Gly Thr Lys Leu Glu Ile Lys His Met Gly
            595                 600                 605

Lys His Leu Cys Pro Ser Pro Leu Phe Pro Gly Pro Ser Lys Pro Phe
        610                 615                 620

Trp Val Leu Val Val Val Gly Gly Val Leu Ala Cys Tyr Ser Leu Leu
625                 630                 635                 640

Val Thr Val Ala Phe Ile Ile Phe Trp Val Arg Ser Lys Arg Ser Arg
                645                 650                 655

Leu Leu His Ser Asp Tyr Met Asn Met Thr Pro Arg Arg Pro Gly Pro
            660                 665                 670

Thr Arg Lys His Tyr Gln Pro Tyr Ala Pro Pro Arg Asp Phe Ala Ala
                675                 680                 685

Tyr Arg Ser Lys Arg Gly Arg Lys Lys Leu Leu Tyr Ile Phe Lys Gln
            690                 695                 700

Pro Phe Met Arg Pro Val Gln Thr Thr Gln Glu Glu Asp Gly Cys Ser
705                 710                 715                 720

Cys Arg Phe Pro Glu Glu Glu Glu Gly Gly Cys Glu Leu
                725                 730
```

<210> SEQ ID NO 16
<211> LENGTH: 2202
<212> TYPE: DNA
<213> ORGANISM: Artificial Sequence
<220> FEATURE:
<223> OTHER INFORMATION: TIM3 CD13 biCAR

<400> SEQUENCE: 16

```
atggccttac cagtgaccgc cttgctcctg ccgctggcct tgctgctcca cgccgccagg     60
ccgggatccg cggcccaggc ggcccaggtg cagctgcagg agtctggggg aggcttggtg    120
cagcctgggg gtctctgag cctctcctgt acagcctctg gattcacgtt cagtagttac    180
tccatggcct gggtccgcca ggctccaggg aagggaccg aatgggtctc agggatttac    240
ccttctgatg gtaagacaag gtatgcagac ttcgtgaagg gccgattcag catctccaga    300
gacaacgcca agaatatgtt gtatctgcaa atgaacaacc tggaacctga ggacacggcc    360
ctatattact gtgcgagagg tatcaccgga ttgggacccc ggggccaggg gacccaggtc    420
accgtctcct cagcggccgc cactagtggc cagaccgtgt ctagcgagtc taagtacggc    480
cctccctgcc ctccttgccc atacatctgg gcgcccttgg ccgggacttg tggggtcctt    540
ctcctgtcac tggttatcac cctttactgc agagtgaagt tcagcaggag cgcagacgcc    600
cccgcgtaca agcagggcca gaaccagctc tataacgagc tcaatctagg acgaagagag    660
```

| | |
|---|---|
| gagtacgatg tttttggacaa gagacgtggc cgggaccctg agatggggggg aaagccgaga | 720 |
| aggaagaacc ctcaggaagg cctgtacaat gaactgcaga aagataagat ggcggaggcc | 780 |
| tacagtgaga ttgggatgaa aggcgagcgc cggaggggca aggggcacga tggcctttac | 840 |
| cagggtctca gtacagccac caaggacacc tacgacgccc ttcacatgca ggccctgccc | 900 |
| cctcgcctcg agggaagcgg agctactaac ttcagcctgc tgaagcaggc tggagacgtg | 960 |
| gaggagaacc ctggacctcc taggatggcc ttaccagtga ccgccttgct cctgccgctg | 1020 |
| gccttgctgc tccacgccgc caggccggga tccgcggccc aggcggccca ggtgcaactg | 1080 |
| cagcagcctg gggctgagct ggtgaagcct ggggcctcag tgaagatgtc ctgcaaggct | 1140 |
| tctggctaca catttaccag ttacaatatg cactggataa agcagacacc tggacagggc | 1200 |
| ctggaatgga ttggagatat ttatccagga aatggtgata cttcctacaa tcagaaattc | 1260 |
| aaaggcaagg ccacattgac tgcagacaaa tcctccagca cagtctacat gcagctcagc | 1320 |
| agcctgacat ctgaggactc tgcggtctat tactgtgcaa gagtggggggg tgccttttcct | 1380 |
| atggactact ggggtcaagg aacctcagtc accgtctcct caggaggcgg aggatctggc | 1440 |
| ggcggaggaa gtggcggagg gggatcaggg ggaggcggat ctgacattgt gctcacccaa | 1500 |
| tctccagctt ctttggctgt gtctctaggg cagagagcca ccatctcctg cagagccagt | 1560 |
| gaaagtgttg aatattatgg cacaagttta atgcagtggt accaacagaa accaggacag | 1620 |
| ccacccaaac tcctcatcta tgctgcatcc aacgtagaat ctggggtccc tgccaggttt | 1680 |
| agtggcagtg ggtctgggac agacttcagc ctcaacatcc atcctgtgga ggaggatgat | 1740 |
| attgcaatat atttctgtca gcaaagtagg aaggatcctt cgacgttcgg tggaggcacc | 1800 |
| aagctggaga tcaaacatat ggggaaacac ctttgtccaa gtcccctatt tcccggacct | 1860 |
| tctaagccct ttgggtgct ggtggtggtt ggtggagtcc tggcttgcta tagcttgcta | 1920 |
| gtaacagtgg cctttattat tttctgggtg aggagtaaga ggagcaggct cctgcacagt | 1980 |
| gactacatga acatgactcc ccgccgcccc gggcccaccc gcaagcatta ccagccctat | 2040 |
| gcccaccac gcgacttcgc agcctatcgc tccaaacggg gcagaaagaa actcctgtat | 2100 |
| atattcaaac aaccatttat gagaccagta caaactactc aagaggaaga tggctgtagc | 2160 |
| tgccgatttc cagaagaaga agaaggagga tgtgaactgt aa | 2202 |

<210> SEQ ID NO 17
<211> LENGTH: 842
<212> TYPE: PRT
<213> ORGANISM: Artificial Sequence
<220> FEATURE:
<223> OTHER INFORMATION: TIM3 PNE inducible bispecific CAR

<400> SEQUENCE: 17

Met Ala Leu Pro Val Thr Ala Leu Leu Leu Pro Leu Ala Leu Leu Leu
1               5                   10                  15

His Ala Ala Arg Pro Gly Ser Ala Ala Gln Ala Ala Gln Val Gln Leu
            20                  25                  30

Gln Gln Pro Gly Ala Glu Leu Val Lys Pro Gly Ala Ser Val Lys Met
        35                  40                  45

Ser Cys Lys Ala Ser Gly Tyr Thr Phe Thr Ser Tyr Asn Met His Trp
    50                  55                  60

Ile Lys Gln Thr Pro Gly Gln Gly Leu Glu Trp Ile Gly Asp Ile Tyr
65                  70                  75                  80

Pro Gly Asn Gly Asp Thr Ser Tyr Asn Gln Lys Phe Lys Gly Lys Ala
                85                  90                  95

-continued

```
Thr Leu Thr Ala Asp Lys Ser Ser Thr Val Tyr Met Gln Leu Ser
            100                 105                 110

Ser Leu Thr Ser Glu Asp Ser Ala Val Tyr Tyr Cys Ala Arg Val Gly
            115                 120                 125

Gly Ala Phe Pro Met Asp Tyr Trp Gly Gln Gly Thr Ser Val Thr Val
130                 135                 140

Ser Ser Gly Gly Gly Gly Ser Gly Gly Gly Ser Gly Gly Gly Gly
145                 150                 155                 160

Ser Gly Gly Gly Ser Asp Ile Val Leu Thr Gln Ser Pro Ala Ser
                165                 170                 175

Leu Ala Val Ser Leu Gly Gln Arg Ala Thr Ile Ser Cys Arg Ala Ser
            180                 185                 190

Glu Ser Val Glu Tyr Tyr Gly Thr Ser Leu Met Gln Trp Tyr Gln Gln
            195                 200                 205

Lys Pro Gly Gln Pro Pro Lys Leu Leu Ile Tyr Ala Ala Ser Asn Val
            210                 215                 220

Glu Ser Gly Val Pro Ala Arg Phe Ser Gly Ser Gly Ser Gly Thr Asp
225                 230                 235                 240

Phe Ser Leu Asn Ile His Pro Val Glu Glu Asp Asp Ile Ala Ile Tyr
            245                 250                 255

Phe Cys Gln Gln Ser Arg Lys Asp Pro Ser Thr Phe Gly Gly Gly Thr
            260                 265                 270

Lys Leu Glu Ile Lys His Met Gly Lys His Leu Cys Pro Ser Pro Leu
            275                 280                 285

Phe Pro Gly Pro Ser Lys Pro Phe Trp Val Leu Val Val Val Gly Gly
            290                 295                 300

Val Leu Ala Cys Tyr Ser Leu Leu Val Thr Val Ala Phe Ile Ile Phe
305                 310                 315                 320

Trp Val Arg Ser Lys Arg Ser Arg Leu Leu His Ser Asp Tyr Met Asn
            325                 330                 335

Met Thr Pro Arg Arg Pro Gly Pro Thr Arg Lys His Tyr Gln Pro Tyr
            340                 345                 350

Ala Pro Pro Arg Asp Phe Ala Ala Tyr Arg Ser Lys Arg Gly Arg Lys
            355                 360                 365

Lys Leu Leu Tyr Ile Phe Lys Gln Pro Phe Met Arg Pro Val Gln Thr
            370                 375                 380

Thr Gln Glu Glu Asp Gly Cys Ser Cys Arg Phe Pro Glu Glu Glu Glu
385                 390                 395                 400

Gly Gly Cys Glu Leu Leu Glu Gly Ser Gly Ala Thr Asn Phe Ser Leu
                405                 410                 415

Leu Lys Gln Ala Gly Asp Val Glu Glu Asn Pro Gly Pro Pro Arg Met
            420                 425                 430

Ala Leu Pro Val Thr Ala Leu Leu Leu Pro Leu Ala Leu Leu Leu His
            435                 440                 445

Ala Ala Arg Pro Asp Ala Val Val Thr Gln Glu Ser Ala Leu Thr Ser
            450                 455                 460

Ser Pro Gly Glu Thr Val Thr Leu Thr Cys Arg Ser Ser Thr Gly Ala
465                 470                 475                 480

Val Thr Thr Ser Asn Tyr Ala Ser Trp Val Gln Glu Lys Pro Asp His
                485                 490                 495

Leu Phe Thr Gly Leu Ile Gly Gly Thr Asn Asn Arg Ala Pro Gly Val
            500                 505                 510
```

```
Pro Ala Arg Phe Ser Gly Ser Leu Ile Gly Asp Lys Ala Leu Thr
            515                 520                 525
Ile Thr Gly Ala Gln Thr Glu Asp Glu Ala Ile Tyr Phe Cys Val Leu
        530                 535                 540
Trp Tyr Ser Asp His Trp Val Phe Gly Gly Gly Thr Lys Leu Thr Val
545                 550                 555                 560
Leu Gly Gly Gly Gly Ser Gly Gly Gly Ser Gly Gly Gly Gly
                565                 570                 575
Ser Gly Gly Gly Gly Ser Asp Val Gln Leu Gln Glu Ser Gly Pro Gly
                580                 585                 590
Leu Val Ala Pro Ser Gln Ser Leu Ser Ile Thr Cys Thr Val Ser Gly
            595                 600                 605
Phe Leu Leu Thr Asp Tyr Gly Val Asn Trp Val Arg Gln Ser Pro Gly
        610                 615                 620
Lys Gly Leu Glu Trp Leu Gly Val Ile Trp Gly Asp Gly Ile Thr Asp
625                 630                 635                 640
Tyr Asn Ser Ala Leu Lys Ser Arg Leu Ser Val Thr Lys Asp Asn Ser
                645                 650                 655
Lys Ser Gln Val Phe Leu Lys Met Asn Ser Leu Gln Ser Gly Asp Ser
            660                 665                 670
Ala Arg Tyr Tyr Cys Val Thr Gly Leu Phe Asp Tyr Trp Gly Gln Gly
        675                 680                 685
Thr Thr Leu Thr Val Ser Ser Glu Ser Lys Tyr Gly Pro Pro Cys Pro
690                 695                 700
Pro Cys Pro Tyr Ile Trp Ala Pro Leu Ala Gly Thr Cys Gly Val Leu
705                 710                 715                 720
Leu Leu Ser Leu Val Ile Thr Leu Tyr Cys Arg Val Lys Phe Ser Arg
                725                 730                 735
Ser Ala Asp Ala Pro Ala Tyr Lys Gln Gly Gln Asn Gln Leu Tyr Asn
            740                 745                 750
Glu Leu Asn Leu Gly Arg Arg Glu Glu Tyr Asp Val Leu Asp Lys Arg
        755                 760                 765
Arg Gly Arg Asp Pro Glu Met Gly Gly Lys Pro Arg Arg Lys Asn Pro
770                 775                 780
Gln Glu Gly Leu Tyr Asn Glu Leu Gln Lys Asp Lys Met Ala Glu Ala
785                 790                 795                 800
Tyr Ser Glu Ile Gly Met Lys Gly Glu Arg Arg Gly Lys Gly His
                805                 810                 815
Asp Gly Leu Tyr Gln Gly Leu Ser Thr Ala Thr Lys Asp Thr Tyr Asp
            820                 825                 830
Ala Leu His Met Gln Ala Leu Pro Pro Arg
        835                 840

<210> SEQ ID NO 18
<211> LENGTH: 2529
<212> TYPE: DNA
<213> ORGANISM: Artificial Sequence
<220> FEATURE:
<223> OTHER INFORMATION: TIM3 PNE inducible bispecific CAR

<400> SEQUENCE: 18
atggccttac cagtgaccgc cttgctcctg ccgctggcct tgctgctcca cgccgccagg     60
ccgggatccg cggcccaggc ggcccaggtg caactgcagc agcctggggc tgagctggtg    120
aagcctgggg cctcagtgaa gatgtcctgc aaggcttctg gctacacatt taccagttac    180
```

-continued

```
aatatgcact ggataaagca gacacctgga cagggcctgg aatggattgg agatatttat    240
ccaggaaatg gtgatacttc ctacaatcag aaattcaaag gcaaggccac attgactgca    300
gacaaatcct ccagcacagt ctacatgcag ctcagcagcc tgacatctga ggactctgcg    360
gtctattact gtgcaagagt gggggtgcc tttcctatgg actactgggg tcaaggaacc    420
tcagtcaccg tctcctcagg aggcggagga tctggcggcg gaggaagtgg cggaggggga    480
tcagggggag gcggatctga cattgtgctc acccaatctc cagcttcttt ggctgtgtct    540
ctagggcaga gagccaccat ctcctgcaga gccagtgaaa gtgttgaata ttatggcaca    600
agtttaatgc agtggtacca acagaaacca ggacagccac ccaaactcct catctatgct    660
gcatccaacg tagaatctgg ggtccctgcc aggtttagtg gcagtgggtc tgggacagac    720
ttcagcctca acatccatcc tgtggaggag gatgatattg caatatattt ctgtcagcaa    780
agtaggaagg atccttcgac gttcggtgga ggcaccaagc tggagatcaa acatatgggg    840
aaacaccttt gtccaagtcc cctatttccc ggaccttcta agcccttttg ggtgctggtg    900
gtggttggtg gagtcctggc ttgctatagc ttgctagtaa cagtggcctt tattattttc    960
tgggtgagga gtaagaggag caggctcctg cacagtgact acatgaacat gactccccgc   1020
cgccccgggc ccacccgcaa gcattaccag ccctatgccc caccacgcga cttcgcagcc   1080
tatcgctcca acggggcag aaagaaactc ctgtatatat tcaaacaacc atttatgaga   1140
ccagtacaaa ctactcaaga ggaagatggc tgtagctgcc gatttccaga agaagaagaa   1200
ggaggatgtg aactgctcga gggaagcgga gctactaact tcagcctgct gaagcaggct   1260
ggagacgtgg aggagaaccc tggacctcct aggatggctc tgcctgtgac agctctgctg   1320
ctgcctctgg ccctgctgct gcatgccgct agacctgatg ccgtcgtgac ccaggaaagc   1380
gccctgacaa gcagccctgg cgagacagtg accctgacct gcagatctag cacaggcgcc   1440
gtgaccacca gcaactacgc cagctgggtg caggaaaagc ccgaccacct gttcaccggc   1500
ctgatcggcg gcaccaacaa tagagcacct ggcgtgcccg ccagattcag cggctctctg   1560
atcggagata aggccgccct gaccatcact ggcgcccaga cagaggacga ggccatctac   1620
ttttgcgtgc tgtggtacag cgaccactgg gtgttcggcg gaggcaccaa gctgacagtg   1680
ctgggcggag gcggaggatc tggcggcgga ggaagtggcg gaggggatc aggggaggc   1740 ggatctgatg tgcagctgca ggaatctggc ccaggactgg tgcccctag ccagagcctg   1800 agcatcacct gtaccgtgtc cggcttcctg ctgaccgact acggcgtgaa ctgggtgcgc   1860
cagtctcctg gcaagggcct ggaatggctg ggagtgatct ggggcgacgg aatcaccgac   1920
tacaactccg ccctgaagtc ccggctgagc gtgaccaagg acaacagcaa gagccaggtg   1980
ttcctgaaga tgaacagcct gcagagcggc gacagcgccc ggtactattg tgtgaccggc   2040
ctgttcgact actggggcca gggcacaacc ctgaccgtgt ctagcgagtc taagtacggc   2100
cctccctgcc ctccttgccc atacatctgg gcgcccttgg ccgggacttg tggggtcctt   2160
ctcctgtcac tggttatcac cctttactgc agagtgaagt tcagcaggag cgcagacgcc   2220
cccgcgtaca gcagggcca gaaccagctc tataacgagc tcaatctagg acgaagagag   2280
gagtacgatg ttttggacaa gagacgtggc cgggaccctg agatgggggg aaagccgaga   2340
aggaagaacc ctcaggaagg cctgtacaat gaactgcaga agataagat ggcggaggcc   2400 tacagtgaga ttgggatgaa aggcgagcgc cggaggggca aggggcacga tggcctttac   2460
cagggtctca gtacagccac caaggacacc tacgacgccc ttcacatgca ggccctgccc   2520
cctcgctaa                                                            2529
```

<210> SEQ ID NO 19
<211> LENGTH: 390
<212> TYPE: DNA
<213> ORGANISM: Artificial Sequence
<220> FEATURE:
<223> OTHER INFORMATION: Anti TIM3 VHH12

<400> SEQUENCE: 19

```
caggtgcagc tgcaggagtc tggaggagga ttggtgcaga ctggggactc tctgagactc        60
tcctgtgtag tctctggagg caccttcaga aactatgtta tgggctggtt ccgccaggct       120
ccagggaagg agcgtgagtt tgtgtctgct atgaactgga gtggcggcat cacagtctat       180
gcagactccg tgaagggccg attcaccatc tccagagaca cgccaagaa cgcggtgtat        240 ctgcaaatgg gcagcctgaa acctggcgac acggccgttt attactgtgc agctgctgca       300
atcgatggtg gaaccgtcag aagcattaac agttatgcct actggggcca ggggacccag       360
gtcaccgtct cctcagcggc cgccactagt                                        390
```

<210> SEQ ID NO 20
<211> LENGTH: 130
<212> TYPE: PRT
<213> ORGANISM: Artificial Sequence
<220> FEATURE:
<223> OTHER INFORMATION: Anti TIM3 VHH12

<400> SEQUENCE: 20

```
Gln Val Gln Leu Gln Glu Ser Gly Gly Gly Leu Val Gln Thr Gly Asp
1               5                   10                  15

Ser Leu Arg Leu Ser Cys Val Val Ser Gly Gly Thr Phe Arg Asn Tyr
            20                  25                  30

Val Met Gly Trp Phe Arg Gln Ala Pro Gly Lys Glu Arg Glu Phe Val
        35                  40                  45

Ser Ala Met Asn Trp Ser Gly Gly Ile Thr Val Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Gly Ser Leu Lys Pro Gly Asp Thr Ala Val Tyr Tyr Cys
                85                  90                  95

Ala Ala Ala Ala Ile Asp Gly Gly Thr Val Arg Ser Ile Asn Ser Tyr
            100                 105                 110

Ala Tyr Trp Gly Gln Gly Thr Gln Val Thr Val Ser Ser Ala Ala Ala
        115                 120                 125

Thr Ser
    130
```

<210> SEQ ID NO 21
<211> LENGTH: 387
<212> TYPE: DNA
<213> ORGANISM: Artificial Sequence
<220> FEATURE:
<223> OTHER INFORMATION: Anti TIM3 VHH13

<400> SEQUENCE: 21

```
caggtgcagc tgcaggagtc tggaggagga ttggtgcagg ctgggggctc tctgagcctc        60
tcctgtgcag cctctggacg caccttcaag aactatctca tggcctggtt ccgccagact       120
ccagggaagg agcgtgagtt tgtggcagct attactcagc ttggtactag atcattaaat       180
gaagacttcg tgaagggccg attcaccatc tccagggaca cgccaagaa cacggtgtat        240
```
ctgcaaatga acgacctgaa aactgacgac acgggcgttt attcttgtgc agcaagccta    300
cagagtgggg ggtcactacg gtacgcgaag tatgactatt ggggccaggg gacccaggtc    360
accgtctcct cagcggccgc cactagt                                        387

<210> SEQ ID NO 22
<211> LENGTH: 129
<212> TYPE: PRT
<213> ORGANISM: Artificial Sequence
<220> FEATURE:
<223> OTHER INFORMATION: Anti TIM3 VHH13

<400> SEQUENCE: 22

Gln Val Gln Leu Gln Glu Ser Gly Gly Gly Leu Val Gln Ala Gly Gly
1               5                   10                  15

Ser Leu Ser Leu Ser Cys Ala Ala Ser Gly Arg Thr Phe Lys Asn Tyr
            20                  25                  30

Leu Met Ala Trp Phe Arg Gln Thr Pro Gly Lys Glu Arg Glu Phe Val
        35                  40                  45

Ala Ala Ile Thr Gln Leu Gly Thr Arg Ser Leu Asn Glu Asp Phe Val
    50                  55                  60

Lys Gly Arg Phe Thr Ile Ser Arg Asp Asn Ala Lys Asn Thr Val Tyr
65                  70                  75                  80

Leu Gln Met Asn Asp Leu Lys Thr Asp Asp Thr Gly Val Tyr Ser Cys
                85                  90                  95

Ala Ala Ser Leu Gln Ser Gly Gly Ser Leu Arg Tyr Ala Lys Tyr Asp
            100                 105                 110

Tyr Trp Gly Gln Gly Thr Gln Val Thr Val Ser Ser Ala Ala Ala Thr
        115                 120                 125

Ser

<210> SEQ ID NO 23
<211> LENGTH: 369
<212> TYPE: DNA
<213> ORGANISM: Artificial Sequence
<220> FEATURE:
<223> OTHER INFORMATION: Anti TIM3 VHH28

<400> SEQUENCE: 23
caggtgcagc tgcaggagtc tgggggagga ttggtgcagg ctgggggctc tctgagactc    60
tcctgtgcag cctctgaagg caccgtcagc acctacacca tggcctggtt ccgccaggct    120
ccagggaagg agcgtgagtt tgtagccagg attactggtg ttagtacggc tgtgaagggc    180
cggttcaccc tctccagaga cgagcccaaa aacacagtgt atctgcaaat gaacagcctg    240
aaacctgagg acacggccgt ctattactgc gcggcacact atttgggtgg tcgtccagat    300
atgccgactc agtatcaata cttgggccag ggacccaggt caccgtctc ctcagcggcc    360 gccactagt                                                            369

<210> SEQ ID NO 24
<211> LENGTH: 123
<212> TYPE: PRT
<213> ORGANISM: Artificial Sequence
<220> FEATURE:
<223> OTHER INFORMATION: Anti TIM3 VHH28

<400> SEQUENCE: 24

Gln Val Gln Leu Gln Glu Ser Gly Gly Gly Leu Val Gln Ala Gly Gly
1               5                   10                  15

Ser Leu Arg Leu Ser Cys Ala Ala Ser Glu Gly Thr Val Ser Thr Tyr
            20                  25                  30

Thr Met Ala Trp Phe Arg Gln Ala Pro Gly Lys Glu Arg Glu Phe Val
            35                  40                  45

Ala Arg Ile Thr Gly Val Ser Thr Ala Val Lys Gly Arg Phe Thr Phe
        50                  55                  60

Ser Arg Asp Glu Pro Lys Asn Thr Val Tyr Leu Gln Met Asn Ser Leu
65                  70                  75                  80

Lys Pro Glu Asp Thr Ala Val Tyr Tyr Cys Ala Ala His Tyr Leu Gly
                85                  90                  95

Gly Arg Pro Asp Met Pro Thr Gln Tyr Gln Tyr Leu Gly Gln Gly Thr
            100                 105                 110

Gln Val Thr Val Ser Ser Ala Ala Ala Thr Ser
            115                 120

<210> SEQ ID NO 25
<211> LENGTH: 402
<212> TYPE: DNA
<213> ORGANISM: Artificial Sequence
<220> FEATURE:
<223> OTHER INFORMATION: Anti TIM3 VHH30

<400> SEQUENCE: 25
caggtgcagc tgcaggagtc tgggggagga ttggtgcagg ctgggggctc tctgagactc      60
tcctgtgcag cctctggatt cacgtttggt agttatgtta tgggctggtt ccgccaggct     120
ccagggaagg agcgtgaatt tgtggcaagt attagtacga gtggtggcat aacatcttat     180
gcagactccg tgaagggccg attcactgtc tccagagaca cgccaagaa tacggtctac     240 ttacaaatga acagcctgaa acctgaggac acggccgttt attactgcgc acgagatctg     300
acatactatc gtactggtgg taggttacca gataacgcta atggatatgc gtactggggc     360
cagggtaccc aggtcaccgt ctcctcagcg gccgccacta gt                         402

<210> SEQ ID NO 26
<211> LENGTH: 134
<212> TYPE: PRT
<213> ORGANISM: Artificial Sequence
<220> FEATURE:
<223> OTHER INFORMATION: Anti TIM3 VHH30

<400> SEQUENCE: 26

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Thr Phe Gly Ser Tyr
            20                  25                  30

Val Met Gly Trp Phe Arg Gln Ala Pro Gly Lys Glu Arg Glu Phe Val
            35                  40                  45

Ala Ser Ile Ser Thr Ser Gly Gly Ile Thr Ser Tyr Ala Asp Ser Val
        50                  55                  60

Lys Gly Arg Phe Thr Val Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Arg Asp Leu Thr Tyr Tyr Arg Thr Gly Gly Arg Leu Pro Asp Asn
            100                 105                 110

Ala Asn Gly Tyr Ala Tyr Trp Gly Gln Gly Thr Gln Val Thr Val Ser
            115                 120                 125

Ser Ala Ala Ala Thr Ser
    130

<210> SEQ ID NO 27
<211> LENGTH: 348
<212> TYPE: DNA
<213> ORGANISM: Artificial Sequence
<220> FEATURE:
<223> OTHER INFORMATION: Anti TIM3 VHH32

<400> SEQUENCE: 27

```
caggtgcagc tgcaggagtc tggaggaggc ttggtgcagg ctgggggggtc tctaaatctc      60
tcctgtgcag cctctggaag ttccttcaga ctctataccg tcggctggca ccgccaggcg     120
ccagggaagc agcgcgagtt ggtcgcatgg attagtggtg cgggcagcac aaactatcat     180
tcgtccgtga agggccgatt caccatctcc agagacaacg ccaagaacac ggcactcctg     240
caaatgaaca acctggcacc tgaagacacg gccgtctatt actgtaatct actgaactac     300
tggggccagg ggacccaggt caccgtctcc tcagcggccg ccactagt                  348
```

<210> SEQ ID NO 28
<211> LENGTH: 116
<212> TYPE: PRT
<213> ORGANISM: Artificial Sequence
<220> FEATURE:
<223> OTHER INFORMATION: Anti TIM3 VHH32

<400> SEQUENCE: 28

Gln Val Gln Leu Gln Glu Ser Gly Gly Gly Leu Val Gln Ala Gly Gly
1               5                   10                  15

Ser Leu Asn Leu Ser Cys Ala Ala Ser Gly Ser Ser Phe Arg Leu Tyr
            20                  25                  30

Thr Val Gly Trp His Arg Gln Ala Pro Gly Lys Gln Arg Glu Leu Val
        35                  40                  45

Ala Trp Ile Ser Gly Ala Gly Ser Thr Asn Tyr His Ser Ser Val Lys
    50                  55                  60

Gly Arg Phe Thr Ile Ser Arg Asp Asn Ala Lys Asn Thr Ala Leu Leu
65                  70                  75                  80

Gln Met Asn Asn Leu Ala Pro Glu Asp Thr Ala Val Tyr Tyr Cys Asn
                85                  90                  95

Leu Leu Asn Tyr Trp Gly Gln Gly Thr Gln Val Thr Val Ser Ser Ala
            100                 105                 110

Ala Ala Thr Ser
        115

<210> SEQ ID NO 29
<211> LENGTH: 378
<212> TYPE: DNA
<213> ORGANISM: Artificial Sequence
<220> FEATURE:
<223> OTHER INFORMATION: Anti TIM3 VHH33

<400> SEQUENCE: 29

```
caggtgcagc tgcaggagtc tgggggaggc ttggtgcagc ctgggggggtc tctgagactc      60
tcctgtgcag tctctggact cacgccggat gcttatgtca tgggctggtt ccgccaggcc     120
ccagggaagg agcgcgaggg ggtctcatgt attagtccta gtggtggtac tacaagctat     180
ccagactccg tgaagggccg attcaccatc tccagagaca tgccaagaa cacggtgtac     240
ctgcaaatga acagcctgaa acctgaggac acgggcgttt attactgtgc ggcagttgcg     300
```

```
ggccgctggt gtgactacgg catgaactac tacggcaaag ggacccaggt caccgtctcc    360
tcagcggccg ccactagt                                                  378
```

<210> SEQ ID NO 30
<211> LENGTH: 126
<212> TYPE: PRT
<213> ORGANISM: Artificial Sequence
<220> FEATURE:
<223> OTHER INFORMATION: Anti TIM3 VHH33

<400> SEQUENCE: 30

Gln Val Gln Leu Gln Glu Ser Gly Gly Gly Leu Val Gln Pro Gly Gly
1               5                   10                  15

Ser Leu Arg Leu Ser Cys Ala Val Ser Gly Leu Thr Pro Asp Ala Tyr
            20                  25                  30

Val Met Gly Trp Phe Arg Gln Ala Pro Gly Lys Glu Arg Glu Gly Val
        35                  40                  45

Ser Cys Ile Ser Pro Ser Gly Gly Thr Thr Ser Tyr Pro Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Ala Val Ala Gly Arg Trp Cys Asp Tyr Gly Met Asn Tyr Tyr Gly
            100                 105                 110

Lys Gly Thr Gln Val Thr Val Ser Ser Ala Ala Ala Thr Ser
        115                 120                 125

<210> SEQ ID NO 31
<211> LENGTH: 381
<212> TYPE: DNA
<213> ORGANISM: Artificial Sequence
<220> FEATURE:
<223> OTHER INFORMATION: Anti TIM3 VHH38

<400> SEQUENCE: 31

```
caggtgcagc tgcaggagtc tgggggaggt tggtgcagg ctggggactc tctgagactc      60
tcctgtgcag tcggacgcac gttcagtgcg tcaaccttgg ctggttccg ccagtctcca    120 gggaaggagc gtgagtttgt cgcagcgatt agttggtggc gtggtgaggc atactatggg    180
gactccgtga agggccgatt caccatctcc agagacaaca ccaagacaac gatcaatctg    240
caaatgaata gcctgaaacc tgaggacacg gccgtttatt actgtgcacg agcccaatttt    300 gatggcgcga cacgggcaga tgactatgac aactggggtc aggggaccca ggtcaccgtc    360
tcctcagcgg ccgccactag t                                              381
```

<210> SEQ ID NO 32
<211> LENGTH: 127
<212> TYPE: PRT
<213> ORGANISM: Artificial Sequence
<220> FEATURE:
<223> OTHER INFORMATION: Anti TIM3 VHH38

<400> SEQUENCE: 32

Gln Val Gln Leu Gln Glu Ser Gly Gly Gly Leu Val Gln Ala Gly Asp
1               5                   10                  15

Ser Leu Arg Leu Ser Cys Ala Val Gly Arg Thr Phe Ser Ala Ser Thr
            20                  25                  30

```
Leu Gly Trp Phe Arg Gln Ser Pro Gly Lys Glu Arg Glu Phe Val Ala
         35                  40                  45

Ala Ile Ser Trp Trp Arg Gly Glu Ala Tyr Tyr Gly Asp Ser Val Lys
 50                  55                  60

Gly Arg Phe Thr Ile Ser Arg Asp Asn Thr Lys Thr Thr Ile Asn Leu
 65                  70                  75                  80

Gln Met Asn Ser Leu Lys Pro Glu Asp Thr Ala Val Tyr Tyr Cys Ala
                 85                  90                  95

Arg Ala Gln Phe Asp Gly Ala Thr Arg Ala Asp Asp Tyr Asp Asn Trp
             100                 105                 110

Gly Gln Gly Thr Gln Val Thr Val Ser Ser Ala Ala Thr Ser
         115                 120                 125
```

<210> SEQ ID NO 33
<211> LENGTH: 9439
<212> TYPE: DNA
<213> ORGANISM: Artificial Sequence
<220> FEATURE:
<223> OTHER INFORMATION: BiCAR VHH12

<400> SEQUENCE: 33

| | | | | | |
|---|---|---|---|---|---|
| gtgcacgagt | gggttacatc | gaactggatc | tcaacagcgg | taagatcctt | gagagttttc | 60 |
| gccccgaaga | acgttttcca | atgatgagca | cttttaaagt | tctgctatgt | ggcgcggtat | 120 |
| tatcccgtat | tgacgccggg | caagagcaac | tcggtcgccg | catacactat | tctcagaatg | 180 |
| acttggttga | gtactcacca | gtcacagaaa | agcatcttac | ggatggcatg | acagtaagag | 240 |
| aattatgcag | tgctgccata | accatgagtg | ataacactgc | ggccaactta | cttctgacaa | 300 |
| cgatcggagg | accgaaggag | ctaaccgctt | ttttgcacaa | catgggggat | catgtaactc | 360 |
| gccttgatcg | ttgggaaccg | gagctgaatg | aagccatacc | aaacgacgag | cgtgacacca | 420 |
| cgatgcctgt | agcaatggca | acaacgttgc | gcaaactatt | aactggcgaa | ctacttactc | 480 |
| tagcttcccg | gcaacaatta | atagactgga | tggaggcgga | taaagttgca | ggaccacttc | 540 |
| tgcgctcggc | ccttccggct | ggctggttta | ttgctgataa | atctggagcc | ggtgagcgtg | 600 |
| ggtctcgcgg | tatcattgca | gcactggggc | cagatggtaa | gccctcccgt | atcgtagtta | 660 |
| tctacacgac | ggggagtcag | gcaactatgg | atgaacgaaa | tagacagatc | gctgagatag | 720 |
| gtgcctcact | gattaagcat | tggtaactgt | cagaccaagt | ttactcatat | atactttaga | 780 |
| ttgatttaaa | acttcatttt | taatttaaaa | ggatctaggt | gaagatcctt | tttgataatc | 840 |
| tcatgaccaa | aatcccttaa | cgtgagtttt | cgttccactg | agcgtcagac | cccgtagaaa | 900 |
| agatcaaagg | atcttcttga | gatccttttt | ttctgcgcgt | aatctgctgc | ttgcaaacaa | 960 |
| aaaaaccacc | gctaccagcg | gtggtttgtt | tgccggatca | agagctacca | actctttttc | 1020 |
| cgaaggtaac | tggcttcagc | agagcgcaga | taccaaatac | tgttcttcta | gtgtagccgt | 1080 |
| agttaggcca | ccacttcaag | aactctgtag | caccgcctac | atacctcgct | ctgctaatcc | 1140 |
| tgttaccagt | ggctgctgcc | agtggcgata | agtcgtgtct | taccgggttg | gactcaagac | 1200 |
| gatagttacc | ggataaggcg | cagcggtcgg | gctgaacggg | gggttcgtgc | acacagccca | 1260 |
| gcttggagcg | aacgacctac | accgaactga | gatacctaca | gcgtgagcta | tgagaaagcg | 1320 |
| ccacgcttcc | cgaagggaga | aaggcggaca | ggtatccggt | aagcggcagg | gtcggaacag | 1380 |
| gagagcgcac | gagggagctt | ccagggggaa | acgcctggta | tctttatagt | cctgtcgggt | 1440 |
| ttcgccacct | ctgacttgag | cgtcgatttt | tgtgatgctc | gtcaggggg | cggagcctat | 1500 |
| ggaaaaacgc | cagcaacgcg | gcctttttac | ggttcctggc | cttttgctgg | ccttttgctc | 1560 |

```
acatgttctt tcctgcgtta tcccctgatt ctgtggataa ccgtattacc gcctttgagt    1620
gagctgatac cgctcgccgc agccgaacga ccgagcgcag cgagtcagtg agcgaggaag    1680
cggaagagcg cccaatacgc aaaccgcctc tccccgcgcg ttggccgatt cattaatgca    1740
gctggcacga caggtttccc gactggaaag cgggcagtga gcgcaacgca attaatgtga    1800
gttagctcac tcattaggca ccccaggctt tacactttat gcttccggct cgtatgttgt    1860
gtggaattgt gagcggataa caatttcaca caggaaacag ctatgaccat gattacgcca    1920
agcgcgcaat taaccctcac taaagggaac aaaagctgga gctgcaagct taatgtagtc    1980
ttatgcaata ctcttgtagt cttgcaacat ggtaacgatg agttagcaac atgccttaca    2040
aggagagaaa aagcaccgtg catgccgatt ggtggaagta aggtggtacg atcgtgcctt    2100
attaggaagg caacagacgg gtctgacatg gattggacga accactgaat tgccgcattg    2160
cagagatatt gtatttaagt gcctagctcg atacataaac gggtctctct ggttagacca    2220
gatctgagcc tgggagctct ctggctaact agggaaccca ctgcttaagc ctcaataaag    2280
cttgccttga gtgcttcaag tagtgtgtgc ccgtctgttg tgtgactctg gtaactagag    2340
atccctcaga cccttttagt cagtgtggaa atctctagc agtggcgccc gaacagggac    2400
ttgaaagcga agggaaacc agaggagctc tctcgacgca ggactcggct tgctgaagcg    2460
cgcacggcaa gaggcgaggg gcggcgactg gtgagtacgc caaaaatttt gactagcgga    2520
ggctagaagg agagagatgg gtgcgagagc gtcagtatta agcggggag aattagatcg    2580 cgatgggaaa aaattcggtt aaggccaggg ggaaagaaaa aatataaatt aaaacatata    2640
gtatgggcaa gcagggagct agaacgattc gcagttaatc ctggcctgtt agaaacatca    2700
gaaggctgta gacaaatact gggacagcta caaccatccc ttcagacagg atcagaagaa    2760
cttagatcat tatataatac agtagcaacc ctctattgtg tgcatcaaag gatagagata    2820
aaagacacca aggaagcttt agacaagata gaggaagagc aaaacaaaag taagaccacc    2880
gcacagcaag cggccgctga tcttcagacc tggaggagga gatatgaggg acaattggag    2940
aagtgaatta tataaatata aagtagtaaa aattgaacca ttaggagtag cacccaccaa    3000
ggcaaagaga agagtggtgc agagagaaaa agagcagtg gaataggag ctttgttcct    3060 tgggttcttg ggagcagcag gaagcactat gggcgcagcg tcaatgacgc tgacggtaca    3120
ggccagacaa ttattgtctg gtatagtgca gcagcagaac aatttgctga gggctattga    3180
ggcgcaacag catctgttgc aactcacagt ctggggcatc aagcagctcc aggcaagaat    3240
cctggctgtg gaaagatacc taaaggatca acagctcctg gggatttggg gttgctctgg    3300
aaaactcatt tgcaccactg ctgtgccttg gaatgctagt tggagtaata atctctgga    3360 acagatttgg aatcacacga cctggatgga gtgggacaga gaaattaaca attacacaag    3420
cttaatacac tccttaattg aagaatcgca aaaccagcaa gaaaagaatg aacaagaatt    3480
attggaatta gataaatggg caagtttgtg gaattggttt aacataacaa attggctgtg    3540
gtatataaaa ttattcataa tgatagtagg aggcttggta ggtttaagaa tagttttgc    3600 tgtactttct atagtgaata gagttaggca gggatattca ccattatcgt ttcagaccca    3660
cctcccaacc ccgagggac ccgacaggcc cgaaggaata agaagaag gtggagagag    3720 agacagagac agatccattc gattagtgaa cggatctcga cggtatcgat tagactgtag    3780
cccaggaata tggcagctag attgtacaca tttagaagga aaagttatct tggtagcagt    3840
tcatgtagcc agtggatata tagaagcaga agtaattcca gcagagacag ggcaagaaac    3900
```

```
agcatacttc ctcttaaaat tagcaggaag atggccagta aaaacagtac atacagacaa    3960
tggcagcaat ttcaccagta ctacagttaa ggccgcctgt tggtgggcgg ggatcaagca    4020
ggaatttggc attccctaca atccccaaag tcaaggagta atagaatcta tgaataaaga    4080
attaaagaaa attataggac aggtaagaga tcaggctgaa catcttaaga cagcagtaca    4140
aatggcagta ttcatccaca attttaaaag aaaaggggg attgggggt acagtgcagg      4200
ggaaagaata gtagacataa tagcaacaga catacaaact aaagaattac aaaaacaaat    4260
tacaaaaatt caaaattttc gggtttatta cagggacagc agagatccag tttggctgca    4320
tacgcgtcgt gaggctccgg tgcccgtcag tgggcagagc gcacatcgcc cacagtcccc    4380
gagaagttgg ggggagggt cggcaattga accggtgcct agagaaggtg gcgcggggta     4440
aactgggaaa gtgatgtcgt gtactggctc cgccttttc ccgagggtgg gggagaaccg     4500
tatataagtg cagtagtcgc cgtgaacgtt cttttcgca acgggtttgc cgccagaaca     4560
caggtaagtg ccgtgtgtgg ttcccgcggg cctggcctct ttacggggta tggcccttgc    4620
gtgccttgaa ttacttccac ctggctgcag tacgtgattc ttgatcccga gcttcgggtt    4680
ggaagtgggt gggagagttc gaggccttgc gcttaaggag ccccttcgcc tcgtgcttga    4740
gttgaggcct ggcctgggcg ctgggccgc cgcgtgcgaa tctggtggca ccttcgcgcc     4800
tgtctcgctg ctttcgataa gtctctagcc atttaaaatt tttgatgacc tgctgcgacg    4860
cttttttct ggcaagatag tcttgtaaat gcgggccaag atctgcacac tggtatttcg     4920
gttttgggg ccgcgggcgg cgacggggcc cgtgcgtccc agcgcacatg ttcggcgagg     4980
cggggcctgc gagcgcggcc accgagaatc ggacgggggg agtctcaagc tggccggcct    5040
gctctggtgc ctggcctcgc gccgccgtgt atcgccccgc cctgggcggc aaggctggcc    5100
cggtcggcac cagttgcgtg agcggaaaga tggccgcttc ccggccctgc tgcagggagc    5160
tcaaaatgga ggacgcggcg ctcgggagag cgggcgggtg agtcacccac acaaaggaaa    5220
agggcctttc cgtcctcagc cgtcgcttca tgtgactcca ctgagtaccg ggcgccgtcc    5280
aggcacctcg attagttctc gtgctttgg agtacgtcgt ctttaggttg gggggagggg      5340
ttttatgcga tggagtttcc ccacactgag tgggtggaga ctgaagttag gccagcttgg    5400
cacttgatgt aattctcctt ggaatttgcc cttttgagt ttggatcttg gttcattctc     5460
aagcctcaga cagtggttca aagttttttt cttccatttc aggtgtcgtg agctagctct    5520
agaatggcct taccagtgac cgccttgctc ctgccgctgg ccttgctgct ccacgccgcc    5580
aggccgcagg tgcagctgca ggagtctggg ggaggcttgg tgcagcctgg ggggtctctg    5640
agcctctcct gtacagcctc tggattcacg ttcagtagtt actccatggc ctgggtccgc    5700
caggctccag ggaagggacc cgaatgggtc tcagggattt acccttctga tggtaagaca    5760
aggtatgcag acttcgtgaa gggccgattc agcatctcca gagacaacgc caagaatatg    5820
ttgtatctgc aaatgaacaa cctgaaacct gaggacacgg ccctatatta ctgtgcgaga    5880
ggtatcaccg gattgggacc ccggggccag gggacccagg tcaccgtctc ctcagcggcc    5940
gccactagtg agtctaagta cggccctccc tgccctcctt gcccatacat ctgggcgccc    6000
ttggccggga cttgtgggt ccttctcctg tcactggtta tcacccttta ctgcaaacgg     6060
ggcagaaaga aactcctgta tatattcaaa caaccatta tgagaccagt acaaactact      6120
caagaggaag atggctgtag ctgccgattt ccagaagaag aagaaggagg atgtgaactg    6180
ctcgagggaa gcggagctac taacttcagc ctgctgaagc aggctggaga cgtggaggag    6240
aaccctggac ctcctaggat ggccttacca gtgaccgcct tgctcctgcc gctggccttg    6300
```

```
ctgctccacg ccgccaggcc gggatcccag gtgcagctgc aggagtctgg aggaggattg      6360
gtgcagactg gggactctct gagactctcc tgtgtagtct ctggaggcac cttcagaaac      6420
tatgttatgg gctggttccg ccaggctcca gggaaggagc gtgagtttgt gtctgctatg      6480
aactggagtg gcggcatcac agtctatgca gactccgtga agggccgatt caccatctcc      6540
agagacaacg ccaagaacgc ggtgtatctg caaatgggca gcctgaaacc tggcgacacg      6600
gccgtttatt actgtgcagc tgctgcaatc gatggtggaa ccgtcagaag cattaacagt      6660
tatgcctact ggggccaggg gacccaggtc accgtctcct cagcggccgc cactagttcc      6720
ggaaccacta caccagcgcc cagaccacct accccggctc ctaccatcgc atctcagccc      6780
ttgagtctta gacccgaggc atgtcggcca gcggcggggg gcgcagtgca cacgaggggg      6840
ctggacttcg cctgtgatta catctgggcg cccttggccg ggacttgtgg ggtccttctc      6900
ctgtcactgg ttatcaccct ttactgcaga gtgaagttca gcaggagcgc agacgccccc      6960
gcgtacaagc agggccagaa ccagctctat aacgagctca atctaggacg aagagaggag      7020
tacgatgttt tggacaagag acgtggccgg accctgaga tggggggaaa gccgagaagg       7080
aagaaccctc aggaaggcct gtacaatgaa ctgcagaaag ataagatggc ggaggcctac      7140
agtgagattg ggatgaaagg cgagcgccgg aggggcaagg ggcacgatgg cctttaccag      7200
ggtctcagta cagccaccaa ggacacctac gacgcccttc acatgcaggc cctgcccct      7260 cgctaagtcg acaatcaacc tctggattac aaaatttgtg aaagattgac tggtattctt      7320
aactatgttg ctccttttac gctatgtgga tacgctgctt taatgccttt gtatcatgct      7380
attgcttccc gtatggcttt cattttctcc tccttgtata atcctggtt gctgtctctt      7440 tatgaggagt tgtggcccgt tgtcaggcaa cgtggcgtgg tgtgcactgt gtttgctgac      7500 gcaacccca ctggttgggg cattgccacc acctgtcagc tcctttccgg gactttcgct       7560 ttcccctcc ctattgccac ggcggaactc atcgccgcct gccttgcccg ctgctggaca       7620
ggggctcggc tgttgggcac tgacaattcc gtggtgttgt cggggaagct gacgtccttt      7680
ccttggctgc tcgcctgtgt tgccacctgg attctgcgcg gacgtccctt ctgctacgtc      7740
ccttcggccc tcaatccagc ggaccttcct tcccgcggcc tgctgccggc tctgcggcct      7800
cttccgcgtc ttcgccttcg ccctcagacg agtcggatct ccctttgggc cgcctccccg      7860
cctggaattc gagctcggta cctttaagac caatgactta caaggcagct gtagatctta      7920 gccactttt aaaagaaaag gggggactgg aagggctaat tcactcccaa cgaagacaag       7980
atctgctttt tgcttgtact gggtctctct ggttagacca gatctgagcc tgggagctct      8040
ctggctaact agggaaccca ctgcttaagc ctcaataaag cttgccttga gtgcttcaag      8100
tagtgtgtgc ccgtctgttg tgtgactctg gtaactagag atccctcaga ccctttagt       8160 cagtgtggaa aatctctagc agtagtagtt catgtcatct tattattcag tatttataac      8220
ttgcaaagaa atgaatatca gagagtgaga ggaacttgtt tattgcagct tataatggtt      8280
acaaataaag caatagcatc acaaatttca caaataaagc attttttca ctgcattcta       8340 gttgtggttt gtccaaactc atcaatgtat cttatcatgt ctggctctag ctatcccgcc      8400
cctaactccg cccagttccg cccattctcc gccccatggc tgactaattt ttttatta       8460 tgcagaggcc gaggccgcct cggcctctga gctattccag aagtagtgag gaggcttttt      8520
tggaggccta gctagggacg tacccaattc gccctatagt gagtcgtatt acgcgcgctc      8580
actggccgtc gttttacaac gtcgtgactg ggaaaaccct ggcgttaccc aacttaatcg      8640
```

| | |
|---|---|
| ccttgcagca catccccctt tcgccagctg gcgtaatagc gaagaggccc gcaccgatcg | 8700 |
| cccttcccaa cagttgcgca gcctgaatgg cgaatgggac gcgccctgta gcggcgcatt | 8760 |
| aagcgcggcg ggtgtggtgg ttacgcgcag cgtgaccgct acacttgcca gcgccctagc | 8820 |
| gcccgctcct ttcgctttct tcccttcctt tctcgccacg ttcgccggct ttccccgtca | 8880 |
| agctctaaat cgggggctcc ctttagggtt ccgatttagt gctttacggc acctcgaccc | 8940 |
| caaaaaactt gattagggtg atggttcacg tagtgggcca tcgccctgat agacggtttt | 9000 |
| tcgccctttg acgttggagt ccacgttctt taatagtgga ctcttgttcc aaactggaac | 9060 |
| aacactcaac cctatctcgg tctattcttt tgatttataa gggattttgc cgatttcggc | 9120 |
| ctattggtta aaaaatgagc tgatttaaca aaaatttaac gcgaatttta acaaaatatt | 9180 |
| aacgcttaca atttaggtgg cacttttcgg ggaaatgtgc gcggaacccc tatttgttta | 9240 |
| tttttctaaa tacattcaaa tatgtatccg ctcatgagac aataaccctg ataaatgctt | 9300 |
| caataatatt gaaaaggaa gagtatgagt attcaacatt tccgtgtcgc ccttattccc | 9360 |
| ttttttgcgg cattttgcct tcctgttttt gctcacccag aaacgctggt gaaagtaaaa | 9420 |
| gatgctgaag atcagttgg | 9439 |

<210> SEQ ID NO 34
<211> LENGTH: 9442
<212> TYPE: DNA
<213> ORGANISM: Artificial Sequence
<220> FEATURE:
<223> OTHER INFORMATION: BiCAR2 VHH13

<400> SEQUENCE: 34

| | |
|---|---|
| gtgcacgagt gggttacatc gaactggatc tcaacagcgg taagatcctt gagagttttc | 60 |
| gccccgaaga cgttttccca atgatgagca cttttaaagt tctgctatgt ggcgcggtat | 120 |
| tatcccgtat tgacgccggg caagagcaac tcggtcgccg catacactat tctcagaatg | 180 |
| acttggttga gtactcacca gtcacagaaa agcatcttac ggatggcatg acagtaagag | 240 |
| aattatgcag tgctgccata accatgagtg ataacactgc ggccaactta cttctgacaa | 300 |
| cgatcggagg accgaaggag ctaaccgctt ttttgcacaa catgggggat catgtaactc | 360 |
| gccttgatcg ttgggaaccg gagctgaatg aagccatacc aaacgacgag cgtgacacca | 420 |
| cgatgcctgt agcaatggca acaacgttgc gcaaactatt aactggcgaa ctacttactc | 480 |
| tagcttcccg gcaacaatta atagactgga tgaggcgga taaagttgca ggaccacttc | 540 |
| tgcgctcggc ccttccggct ggctggttta ttgctgataa atctggagcc ggtgagcgtg | 600 |
| ggtctcgcgg tatcattgca gcactggggc cagatggtaa gccctcccgt atcgtagtta | 660 |
| tctacacgac ggggagtcag gcaactatgg atgaacgaaa tagacagatc gctgagatag | 720 |
| gtgcctcact gattaagcat tggtaactgt cagaccaagt ttactcatat atactttaga | 780 |
| ttgatttaaa acttcatttt taatttaaaa ggatctaggt gaagatcctt tttgataatc | 840 |
| tcatgaccaa atcccttaa cgtgagtttt cgttccactg agcgtcagac cccgtagaaa | 900 |
| agatcaaagg atcttcttga tccttttt ttctgcgcgt aatctgctgc ttgcaaacaa | 960 |
| aaaaaccacc gctaccagcg gtggtttgtt tgccggatca agagctacca actctttttc | 1020 |
| cgaaggtaac tggcttcagc agagcgcaga taccaaatac tgttcttcta gtgtagccgt | 1080 |
| agttaggcca ccacttcaag aactctgtag caccgcctac atacctcgct ctgctaatcc | 1140 |
| tgttaccagt ggctgctgcc agtggcgata agtcgtgtct taccgggttg gactcaagac | 1200 |
| gatagttacc ggataaggcg cagcggtcgg gctgaacggg gggttcgtgc acacagccca | 1260 |

```
gcttggagcg aacgacctac accgaactga gatacctaca gcgtgagcta tgagaaagcg    1320
ccacgcttcc cgaagggaga aaggcggaca ggtatccggt aagcggcagg gtcggaacag    1380
gagagcgcac gagggagctt ccaggggaa acgcctggta tctttatagt cctgtcgggt    1440
ttcgccacct ctgacttgag cgtcgatttt tgtgatgctc gtcaggggg cggagcctat    1500 ggaaaaacgc cagcaacgcg gccttttac ggttcctggc cttttgctgg ccttttgctc    1560
acatgttctt tcctgcgtta tcccctgatt ctgtggataa ccgtattacc gcctttgagt    1620
gagctgatac cgctcgccgc agccgaacga ccgagcgcag cgagtcagtg agcgaggaag    1680
cggaagagcg cccaatacgc aaaccgcctc tccccgcgcg ttggccgatt cattaatgca    1740
gctggcacga caggtttccc gactggaaag cgggcagtga gcgcaacgca attaatgtga    1800
gttagctcac tcattaggca ccccaggctt tacactttat gcttccggct cgtatgttgt    1860
gtggaattgt gagcggataa caatttcaca caggaaacag ctatgaccat gattacgcca    1920
agcgcgcaat taaccctcac taaagggaac aaaagctgga gctgcaagct taatgtagtc    1980
ttatgcaata ctcttgtagt cttgcaacat ggtaacgatg agttagcaac atgccttaca    2040
aggagagaaa aagcaccgtg catgccgatt ggtggaagta aggtggtacg atcgtgcctt    2100
attaggaagg caacagacgg gtctgacatg gattggacga accactgaat tgccgcattg    2160
cagagatatt gtatttaagt gcctagctcg atacataaac gggtctctct ggttagacca    2220
gatctgagcc tgggagctct ctggctaact agggaaccca ctgcttaagc ctcaataaag    2280
cttgccttga gtgcttcaag tagtgtgtgc ccgtctgttg tgtgactctg gtaactagag    2340
atccctcaga ccctttagt cagtgtggaa atctctagc agtggcgccc gaacagggac    2400
ttgaaagcga aagggaaacc agaggagctc tctcgacgca ggactcggct tgctgaagcg    2460
cgcacggcaa gaggcgaggg gcggcgactg gtgagtacgc caaaaatttt gactagcgga    2520
ggctagaagg agagagatgg gtgcgagagc gtcagtatta gcggggggag aattagatcg    2580
cgatgggaaa aaattcggtt aaggccaggg ggaaagaaaa aatataaatt aaaacatata    2640
gtatgggcaa gcagggagct agaacgattc gcagttaatc ctggcctgtt agaaacatca    2700
gaaggctgta gacaaatact gggacagcta caaccatccc ttcagacagg atcagaagaa    2760
cttagatcat tatataatac agtagcaacc ctctattgtg tgcatcaaag gatagagata    2820
aaagacacca aggaagcttt agacaagata gaggaagagc aaaacaaaag taagaccacc    2880
gcacagcaag cggccgctga tcttcagacc tggaggagga gatatgaggg acaattggag    2940
aagtgaatta tataaatata aagtagtaaa aattgaacca ttaggagtag cacccaccaa    3000
ggcaaagaga agagtggtgc agagagaaaa aagagcagtg ggaataggag ctttgttcct    3060
tgggttcttg ggagcagcag gaagcactat gggcgcagcg tcaatgacgc tgacggtaca    3120
ggccagacaa ttattgtctg gtatagtgca gcagcagaac aatttgctga ggctattga    3180 ggcgcaacag catctgttgc aactcacagt ctggggcatc aagcagctcc aggcaagaat    3240
cctggctgtg gaaagatacc taaggatca acagctcctg gggatttggg gttgctctgg    3300
aaaactcatt tgcaccactg ctgtgccttg gaatgctagt tggagtaata atctctggga    3360
acagatttgg aatcacacga cctggatgga gtgggacaga gaaattaaca attacacaag    3420
cttaatacac tccttaattg aagaatcgca aaaccagcaa gaaaagaatg aacaagaatt    3480
attggaatta gataaatggg caagtttgtg gaattggttt aacataacaa attggctgtg    3540
gtatataaaa ttattcataa tgatagtagg aggcttggta ggtttaagaa tagttttgc    3600
```

```
tgtactttct atagtgaata gagttaggca gggatattca ccattatcgt ttcagaccca    3660
cctcccaacc ccgaggggac ccgacaggcc cgaaggaata gaagaagaag gtggagagag    3720
agacagagac agatccattc gattagtgaa cggatctcga cggtatcgat tagactgtag    3780
cccaggaata tggcagctag attgtacaca tttagaagga aaagttatct tggtagcagt    3840
tcatgtagcc agtggatata tagaagcaga agtaattcca gcagagacag ggcaagaaac    3900
agcatacttc ctcttaaaat tagcaggaag atggccagta aaaacagtac atacagacaa    3960
tggcagcaat tcaccagta ctacagttaa ggccgcctgt tggtgggcgg ggatcaagca    4020
ggaatttggc attccctaca atccccaaag tcaaggagta atagaatcta tgaataaaga    4080
attaaagaaa attataggac aggtaagaga tcaggctgaa catcttaaga cagcagtaca    4140
aatggcagta ttcatccaca attttaaaag aaaaggggggg attggggggt acagtgcagg    4200
ggaaagaata gtagacataa tagcaacaga catacaaact aaagaattac aaaaacaaat    4260
tacaaaaatt caaaattttc gggtttatta cagggacagc agagatccag tttggctgca    4320
tacgcgtcgt gaggctccgg tgcccgtcag tgggcagagc gcacatcgcc cacagtcccc    4380
gagaagttgg ggggagggggt cggcaattga accggtgcct agagaaggtg gcgcggggta    4440
aactgggaaa gtgatgtcgt gtactggctc cgccttttc ccgagggtgg gggagaaccg    4500
tatataagtg cagtagtcgc cgtgaacgtt ctttttcgca acgggtttgc cgccagaaca    4560
caggtaagtg ccgtgtgtgg ttcccgcggg cctggcctct ttacgggtta tggcccttgc    4620
gtgccttgaa ttacttccac ctggctgcag tacgtgattc ttgatcccga gcttcgggtt    4680
ggaagtgggt gggagagttc gaggccttgc gcttaaggag ccccttcgcc tcgtgcttga    4740
gttgaggcct ggcctgggcg ctggggccgc cgcgtgcgaa tctggtggca ccttcgcgcc    4800
tgtctcgctg ctttcgataa gtctctagcc atttaaaatt tttgatgacc tgctgcgacg    4860 cttttttttct ggcaagatag tcttgtaaat gcgggccaag atctgcacac tggtatttcg    4920 gttttttgggg ccgcgggcgg cgacggggcc cgtgcgtccc agcgcacatg ttcggcgagg    4980
cggggcctgc gagcgcggcc accgagaatc ggacgggggt agtctcaagc tggccggcct    5040
gctctggtgc ctggcctcgc gccgccgtgt atcgccccgc cctgggcggc aaggctggcc    5100
cggtcggcac cagttgcgtg agcggaaaga tggccgcttc ccggccctgc tgcagggagc    5160
tcaaaatgga ggacgcggcg ctcgggagag cgggcgggtg agtcacccac acaaaggaaa    5220 agggccttc cgtcctcagc cgtcgcttca tgtgactcca ctgagtaccg ggcgccgtcc    5280
aggcacctcg attagttctc gtgctttttgg agtacgtcgt ctttaggttg ggggggagggg    5340 ttttatgcga tggagtttcc ccacactgag tgggtggaga ctgaagttag gccagcttgg    5400
cacttgatgt aattctcctt ggaatttgcc ctttttgagt ttggatcttg gttcattctc    5460
aagcctcaga cagtggttca agtttttttt cttccatttc aggtgtcgtg agctagctct    5520
agagccagca tggccttacc agtgaccgcc ttgctcctgc cgctggcctt gctgctccac    5580
gccgccaggc cgcaggtgca gctgcaggag tctgggggag gcttggtgca gcctgggggg    5640
tctctgagcc tctcctgtac agcctctgga ttcacgttca gtagttactc catggcctgg    5700
gtccgccagg ctcagggaa gggacccgaa tgggtctcag ggatttaccc ttctgatggt    5760
aagacaaggt atgcagactt cgtgaagggc cgattcagca tctccagaga caacgccaag    5820
aatatgttgt atctgcaaat gaacaacctg gaacctgagg acacggccct atattactgt    5880
gcgagaggta tcaccggatt gggacccccgg ggccagggga cccaggtcac cgtctcctca    5940
gcggccgcca ctagtgagtc taagtacggc cctccctgcc ctccttgccc atacatctgg    6000
```

```
gcgcccttgg ccgggacttg tggggtcctt ctcctgtcac tggttatcac cctttactgc    6060
aaacggggca gaaagaaact cctgtatata ttcaaacaac catttatgag accagtacaa    6120
actactcaag aggaagatgg ctgtagctgc cgatttccag aagaagaaga aggaggatgt    6180
gaactgctcg agggaagcgg agctactaac ttcagcctgc tgaagcaggc tggagacgtg    6240
gaggagaacc ctggacctcc taggatggcc ttaccagtga ccgccttgct cctgccgctg    6300
gccttgctgc tccacgccgc caggccggga tcccaggtgc agctgcagga gtctggagga    6360
ggattggtgc aggctggggg ctctctgagc ctctcctgtg cagcctctgg acgcaccttc    6420
aagaactatc tcatggcctg gttccgccag actccaggga aggagcgtga gtttgtggca    6480
gctattactc agcttggtac tagatcatta aatgaagact cgtgaaggg ccgattcacc     6540 atctccaggg acaacgccaa gaacacggtg tatctgcaaa tgaacgacct gaaaactgac    6600
gacacgggcg tttattcttg tgcagcaagc ctacagagtg gggggtcact acggtacgcg    6660
aagtatgact attggggcca ggggacccag gtcaccgtct cctcagcggc cgccactagt    6720
tccggaacca ctacaccagc gcccagacca cctaccccgg ctcctaccat cgcatctcag    6780
cccttgagtc ttagacccga ggcatgtcgg ccagcggcgg ggggcgcagt gcacacgagg    6840
gggctggact tcgcctgtga ttacatctgg gcgcccttgg ccgggacttg tggggtcctt    6900
ctcctgtcac tggttatcac cctttactgc agagtgaagt tcagcaggag cgcagacgcc    6960
cccgcgtaca agcagggcca gaaccagctc tataacgagc tcaatctagg acgaagagag    7020
gagtacgatg ttttggacaa gagacgtggc cgggaccctg agatgggggg aaagccgaga    7080
aggaagaacc ctcaggaagg cctgtacaat gaactgcaga agataagat ggcggaggcc     7140 tacagtgaga ttgggatgaa aggcgagcgc cggaggggca aggggcacga tggcctttac    7200
cagggtctca gtacagccac caaggacacc tacgacgccc ttcacatgca ggccctgccc    7260
cctcgctaag tcgacaatca acctctggat tacaaaattt gtgaaagatt gactggtatt    7320
cttaactatg ttgctccttt tacgctatgt ggatacgctg ctttaatgcc tttgtatcat    7380
gctattgctt cccgtatggc tttcattttc tcctccttgt ataaatcctg gttgctgtct    7440
ctttatgagg agttgtggcc cgttgtcagg caacgtggcg tggtgtgcac tgtgtttgct    7500
gacgcaaccc ccactggttg ggcattgcca ccacctgtc agctcctttc cgggactttc     7560
gctttccccc tccctattgc cacggcggaa ctcatcgccg cctgccttgc ccgctgctgg    7620 acagggctc ggctgttggg cactgacaat tccgtggtgt tgtcgggaa gctgacgtcc      7680 tttccttggc tgctcgcctg tgttgccacc tggattctgc gcgggacgtc cttctgctac    7740
gtcccttcgg ccctcaatcc agcggacctt ccttcccgcg gcctgctgcc ggctctgcgg    7800
cctcttccgc gtcttcgcct tcgccctcag acgagtcgga tctcccttg gccgcctcc     7860 ccgcctggaa ttcgagctcg gtacctttaa gaccaatgac ttacaaggca gctgtagatc    7920
ttagccactt tttaaaagaa aagggggac tggaagggct aattcactcc caacgaagac     7980
aagatctgct ttttgcttgt actgggtctc tctggttaga ccagatctga gcctgggagc    8040
tctctggcta actagggaac ccactgctta agcctcaata agcttgcct tgagtgcttc     8100 aagtagtgtg tgcccgtctg ttgtgtgact ctggtaacta gagatccctc agacccttt     8160 agtcagtgtg aaaatctct agcagtagta gttcatgtca tcttattatt cagtatttat     8220
aacttgcaaa gaaatgaata tcagagagtg agaggaactt gttttattgca gcttataatg    8280 gttacaaata aagcaatagc atcacaaatt tcacaaataa agcatttttt tcactgcatt    8340
```

| | |
|---|---|
| ctagttgtgg tttgtccaaa ctcatcaatg tatcttatca tgtctggctc tagctatccc | 8400 |
| gccccctaact ccgcccagtt ccgcccattc tccgcccat ggctgactaa ttttttttat | 8460 |
| ttatgcagag gccgaggccg cctcggcctc tgagctattc cagaagtagt gaggaggctt | 8520 |
| ttttggaggc ctagctaggg acgtacccaa ttcgccctat agtgagtcgt attacgcgcg | 8580 |
| ctcactggcc gtcgttttac aacgtcgtga ctgggaaaac cctggcgtta cccaacttaa | 8640 |
| tcgccttgca gcacatcccc ctttcgccag ctggcgtaat agcgaagagg cccgcaccga | 8700 |
| tcgcccttcc caacagttgc gcagcctgaa tggcgaatgg gacgcgccct gtagcggcgc | 8760 |
| attaagcgcg gcgggtgtgg tggttacgcg cagcgtgacc gctacacttg ccagcgccct | 8820 |
| agcgcccgct cctttcgctt tcttcccttc ctttctcgcc acgttcgccg gctttccccg | 8880 |
| tcaagctcta aatcggggc tcccttagg gttccgattt agtgctttac ggcacctcga | 8940 |
| ccccaaaaaa cttgattagg gtgatggttc acgtagtggg ccatcgccct gatagacggt | 9000 |
| ttttcgccct ttgacgttgg agtccacgtt ctttaatagt ggactcttgt tccaaactgg | 9060 |
| aacaacactc aaccctatct cggtctatte ttttgattta aagggattt tgccgatttc | 9120 |
| ggcctattgg ttaaaaaatg agctgattta acaaaaattt aacgcgaatt ttaacaaaat | 9180 |
| attaacgctt acaatttagg tggcactttt cggggaaatg tgcgcggaac ccctatttgt | 9240 |
| ttatttttct aaatacattc aaatatgtat ccgctcatga gacaataacc ctgataaatg | 9300 |
| cttcaataat attgaaaaag gaagagtatg agtattcaac atttccgtgt cgcccttatt | 9360 |
| cccttttttg cggcattttg ccttcctgtt tttgctcacc cagaaacgct ggtgaaagta | 9420 |
| aaagatgctg aagatcagtt gg | 9442 |

<210> SEQ ID NO 35
<211> LENGTH: 9424
<212> TYPE: DNA
<213> ORGANISM: Artificial Sequence
<220> FEATURE:
<223> OTHER INFORMATION: BiCAR2 VHH28

<400> SEQUENCE: 35

| | |
|---|---|
| gtgcacgagt gggttacatc gaactggatc tcaacagcgg taagatcctt gagagttttc | 60 |
| gccccgaaga acgttttcca atgatgagca cttttaaagt tctgctatgt ggcgcggtat | 120 |
| tatcccgtat tgacgccggg caagagcaac tcggtcgccg catacactat tctcagaatg | 180 |
| acttggttga gtactcacca gtcacagaaa agcatcttac ggatggcatg acagtaagag | 240 |
| aattatgcag tgctgccata accatgagtg ataacactgc ggccaactta cttctgacaa | 300 |
| cgatcggagg accgaaggag ctaaccgctt ttttgcacaa catgggggat catgtaactc | 360 |
| gccttgatcg ttgggaaccg gagctgaatg aagccatacc aaacgacgag cgtgacacca | 420 |
| cgatgcctgt agcaatggca acaacgttgc gcaaactatt aactggcgaa ctacttactc | 480 |
| tagcttcccg gcaacaatta atagactgga tggaggcgga taaagttgca ggaccacttc | 540 |
| tgcgctcggc ccttccggct ggctggttta ttgctgataa atctggagcc ggtgagcgtg | 600 |
| ggtctcgcgg tatcattgca gcactggggc cagatggtaa gccctcccgt atcgtagtta | 660 |
| tctacacgac ggggagtcag gcaactatgg atgaacgaaa tagacagatc gctgagatag | 720 |
| gtgcctcact gattaagcat tggtaactgt cagaccaagt ttactcatat atactttaga | 780 |
| ttgatttaaa acttcatttt taatttaaaa ggatctaggt gaagatcctt tttgataatc | 840 |
| tcatgaccaa aatcccttaa cgtgagtttt cgttccactg agcgtcagac cccgtagaaa | 900 |
| agatcaaagg atcttcttga tccttttttt ttctgcgcgt aatctgctgc ttgcaaacaa | 960 |

-continued

| | |
|---|---|
| aaaaaccacc gctaccagcg gtggtttgtt tgccggatca agagctacca actcttttc | 1020 |
| cgaaggtaac tggcttcagc agagcgcaga taccaaatac tgttcttcta gtgtagccgt | 1080 |
| agttaggcca ccacttcaag aactctgtag caccgcctac atacctcgct ctgctaatcc | 1140 |
| tgttaccagt ggctgctgcc agtggcgata agtcgtgtct taccgggttg gactcaagac | 1200 |
| gatagttacc ggataaggcg cagcggtcgg gctgaacggg gggttcgtgc acacagccca | 1260 |
| gcttggagcg aacgacctac accgaactga gatacctaca gcgtgagcta tgagaaagcg | 1320 |
| ccacgcttcc cgaagggaga aggcggaca ggtatccggt aagcggcagg gtcggaacag | 1380 |
| gagagcgcac gagggagctt ccaggggaa acgcctggta tctttatagt cctgtcgggt | 1440 |
| ttcgccacct ctgacttgag cgtcgatttt tgtgatgctc gtcagggggg cggagcctat | 1500 |
| ggaaaaacgc cagcaacgcg gccttttac ggttcctggc cttttgctgg ccttttgctc | 1560 |
| acatgttctt tcctgcgtta tccctgatt ctgtggataa ccgtattacc gcctttgagt | 1620 |
| gagctgatac cgctcgccgc agccgaacga ccgagcgcag cgagtcagtg agcgaggaag | 1680 |
| cggaagagcg cccaatacgc aaaccgcctc tccccgcgcg ttggccgatt cattaatgca | 1740 |
| gctggcacga caggtttccc gactggaaag cgggcagtga gcgcaacgca attaatgtga | 1800 |
| gttagctcac tcattaggca ccccaggctt tacactttat gcttccggct cgtatgttgt | 1860 |
| gtggaattgt gagcggataa caatttcaca caggaaacag ctatgaccat gattacgcca | 1920 |
| agcgcgcaat taaccctcac taaagggaac aaaagctgga gctgcaagct taatgtagtc | 1980 |
| ttatgcaata ctcttgtagt cttgcaacat ggtaacgatg agttagcaac atgccttaca | 2040 |
| aggagagaaa aagcaccgtg catgccgatt ggtggaagta aggtggtacg atcgtgcctt | 2100 |
| attaggaagg caacagacgg gtctgacatg gattggacga accactgaat tgccgcattg | 2160 |
| cagagatatt gtatttaagt gcctagctcg atacataaac gggtctctct ggttagacca | 2220 |
| gatctgagcc tgggagctct ctggctaact agggaaccca ctgcttaagc ctcaataaag | 2280 |
| cttgccttga gtgcttcaag tagtgtgtgc ccgtctgttg tgtgactctg gtaactagag | 2340 |
| atccctcaga ccctttagt cagtgtggaa aatctctagc agtggcgccc gaacagggac | 2400 |
| ttgaaagcga aagggaaacc agaggagctc tctcgacgca ggactcggct tgctgaagcg | 2460 |
| cgcacggcaa gaggcgaggg gcggcgactg gtgagtacgc caaaaatttt gactagcgga | 2520 |
| ggctagaagg agagagatgg gtgcgagagc gtcagtatta gcggggggag aattagatcg | 2580 |
| cgatgggaaa aaattcggtt aaggccaggg ggaagaaaa aatataaatt aaaacatata | 2640 |
| gtatgggcaa gcagggagct agaacgattc gcagttaatc ctggcctgtt agaaacatca | 2700 |
| gaaggctgta gacaaatact gggacagcta caaccatccc ttcagacagg atcagaagaa | 2760 |
| cttagatcat tatataatac agtagcaacc ctctattgtg tgcatcaaag gatagagata | 2820 |
| aaagacacca aggaagcttt agacaagata gaggaagagc aaaacaaaag taagaccacc | 2880 |
| gcacagcaag cggccgctga tcttcagacc tggaggagga gatatgaggg acaattggag | 2940 |
| aagtgaatta tataaatata agtagtaaa aattgaacca ttaggagtag cacccaccaa | 3000 |
| ggcaaagaga agagtggtgc agagagaaaa aagagcagtg ggaataggag ctttgttcct | 3060 |
| tgggttcttg ggagcagcag gaagcactat gggcgcagcg tcaatgacgc tgacggtaca | 3120 |
| ggccagacaa ttattgtctg gtatagtgca gcagcagaac aatttgctga ggctattga | 3180 |
| ggcgcaacag catctgttgc aactcacagt ctggggcatc aagcagctcc aggcaagaat | 3240 |
| cctggctgtg gaaagatacc taaaggatca acagctcctg gggatttggg gttgctctgg | 3300 |

```
aaaactcatt tgcaccactg ctgtgccttg aatgctagt tggagtaata aatctctgga    3360
acagatttgg aatcacacga cctggatgga gtgggacaga gaaattaaca attacacaag    3420
cttaatacac tccttaattg aagaatcgca aaaccagcaa gaaaagaatg aacaagaatt    3480
attggaatta gataaatggg caagtttgtg gaattggttt aacataacaa attggctgtg    3540
gtatataaaa ttattcataa tgatagtagg aggcttggta ggtttaagaa tagttttgc     3600 tgtactttct atagtgaata gagttaggca gggatattca ccattatcgt ttcagaccca    3660
cctcccaacc ccgaggggac ccgacaggcc cgaaggaata agaagaag gtggagagag     3720 agacagagac agatccattc gattagtgaa cggatctcga cggtatcgat tagactgtag    3780
cccaggaata tggcagctag attgtacaca tttagaagga aaagttatct tggtagcagt    3840
tcatgtagcc agtggatata tagaagcaga agtaattcca gcagagacag ggcaagaaac    3900
agcatacttc ctcttaaaat tagcaggaag atggccagta aaaacagtac atacagacaa    3960
tggcagcaat ttcaccagta ctacagttaa ggccgcctgt tggtgggcgg ggatcaagca    4020
ggaatttggc attccctaca atccccaaag tcaaggagta atagaatcta tgaataaaga    4080
attaaagaaa attataggac aggtaagaga tcaggctgaa catcttaaga cagcagtaca    4140
aatggcagta ttcatccaca attttaaaag aaaagggggg attgggggt acagtgcagg     4200 ggaaagaata gtagacataa tagcaacaga catacaaact aaagaattac aaaaacaaat    4260
tacaaaaatt caaaattttc gggtttatta cagggacagc agagatccag tttggctgca    4320
tacgcgtcgt gaggctccgg tgcccgtcag tgggcagagc gcacatcgcc cacagtcccc    4380
gagaagttgg ggggagggt cggcaattga accggtgcct agagaaggtg gcgcggggta    4440
aactgggaaa gtgatgtcgt gtactggctc cgccttttc ccgagggtgg gggagaaccg    4500
tatataagtg cagtagtcgc cgtgaacgtt ctttttcgca acgggtttgc cgccagaaca    4560
caggtaagtg ccgtgtgtgg ttcccgcggg cctggcctct ttacgggtta tggcccttgc    4620
gtgccttgaa ttacttccac ctggctgcag tacgtgattc ttgatcccga gcttcgggtt    4680
ggaagtgggt gggagagttc gaggccttgc gcttaaggag ccccttcgcc tcgtgcttga    4740
gttgaggcct ggcctgggcg ctgggccgc cgcgtgcgaa tctggtggca ccttcgcgcc     4800
tgtctcgctg ctttcgataa gtctctagcc atttaaaatt tttgatgacc tgctgcgacg    4860 cttttttct ggcaagatag tcttgtaaat gcgggccaag atctgcacac tggtatttcg     4920
gttttttggg ccgcgggcgg cgacggggcc cgtgcgtccc agcgcacatg ttcggcgagg    4980
cggggcctgc gagcgcggcc accgagaatc ggacgggggt agtctcaagc tggccggcct    5040
gctctggtgc ctggcctcgc gccgccgtgt atcgccccgc cctgggcggc aaggctggcc    5100
cggtcggcac cagttgcgtg agcggaaaga tggccgcttc ccggccctgc tgcagggagc    5160
tcaaaatgga ggacgcggcg ctcgggagag cgggcgggtg agtcacccac acaaaggaaa    5220
agggcctttc cgtcctcagc cgtcgcttca tgtgactcca ctgagtaccg ggcgccgtcc    5280
aggcacctcg attagttctc gtgcttttgg agtacgtcgt ctttaggttg ggggagggg     5340 ttttatgcga tggagtttcc ccacactgag tgggtggaga ctgaagttag gccagcttgg    5400
cacttgatgt aattctcctt ggaatttgcc cttttgagt ttggatcttg gttcattctc     5460
aagcctcaga cagtggttca agtttttttt cttccatttc aggtgtcgtg agctagctct    5520
agagccagca tggccttacc agtgaccgcc ttgctcctgc cgctggcctt gctgctccac    5580
gccgccaggc cgcaggtgca gctgcaggag tctggggag gcttggtgca gcctggggg      5640 tctctgagcc tctcctgtac agcctctgga ttcacgttca gtagttactc catggcctgg    5700
```

-continued

| | | | | |
|---|---|---|---|---|
| gtccgccagg | ctccagggaa | gggacccgaa | tgggtctcag | ggatttaccc ttctgatggt | 5760 |
| aagacaaggt | atgcagactt | cgtgaagggc | cgattcagca | tctccagaga caacgccaag | 5820 |
| aatatgttgt | atctgcaaat | gaacaacctg | gaacctgagg | acacggccct atattactgt | 5880 |
| gcgagaggta | tcaccggatt | gggacccggg | gccaggggaa | cccaggtcac cgtctcctca | 5940 |
| gcggccgcca | ctagtgagtc | taagtacggc | cctccctgcc | ctccttgccc atacatctgg | 6000 |
| gcgcccttgg | ccgggacttg | tggggtcctt | ctcctgtcac | tggttatcac cctttactgc | 6060 |
| aaacggggca | gaaagaaact | cctgtatata | ttcaaacaac | catttatgag accagtacaa | 6120 |
| actactcaag | aggaagatgg | ctgtagctgc | cgatttccag | aagaagaaga aggaggatgt | 6180 |
| gaactgctcg | agggaagcgg | agctactaac | ttcagcctgc | tgaagcaggc tggagacgtg | 6240 |
| gaggagaacc | ctggacctcc | taggatggcc | ttaccagtga | ccgccttgct cctgccgctg | 6300 |
| gccttgctgc | tccacgccgc | caggccggga | tcccaggtgc | agctgcagga gtctggggga | 6360 |
| ggattggtgc | aggctggggg | ctctctgaga | ctctcctgtg | cagcctctga aggcaccgtc | 6420 |
| agcacctaca | ccatggcctg | gttccgccag | gctccaggga | aggagcgtga gtttgtagcc | 6480 |
| aggattactg | tgttagtac | ggctgtgaag | ggccggttca | ccttctccag agacgagccc | 6540 |
| aaaaacacag | tgtatctgca | aatgaacagc | ctgaaacctg | aggacacggc cgtctattac | 6600 |
| tgcgcggcac | actatttggg | tggtcgtcca | gatatgccga | ctcagtatca atacttgggc | 6660 |
| caggggaccc | aggtcaccgt | ctcctcagcg | gccgccacta | gttccggaac cactacacca | 6720 |
| gcgcccagac | cacctacccc | ggctcctacc | atcgcatctc | agcccttgag tcttagaccc | 6780 |
| gaggcatgtc | ggccagcggc | gggggcgca | gtgcacacga | ggggctgga cttcgcctgt | 6840 |
| gattacatct | gggcgccctt | ggccgggact | tgtggggtcc | ttctcctgtc actggttatc | 6900 |
| accctttact | gcagagtgaa | gttcagcagg | agcgcagacg | cccccgcgta caagcagggc | 6960 |
| cagaaccagc | tctataacga | gctcaatcta | ggacgaagag | aggagtacga tgttttggac | 7020 |
| aagagacgtg | gccgggaccc | tgagatgggg | ggaaagccga | aaggaagaa ccctcaggaa | 7080 |
| ggcctgtaca | atgaactgca | gaaagataag | atggcggagg | cctacagtga gattgggatg | 7140 |
| aaaggcgagc | gccggagggg | caaggggcac | gatggccttt | accagggtct cagtacagcc | 7200 |
| accaaggaca | cctacgacgc | ccttcacatg | caggccctgc | cccctcgcta agtcgacaat | 7260 |
| caacctctgg | attacaaaat | ttgtgaaaga | ttgactggta | ttcttaacta tgttgctcct | 7320 |
| tttacgctat | gtggatacgc | tgctttaatg | cctttgtatc | atgctattgc ttcccgtatg | 7380 |
| gctttcattt | tctcctcctt | gtataaatcc | tggttgctgt | ctctttatga ggagttgtgg | 7440 |
| cccgttgtca | ggcaacgtgg | cgtggtgtgc | actgtgtttg | ctgacgcaac ccccactggt | 7500 |
| tggggcattg | ccaccacctg | tcagctcctt | tccgggactt | tcgctttccc cctccctatt | 7560 |
| gccacggcgg | aactcatcgc | cgcctgcctt | gcccgctgct | ggacaggggc tcggctgttg | 7620 |
| ggcactgaca | attccgtggt | gttgtcgggg | aagctgacgt | cctttccttg ctgctcgcc | 7680 |
| tgtgttgcca | cctggattct | gcgcgggacg | tccttctgct | acgtcccttc ggccctcaat | 7740 |
| ccagcggacc | ttccttcccg | cggcctgctg | ccggctctgc | ggcctcttcc gcgtcttcgc | 7800 |
| cttcgccctc | agacgagtcg | gatctccctt | gggccgcct | cccgcctgg aattcgagct | 7860 |
| cggtaccttt | aagaccaatg | acttacaagg | cagctgtaga | tcttagccac ttttttaaaag | 7920 |
| aaaaggggg | actggaaggg | ctaattcact | cccaacgaag | acaagatctg cttttttgctt | 7980 |
| gtactgggtc | tctctggtta | gaccagatct | gagcctggga | gctctctggc taactaggga | 8040 |

```
acccactgct taagcctcaa taaagcttgc cttgagtgct tcaagtagtg tgtgcccgtc    8100
tgttgtgtga ctctggtaac tagagatccc tcagacccTT ttagtcagtg tggaaaatct    8160
ctagcagtag tagttcatgt catcttatta ttcagtattt ataacttgca aagaaatgaa    8220
tatcagagag tgagaggaac ttgtttattg cagcttataa tggttacaaa taaagcaata    8280
gcatcacaaa tttcacaaat aaagcatttt tttcactgca ttctagttgt ggtttgtcca    8340
aactcatcaa tgtatcttat catgtctggc tctagctatc ccgcccctaa ctccgcccag    8400
ttccgcccat tctccgcccc atggctgact aatttttttt atttatgcag aggccgaggc    8460
cgcctcggcc tctgagctat tccagaagta gtgaggaggc ttttttggag gcctagctag    8520
ggacgtaccc aattcgccct atagtgagtc gtattacgcg cgctcactgg ccgtcgtttt    8580
acaacgtcgt gactgggaaa accctggcgt tacccaactt aatcgccttg cagcacatcc    8640
ccctttcgcc agctggcgta atagcgaaga ggcccgcacc gatcgccctt cccaacagtt    8700
gcgcagcctg aatggcgaat gggacgcgcc ctgtagcggc gcattaagcg cggcgggtgt    8760
ggtggttacg cgcagcgtga ccgctacact tgccagcgcc ctagcgcccg ctcctttcgc    8820
tttcttccct cctttctcg ccacgttcgc cggctttccc cgtcaagctc taaatcgggg    8880
gctcccttta gggttccgat ttagtgcttt acggcacctc gaccccaaaa aacttgatta    8940
gggtgatggt tcacgtagtg ggccatcgcc ctgatagacg ttttttcgcc ctttgacgtt    9000
ggagtccacg ttctttaata gtggactctt gttccaaact ggaacaacac tcaaccctat    9060
ctcggtctat tcttttgatt tataagggat tttgccgatt tcggcctatt ggttaaaaaa    9120
tgagctgatt taacaaaaat ttaacgcgaa ttttaacaaa atattaacgc ttacaattta    9180
ggtggcactt ttcggggaaa tgtgcgcgga accctattt gtttattttt ctaaatacat    9240
tcaaatatgt atccgctcat gagacaataa ccctgataaa tgcttcaata atattgaaaa    9300
aggaagagta tgagtattca acatttccgt gtcgccctta ttcccttttt tgcggcattt    9360
tgccttcctg ttttgctca cccagaaacg ctggtgaaag taaaagatgc tgaagatcag    9420
ttgg                                                                   9424
```

<210> SEQ ID NO 36
<211> LENGTH: 9457
<212> TYPE: DNA
<213> ORGANISM: Artificial Sequence
<220> FEATURE:
<223> OTHER INFORMATION: BiCAR2 VHH30

<400> SEQUENCE: 36

```
gtgcacgagt gggttacatc gaactggatc tcaacagcgg taagatcctt gagagttttc     60
gccccgaaga cgttttcca atgatgagca cttttaaagt tctgctatgt ggcgcggtat    120
tatcccgtat tgacgccggg caagagcaac tcggtcgccg catacactat tctcagaatg    180
acttggttga gtactcacca gtcacagaaa agcatcttac ggatggcatg acagtaagag    240
aattatgcag tgctgccata accatgagtg ataacactgc ggccaactta cttctgacaa    300
cgatcggagg accgaaggag ctaaccgctt ttttgcacaa catgggggat catgtaactc    360
gccttgatcg ttgggaaccg gagctgaatg aagccatacc aaacgacgag cgtgacacca    420
cgatgcctgt agcaatggca acaacgttgc gcaaactatt aactggcgaa ctacttactc    480
tagcttcccg gcaacaatta atagactgga tggaggcgga taagttgca ggaccacttc    540 tgcgctcggc ccttccggct ggctggttta ttgctgataa atctggagcc ggtgagcgtg    600
ggtctcgcgg tatcattgca gcactggggc cagatggtaa gccctcccgt atcgtagtta    660
```

```
tctacacgac ggggagtcag gcaactatgg atgaacgaaa tagacagatc gctgagatag     720
gtgcctcact gattaagcat tggtaactgt cagaccaagt ttactcatat atactttaga     780
ttgatttaaa acttcatttt taatttaaaa ggatctaggt gaagatcctt tttgataatc     840
tcatgaccaa aatcccttaa cgtgagtttt cgttccactg agcgtcagac cccgtagaaa     900
agatcaaagg atcttcttga tcctttttt ttctgcgcgt aatctgctgc ttgcaaacaa     960
aaaaaccacc gctaccagcg gtggtttgtt tgccggatca agagctacca actctttttc    1020
cgaaggtaac tggcttcagc agagcgcaga taccaaatac tgttcttcta gtgtagccgt    1080
agttaggcca ccacttcaag aactctgtag caccgcctac atacctcgct ctgctaatcc    1140
tgttaccagt ggctgctgcc agtggcgata agtcgtgtct taccgggttg gactcaagac    1200
gatagttacc ggataaggcg cagcggtcgg gctgaacggg gggttcgtgc acacagccca    1260
gcttggagcg aacgacctac accgaactga gatacctaca gcgtgagcta tgagaaagcg    1320
ccacgcttcc cgaagggaga aaggcggaca ggtatccggt aagcggcagg gtcggaacag    1380
gagagcgcac gagggagctt ccaggggaa acgcctggta tctttatagt cctgtcgggt    1440
ttcgccacct ctgacttgag cgtcgatttt tgtgatgctc gtcagggggg cggagcctat    1500
ggaaaaacgc cagcaacgcg gcctttttac ggttcctggc cttttgctgg ccttttgctc    1560
acatgttctt cctgcgtta tcccctgatt ctgtggataa ccgtattacc gcctttgagt    1620
gagctgatac cgctcgccgc agccgaacga ccgagcgcag cgagtcagtg agcgaggaag    1680
cggaagagcg cccaatacgc aaaccgcctc tccccgcgcg ttggccgatt cattaatgca    1740
gctggcacga caggtttccc gactggaaag cgggcagtga gcgcaacgca attaatgtga    1800
gttagctcac tcattaggca ccccaggctt tacactttat gcttccggct cgtatgttgt    1860
gtggaattgt gagcggataa caatttcaca caggaaacag ctatgaccat gattacgcca    1920
agcgcgcaat taaccctcac taaagggaac aaaagctgga gctgcaagct taatgtagtc    1980
ttatgcaata ctcttgtagt cttgcaacat ggtaacgatg agttagcaac atgccttaca    2040
aggagagaaa aagcaccgtg catgccgatt ggtggaagta aggtggtacg atcgtgcctt    2100
attaggaagg caacagacgg gtctgacatg gattggacga accactgaat tgccgcattg    2160
cagagatatt gtatttaagt gcctagctcg atacataaac gggtctctct ggttagacca    2220
gatctgagcc tgggagctct ctggctaact agggaaccca ctgcttaagc ctcaataaag    2280
cttgccttga gtgcttcaag tagtgtgtgc ccgtctgttg tgtgactctg gtaactagag    2340
atccctcaga ccctttagt cagtgtggaa aatctctagc agtggcgccc gaacagggac    2400
ttgaaagcga aagggaaacc agaggagctc tctcgacgca ggactcggct tgctgaagcg    2460
cgcacggcaa gaggcgaggg gcggcgactg gtgagtacgc caaaaatttt gactagcgga    2520
ggctagaagg agagagatgg gtgcgagagc gtcagtatta gcgggggag aattagatcg    2580 cgatgggaaa aaattcggtt aaggccaggg ggaaagaaaa aatataaatt aaaacatata    2640
gtatgggcaa gcagggagct agaacgattc gcagttaatc ctggcctgtt agaaacatca    2700
gaaggctgta gacaaatact gggacagcta caaccatccc ttcagacagg atcagaagaa    2760
cttagatcat tatataatac agtagcaacc ctctattgtg tgcatcaaag gatagagata    2820
aaagacacca aggaagcttt agacaagata gaggaagagc aaaacaaaag taagaccacc    2880
gcacagcaag cggccgctga tcttcagacc tggaggagga gatatgaggg acaattggag    2940
aagtgaatta tataaatata aagtagtaaa aattgaacca ttaggagtag cacccaccaa    3000
```

-continued

```
ggcaaagaga agagtggtgc agagagaaaa aagagcagtg ggaataggag ctttgttcct    3060
tgggttcttg ggagcagcag gaagcactat gggcgcagcg tcaatgacgc tgacggtaca    3120
ggccagacaa ttattgtctg gtatagtgca gcagcagaac aatttgctga gggctattga    3180
ggcgcaacag catctgttgc aactcacagt ctggggcatc aagcagctcc aggcaagaat    3240
cctggctgtg gaaagatacc taaaggatca acagctcctg gggatttggg gttgctctgg    3300
aaaactcatt tgcaccactg ctgtgccttg gaatgctagt tggagtaata atctctgga    3360 acagatttgg aatcacacga cctggatgga gtgggacaga gaaattaaca attacacaag    3420
cttaatacac tccttaattg aagaatcgca aaaccagcaa gaaaagaatg aacaagaatt    3480
attggaatta gataaatggg caagtttgtg gaattggttt aacataacaa attggctgtg    3540
gtatataaaa ttattcataa tgatagtagg aggcttggta ggtttaagaa tagttttgc     3600 tgtactttct atagtgaata gagttaggca gggatattca ccattatcgt ttcagaccca    3660
cctcccaacc ccgaggggac ccgacaggcc cgaaggaata agaagaag gtggagagag      3720 agacagagac agatccattc gattagtgaa cggatctcga cggtatcgat tagactgtag    3780
cccaggaata tggcagctag attgtacaca tttagaagga aaagttatct tggtagcagt    3840
tcatgtagcc agtggatata tagaagcaga agtaattcca gcagagacag ggcaagaaac    3900
agcatacttc ctcttaaaat tagcaggaag atggccagta aaaacagtac atacagacaa    3960
tggcagcaat ttcaccagta ctacagttaa ggccgcctgt tggtgggcgg ggatcaagca    4020
ggaatttggc attccctaca atccccaaag tcaaggagta atagaatcta tgaataaaga    4080
attaagaaaa attataggac aggtaagaga tcaggctgaa catcttaaga cagcagtaca    4140
aatggcagta ttcatccaca attttaaaag aaaagggggg attgggggt acagtgcagg    4200 ggaaagaata gtagacataa tagcaacaga catacaaact aaagaattac aaaaacaaat    4260
tacaaaaatt caaaattttc gggtttatta cagggacagc agagatccag tttggctgca    4320
tacgcgtcgt gaggctccgg tgcccgtcag tgggcagagc gcacatcgcc cacagtcccc    4380
gagaagttgg ggggaggggt cggcaattga accggtgcct agagaaggtg gcgcggggta    4440
aactgggaaa gtgatgtcgt gtactggctc cgccttttc ccgagggtgg gggagaaccg    4500
tatataagtg cagtagtcgc cgtgaacgtt cttttcgca acgggtttgc cgccagaaca    4560
caggtaagtg ccgtgtgtgg ttcccgcggg cctggcctct ttacgggtta tggcccttgc    4620
gtgccttgaa ttacttccac ctggctgcag tacgtgattc ttgatcccga gcttcgggtt    4680
ggaagtgggt gggagagttc gaggccttgc gcttaaggag ccccttcgcc tcgtgcttga    4740
gttgaggcct ggcctgggcg ctggggccgc cgcgtgcgaa tctggtggca ccttcgcgcc    4800
tgtctcgctg ctttcgataa gtctctagcc atttaaaatt tttgatgacc tgctgcgacg    4860
ctttttttct ggcaagatag tcttgtaaat gcgggccaag atctgcacac tggtatttcg    4920
gtttttgggg ccgcgggcgg cgacgggggcc cgtgcgtccc agcgcacatg ttcggcgagg    4980
cggggcctgc gagcgcggcc accgagaatc ggacgggggt agtctcaagc tggccggcct    5040
gctctggtgc ctggcctcgc gccgccgtgt atcgccccgc cctgggcggc aaggctggcc    5100
cggtcggcac cagttgcgtg agcggaaaga tggccgcttc ccggccctgc tgcagggagc    5160
tcaaaatgga ggacgcggcg ctcgggagag cgggcgggtg agtcacccac acaaaggaaa    5220
agggcctttc cgtcctcagc cgtcgcttca tgtgactcca ctgagtaccg ggcgccgtcc    5280
aggcacctcg attagttctc gtgcttttgg agtacgtcgt ctttaggttg ggggagggg     5340 ttttatgcga tggagtttcc ccacactgag tgggtggaga ctgaagttag gccagcttgg    5400
```

```
cacttgatgt aattctcctt ggaatttgcc cttttttgagt ttggatcttg gttcattctc    5460
aagcctcaga cagtggttca aagttttttt cttccatttc aggtgtcgtg agctagctct    5520
agagccagca tggccttacc agtgaccgcc ttgctcctgc cgctggcctt gctgctccac    5580
gccgccaggc cgcaggtgca gctgcaggag tctgggggag gcttggtgca gcctgggggg    5640
tctctgagcc tctcctgtac agcctctgga ttcacgttca gtagttactc catggcctgg    5700
gtccgccagg ctccagggaa gggacccgaa tgggtctcag ggatttaccc ttctgatggt    5760
aagacaaggt atgcagactt cgtgaagggc cgattcagca tctccagaga caacgccaag    5820
aatatgttgt atctgcaaat gaacaacctg gaacctgagg acacggccct atattactgt    5880
gcgagaggta tcaccggatt gggaccccgg ggccagggga cccaggtcac cgtctcctca    5940
gcggccgcca ctagtgagtc taagtacggc cctcccctgcc ctccttgccc atacatctgg    6000
gcgcccttgg ccgggacttg tggggtcctt ctcctgtcac tggttatcac cctttactgc    6060
aaacggggca gaaagaaact cctgtatata ttcaaacaac catttatgag accagtacaa    6120
actactcaag aggaagatgg ctgtagctgc cgatttccag aagaagaaga aggaggatgt    6180
gaactgctcg agggaagcgg agctactaac ttcagcctgc tgaagcaggc tggagacgtg    6240
gaggagaacc ctggacctcc taggatggcc ttaccagtga ccgccttgct cctgccgctg    6300
gccttgctgc tccacgccgc caggccggga tcccaggtgc agctgcagga gtctggggga    6360
ggattggtgc aggctggggg ctctctgaga ctctcctgtg cagcctctgg attcacgttt    6420
ggtagttatg ttatgggctg gttccgccag gctccaggga aggagcgtga atttgtggca    6480
agtattagta cgagtggtgg cataacatct tatgcagact ccgtgaaggg ccgattcact    6540
gtctccagag acaacgccaa gaatacggtc tacttacaaa tgaacagcct gaaacctgag    6600
gacacggccg tttattactg cgcacgagat ctgacatact atcgtactgg tggtaggtta    6660
ccagataacg ctaatggata tgcgtactgg ggccagggta cccaggtcac cgtctcctca    6720
gcggccgcca ctagttccgg aaccactaca ccagcgccca gaccacctac cccggctcct    6780
accatcgcat ctcagccctt gagtcttaga cccgaggcat gtcggccagc ggcgggggc    6840 gcagtgcaca cgagggggct ggacttcgcc tgtgattaca tctgggcgcc cttggccggg    6900
acttgtgggg tccttctcct gtcactggtt atcaccccttt actgcagagt gaagttcagc    6960
aggagcgcag acgcccccgc gtacaagcag gccagaacc agctctataa cgagctcaat    7020
ctaggacgaa gagaggagta cgatgttttg acaagagac gtggccggga ccctgagatg    7080
gggggaaagc cgagaaggaa gaaccctcag gaaggcctgt acaatgaact gcagaaagat    7140
aagatggcgg aggcctacag tgagattggg atgaaaggcg agcgccggag gggcaagggg    7200
cacgatggcc tttaccaggg tctcagtaca gccaccaagg acacctacga cgcccttcac    7260
atgcaggccc tgccccctcg ctaagtcgac aatcaacctc tggattacaa atttgtgaa    7320 agattgactg gtattcttaa ctatgttgct ccttttacgc tatgtggata cgctgcttta    7380
atgcctttgt atcatgctat tgcttcccgt atggctttca ttttctcctc cttgtataaa    7440
tcctggttgc tgtctcttta tgaggagttg tggcccgttg tcaggcaacg tggcgtggtg    7500
tgcactgtgt ttgctgacgc aaccccccact ggttggggca ttgccaccac ctgtcagctc    7560
ctttccggga cttttgctttt ccccctccct attgccacgg cggaactcat cgccgcctgc    7620
cttgcccgct gctggacagg ggctcggctg ttgggcactg acaattccgt ggtgttgtcg    7680
gggaagctga cgtcctttcc ttggctgctc gcctgtgttg ccacctggat tctgcgcggg    7740
```

```
acgtccttct gctacgtccc ttcggccctc aatccagcgg accttccttc ccgcggcctg   7800
ctgccggctc tgcggcctct tccgcgtctt cgccttcgcc ctcagacgag tcggatctcc   7860
ctttgggccg cctccccgcc tggaattcga gctcggtacc tttaagacca atgacttaca   7920
aggcagctgt agatcttagc cacttttttaa aagaaaaggg gggactggaa gggctaattc   7980
actcccaacg aagacaagat ctgcttttttg cttgtactgg gtctctctgg ttagaccaga   8040
tctgagcctg ggagctctct ggctaactag ggaacccact gcttaagcct caataaagct   8100
tgccttgagt gcttcaagta gtgtgtgccc gtctgttgtg tgactctggt aactagagat   8160
ccctcagacc cttttagtca gtgtggaaaa tctctagcag tagtagttca tgtcatctta   8220
ttattcagta tttataactt gcaaagaaat gaatatcaga gagtgagagg aacttgttta   8280
ttgcagctta taatggttac aaataaagca atagcatcac aaatttcaca aataaagcat   8340
ttttttcact gcattctagt tgtggtttgt ccaaactcat caatgtatct tatcatgtct   8400
ggctctagct atcccgcccc taactccgcc cagttccgcc cattctccgc cccatggctg   8460
actaattttt tttatttatg cagaggccga ggccgcctcg gcctctgagc tattccagaa   8520
gtagtgagga ggcttttttg gaggcctagc tagggacgta cccaattcgc cctatagtga   8580
gtcgtattac gcgcgctcac tggccgtcgt tttacaacgt cgtgactggg aaaaccctgg   8640
cgttacccaa cttaatcgcc ttgcagcaca tccccctttc gccagctggc gtaatagcga   8700
agaggcccgc accgatcgcc cttcccaaca gttgcgcagc ctgaatggcg aatgggacgc   8760
gccctgtagc ggcgcattaa gcgcggcggg tgtggtggtt acgcgcagcg tgaccgctac   8820
acttgccagc gccctagcgc ccgctccttt cgctttcttc ccttcctttc tcgccacgtt   8880
cgccggcttt ccccgtcaag ctctaaatcg ggggctccct ttagggttcc gatttagtgc   8940
tttacggcac ctcgacccca aaaaacttga ttagggtgat ggttcacgta gtgggccatc   9000
gccctgatag acggtttttc gccctttgac gttggagtcc acgttcttta atagtggact   9060
cttgttccaa actggaacaa cactcaaccc tatctcggtc tattcttttg atttataagg   9120
gattttgccg atttcggcct attggttaaa aaatgagctg atttaacaaa aatttaacgc   9180
gaattttaac aaaatattaa cgcttacaat ttaggtggca cttttcgggg aaatgtgcgc   9240
ggaacccta tttgtttatt tttctaaata cattcaaata tgtatccgct catgagacaa   9300
taaccctgat aaatgcttca ataatattga aaaaggaaga gtatgagtat tcaacatttc   9360
cgtgtcgccc ttattccctt ttttgcggca ttttgccttc ctgtttttgc tcacccagaa   9420
acgctggtga agtaaaaga tgctgaagat cagttgg                             9457
```

<210> SEQ ID NO 37
<211> LENGTH: 9403
<212> TYPE: DNA
<213> ORGANISM: Artificial Sequence
<220> FEATURE:
<223> OTHER INFORMATION: BiCAR2 VHH32

<400> SEQUENCE: 37

```
gtgcacgagt gggttacatc gaactggatc tcaacagcgg taagatcctt gagagttttc     60
gccccgaaga cgttttcca atgatgagca ctttttaaagt tctgctatgt ggcgcggtat    120
tatcccgtat tgacgccggg caagagcaac tcggtcgccg catacactat tctcagaatg    180
acttggttga gtactcacca gtcacagaaa agcatcttac ggatggcatg acagtaagag    240
aattatgcag tgctgccata accatgagtg ataaacactgc ggccaactta cttctgacaa    300
cgatcggagg accgaaggag ctaaccgctt ttttgcacaa catgggggat catgtaactc    360
```

-continued

```
gccttgatcg ttgggaaccg gagctgaatg aagccatacc aaacgacgag cgtgacacca    420
cgatgcctgt agcaatggca acaacgttgc gcaaactatt aactggcgaa ctacttactc    480
tagcttcccg gcaacaatta atagactgga tggaggcgga taaagttgca ggaccacttc    540
tgcgctcggc ccttccggct ggctggttta ttgctgataa atctggagcc ggtgagcgtg    600
ggtctcgcgg tatcattgca gcactggggc cagatggtaa gccctcccgt atcgtagtta    660
tctacacgac ggggagtcag gcaactatgg atgaacgaaa tagacagatc gctgagatag    720
gtgcctcact gattaagcat tggtaactgt cagaccaagt ttactcatat atactttaga    780
ttgatttaaa acttcatttt taatttaaaa ggatctaggt gaagatcctt tttgataatc    840
tcatgaccaa aatcccttaa cgtgagtttt cgttccactg agcgtcagac cccgtagaaa    900
agatcaaagg atcttcttga tccttttttt tctgcgcgt aatctgctgc ttgcaaacaa    960
aaaaaccacc gctaccagcg gtggtttgtt tgccggatca agagctacca actcttttc    1020 cgaaggtaac tggcttcagc agagcgcaga taccaaatac tgttcttcta gtgtagccgt    1080
agttaggcca ccacttcaag aactctgtag caccgcctac atacctcgct ctgctaatcc    1140
tgttaccagt ggctgctgcc agtggcgata agtcgtgtct taccgggttg gactcaagac    1200
gatagttacc ggataaggcg cagcggtcgg gctgaacggg gggttcgtgc acacagccca    1260
gcttggagcg aacgacctac accgaactga gatacctaca gcgtgagcta tgagaaagcg    1320
ccacgcttcc cgaagggaga aaggcggaca ggtatccggt aagcggcagg gtcggaacag    1380
gagagcgcac gagggagctt ccaggggaa acgcctggta tctttatagt cctgtcgggt    1440
ttcgccacct ctgacttgag cgtcgatttt tgtgatgctc gtcaggggg cggagcctat    1500 ggaaaaacgc cagcaacgcg gcctttttac ggttcctggc cttttgctgg ccttttgctc    1560
acatgttctt cctgcgtta tcccctgatt ctgtggataa ccgtattacc gcctttgagt    1620
gagctgatac cgctcgccgc agccgaacga ccgagcgcag cgagtcagtg agcgaggaag    1680
cggaagagcg cccaatacgc aaaccgcctc tccccgcgcg ttggccgatt cattaatgca    1740
gctggcacga caggtttccc gactggaaag cgggcagtga gcgcaacgca attaatgtga    1800
gttagctcac tcattaggca ccccaggctt tacactttat gcttccggct cgtatgttgt    1860
gtggaattgt gagcggataa caatttcaca caggaaacag ctatgaccat gattacgcca    1920
agcgcgcaat taaccctcac taaagggaac aaaagctgga gctgcaagct taatgtagtc    1980
ttatgcaata ctcttgtagt cttgcaacat ggtaacgatg agttagcaac atgccttaca    2040
aggagagaaa aagcaccgtg catgccgatt ggtggaagta aggtggtacg atcgtgcctt    2100
attaggaagg caacagacgg gtctgacatg gattggacga accactgaat tgccgcattg    2160
cagagatatt gtatttaagt gcctagctcg atacataaac gggtctctct ggttagacca    2220
gatctgagcc tgggagctct ctggctaact agggaaccca ctgcttaagc ctcaataaag    2280
cttgccttga gtgcttcaag tagtgtgtgc ccgtctgttg tgtgactctg gtaactagag    2340
atccctcaga cccttttagt cagtgtggaa atctctagc agtggcgccc gaacagggac    2400
ttgaaagcga aagggaaacc agaggagctc tctcgacgca ggactcggct tgctgaagcg    2460
cgcacggcaa gaggcgaggg gcggcgactg gtgagtacgc caaaaatttt gactagcgga    2520
ggctagaagg agagagatgg gtgcgagagc gtcagtatta agcggggag aattagatcg    2580 cgatgggaaa aaattcggtt aaggccaggg ggaaagaaaa atataaatt aaacatata    2640 gtatgggcaa gcagggagct agaacgattc gcagttaatc ctggcctgtt agaaacatca    2700
```

```
gaaggctgta gacaaatact gggacagcta caaccatccc ttcagacagg atcagaagaa    2760
cttagatcat tatataatac agtagcaacc ctctattgtg tgcatcaaag gatagagata    2820
aaagacacca aggaagcttt agacaagata gaggaagagc aaaacaaaag taagaccacc    2880
gcacagcaag cggccgctga tcttcagacc tggaggagga gatatgaggg acaattggag    2940
aagtgaatta tataaatata aagtagtaaa aattgaacca ttaggagtag cacccaccaa    3000
ggcaaagaga agagtggtgc agagagaaaa aagagcagtg gaataggag ctttgttcct     3060 tgggttcttg ggagcagcag gaagcactat gggcgcagcg tcaatgacgc tgacggtaca    3120
ggccagacaa ttattgtctg gtatagtgca gcagcagaac aatttgctga ggctattga     3180 ggcgcaacag catctgttgc aactcacagt ctggggcatc aagcagctcc aggcaagaat    3240
cctggctgtg gaaagatacc taaaggatca acagctcctg gggatttggg gttgctctgg    3300
aaaactcatt tgcaccactg ctgtgccttg gaatgctagt tggagtaata atctctgga     3360 acagatttgg aatcacacga cctggatgga gtgggacaga gaaattaaca attacacaag    3420
cttaatacac tccttaattg aagaatcgca aaaccagcaa gaaaagaatg aacaagaatt    3480
attggaatta gataaatggg caagtttgtg gaattggttt aacataacaa attggctgtg    3540
gtatataaaa ttattcataa tgatagtagg aggcttggta ggtttaagaa tagttttgc     3600 tgtactttct atagtgaata gagttaggca gggatattca ccattatcgt ttcagaccca    3660
cctcccaacc ccgaggggac ccgacaggcc cgaaggaata agaagaag gtggagagag      3720 agacagagac agatccattc gattagtgaa cggatctcga cggtatcgat tagactgtag    3780
cccaggaata tggcagctag attgtacaca tttagaagga aaagttatct tggtagcagt    3840
tcatgtagcc agtggatata tagaagcaga gtaattcca gcagagacag ggcaagaaac     3900
agcatacttc ctcttaaaat tagcaggaag atggccagta aaaacagtac atacagacaa    3960
tggcagcaat ttcaccagta ctacagttaa ggccgcctgt tggtgggcgg ggatcaagca    4020
ggaatttggc attccctaca atccccaaag tcaaggagta atagaatcta tgaataaaga    4080
attaaagaaa attataggac aggtaagaga tcaggctgaa catcttaaga cagcagtaca    4140
aatggcagta ttcatccaca attttaaaag aaaagggggg attgggggt acagtgcagg     4200 ggaaagaata gtagacataa tagcaacaga catacaaact aaagaattac aaaaacaaat    4260
tacaaaaatt caaaattttc gggtttatta caggacagc agagatccag tttggctgca    4320
tacgcgtcgt gaggctccgg tgcccgtcag tgggcagagc gcacatcgcc cacagtcccc    4380
gagaagttgg ggggagggt cggcaattga accggtgcct agagaaggtg gcgcggggta     4440
aactgggaaa gtgatgtcgt gtactggctc cgcctttttc ccgagggtgg gggagaaccg    4500
tatataagtg cagtagtcgc cgtgaacgtt ctttttcgca acgggtttgc cgccagaaca    4560
caggtaagtg ccgtgtgtgg ttcccgcggg cctggcctct ttacgggtta tggcccttgc    4620
gtgccttgaa ttacttccac ctggctgcag tacgtgattc ttgatcccga gcttcgggtt    4680
ggaagtgggt gggagagttc gaggccttgc gcttaaggag ccccttcgcc tcgtgcttga    4740
gttgaggcct ggcctgggcg ctggggccgc cgcgtgcgaa tctggtggca cttcgcgcc     4800 tgtctcgctg ctttcgataa gtctctagcc atttaaaatt tttgatgacc tgctgcgacg    4860 cttttttttct ggcaagatag tcttgtaaat gcgggccaag atctgcacac tggtatttcg   4920
gtttttgggg ccgcgggcgg cgacgggcc cgtgcgtccc agcgcacatg ttcggcgagg     4980
cggggcctgc gagcgcggcc accgagaatc ggacgggggt agtctcaagc tggccggcct    5040
gctctggtgc ctggcctcgc gccgccgtgt atcgccccgc cctgggcggc aaggctggcc    5100
```

```
cggtcggcac cagttgcgtg agcggaaaga tggccgcttc ccggccctgc tgcagggagc    5160
tcaaaatgga ggacgcggcg ctcgggagag cgggcggGtg agtcacccac acaaaggaaa    5220
agggcctttc cgtcctcagc cgtcgcttca tgtgactcca ctgagtaccg ggcgccgtcc    5280
aggcacctcg attagttctc gtgcttttgg agtacgtcgt ctttaggttg gggggagggg    5340
ttttatgcga tggagtttcc ccacactgag tgggtggaga ctgaagttag gccagcttgg    5400
cacttgatgt aattctcctt ggaatttgcc cttttTgagt ttggatcttg gttcattctc    5460
aagcctcaga cagtggttca aagtttttTt cttccatttc aggtgtcgtg agctagctct    5520
agagccagca tggccttacc agtgaccgcc ttgctcctgc cgctggcctt gctgctccac    5580
gccgccaggc cgcaggtgca gctgcaggag tctgggggag gcttggtgca gcctgggggg    5640
tctctgagcc tctcctgtac agcctctgga ttcacgttca gtagttactc catggcctgg    5700
gtccgccagg ctccagggaa gggacccgaa tgggtctcag ggatttaccc ttctgatggt    5760
aagacaaggt atgcagactt cgtgaagggc cgattcagca tctccagaga caacgccaag    5820
aatatgttgt atctgcaaat gaacaacctg gaacctgagg acacggccct atattactgt    5880
gcgagaggta tcaccggatt gggacccagg ggccagggga cccaggtcac cgtctcctca    5940
gcggccgcca ctagtgagtc taagtacggc cctccctgcc ctccttgccc atacatctgg    6000
gcgcccttgg ccgggacttg tggggtcctt ctcctgtcac tggttatcac cctttactgc    6060
aaacggggca gaaagaaact cctgtatata ttcaaacaac catttatgag accagtacaa    6120
actactcaag aggaagatgg ctgtagctgc cgatttccag aagaagaaga aggaggatgt    6180
gaactgctcg agggaagcgg agctactaac ttcagcctgc tgaagcaggc tggagacgtg    6240
gaggagaacc ctggacctcc taggatggcc ttaccagtga ccgccttgct cctgccgctg    6300
gccttgctgc tccacgccgc caggccggga tcccaggtgc agctgcagga gtctggagga    6360
ggcttggtgc aggctggggg gtctctaaat ctctcctgtg cagcctctgg aagttccttc    6420
agactctata ccgtcggctg gcaccgccag gcgccaggga agcagcgcga gttggtcgca    6480
tggattagtg gtgcgggcag cacaaactat cattcgtccg tgaagggccg attcaccatc    6540
tccagagaca acgccaagaa cacggcactc ctgcaaatga caacctggcc acctgaagac    6600
acggccgtct attactgtaa tctactgaac tactggggcc aggggaccca ggtcaccgtc    6660
tcctcagcgg ccgccactag ttccggaacc actacaccag cgcccagacc acctaccccg    6720
gctcctacca tcgcatctca gcccttgagt cttagacccg aggcatgtcg gccagcggcg    6780
gggggcgcag tgcacacgag ggggctggac ttcgcctgtg attacatctg ggcgcccttg    6840
gccgggactt gtggggtcct tctcctgtca ctggttatca cccttTactg cagagtgaag    6900
ttcagcagga gcgcagacgc ccccgcgtac aagcagggcc agaaccagct ctataacgag    6960
ctcaatctag gacgaagaga ggagtacgat gttttggaca gagacgtgg ccgggaccct     7020 gagatggggg gaaagccgag aaggaagaac cctcaggaag gcctgtacaa tgaactgcag    7080
aaagataaga tggcggaggc ctacagtgag attgggatga aggcgagcg ccggagggc     7140 aaggggcacg atggccttta ccagggtctc agtacagcca ccaaggacac ctacgacgcc    7200
cttcacatgc aggccctgcc ccctcgctaa gtcgacaatc aacctctgga ttacaaaatt    7260
tgtgaaagat tgactggtat tcttaactat gttgctcctt ttacgctatg tggatacgct    7320
gctttaatgc ctttgtatca tgctattgct tcccgtatgg ctttcatttt ctcctccttg    7380
tataaatcct ggttgctgtc tctttatgag gagttgtggc ccgttgtcag caacgtggc     7440
```

```
gtggtgtgca ctgtgtttgc tgacgcaacc cccactggtt ggggcattgc caccacctgt    7500
cagctccttt ccgggacttt cgctttcccc ctccctattg ccacggcgga actcatcgcc    7560
gcctgccttg cccgctgctg acaggggct cggctgttgg gcactgacaa ttccgtggtg     7620
ttgtcgggga agctgacgtc ctttccttgg ctgctcgcct gtgttgccac ctggattctg    7680
cgcgggacgt ccttctgcta cgtcccttcg gccctcaatc cagcggacct tccttcccgc    7740
ggcctgctgc cggctctgcg gcctcttccg cgtcttcgcc ttcgccctca gacgagtcgg    7800
atctcccttt gggccgcctc cccgcctgga attcgagctc ggtacctttta agaccaatga   7860 cttacaaggc agctgtagat cttagccact ttttaaaaga aaggggggga ctggaagggc    7920
taattcactc ccaacgaaga caagatctgc ttttgcttg tactgggtct ctctggttag     7980
accagatctg agcctgggag ctctctggct aactagggaa cccactgctt aagcctcaat    8040
aaagcttgcc ttgagtgctt caagtagtgt gtgcccgtct gttgtgtgac tctggtaact    8100
agagatccct cagaccctt tagtcagtgt ggaaaatctc tagcagtagt agttcatgtc     8160
atcttattat tcagtattta aacttgcaa agaaatgaat atcagagagt gagaggaact     8220
tgtttattgc agcttataat ggttacaaat aaagcaatag catcacaaat ttcacaaata   8280
aagcattttt ttcactgcat tctagttgtg gtttgtccaa actcatcaat gtatcttatc   8340
atgtctggct ctagctatcc cgcccctaac tccgcccagt tccgcccatt ctccgcccca   8400
tggctgacta attttttta tttatgcaga ggccgaggcc gcctcggcct ctgagctatt    8460
ccagaagtag tgaggaggct tttttggagg cctagctagg gacgtaccca attcgcccta   8520
tagtgagtcg tattacgcgc gctcactggc cgtcgtttta caacgtcgtg actgggaaaa   8580
ccctggcgtt acccaactta atcgccttgc agcacatccc ctttcgcca gctggcgtaa    8640 tagcgaagag gcccgcaccg atcgcccttc ccaacagttg cgcagcctga atggcgaatg    8700
ggacgcgccc tgtagcggcg cattaagcgc ggcgggtgtg gtggttacgc gcagcgtgac    8760
cgctacactt gccagcgccc tagcgcccgc tcctttcgct ttcttccctt ctttctcgc    8820 cacgttcgcc ggctttcccc gtcaagctct aaatcggggg ctcccttag ggttccgatt    8880 tagtgcttta cggcacctcg accccaaaaa acttgattag ggtgatggtt cacgtagtgg    8940
gccatcgccc tgatagacgg ttttttcgccc tttgacgttg gagtccacgt tctttaatag   9000
tggactcttg ttccaaactg gaacaacact caacccctatc tcggtctatt cttttgattt   9060
ataagggatt ttgccgattt cggcctattg gttaaaaaat gagctgattt aacaaaaatt   9120
taacgcgaat tttaacaaaa tattaacgct acaatttag gtggcacttt tcggggaaat    9180
gtgcgcggaa cccctatttg tttatttttc taaatacatt caaatatgta tccgctcatg   9240
agacaataac cctgataaat gcttcaataa tattgaaaaa ggaagagtat gagtattcaa    9300
catttccgtg tcgcccttat cccttttttt gcggcatttt gccttcctgt ttttgctcac   9360
ccagaaacgc tggtgaaagt aaaagatgct gaagatcagt tgg                      9403
```

<210> SEQ ID NO 38
<211> LENGTH: 9433
<212> TYPE: DNA
<213> ORGANISM: Artificial Sequence
<220> FEATURE:
<223> OTHER INFORMATION: BiCAR2 VHH33

<400> SEQUENCE: 38

```
gtgcacgagt gggttacatc gaactggatc tcaacagcgg taagatcctt gagagttttc     60
gccccgaaga acgttttcca atgatgagca cttttaaagt tctgctatgt ggcgcggtat    120
```

```
tatcccgtat tgacgccggg caagagcaac tcggtcgccg catacactat tctcagaatg    180
acttggttga gtactcacca gtcacagaaa agcatcttac ggatggcatg acagtaagag    240
aattatgcag tgctgccata accatgagtg ataacactgc ggccaactta cttctgacaa    300
cgatcggagg accgaaggag ctaaccgctt ttttgcacaa catgggggat catgtaactc    360
gccttgatcg ttgggaaccg gagctgaatg aagccatacc aaacgacgag cgtgacacca    420
cgatgcctgt agcaatggca acaacgttgc gcaaactatt aactggcgaa ctacttactc    480
tagcttcccg gcaacaatta atagactgga tggaggcgga taaagttgca ggaccacttc    540
tgcgctcggc ccttccggct ggctggttta ttgctgataa atctggagcc ggtgagcgtg    600
ggtctcgcgg tatcattgca gcactggggc cagatggtaa gccctcccgt atcgtagtta    660
tctacacgac ggggagtcag gcaactatgg atgaacgaaa tagacagatc gctgagatag    720
gtgcctcact gattaagcat tggtaactgt cagaccaagt ttactcatat atactttaga    780
ttgatttaaa acttcatttt taatttaaaa ggatctaggt gaagatcctt tttgataatc    840
tcatgaccaa aatcccttaa cgtgagtttt cgttccactg agcgtcagac cccgtagaaa    900
agatcaaagg atcttcttga gatcctttt ttctgcgcgt aatctgctgc ttgcaaacaa    960
aaaaaccacc gctaccagcg gtggtttgtt tgccggatca agagctacca actctttttc   1020
cgaaggtaac tggcttcagc agagcgcaga taccaaatac tgttcttcta gtgtagccgt   1080
agttaggcca ccacttcaag aactctgtag caccgcctac atacctcgct ctgctaatcc   1140
tgttaccagt ggctgctgcc agtggcgata agtcgtgtct taccgggttg gactcaagac   1200
gatagttacc ggataaggcg cagcggtcgg gctgaacggg gggttcgtgc acacagccca   1260
gcttggagcg aacgacctac accgaactga gatacctaca gcgtgagcta tgagaaagcg   1320
ccacgcttcc cgaagggaga aaggcggaca ggtatccggt aagcggcagg gtcggaacag   1380
gagagcgcac gagggagctt ccagggggaa acgcctggta tctttatagt cctgtcgggt   1440
ttcgccacct ctgacttgag cgtcgatttt tgtgatgctc gtcagggggg cggagcctat   1500
ggaaaaacgc cagcaacgcg gcctttttac ggttcctggc cttttgctgg ccttttgctc   1560
acatgttctt tcctgcgtta tcccctgatt ctgtggataa ccgtattacc gcctttgagt   1620
gagctgatac cgctcgccgc agccgaacga ccgagcgcag cgagtcagtg agcgaggaag   1680
cggaagagcg cccaatacgc aaaccgcctc tccccgcgcg ttggccgatt cattaatgca   1740
gctggcacga caggtttccc gactggaaag cgggcagtga gcgcaacgca attaatgtga   1800
gttagctcac tcattaggca ccccaggctt tacactttat gcttccggct cgtatgttgt   1860
gtggaattgt gagcggataa caatttcaca caggaaacag ctatgaccat gattacgcca   1920
agcgcgcaat taaccctcac taaagggaac aaaagctgga gctgcaagct taatgtagtc   1980
ttatgcaata ctcttgtagt cttgcaacat ggtaacgatg agttagcaac atgccttaca   2040
aggagagaaa aagcaccgtg catgccgatt ggtggaagta aggtggtacg atcgtgcctt   2100
attaggaagg caacagacgg gtctgacatg gattggacga accactgaat tgccgcattg   2160
cagagatatt gtatttaagt gcctagctcg atacataaac gggtctctct ggttagacca   2220
gatctgagcc tgggagctct ctggctaact agggaaccca ctgcttaagc ctcaataaag   2280
cttgccttga gtgcttcaag tagtgtgtgc ccgtctgttg tgtgactctg gtaactagag   2340
atccctcaga cccttttagt cagtgtggaa aatctctagc agtggcgccc gaacagggac   2400
ttgaaagcga aagggaaacc agaggagctc tctcgacgca ggactcggct tgctgaagcg   2460
```

```
cgcacggcaa gaggcgaggg gcggcgactg gtgagtacgc caaaaatttt gactagcgga   2520
ggctagaagg agagagatgg gtgcgagagc gtcagtatta agcggggggag aattagatcg   2580
cgatgggaaa aaattcggtt aaggccaggg ggaaagaaaa aatataaatt aaaacatata   2640
gtatgggcaa gcagggagct agaacgattc gcagttaatc ctggcctgtt agaaacatca   2700
gaaggctgta gacaaatact gggacagcta caaccatccc ttcagacagg atcagaagaa   2760
cttagatcat tatataatac agtagcaacc ctctattgtg tgcatcaaag gatagagata   2820
aaagacacca aggaagcttt agacaagata gaggaagagc aaaacaaaag taagaccacc   2880
gcacagcaag cggccgctga tcttcagacc tggaggagga gatatgaggg acaattggag   2940
aagtgaatta tataaatata agtagtaaaa aattgaacca ttaggagtag cacccaccaa   3000
ggcaaagaga agagtggtgc agagagaaaa aagagcagtg gaataggag ctttgttcct   3060
tgggttcttg ggagcagcag gaagcactat gggcgcagcg tcaatgacgc tgacggtaca   3120
ggccagacaa ttattgtctg gtatagtgca gcagcagaac aatttgctga gggctattga   3180
ggcgcaacag catctgttgc aactcacagt ctggggcatc aagcagctcc aggcaagaat   3240
cctggctgtg gaaagatacc taaaggatca acagctcctg gggatttggg gttgctctgg   3300
aaaactcatt tgcaccactg ctgtgccttg gaatgctagt tggagtaata atctctgga   3360
acagatttgg aatcacacga cctggatgga gtgggacaga gaaattaaca attacacaag   3420
cttaatacac tccttaattg aagaatcgca aaaccagcaa gaaaagaatg aacaagaatt   3480
attggaatta gataaatggg caagtttgtg gaattggttt aacataacaa attggctgtg   3540
gtatataaaa ttattcataa tgatagtagg aggcttggta ggtttaagaa tagttttgc   3600
tgtactttct atagtgaata gagttaggca gggatattca ccattatcgt ttcagaccca   3660
cctcccaacc ccgaggggac ccgacaggcc cgaaggaata agaagaag gtggagagag   3720
agacagagac agatccattc gattagtgaa cggatctcga cggtatcgat tagactgtag   3780
cccaggaata tggcagctag attgtacaca tttagaagga aaagttatct tggtagcagt   3840
tcatgtagcc agtggatata tagaagcaga agtaattcca gcagagacag ggcaagaaac   3900
agcatacttc ctcttaaaat tagcaggaag atggccagta aaaacagtac atacagacaa   3960
tggcagcaat ttcaccagta ctacagttaa ggccgcctgt tggtgggcgg ggatcaagca   4020
ggaatttggc attccctaca atccccaaag tcaaggagta atagaatcta tgaataaaga   4080
attaaagaaa attataggac aggtaagaga tcaggctgaa catcttaaga cagcagtaca   4140
aatggcagta ttcatccaca atttaaaag aaaaggggg attgggggt acagtgcagg   4200
ggaaagaata gtagacataa tagcaacaga catacaaact aaagaattac aaaaacaaat   4260
tacaaaaatt caaaattttc gggtttatta caggacagc agagatccag tttggctgca   4320
tacgcgtcgt gaggctccgg tgcccgtcag tgggcagagc gcacatcgcc cacagtcccc   4380
gagaagttgg ggggagggt cggcaattga accggtgcct agagaaggtg gcgcggggta   4440
aactgggaaa gtgatgtcgt gtactggctc cgcctttttc ccgagggtgg gggagaaccg   4500
tatataagtg cagtagtcgc cgtgaacgtt ctttttcgca acgggtttgc cgccagaaca   4560
caggtaagtg ccgtgtgtgg ttcccgcggg cctggcctct ttacgggtta tggcccttgc   4620
gtgccttgaa ttacttccac ctggctgcag tacgtgattc ttgatcccga gcttcgggtt   4680
ggaagtgggt gggagagttc gaggccttgc gcttaaggag cccttcgcc tcgtgcttga   4740
gttgaggcct ggcctgggcg ctggggccgc cgcgtgcgaa tctggtggca ccttcgcgcc   4800
tgtctcgctg ctttcgataa gtctctagcc atttaaaatt tttgatgacc tgctgcgacg   4860
```

```
cttttttttct ggcaagatag tcttgtaaat gcgggccaag atctgcacac tggtatttcg   4920
gtttttgggg ccgcgggcgg cgacggggcc cgtgcgtccc agcgcacatg ttcggcgagg   4980
cggggcctgc gagcgcggcc accgagaatc ggacgggggt agtctcaagc tggccggcct   5040
gctctggtgc ctggcctcgc gccgccgtgt atcgccccgc cctgggcggc aaggctggcc   5100
cggtcggcac cagttgcgtg agcggaaaga tggccgcttc ccggccctgc tgcagggagc   5160
tcaaaatgga ggacgcggcg ctcggggagg cgggcgggtg agtcacccac acaaaggaaa   5220
agggcctttc cgtcctcagc cgtcgcttca tgtgactcca ctgagtaccg ggcgccgtcc   5280
aggcacctcg attagttctc gtgctttttgg agtacgtcgt ctttaggttg gggggagggg   5340
ttttatgcga tggagtttcc ccacactgag tgggtggaga ctgaagttag gccagcttgg   5400
cacttgatgt aattctcctt ggaatttgcc cttttttgagt ttggatcttg gttcattctc   5460
aagcctcaga cagtggttca aagtttttttt cttccatttc aggtgtcgtg agctagctct   5520
agagccagca tggccttacc agtgaccgcc ttgctcctgc cgctggcctt gctgctccac   5580
gccgccaggc cgcaggtgca gctgcaggag tctgggggag gcttggtgca gcctgggggg   5640
tctctgagcc tctcctgtac agcctctgga ttcacgttca gtagttactc catggcctgg   5700
gtccgccagg ctccagggaa gggacccgaa tgggtctcag ggatttaccc ttctgatggt   5760
aagacaaggt atgcagactt cgtgaagggc cgattcagca tctccagaga caacgccaag   5820
aatatgttgt atctgcaaat gaacaacctg gaacctgagg acacggccct atattactgt   5880
gcgagaggta tcaccggatt gggacccggg gccaggggga cccaggtcac cgtctcctca   5940
gcggccgcca ctagtgagtc taagtacggc cctccctgcc ctccttgccc atacatctgg   6000
gcgcccttgg ccgggacttg tggggtcctt ctcctgtcac tggttatcac cctttactgc   6060
aaacggggca gaaagaaact cctgtatata ttcaaacaac catttatgag accagtacaa   6120
actactcaag aggaagatgg ctgtagctgc cgatttccag aagaagaaga aggaggatgt   6180
gaactgctcg agggaagcgg agctactaac ttcagcctgc tgaagcaggc tggagacgtg   6240
gaggagaacc ctggacctcc taggatggcc ttaccagtga ccgccttgct cctgccgctg   6300
gccttgctgc tccacgccgc caggccggga tcccaggtgc agctgcagga gtctggggga   6360
ggcttggtgc agcctggggg gtctctgaga ctctcctgtg cagtctctgg actcacgccg   6420
gatgcttatg tcatgggctg gttccgccag gccccaggga aggagcgcga gggggtctca   6480
tgtattagtc ctagtggtgg tactacaagc tatccagact ccgtgaaggg ccgattcacc   6540
atctccagag acaatgccaa gaacacggtg tacctgcaaa tgaacagcct gaaacctgag   6600
gacacgggcg tttattactg tgcggcagtt gcgggccgct ggtgtgacta cggcatgaac   6660
tactacggca aagggaccca ggtcaccgtc tcctcagcgg ccgccactag ttccggaacc   6720
actacaccag cgcccagacc acctaccccg gctcctacca tcgcatctca gcccttgagt   6780
cttagacccg aggcatgtcg gccagcggcg ggggcgcag tgcacacgag ggggctggac   6840
ttcgcctgtg attacatctg ggcgcccttg gccgggactt gtggggtcct tctcctgtca   6900
ctggttatca ccctttactg cagagtgaag ttcagcagga gcgcagacgc cccgcgtac   6960 aagcagggcc agaaccagct ctataacgag ctcaatctag gacgaagaga ggagtacgat   7020
gttttggaca gagacgtggc ccgggaccct gagatggggg gaaagccgag aaggaagaac   7080
cctcaggaag gcctgtacaa tgaactgcag aaagataaga tggcggaggc ctacagtgag   7140
attgggatga aaggcgagcg ccggagggga aaggggcacg atggccttta ccagggtctc   7200
```

-continued

| | |
|---|---|
| agtacagcca ccaaggacac ctacgacgcc cttcacatgc aggccctgcc ccctcgctaa | 7260 |
| gtcgacaatc aacctctgga ttacaaaatt tgtgaaagat tgactggtat tcttaactat | 7320 |
| gttgctcctt ttacgctatg tggatacgct gctttaatgc ctttgtatca tgctattgct | 7380 |
| tcccgtatgg cttteatttt ctcctccttg tataaatcct ggttgctgtc tctttatgag | 7440 |
| gagttgtggc ccgttgtcag gcaacgtggc gtggtgtgca ctgtgtttgc tgacgcaacc | 7500 |
| cccactggtt ggggcattgc caccacctgt cagctccttt ccgggacttt cgctttcccc | 7560 |
| ctccctattg ccacggcgga actcatcgcc gcctgccttg cccgctgctg acagggggct | 7620 |
| cggctgttgg gcactgacaa ttccgtggtg ttgtcgggga agctgacgtc ctttccttgg | 7680 |
| ctgctcgcct gtgttgccac ctggattctg cgcgggacgt ccttctgcta cgtcccttcg | 7740 |
| gccctcaatc cagcggacct tccttcccgc ggcctgctgc cggctctgcg gcctcttccg | 7800 |
| cgtcttcgcc ttcgccctca gacgagtcgg atctcccttt gggccgcctc cccgcctgga | 7860 |
| attcgagctc ggtacccttta agaccaatga cttacaaggc agctgtagat cttagccact | 7920 |
| tttaaaga aaggggga ctggaagggc taattcactc ccaacgaaga caagatctgc | 7980 |
| tttttgcttg tactgggtct ctctggttag accagatctg agcctgggag ctctctggct | 8040 |
| aactagggaa cccactgctt aagcctcaat aaagcttgcc ttgagtgctt caagtagtgt | 8100 |
| gtgcccgtct gttgtgtgac tctggtaact agagatccct cagacccttt tagtcagtgt | 8160 |
| ggaaaatctc tagcagtagt agttcatgtc atcttattat tcagtattta aacttgcaa | 8220 |
| agaaatgaat atcagagagt gagaggaact tgtttattgc agcttataat ggttacaaat | 8280 |
| aaagcaatag catcacaaat ttcacaaata agcatttttt ttcactgcat tctagttgtg | 8340 |
| gtttgtccaa actcatcaat gtatcttatc atgtctggct ctagctatcc cgcccctaac | 8400 |
| tccgcccagt tccgcccatt ctccgcccca tggctgacta atttttttta tttatgcaga | 8460 |
| ggccgaggcc gcctcggcct ctgagctatt ccagaagtag tgaggaggct ttttggagg | 8520 |
| cctagctagg gacgtaccca attcgcccta tagtgagtcg tattacgcgc gctcactggc | 8580 |
| cgtcgtttta caacgtcgtg actgggaaaa cctggcgtt acccaactta atcgccttgc | 8640 |
| agcacatccc cctttcgcca gctggcgtaa tagcgaagag gcccgcaccg atcgcccttc | 8700 |
| ccaacagttg cgcagcctga atggcgaatg ggacgcgccc tgtagcggcg cattaagcgc | 8760 |
| ggcgggtgtg gtggttacgc gcagcgtgac cgctacactt gccagcgccc tagcgcccgc | 8820 |
| tcctttcgct ttcttccctt cctttctcgc cacgttcgcc ggctttcccc gtcaagctct | 8880 |
| aaatcggggg ctccctttag ggttccgatt tagtgcttta cggcacctcg accccaaaaa | 8940 |
| acttgattag ggtgatggtt cacgtagtgg gccatcgccc tgatagacgg ttttcgccc | 9000 |
| tttgacgttg gagtccacgt tctttaatag tggactcttg ttccaaactg gaacaacact | 9060 |
| caaccctatc tcggtctatt cttttgattt ataagggatt ttgccgattt cggcctattg | 9120 |
| gttaaaaaat gagctgattt aacaaaaatt taacgcgaat tttaacaaaa tattaacgct | 9180 |
| tacaatttag gtggcacttt tcggggaaat gtgcgcggaa cccctatttg tttatttttc | 9240 |
| taaatacatt caaatatgta tccgctcatg agacaataac cctgataaat gcttcaataa | 9300 |
| tattgaaaaa ggaagagtat gagtattcaa catttccgtg tcgcccttat tccctttttt | 9360 |
| gcggcatttt gccttcctgt ttttgctcac ccagaaacgc tggtgaaagt aaaagatgct | 9420 |
| gaagatcagt tgg | 9433 |

<210> SEQ ID NO 39
<211> LENGTH: 9436

```
<212> TYPE: DNA
<213> ORGANISM: Artificial Sequence
<220> FEATURE:
<223> OTHER INFORMATION: BiCAR2 VHH38

<400> SEQUENCE: 39
gtgcacgagt gggttacatc gaactggatc tcaacagcgg taagatcctt gagagttttc      60
gccccgaaga acgttttcca atgatgagca cttttaaagt tctgctatgt ggcgcggtat     120
tatcccgtat tgacgccggg caagagcaac tcggtcgccg catacactat tctcagaatg     180
acttggttga gtactcacca gtcacagaaa agcatcttac ggatggcatg acagtaagag     240
aattatgcag tgctgccata accatgagtg ataacactgc ggccaactta cttctgacaa     300
cgatcggagg accgaaggag ctaaccgctt ttttgcacaa catggggggat catgtaactc     360
gccttgatcg ttgggaaccg gagctgaatg aagccatacc aaacgacgag cgtgacacca     420
cgatgcctgt agcaatggca acaacgttgc gcaaactatt aactggcgaa ctacttactc     480
tagcttcccg gcaacaatta atagactgga tggaggcgga taaagttgca ggaccacttc     540
tgcgctcggc ccttccggct ggctggttta ttgctgataa atctggagcc ggtgagcgtg     600
ggtctcgcgg tatcattgca gcactggggc cagatggtaa gccctcccgt atcgtagtta     660
tctacacgac ggggagtcag gcaactatgg atgaacgaaa tagacagatc gctgagatag     720
gtgcctcact gattaagcat tggtaactgt cagaccaagt ttactcatat atactttaga     780
ttgatttaaa acttcatttt taatttaaaa ggatctaggt gaagatcctt tttgataatc     840
tcatgaccaa aatcccttaa cgtgagtttt cgttccactg agcgtcagac cccgtagaaa     900
agatcaaagg atcttcttga tccttttttt tctgcgcgt aatctgctgc ttgcaaacaa     960
aaaaaccacc gctaccagcg gtggtttgtt tgccggatca agagctacca actctttttc    1020
cgaaggtaac tggcttcagc agagcgcaga taccaaatac tgttcttcta gtgtagccgt    1080
agttaggcca ccacttcaag aactctgtag caccgcctac atacctcgct ctgctaatcc    1140
tgttaccagt ggctgctgcc agtggcgata agtcgtgtct taccgggttg gactcaagac    1200
gatagttacc ggataaggcg cagcggtcgg gctgaacggg gggttcgtgc acacagccca    1260
gcttggagcg aacgacctac accgaactga gatacctaca gcgtgagcta tgagaaagcg    1320
ccacgcttcc cgaagggaga aaggcggaca ggtatccggt aagcggcagg gtcggaacag    1380
gagagcgcac gagggagctt ccagggggaa acgcctggta tctttatagt cctgtcgggt    1440
ttcgccacct ctgacttgag cgtcgatttt tgtgatgctc gtcaggggggg cggagcctat    1500
ggaaaaacgc cagcaacgcg gcctttttac ggttcctggc cttttgctgg ccttttgctc    1560
acatgttctt tcctgcgtta tcccctgatt ctgtggataa ccgtattacc gcctttgagt    1620
gagctgatac cgctcgccgc agccgaacga ccgagcgcag cgagtcagtg agcgaggaag    1680
cggaagagcg cccaatacgc aaaccgcctc tccccgcgcg ttggccgatt cattaatgca    1740
gctggcacga caggtttccc gactggaaag cgggcagtga gcgcaacgca attaatgtga    1800
gttagctcac tcattaggca ccccaggctt tacactttat gcttccggct cgtatgttgt    1860
gtggaattgt gagcggataa caatttcaca caggaaacag ctatgaccat gattacgcca    1920
agcgcgcaat taaccctcac taaagggaac aaaagctgga gctgcaagct taatgtagtc    1980
ttatgcaata ctcttgtagt cttgcaacat ggtaacgatg agttagcaac atgccttaca    2040
aggagagaaa aagcaccgtg catgccgatt ggtggaagta aggtggtacg atcgtgcctt    2100
attaggaagg caacagacgg gtctgacatg gattggacga accactgaat tgccgcattg    2160
```

```
cagagatatt gtatttaagt gcctagctcg atacataaac gggtctctct ggttagacca    2220
gatctgagcc tgggagctct ctggctaact agggaaccca ctgcttaagc ctcaataaag    2280
cttgccttga gtgcttcaag tagtgtgtgc ccgtctgttg tgtgactctg gtaactagag    2340
atccctcaga ccctttagt cagtgtggaa aatctctagc agtggcgccc gaacagggac     2400
ttgaaagcga agggaaacc agaggagctc tctcgacgca ggactcggct tgctgaagcg     2460
cgcacggcaa gaggcgaggg gcggcgactg gtgagtacgc caaaaatttt gactagcgga    2520
ggctagaagg agagagatgg gtgcgagagc gtcagtatta agcggggag aattagatcg     2580 cgatgggaaa aaattcggtt aaggccaggg ggaaagaaaa aatataaatt aaaacatata    2640
gtatgggcaa gcagggagct agaacgattc gcagttaatc ctggcctgtt agaaacatca    2700
gaaggctgta gacaaatact gggacagcta caaccatccc ttcagacagg atcagaagaa    2760
cttagatcat tatataatac agtagcaacc ctctattgtg tgcatcaaag gatagagata    2820
aaagacacca aggaagcttt agacaagata gaggaagagc aaaacaaaag taagaccacc    2880
gcacagcaag cggccgctga tcttcagacc tggaggagga gatatgaggg acaattggag    2940
aagtgaatta tataaatata aagtagtaaa aattgaacca ttaggagtag cacccaccaa    3000
ggcaaagaga agagtggtgc agagagaaaa aagagcagtg gaataggag ctttgttcct     3060 tgggttcttg ggagcagcag gaagcactat gggcgcagcg tcaatgacgc tgacggtaca    3120
ggccagacaa ttattgtctg gtatagtgca gcagcagaac aatttgctga gggctattga    3180
ggcgcaacag catctgttgc aactcacagt ctggggcatc aagcagctcc aggcaagaat    3240
cctggctgtg gaaagatacc taaaggatca acagctcctg gggatttggg gttgctctgg    3300
aaaactcatt tgcaccactg ctgtgccttg gaatgctagt tggagtaata atctctgga     3360 acagatttgg aatcacacga cctggatgga gtgggacaga gaaattaaca attacacaag    3420
cttaatacac tccttaattg aagaatcgca aaaccagcaa gaaaagaatg aacaagaatt    3480
attggaatta gataaatggg caagtttgtg gaattggttt aacataacaa attggctgtg    3540
gtatataaaa ttattcataa tgatagtagg aggcttggta ggtttaagaa tagttttgc     3600 tgtactttct atagtgaata gagttaggca gggatattca ccattatcgt ttcagaccca    3660
cctcccaacc ccgagggac ccgacaggcc cgaaggaata gaagaagaag gtggagagag     3720
agacagagac agatccattc gattagtgaa cggatctcga cggtatcgat tagactgtag    3780
cccaggaata tggcagctag attgtacaca tttagaagga aaagttatct tggtagcagt    3840
tcatgtagcc agtggatata tagaagcaga agtaattcca gcagagacag ggcaagaaac    3900
agcatacttc ctcttaaaat tagcaggaag atggccagta aaaacagtac atacagacaa    3960
tggcagcaat ttcaccagta ctacagttaa ggccgcctgt tggtgggcgg ggatcaagca    4020
ggaatttggc attccctaca atccccaaag tcaaggagta atagaatcta tgaataaaga    4080
attaaagaaa attataggac aggtaagaga tcaggctgaa catcttaaga cagcagtaca    4140
aatggcagta ttcatccaca attttaaaag aaaaggggg attgggggt acagtgcagg      4200 ggaaagaata gtagacataa tagcaacaga catacaaact aaagaattac aaaaacaaat    4260
tacaaaaatt caaaattttc gggtttatta caggacagc agagatccag tttggctgca     4320
tacgcgtcgt gaggctccgg tgcccgtcag tgggcagagc gcacatcgcc cacagtcccc    4380
gagaagttgg ggggaggggt cggcaattga accggtgcct agagaaggtg gcgcgggta     4440 aactgggaaa gtgatgtcgt gtactggctc cgccttttc ccgagggtgg gggagaaccg     4500
tatataagtg cagtagtcgc cgtgaacgtt ctttttcgca acgggtttgc cgccagaaca    4560
```

```
caggtaagtg ccgtgtgtgg ttcccgcggg cctggcctct ttacgggtta tggcccttgc    4620
gtgccttgaa ttacttccac ctggctgcag tacgtgattc ttgatcccga gcttcgggtt    4680
ggaagtgggt gggagagttc gaggccttgc gcttaaggag ccccttcgcc tcgtgcttga    4740
gttgaggcct ggcctgggcg ctgggccgc cgcgtgcgaa tctggtggca ccttcgcgcc     4800
tgtctcgctg ctttcgataa gtctctagcc atttaaaatt tttgatgacc tgctgcgacg    4860
cttttttcct ggcaagatag tcttgtaaat gcgggccaag atctgcacac tggtatttcg    4920 gttttgggg ccgcgggcgg cgacggggcc cgtgcgtccc agcgcacatg ttcggcgagg     4980
cggggcctgc gagcgcggcc accgagaatc ggacgggggt agtctcaagc tggccggcct    5040
gctctggtgc ctggcctcgc gccgccgtgt atcgccccgc cctgggcggc aaggctggcc    5100
cggtcggcac cagttgcgtg agcggaaaga tggccgcttc ccggccctgc tgcagggagc    5160
tcaaaatgga ggacgcggcg ctcgggagag cgggcgggtg agtcacccac acaaaggaaa    5220
agggcctttc cgtcctcagc cgtcgcttca tgtgactcca ctgagtaccg ggcgccgtcc    5280
aggcacctcg attagttctc gtgctttggg agtacgtcgt ctttaggttg gggggagggg    5340
ttttatgcga tggagtttcc ccacactgag tgggtggaga ctgaagttag gccagccttgg   5400 cacttgatgt aattctcctt ggaatttgcc cttttgagt ttggatcttg gttcattctc     5460
aagcctcaga cagtggttca aagtttttt cttccatttc aggtgtcgtg agctagctct     5520
agagccagca tggccttacc agtgaccgcc ttgctcctgc cgctggcctt gctgctccac    5580
gccgccaggc cgcaggtgca gctgcaggag tctgggggag gcttggtgca gcctgggggg    5640
tctctgagcc tctcctgtac agcctctgga ttcacgttca gtagttactc catggcctgg    5700
gtccgccagg ctccagggaa gggacccgaa tgggtctcag ggatttaccc ttctgatggt    5760
aagacaaggt atgcagactt cgtgaagggc cgattcagca tctccagaga caacgccaag    5820
aatatgttgt atctgcaaat gaacaacctg gaacctgagg acacggccct atattactgt    5880
gcgagaggta tcaccggatt gggaccccgg ggccagggga cccaggtcac cgtctcctca    5940
gcggccgcca ctagtgagtc taagtacggc cctcccctgcc ctccttgccc atacatctgg   6000
gcgcccttgg ccgggacttg tggggtcctt ctcctgtcac tggttatcac cctttactgc    6060
aaacggggca gaaagaaact cctgtatata ttcaaacaac catttatgag accagtacaa    6120
actactcaag aggaagatgg ctgtagctgc cgatttccag aagaagaaga aggaggatgt    6180
gaactgctcg agggaagcgg agctactaac ttcagcctgc tgaagcaggc tggagacgtg    6240
gaggagaacc ctggacctcc taggatggcc ttaccagtga ccgccttgct cctgccgctg    6300
gccttgctgc tccacgccgc caggccggga tcccaggtgc agctgcagga gtctggggga    6360 ggttggtgc aggctgggga ctctctgaga ctctcctgtg cagtcggacg cacgttcagt     6420
gcgtcaacct gggctggtt ccgccagtct ccagggaagg agcgtgagtt tgtcgcagcg     6480
attagttggt ggcgtggtga ggcatactat ggggactccg tgaagggccg attccaccatc   6540 tccagagaca acaccaagac aacgatcaat ctgcaaatga atagcctgaa acctgaggac    6600
acggccgttt attactgtgc acgagcccaa tttgatggcg cgacacgggc agatgactat    6660
gacaactggg gtcaggggac ccaggtcacc gtctcctcag cggccgccac tagttccgga    6720
accactacac cagcgcccag accacctacc ccggctccta ccatcgcatc tcagcccttg    6780
agtcttagac ccgaggcatg tcggccagcg gcggggggcg cagtgcacac gaggggggctg   6840 gacttcgcct gtgattacat ctgggcgccc ttggccggga cttgtggggt ccttctcctg    6900
```

```
tcactggtta tcacccttta ctgcagagtg aagttcagca ggagcgcaga cgccccgcg    6960 tacaagcagg gccagaacca gctctataac gagctcaatc taggacgaag agaggagtac   7020
gatgttttgg acaagagacg tggccgggac cctgagatgg ggggaaagcc gagaaggaag   7080
aaccctcagg aaggcctgta caatgaactg cagaaagata agatggcgga ggcctacagt   7140
gagattggga tgaaaggcga gcgccggagg ggcaaggggc acgatggcct ttaccagggt   7200
ctcagtacag ccaccaagga cacctacgac gcccttcaca tgcaggccct gcccctcgc    7260 taagtcgaca atcaacctct ggattacaaa atttgtgaaa gattgactgg tattcttaac   7320
tatgttgctc cttttacgct atgtggatac gctgctttaa tgcctttgta tcatgctatt   7380
gcttcccgta tggctttcat tttctcctcc ttgtataaat cctggttgct gtctctttat   7440
gaggagttgt ggcccgttgt caggcaacgt ggcgtggtgt gcactgtgtt tgctgacgca   7500 accccactg gttgggcat tgccaccacc tgtcagctcc tttccgggac tttcgctttc    7560 cccctccta ttgccacggc ggaactcatc gccgcctgcc ttgcccgctg ctggacaggg   7620
gctcggctgt tgggcactga caattccgtg gtgttgtcgg ggaagctgac gtcctttcct   7680
tggctgctcg cctgtgttgc cacctggatt ctgcgcggga cgtccttctg ctacgtccct   7740
tcggccctca atccagcgga ccttccttcc cgcggcctgc tgccggctct gcggcctctt   7800
ccgcgtcttc gccttcgccc tcagacgagt cggatctccc tttgggccgc ctccccgcct   7860
ggaattcgag ctcggtacct ttaagaccaa tgacttacaa gcagctgta gatcttagcc    7920 acttttaaa agaaaagggg ggactggaag ggctaattca ctcccaacga agacaagatc   7980 tgcttttgc ttgtactggg tctctctggt tagaccagat ctgagcctgg gagctctctg    8040
gctaactagg gaacccactg cttaagcctc aataaagctt gccttgagtg cttcaagtag   8100
tgtgtgcccg tctgttgtgt gactctggta actagagatc cctcagaccc ttttagtcag   8160
tgtggaaaat ctctagcagt agtagttcat gtcatcttat tattcagtat ttataacttg   8220
caaagaaatg aatatcagag agtgagagga acttgtttat tgcagcttat aatggttaca   8280
aataaagcaa tagcatcaca aatttcacaa ataaagcatt ttttcactg cattctagtt   8340 gtggtttgtc caaactcatc aatgtatctt atcatgtctg gctctagcta tcccgcccct   8400
aactccgccc agttccgccc attctccgcc ccatggctga ctaatttttt ttatttatgc   8460
agaggccgag gccgcctcgg cctctgagct attccagaag tagtgaggag gcttttttgg   8520
aggcctagct agggacgtac ccaattcgcc ctatagtgag tcgtattacg cgcgctcact   8580
ggccgtcgtt ttacaacgtc gtgactggga aaaccctggc gttacccaac ttaatcgcct   8640
tgcagcacat ccccctttcg ccagctggcg taatagcgaa gaggcccgca ccgatcgccc   8700
ttcccaacag ttgcgcagcc tgaatggcga atgggacgcg ccctgtagcg gcgcattaag   8760
cgcggcgggt gtggtggtta cgcgcagcgt gaccgctaca cttgccagcg ccctagcgcc   8820
cgctcctttc gctttcttcc cttcctttct cgccacgttc gccggctttc ccgtcaagc    8880 tctaaatcgg gggctccctt tagggttccg atttagtgct ttacggcacc tcgaccccaa   8940
aaaacttgat tagggtgatg gttcacgtag tgggccatcg ccctgataga cggttttttcg   9000 cccctttgacg ttggagtcca cgttctttaa tagtggactc ttgttccaaa ctggaacaac   9060
actcaaccct atctcggtct attcttttga tttataaggg attttgccga tttcggccta   9120
ttggttaaaa aatgagctga tttaacaaaa atttaacgcg aatttttaaca aaatattaac   9180 gcttacaatt taggtggcac ttttcgggga aatgtgcgcg gaacccctat ttgtttattt   9240
ttctaaatac attcaaatat gtatccgctc atgagacaat aaccctgata aatgcttcaa   9300
```

```
taatattgaa aaaggaagag tatgagtatt caacatttcc gtgtcgccct tattcccttt    9360
tttgcggcat tttgccttcc tgtttttgct cacccagaaa cgctggtgaa agtaaaagat    9420
gctgaagatc agttgg                                                    9436

<210> SEQ ID NO 40
<211> LENGTH: 8
<212> TYPE: PRT
<213> ORGANISM: Artificial Sequence
<220> FEATURE:
<223> OTHER INFORMATION: Octretotide
<220> FEATURE:
<221> NAME/KEY: SITE
<222> LOCATION: (1)..(1)
<223> OTHER INFORMATION: Phe is a D-amino acid.
<220> FEATURE:
<221> NAME/KEY: SITE
<222> LOCATION: (4)..(4)
<223> OTHER INFORMATION: Trp is a D-amino acid.

<400> SEQUENCE: 40

Phe Cys Phe Trp Lys Thr Cys Thr
1               5
```